(12) United States Patent
Hirai et al.

(10) Patent No.: US 7,700,786 B2
(45) Date of Patent: Apr. 20, 2010

(54) PYRAZOLE DERIVATIVE, INTERMEDIATE THEREFOR, PROCESSES FOR PRODUCING THESE, AND HERBICIDE CONTAINING THESE AS ACTIVE INGREDIENT

(75) Inventors: Kenji Hirai, Sagamihara (JP); Atsushi Uchida, Machida (JP); Atsuko Watanabe, Yokohama (JP); Taeko Abe, Sagamihara (JP); Takuya Ueda, Abiko (JP); Hiroshi Sakurai, Fujieda (JP)

(73) Assignees: Sagami Chemical Research Center (JP); Kaken Pharmaceutical Co., Ltd. (JP)

( * ) Notice: Subject to any disclaimer, the term of this patent is extended or adjusted under 35 U.S.C. 154(b) by 1245 days.

(21) Appl. No.: 10/468,527

(22) PCT Filed: Feb. 19, 2002

(86) PCT No.: PCT/JP02/01411

§ 371 (c)(1),
(2), (4) Date: Mar. 2, 2004

(87) PCT Pub. No.: WO02/066439

PCT Pub. Date: Aug. 29, 2002

(65) Prior Publication Data

US 2005/0070441 A1    Mar. 31, 2005

(30) Foreign Application Priority Data

Feb. 20, 2001    (JP)    ............... 2001-043199

(51) Int. Cl.
*C07D 231/12*    (2006.01)
*C07D 231/20*    (2006.01)
*A01N 43/56*    (2006.01)

(52) U.S. Cl. ............... 548/377.1; 548/376; 548/366.1; 548/367.1; 504/169

(58) Field of Classification Search ............... 504/130, 504/193, 169; 548/377, 366.1, 377.1, 376, 548/367.1
See application file for complete search history.

(56) References Cited

U.S. PATENT DOCUMENTS

| 3,923,789 | A |   | 12/1975 | Schrock et al. |
| 3,991,073 | A |   | 11/1976 | Mulder et al. |
| 4,008,249 | A | * | 2/1977  | Fischer et al. ............ 548/366.1 |
| 4,070,365 | A |   | 1/1978  | Van Daalen et al. |
| 4,316,040 | A |   | 2/1982  | Plath et al. |
| 4,620,865 | A | * | 11/1986 | Beck et al. ................ 504/130 |
| 4,885,022 | A | * | 12/1989 | Baba et al. ................ 504/193 |
| 5,032,165 | A | * | 7/1991  | Miura et al. .............. 504/193 |
| 5,185,025 | A |   | 2/1993  | Moedritzer et al. |
| 5,424,279 | A |   | 6/1995  | Sugai et al. |
| 5,962,694 | A | * | 10/1999 | Zagar et al. ............. 548/366.1 |
| 6,075,149 | A |   | 6/2000  | Kirstgen et al. |

FOREIGN PATENT DOCUMENTS

| EP | 256 667 A2 | 7/1987 |
| EP | 295 233 A1 | 6/1988 |
| EP | 370 990 A1 | 11/1989 |
| EP | 508 469 A1 | 4/1992 |
| EP | 647 612 A1 | 9/1994 |
| JP | 55-9062    | 1/1980 |
| JP | 05112532   | 5/1993 |
| JP | 07-285962  | 10/1995 |
| JP | 08-245594  | 9/1996 |

OTHER PUBLICATIONS

Freche, P et al., Tetrahedron, 33:2069-2077 (1977).
Clark, RD, J. Agric. Food Chem. 44:3643-3652 (1996).
Nandihalli, UB, Pestic. Sci. 40:265-277 (1994).
Allah, HM et al., Pharmazie 35(12):799-800 (1980).
Abuzar, S. et al., Indian J. Chem., Sect. B, 19B:211-212 (1980).
Moedritzer, K. et al, "Synthesis and chemistry of agrochemicals III." ACS Symposium Series 504:147-160, 1992.

* cited by examiner

*Primary Examiner*—Sabiha Qazi
(74) *Attorney, Agent, or Firm*—Nixon Peabody LLP

(57) ABSTRACT

The present invention provides a pyrazole derivative of the general formula (1),

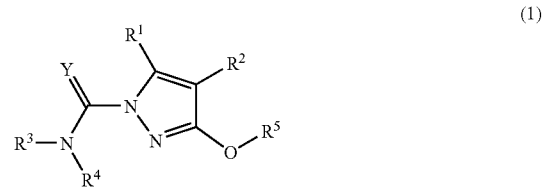

which has an excellent efficacy as an active component for a herbicide, an intermediate for the production thereof, processes for the production thereof, and a herbicide containing the derivative as an active ingredient.

8 Claims, No Drawings

PYRAZOLE DERIVATIVE, INTERMEDIATE THEREFOR, PROCESSES FOR PRODUCING THESE, AND HERBICIDE CONTAINING THESE AS ACTIVE INGREDIENT

CROSS-REFERENCE TO RELATED APPLICATIONS

This application is a National Phase Entry of co-pending International Application No. PCT/JP02/01411, filed Feb. 19, 2002 which designated the U.S. and which claims the benefit of Japanese Application No. 2001-43199, filed Feb. 20, 2001.

TECHNICAL FIELD

The present invention relates to a novel pyrazole derivative, an intermediate thereof, processes for the preparation thereof and a herbicide containing any one of them as an active ingredient.

TECHNICAL BACKGROUND

Conventionally, there are known a number of pyrazole derivatives having pesticidal activity such as herbicidal activity or insecticidal activity. However, nothing has been reported on any pyrazole derivative having a substituted oxy group at the 3-position of a pyrazole ring and a substituted carbamoyl group or a substituted thiocarbamoyl group on a nitrogen atom at the 1-position as shown in the following general formula (1) in the present invention, nor is there any report on biological activities thereof. As pyrazole derivatives structurally similar to the pyrazole derivative (1) of the present invention, there are known pyrazole derivatives described in WO97/24332 (EP876351, JP2000/502686, U.S. Pat. No. 6,075,149) and EP256667 (JP63/044571, U.S. Pat. No. 5,374,644). However, these pyrazole derivatives are completely different from the pyrazole derivative (1) of the present invention in that they have an alkyl group on a nitrogen atom of their pyrazole ring. Further, it is described that the pyrazole derivatives described in the above WO97/24332 and EP256667 have pesticidal activity against fungi and harmful insects, but these Publications describe nothing concerning any other biological activity.

DISCLOSURE OF THE INVENTION

The present invention provides a novel pyrazole derivative having excellent herbicidal activity and high selectivity to crops, an intermediate thereof and processes for the preparation thereof, and further provides a herbicide containing the derivative as an active ingredient.

The present inventors have made diligent studies for herbicides having excellent herbicidal activity and crop selectivity. As a result, it has been found that the pyrazole derivative of the following general formula (1) in the present invention exhibits excellent herbicidal activity at a low dosage without causing phytotoxicity, and a simple process for the preparation thereof has been also found. The present invention has been accordingly completed.

That is, the present invention is directed to a pyrazole derivative of the general formula (1),

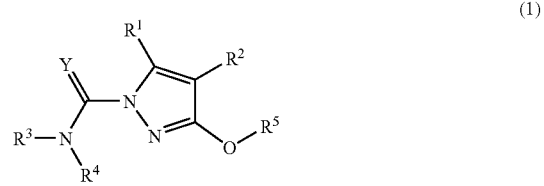

wherein $R^1$ is a hydrogen atom, an optionally substituted alkyl group having 1 to 6 carbon atoms, an optionally substituted cycloalkyl group having 3 to 8 carbon atoms, an alkyloxycarbonyl group having 1 to 6 carbon atoms or an optionally substituted phenyl group, $R^2$ is a hydrogen atom, a halogen atom or an optionally substituted alkyl group having 1 to 6 carbon atoms, $R^3$ is a hydrogen atom, an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group, $R^4$ is a hydrogen atom, an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms or an optionally substituted phenyl group, or, $R^3$ and $R^4$ may form a heterocyclic ring together with a nitrogen atom to which they bond, $R^5$ is an optionally substituted phenyl group or an optionally substituted pyridyl group, and Y is an oxygen atom or a sulfur atom.

Further, the present invention is also directed to a pyrazole derivative of the general formula (2),

wherein $R^1$, $R^2$ and $R^5$ are as defined above.

Further, the present invention is directed to a process for the preparation of a pyrazole derivative of the general formula (2),

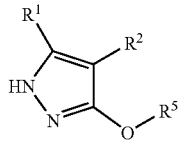
(2)

wherein $R^1$, $R^2$ and $R^5$ are as defined above, which comprises reacting a 3-hydroxypyrazole derivative of the general formula (3),

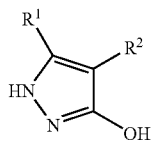
(3)

wherein $R^1$ and $R^2$ are as defined above, and a compound of the general formula (4), $$R^5-Z \qquad (4)$$

wherein $R^5$ is as defined above and Z is a leaving group, in the presence of a base.

Further, the present invention is directed to a process for the preparation of a pyrazole derivative of the general formula (2b),

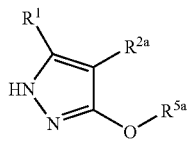
(2b)

wherein $R^1$ is as defined above, $R^{5a}$ is a hydrogen atom, an optionally substituted phenyl group or an optionally substituted pyridyl group and $R^{2a}$ is a halogen atom, which comprises halogenating a pyrazole derivative of the general formula (2a),

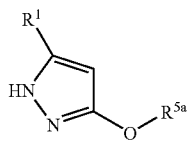
(2a)

wherein $R^1$ and $R^{5a}$ are as defined above.

Further, the present invention is directed to a process for the preparation of a pyrazole derivative of the general formula (1a) in the present invention,

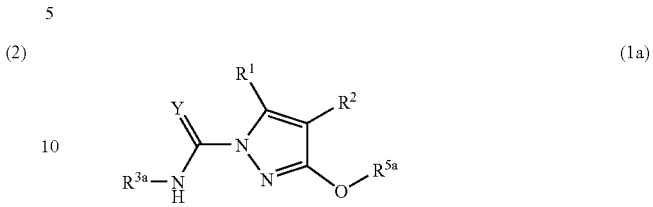
(1a)

wherein $R^1$, $R^2$, $R^{5a}$ and Y are as defined above, and $R^{3a}$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group, which comprises reacting a pyrazole derivative of the general formula (2c),

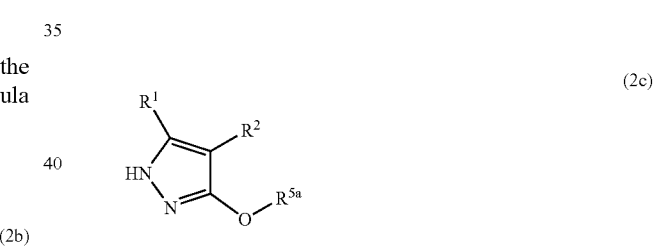
(2c)

wherein $R^1$, $R^2$ and $R^{5a}$ are as defined above, and isocyanates or isothiocyanates of the general formula (5), $$R^{3a}-NCY \qquad (5)$$

wherein $R^{3a}$ and Y are as defined above, optionally in the presence of a base.

Further, the present invention is directed to a process for the preparation of a pyrazole derivative of the general formula (1b),

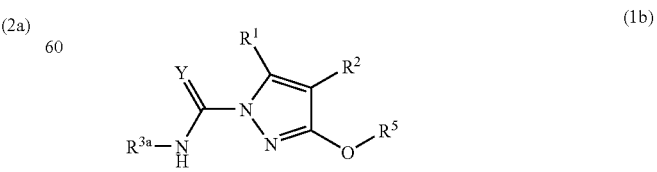
(1b)

wherein $R^1$, $R^2$, $R^{3a}$ and $R^5$ are as defined above, which comprises reacting a 3-hydroxypyrazole derivative of the general formula (3a),

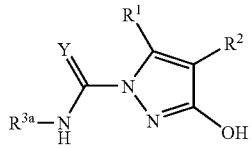
(3a)

wherein $R^1$, $R^2$ and $R^{3a}$ are as defined above, and a compound of the general formula (4), $$R^5-Z \qquad (4)$$

wherein $R^5$ is as defined above and Z is a leaving group, in the presence of a base.

Further, the present invention is directed to a process for the preparation of a pyrazole derivative of the general formula (1c),

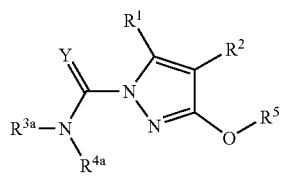
(1c)

wherein $R^1$, $R^2$, $R^{3a}$, $R^5$ and Y are as defined above, and $R^{4a}$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms or an optionally substituted alkynyl group having 3 to 6 carbon atoms, which comprises reacting the thus-obtained pyrazole derivative of the general formula (1b),

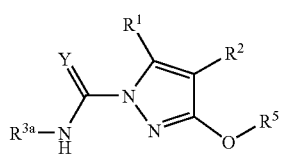
(1b)

wherein $R^1$, $R^2$, $R^{3a}$, $R^5$ and Y are as defined above, and a compound of the general formula (6), $$R^{4a}-Z \qquad (6)$$

wherein $R^{4a}$ is as defined above and Z is a leaving group.

Further, the present invention is directed to a process for the preparation of a pyrazole-1-carboxamide derivative of the general formula (1d) in the present invention,

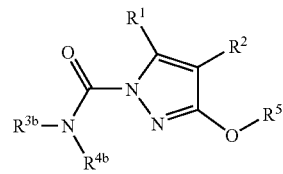
(1d)

wherein $R^1$, $R^2$ and $R^5$ are as defined above and each of $R^{3b}$ and $R^{4b}$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms or an optionally substituted phenyl group, or $R^{3b}$ and $R^{4b}$ may form a heterocyclic ring together with a nitrogen atom to which they bond, which comprises reacting a pyrazole derivative of the general formula (2),

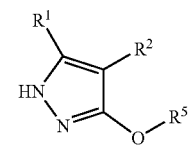
(2)

wherein $R^1$, $R^2$ and $R^5$ are as defined above, and carbamic acid chlorides of the general formula (7),

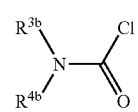
(7)

wherein $R^{3b}$ and $R^{4b}$ are as defined above, in the presence of a base.

Further, the present invention is directed to a pyrazole derivative of the general formula (2d),

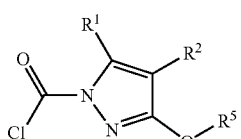
(2d)

wherein $R^1$, $R^2$ and $R^5$ are as defined above, which is an intermediate in the production of a pyrazole-1-carboxamide derivative in the present invention, and, said pyrazole derivative can be produced by reacting a pyrazole derivative of the general formula (2),

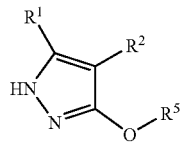
(2)

wherein $R^1$, $R^2$ and $R^5$ are as defined above, with phosgene or a material equivalent to phosgene.

Further, the present invention is directed to a process for the preparation of a pyrazole-1-carboxamide derivative of the general formula (1e) in the present invention,

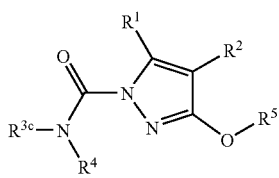
(1e)

wherein $R^1$, $R^2$, $R^4$ and $R^5$ are as defined above and $R^{3c}$ is a hydrogen atom, an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group, or $R^{3c}$ and $R^4$ may form a heterocyclic ring together with a nitrogen atom to which they bond, which comprises reacting a pyrazole derivative of the general formula (2d) as an intermediate in production,

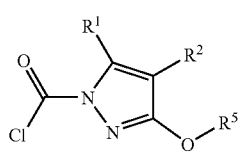
(2d)

wherein $R^1$, $R^2$ and $R^5$ are as defined above, with amines of the general formula (8).

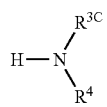
(8)

wherein $R^{3c}$ and $R^4$ are as defined above, optionally in the presence of a base.

Further, the present invention is directed to a process for the preparation of a pyrazole derivative of the general formula (1g),

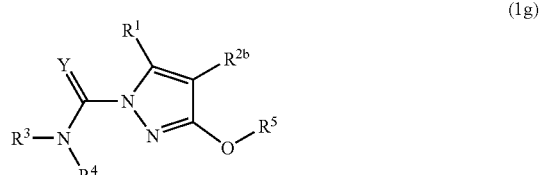
(1g)

wherein $R^1$, $R^3$, $R^4$, $R^5$ and Y are as defined above and $R^{2b}$ is a halogen atom, which comprises halogenating a pyrazole derivative of the general formula (1f),

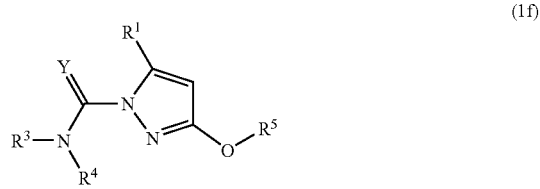
(1f)

wherein $R^1$, $R^3$, $R^4$, $R^5$ and Y are as defined above.

Further, the present invention is directed to a process for the preparation of a pyrazole-1-carboxamide derivative of the general formula (1i),

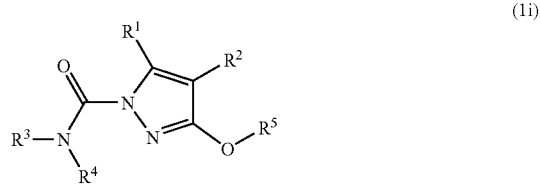
(1i)

wherein $R^1$, $R^2$, $R^3$, $R^4$ and $R^5$ are as defined above, which comprises oxidizing a pyrazole-1-carbothioamide derivative of the general formula (1h),

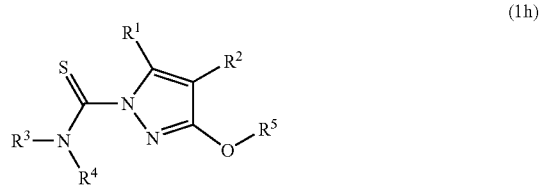
(1h)

wherein $R^1$, $R^2$, $R^3$, $R^4$ and $R^5$ are as defined above.

Further, the present invention is directed to a herbicide containing, as an active ingredient, a pyrazole derivative of the general formula (1),

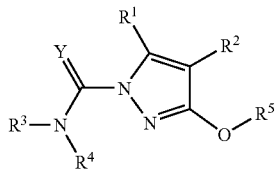

(1)

wherein $R^1$, $R^2$, $R^3$, $R^4$, $R^5$ and Y are as defined above.

PREFERRED EMBODIMENTS OF THE INVENTION

In compounds of the present invention, definitions of substituents represented by $R^1$ to $R^5$, Y and Z are as follows.

The alkyl group having 1 to 6 carbon atoms, represented by $R^1$, $R^2$ and $R^{2a}$, may be linear or branched, and examples thereof include methyl, ethyl, propyl, isopropyl, butyl, isobutyl, s-butyl, tert-butyl, pentyl, isoamyl, neopentyl, 1-ethylpropyl, 1-methylbutyl, 2-methylbutyl, hexyl, isohexyl, 2-ethylbutyl and 4-methylpentyl. The above alkyl group may have at least one substituent such as a halogen atom, an alkyloxy group having 1 to 6 carbon atoms, a formyl group, an alkyloxycarbonyl group having 1 to 6 carbon atoms or a heterocyclic ring. More specifically, examples of such alkyl groups include trichloromethyl, trifluoromethyl, methoxymethyl, ethoxymethyl, 2-methoxyethyl, formylmethyl, methoxycarbonylmethyl, ethoxycarbonylmethyl, furfuryl, tetrahydrofurfuryl, 2-picolyl, 3-picolyl, 4-picolyl, 2-thienylmethyl and 2-morpholinoethyl.

The alkyl group having 1 to 12 carbon atoms, represented by $R^3$, $R^{3a}$, $R^{3b}$, $R^{3c}$, $R^4$, $R^{4a}$ and $R^{4b}$, may be linear or branched, and examples thereof include methyl, ethyl, propyl, isopropyl, butyl, isobutyl, s-butyl, tert-butyl, pentyl, isoamyl, neopentyl, 1-ethylpropyl, 1-methylbutyl, 2-methylbutyl, hexyl, isohexyl, 2-ethylbutyl, 4-methylpentyl, heptyl, 1-methylhexyl, octyl, decyl, undecyl and dodecyl. The above alkyl group may have at least one substituent such as a halogen atom, a cycloalkyl group having 3 to 8 carbon atoms, a cyano group, a nitro group, an alkylthio group having 1 to 6 carbon atoms, an alkyloxy group having 1 to 6 carbon atoms, an alkyloxycarbonyl group having 1 to 6 carbon atoms, a carboxy group or an acyl group. More specifically, examples of such alkyl groups include 2-chloroethyl, 2-bromoethyl, 3-chloropropyl, 3-fluoropropyl, cyclopropylmethyl, cyclopentylmethyl, cyclohexylmethyl, cyanomethyl, 2-cyanoethyl, 3-cyanopropyl, nitromethyl, 2-methylthioethyl, methoxymethyl, ethoxymethyl, 2-methoxyethyl, 2-chloroethoxymethyl, methoxycarbonylmethyl, ethoxycarbonylmethyl, 1-methoxycarbonylethyl, 1-ethoxycarbonylethyl, 2-ethoxycarbonylethyl, carboxymethyl, acetonyl, 1-acetylethyl, 3-acetylpropyl, phenacyl, 4-chlorophenacyl, 2,4-difluorophenacyl, 4-methylphenacyl, 4-isopropylphenacyl, 4-isobutylphenacyl, 4-cyclohexylphenacyl, 4-cyanophenacyl and 4-nitrophenacyl.

Examples of the cycloalkyl group having 3 to 8 carbon atoms, represented by $R^1$, $R^3$, $R^{3a}$, $R^{3b}$, $R^{3c}$, $R^4$, $R^{4a}$ and $R^{4b}$, include cyclopropyl, cyclobutyl, cyclopentyl, cyclohexyl and cyclooctyl. The above cycloalkyl group may have a substituent such as a halogen atom, an alkyl group having 1 to 4 carbon atoms, an alkyloxycarboyl group having 1 to 4 carbon atoms or a cyano group. More specifically, examples of such cycloalkyl groups include 1-methylcyclopropyl, 2,2-dimethylcyclopropyl, 2-chlorocyclopropyl, 2,2-dichlorocyclopropyl, 2-methoxycarbonylcyclopropyl, 2-cyanocyclopropyl, 2-methylcyclopentyl and 3-methylcyclopentyl.

Examples of the aralkyl group having 7 to 11 carbon atoms, represented by $R^3$, $R^{3a}$, $R^{3b}$, $R^{3c}$, $R^4$, $R^{4a}$ and $R^{4b}$, include benzyl, 1-phenylethyl, 2-phenylethyl, 1-phenylpropyl, 1-naphthylmethyl and 2-naphthylmethyl. The above aralkyl group may have, on its aromatic ring, at least one substituent such as a halogen atom, an alkyl group having 1 to 12 carbon atoms, a haloalkyl group having 1 to 6 carbon atoms, an alkyloxy group having 1 to 6 carbon atoms, a haloalkyloxy group having 1 to 6 carbon atoms, an alkylthio group having 1 to 6 carbon atoms, an alkylsulfonyl group having 1 to 6 carbon atoms, an alkyloxycarbonyl group having 1 to 6 carbon atoms, an carboxy group, an optionally substituted carbamoyl group, a cyano group or a nitro group. More specifically, examples of such aralkyl groups include benzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 3,5-dichlorobenzyl, 3,5-dibromobenzyl, 2-methylbenzyl, 3-methylbenzyl, 4-methylbenzyl, 2,4-dimethylbenzyl, 3,5-dimethylbenzyl, 2-trifluoromethylbenzyl, 3-trifluoromethylbenzyl, 4-trifluoromethylbenzyl, 3,5-bis(trifluoromethyl)benzyl, 2,4-bis(trifluoromethyl)benzyl, 2-methoxycarbonylbenzyl, 3-methoxycarbonylbenzyl, 4-methoxycarbonylbenzyl, 3-carboxybenzyl, 4-carboxybenzyl, 3-(N,N-dimethylcarbamoyl)benzyl, 4-(N,N-dimethylcarbamoyl)benzyl, 3-(N,N-diethylcarbamoyl)benzyl, 3-(N-ethyl-N-propylcarbamoyl)benzyl, 3-cyanobenzyl, 4-cyanobenzyl, 2-methoxybenzyl, 3-methoxybenzyl, 4-methoxybenzyl, 3,4-dimethoxybenzyl, 4-trifluoromethoxybenzyl, 4-phenoxybenzyl, 4-methylthiobenzyl, 4-methylsulfonylbenzyl, 2-nitrobenzyl, 3-nitrobenzyl, 4-nitrobenzyl, 1-(2-fluorophenyl)ethyl, 1-(2-chlorophenyl)ethyl, 1-(2-bromophenyl)ethyl, 1-(3-fluorophenyl)ethyl, 1-(3-chlorophenyl)ethyl, 1-(3-bromophenyl)ethyl, 1-(4-fluorophenyl)ethyl, 1-(4-chlorophenyl)ethyl, 1-(4-bromophenyl)ethyl, 1-(2-trifluoromethylphenyl)ethyl, 1-(3-trifluoromethylphenyl)ethyl, 1-(4-trifluoromethylphenyl)ethyl, 2-(3-bromophenyl)ethyl, 2-(3-trifluoromethylphenyl)ethyl, 3-phenylpropyl and 4-phenylbutyl.

Examples of the alkenyl group having 3 to 6 carbon atoms, represented by $R^3$, include allyl, 2-methyl-2-propenyl, 2-butenyl, 3-butenyl, 2-pentenyl, 3-pentenyl, 2-hexenyl and 3-hexenyl. The alkenyl group may be substituted with a halogen atom or the like. Examples of the substituted alkenyl group include 2-chloro-2-propenyl, 3-chloropropenyl and 4-chloro-2-butenyl.

Examples of the alkenyl group having 3 to 6 carbon atoms, represented by $R^{3a}$, $R^{3b}$, $R^{3c}$, $R^4$, $R^{4a}$ and $R^{4b}$, include allyl, 2-methyl-2-propenyl, 2-butenyl, 3-butenyl, 2-pentenyl, 3-pentenyl, 2-hexenyl and 3-hexenyl. The alkenyl group may be substituted with a halogen atom or the like. Examples of the substituted alkenyl group include 2-chloro-2-propenyl, 3-chloropropenyl and 4-chloro-2-butenyl.

The alkynyl group having 3 to 6 carbon atoms, represented by $R^3$, $R^{3a}$, $R^{3b}$, $R^{3c}$, $R^4$, $R^{4a}$ and $R^{4b}$, may be linear or branched, and examples thereof include propargyl, 1-butyn-3-yl, 3-methyl-1-butyn-3-yl, 2-butynyl, 2-pentynyl and 3-pentynyl. The alkynyl group may be substituted with a halogen atom, or the like. Examples of the substituted alkynyl group include 3-fluoro-2-propynyl, 3-chloro-2-propynyl, 3-bromo-2-propynyl, 4-bromo-2-butynyl and 4-bromo-3-butynyl.

The optionally substituted phenyl group represented by $R^1$, $R^3$, $R^{3a}$, $R^{3b}$, $R^{3c}$, $R^4$ and $R^{4b}$ is, for example, a phenyl group having, as a substituent on a benzene ring, a halogen atom, an alkyl group having 1 to 12 carbon atoms, a haloalkyl group having 1 to 6 carbon atoms, an acyl group having 1 to 6 carbon atoms, an alkyl group having 1 to 12 carbon atoms and being substituted with an alkyloxyimino group having 1 to 4 carbon atoms, an alkyloxycarbonyl group having 1 to 6 carbon atoms, a carboxy group, a cyano group, an alkyloxy group having 1 to 6 carbon atoms, an aryloxy group, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, a haloalkylthio group having 1 to 6 carbon atoms, a haloalkylsulfinyl group having 1 to 6 carbon atoms, a haloalkylsulfonyl group having 1 to 6 carbon atoms or a nitro group. More specifically, examples of such optionally substituted phenyl group include 2-fluorophenyl, 2-chlorophenyl, 2-bromophenyl, 3-fluorophenyl, 3-chlorophenyl, 4-fluorophenyl, 4-chlorophenyl, 4-bromophenyl, 2,4-difluorophenyl, 2,4-dichlorophenyl, 3,5-difluorophenyl, 3,5-dichlorophenyl, 3-chloro-2,4-difluorophenyl, 2,4,5-trichlorophenyl, 2,4-dichloro-3-methylphenyl, 2,4-dichloro-5-methoxyphenyl, 2,4-dichloro-5-isopropyloxyphenyl, 2-fluoro-4-chloro-5-methoxyphenyl, 2-fluoro-4-chloro-5-isopropyloxyphenyl, 2-fluoro-4-chloro-5-cyclopentyloxyphenyl, 2-fluoro-4-chloro-5-propargyloxyphenyl, 2-fluoro-4-chloro-5-(1-butyn-3-yloxy)phenyl, 2-fluoro-4-trifluoromethylphenyl, 2-chloro-4-trifluoromethylphenyl, 2-chloro-5-trifluoromethylphenyl, 4-fluoro-3-phenoxyphenyl, 2-fluoro-5-nitrophenyl, 2,4-difluoro-5-nitrophenyl, 2-methylphenyl, 3-methylphenyl, 4-methylphenyl, 2,4-dimethylphenyl, 4-ethylphenyl, 4-isopropylphenyl, 4-tert-butylphenyl, 2-trifluoromethylphenyl, 3-trifluoromethylphenyl, 4-trifluoromethylphenyl, 2,4-bis(trifluoromethyl)phenyl, 3,5-bis(trifluoromethyl)phenyl, 2-acetylphenyl, 4-acetylphenyl, 4-isovalerylphenyl, 2-methoxycarbonylphenyl, 2-ethoxycarbonylphenyl, 3-methoxycarbonylphenyl, 4-methoxycarbonylphenyl, 2-carboxyphenyl, 4-carboxyphenyl, 2-cyanophenyl, 4-cyanophenyl, 2-methoxyphenyl, 3-methoxyphenyl, 4-methoxyphenyl, 3,4-dimethoxyphenyl, 4-isopropyloxyphenyl, 4-tert-butyloxyphenyl, 3-trifluoromethyloxyphenyl, 4-trifluoromethyloxyphenyl, 3-phenoxyphenyl, 4-phenoxyphenyl, 2-methylthiophenyl, 4-methylthiophenyl, 2-methylsulfinylphenyl, 4-methylsulfinylphenyl, 2-methylsulfonylphenyl, 4-methylsulfonylphenyl, 4-trifluoromethylthiophenyl, 4-trifluoromethylsulfinylphenyl, 4-trifluoromethylsulfonylphenyl, 2-nitrophenyl and 4-nitrophenyl.

The optionally substituted phenyl group represented by $R^5$ and $R^{5a}$ is, for example, a phenyl group having, as a substituent on a benzene ring, a halogen atom, an alkyl group having 1 to 12 carbon atoms, a haloalkyl group having 1 to 6 carbon atoms, an acyl group having 1 to 6 carbon atoms, an alkyl group having 1 to 12 carbon atoms and being substituted with an alkyloxyimino group having 1 to 4 carbon atoms, an alkyloxycarbonyl group having 1 to 6 carbon atoms, a carboxy group, a cyano group, a substituted amino group, an alkyloxy group having 1 to 6 carbon atoms, an aryloxy group, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, a haloalkylthio group having 1 to 6 carbon atoms, a haloalkylsulfinyl group having 1 to 6 carbon atoms, a haloalkylsulfonyl group having 1 to 6 carbon atoms or a nitro group. As a substituent on a benzene ring, electron-withdrawing groups such as a trifluoromethyl group, a nitro group, a cyano group, a chlorine atom, a fluorine atom and an alkyloxycarbonyl group are preferred, since a good reaction yield is attained and since raw materials can be easily obtained. Further, such electron-withdrawing groups are preferably substituted at an o-position and/or p-position. More specifically, examples of the above substituted phenyl include 4-fluorophenyl, 4-chlorophenyl, 4-bromophenyl, 2,4-difluorophenyl, 2,4-dichlorophenyl, 2,4,5-trichlorophenyl, 2-chloro-5-trifluoromethylphenyl, 2-trifluoromethylphenyl, 4-trifluoromethylphenyl, 2,4-bis(trifluoromethyl)phenyl, 2,6-dichloro-4-trifluoromethylphenyl, 4-cyanophenyl, 4-cyano-2-trifluoromethylphenyl, 2-methylthiophenyl, 4-methylthiophenyl, 2-methylsulfinylphenyl, 4-methylsulfinylphenyl, 2-methylsulfonylphenyl, 4-methylsulfonylphenyl, 4-trifluoromethylthiophenyl, 4-trifluoromethylsulfinylphenyl, 4-trifluoromethylsulfonylphenyl, 2-nitrophenyl, 4-nitrophenyl, 2-nitro-4-trifluoromethylphenyl, 4-nitro-2-trifluoromethylphenyl, 4-nitro-3-trifluoromethylphenyl, 2,6-dichloro-4-trifluoromethylphenyl, 2-chloro-6-fluoro-4-trifluoromethylphenyl, 2-chloro-6-nitro-4-trifluoromethylphenyl and 2,4-dinitro-6-trifluoromethylphenyl. Concerning these substituents on a benzene ring, for example, a nitro group is convertible to an amino group by reduction, and the amino group is further convertible to a halogen atom or a substituted alkyl group through a diazonium salt, and these can be included in the substituents on a benzene ring.

The optionally substituted pyridyl group represented by $R^5$ and $R^{5a}$ is, for example, a pyridyl group having, as a substituent on a pyridine ring, a halogen atom, an alkyl group having 1 to 12 carbon atoms, a haloalkyl group having 1 to 6 carbon atoms, an acyl group having 1 to 6 carbon atoms, an alkyl group having 1 to 12 carbon atoms and being substituted with an alkyloxyimino group having 1 to 4 carbon atoms, an alkyloxycarbonyl group having 1 to 6 carbon atoms, a carboxy group, a cyano group, an alkyloxy group having 1 to 6 carbon atoms, an aryloxy group, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, a haloalkylthio group having 1 to 6 carbon atoms, a haloalkylsulfinyl group having 1 to 6 carbon atoms, a haloalkylsulfonyl group having 1 to 6 carbon atoms or a nitro group. As a substituent on a pyridine ring, electron-withdrawing groups such as a trifluoromethyl group, a nitro group, a cyano group, a chlorine atom, a fluorine atom and an alkyloxycarbonyl group are preferred, since a good reaction yield is attained and since raw materials can be easily obtained. Further, such electron-withdrawing groups are preferably substituted at the 3-position and/or the 5-position of a pyridine ring. More specifically, examples of the substituted pyridyl group include 3-chloropyridin-2-yl, 5-chloropyridin-2-yl, 3,5-dichloropyridin-2-yl, 4-amino-3,5-dichloropyridin-2-yl, 3-cyano-6-methylpyridin-2-yl, 5-trifluoromethylpyridin-2-yl, 3-chloro-5-trifluoromethylpyridin-2-yl, 3-nitropyridin-2-yl, 5-nitropyridin-2-yl, 3-nitro-4-methylpyridin-2-yl, 3-nitro-6-methoxypyridin-2-yl, 2-chloro-3-nitropyridin-6-yl, 6-chloro-3-nitropyridin-2-yl and 3,5-dinitropyridin-2-yl. Concerning these substituents on a pyridine ring, for example, a nitro group is convertible to an amino group by reduction, and the amino group is further convertible to a halogen atom or a substituted alkyl group through a diazonium salt, and these can be included in the substituents on a pyridine ring.

Examples of the alkyloxy group having 1 to 6 carbon atoms, represented by $R^3$, $R^{3a}$ and $R^{3c}$, include methoxy, ethoxy, propyloxy, isopropyloxy, butyloxy, isobutyloxy, sec-butyloxy, tert-butyloxy, pentyloxy and hexyloxy. The alkyl group constituting such an alkyloxy group may be substituted with at least one of a halogen atom, a cycloalkyl group having 3 to 8 carbon atoms, an alkyloxy group having 1 to 6 carbon atoms, an alkylthio group having 1 to 6 carbon atoms, an alkyloxycarbonyl group having 1 to 6 carbon atoms, a carboxy group, a cyano group, a nitro group, an optionally substituted amino group and an optionally substituted phenyl group.

Examples of the cycloalkyloxy group having 3 to 8 carbon atoms, represented by $R^3$, $R^{3a}$ and $R^{3c}$, include cyclopropyloxy, cyclobutyloxy, cyclopentyloxy, cyclohexyloxy and cyclooctyloxy. These cycloalkyl groups may be substituted with a halogen atom, an alkyl group having 1 to 4 carbon atoms, an alkyloxycarbonyl group having 1 to 4 carbon atoms or a cyano group. More specifically, examples of such substituted cycloalkyloxy groups include 1-methylcyclopropyloxy, 2,2-dimethylcyclopropyloxy, 2-chlorocyclopropyloxy, 2,2-dichlorocyclopropyloxy, 2-methoxycarbonylcyclopropyloxy, 2-cyanocyclopropyloxy, 2-methylcyclopentyloxy and 3-methylcyclopentyloxy.

Examples of the aralkyloxy group having 7 to 11 carbon atoms, represented by $R^3$, $R^{3a}$ and $R^{3c}$, include benzyloxy, 1-phenylethyloxy, 2-phenylethyloxy, 1-phenylpropyloxy, 1-naphthylmethyloxy and 2-naphthylmethyloxy. The aromatic ring of the aralkyloxy group may be substituted with at least one of a halogen atom, an alkyl group having 1 to 12 carbon atoms, a haloalkyl group having 1 to 6 carbon atoms, an alkyloxy group having 1 to 6 carbon atoms, a haloalkyloxy group having 1 to 6 carbon atoms, an alkylthio group having 1 to 6 carbon atoms, an alkylsulfonyl group having 1 to 6 carbon atoms, an alkyloxycarbonyl group having 1 to 6 carbon atoms, a carboxy group, an optionally substituted carbamoyl group, a cyano group and a nitro group.

The alkenyloxy group having 3 to 12 carbon atoms, represented by $R^3$, $R^{3a}$ and $R^{3c}$, may be linear or branched, and examples thereof include 1-propenyloxy, allyloxy, 2-methyl-2-propenyloxy, 2-butenyloxy, 3-butenyloxy, 2-pentenyloxy, 3-pentenyloxy, 1-cyclopentenyloxy, 2-hexenyloxy, 3-hexenyloxy, 1-cyclohexenyloxy, 2-heptenyloxy and 1-cyclooctenyloxy. The alkenyloxy group may be substituted with a halogen atom, or the like, and examples of the substituted alkenyloxy group include 2-chloro-2-propenyloxy, 3-chloropropenyloxy and 4-chloro-2-butenyloxy.

The alkynyloxy group having 3 to 6 carbon atoms, represented by $R^3$, $R^{3a}$ and $R^{3c}$, may be linear or branched, and examples thereof include propargyloxy, 1-butyn-3-yloxy, 3-methyl-1-butyn-3-yloxy, 2-butynyloxy, 2-pentynyloxy and 3-pentynyloxy. The above alkynyloxy group may be substituted with a halogen atom, or the like, and examples of the substituted alkynyloxy group include 3-fluoro-2-propynyloxy, 3-chloro-2-propynyloxy, 3-bromo-2-propynyloxy, 4-bromo-2-butynyloxy and 4-bromo-3-butynyloxy.

Examples of the heterocyclic ring that a combination of $R^3$ and $R^4$, a combination of $R^{3c}$ and $R^4$ or a combination of $R^{3b}$ and $R^{4b}$ forms together with a nitrogen atom to which they bond include pyrrole, pyrroline, pyrrolidine, imidazole, imidazoline, imidazolioine, pyrazole, pyrazoline, pyrazolidine, piperidine, piperazine, indole, indoline, isoindole, 1H-indazole, purine, oxazoline, isoxazoline, isoxazolidine, thiazoline, morpholine, thiomorpholine, aziridine, azocane and tetrahydrooxazine. The above heterocyclic ring may be substituted with at least one of an alkyl group having 1 to 6 carbon atoms, a haloalkyl group having 1 to 6 carbon atoms, a halogen atom and a cyano group.

Examples of the halogen atom represented by $R^2$ and $R^{2b}$ include a chlorine atom, a bromine atom and a fluorine atom.

Examples of the leaving group represented by Z include halogen atoms such as a chlorine atom, a bromine atom and iodine atom and alkyl- or arylsulfonyloxy groups such as methylsulfonyloxy, trifluoromethylsulfonyloxy, phenylsulfonyloxy and p-tolylsulfonyloxy.

The method of producing the pyrazole derivative of the present invention and the intermediate thereof will be explained in detail below.

Production method-1 (Step-1) shows a method in which a reaction of a pyrazole derivative (3) and a compound (4) is carried out in the presence of a base, to produce a pyrazole derivative (2) of the present invention.

[Production Method-1]

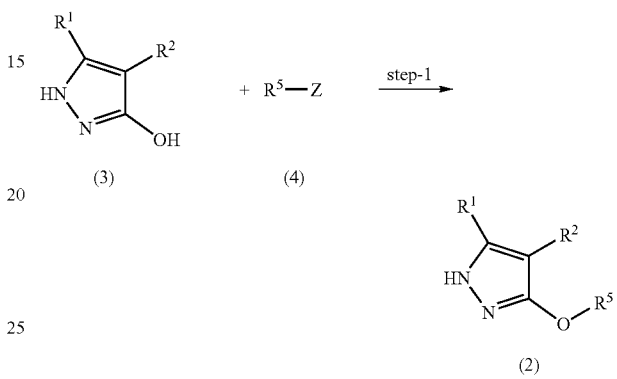

wherein $R^1$, $R^2$, $R^5$ and Z are as defined above.

The above reaction is essentially carried out in the presence of a base. The base can be selected from alkali metal bases such as sodium hydride, sodium amide, sodium carbonate, potassium carbonate, sodium methoxide, sodium ethoxide, potassium-t-butoxide, sodium hydroxide and potassium hydroxide, and organic amines such as triethylamine, tributylamine, N-methylmorpholine, pyridine and dimethylaniline. The base is preferably used in an amount of one to excess equivalents to the reaction substrate, since a good yield is attained.

The reaction is preferably carried out in a solvent, and any solvent can be used so long as it has no adversary effect on the reaction. For example, the solvent can be selected from ether solvents such as diethyl ether, tetrahydrofuran (THF), dioxane and 1,2-dimethoxyethane (DME), nitriles such as acetonitrile and propionitrile, esters such as ethyl acetate and ethyl propionate, aromatic hydrocarbon solvents such as benzene, toluene, xylene and chlorobenzene, amides such as N,N-dimethylformamide (DMF) and N-methylpyrrolidone, dimethylsulfoxide (DMSO), water or mixtures of these. While the reaction temperature is not specially limited, the desired product can be obtained in good yield by carrying out the reaction at a temperature that is determined in the range of 0° C. to 150° C. as required. After completion of the reaction, the desired product can be obtained by ordinary post-treatment procedures. The product can be purified by column chromatography or recrystallization as required.

The pyrazole derivative represented by the general formula (3), as a raw material in the above step, can be easily prepared by a cyclization reaction of hydrazine and a β-ketoester derivative as described, for example, in Organic Synthesis Vol. 6, 791 (1988). While the thus-obtained 3-hydroxypyrazole derivative (3) is present in the form of an equilibrium mixture with a tautomer, the general formula shows a structure of an alcohol form (3) for the convenience.

Production method-2 (step-2) is a method in which a pyrazole derivative (2a) is halogenated to produce a pyrazole derivative (2b) of the present invention.

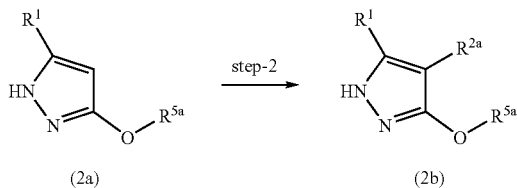

wherein $R^1$, $R^{2a}$ and $R^{5a}$ are as defined above.

The halogenation can be carried out with a halogenating reagent. The halogenating reagent can be selected from sulfuryl chloride, N-chlorosuccinimide or N-bromosuccinimide.

The reaction is preferably carried out in a solvent, and any solvent can be used so long as it has no adversary effect on the reaction. Examples of the solvent include aliphatic hydrocarbon solvents such as pentane, hexane and octane, ether solvents such as diethyl ether, tetrahydrofuran, dioxane and DME, halogen-containing solvents such as dichloromethane, chloroform and carbon tetrachloride, aromatic hydrocarbon solvents such as chlorobenzene and dichlorobenzene, organic acid solvents such as acetic acid and propionic acid, water and mixtures of these.

While the reaction temperature differs depending upon the halogenating reagent used, it is determined at a temperature in the range of –10° C. to 150° C. The reaction is preferably carried out at a temperature determined in the range of 0° C. to the reflux temperature of a solvent as required, since it gives a good yield. After completion of the reaction, the desired product can be obtained by ordinary post-treatment procedures. The product can be purified by column chromatography or recrystallization as required.

Production method-3 (step-3) is a step in which a pyrazole derivative (2c) reacts with isocyanates or isothiocyanates (5), to produce a pyrazole derivative (1a) of the present invention.

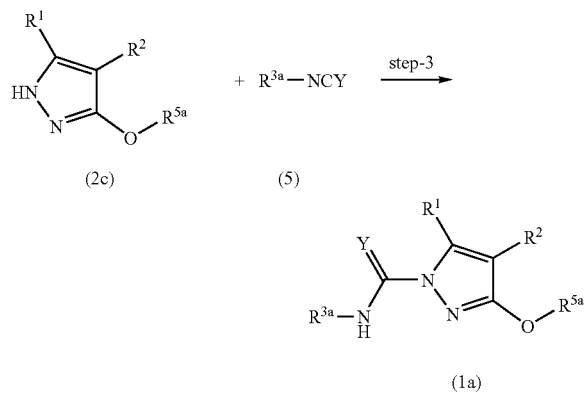

wherein $R^1$, $R^2$, $R^{3a}$, $R^{5a}$ and Y are as defined above.

The above reaction can be carried out in the presence of a base, and the base can be selected from alkali metal bases such as sodium hydride, sodium amide, sodium carbonate, potassium carbonate, sodium methoxide, sodium ethoxide, potassium-t-butoxide, sodium hydroxide and potassium hydroxide, and organic amines such as triethylamine, tributylamine, N-methylmorpholine, pyridine and dimethylaniline. The amount of the base is not specially limited.

The reaction can be carried out in a solvent, and any solvent can be used so long as it has no adversary effect on the reaction. Examples of the solvent include ether solvents such as diethyl ether, THF, dioxane and DME, nitriles such as acetonitrile and propionitrile, esters such as ethyl acetate and ethyl propionate, aromatic hydrocarbon solvents such as benzene, toluene, xylene and chlorobenzene, halogen-containing solvents such as dichloromethane, chloroform and carbon tetrachloride, amides such as DMF and N-methylpyrrolidone, DMSO or mixtures of these. While the reaction temperature is not specially limited, the desired product can be obtained in good yield by carrying out the reaction at a temperature that is determined in the range of 0° C. to 150° C. as required. After completion of the reaction, the desired product can be obtained by ordinary post-treatment procedures. The product can be purified by column chromatography or recrystallization as required.

Production-4 (step-4) shows a method in which a reaction of a pyrazole derivative (3a) and a compound (4) is carried out in the presence of a base, to produce a pyrazole derivative (1b) of the present invention.

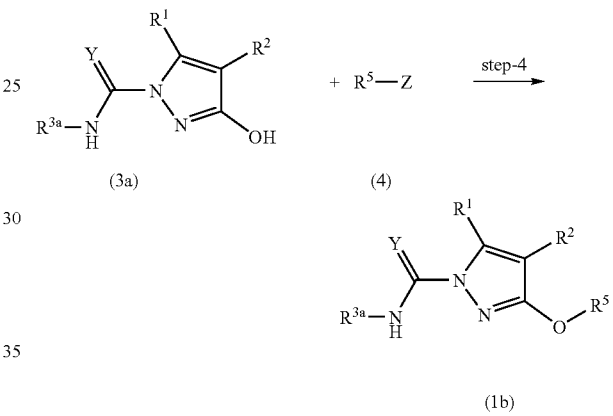

wherein $R^1$, $R^2$, $R^{3a}$, $R^5$ and Z are as defined above.

It is essential to carry out the above reaction in the presence of a base. The base can be selected from alkali metal bases such as sodium hydride, sodium amide, sodium carbonate, potassium carbonate, sodium methoxide, sodium ethoxide, potassium-t-butoxide, sodium hydroxide and potassium hydroxide, and organic amines such as triethylamine, tributylamine, N-methylmorpholine, pyridine and dimethylaniline. The base is preferably used in an amount of one to excess equivalents to the reaction substrate, since a good yield is attained.

The reaction is preferably carried out in a solvent, and any solvent can be used so long as it has no adversary effect on the reaction. For example, the solvent can be selected from ether solvents such as diethyl ether, tetrahydrofuran (THF), dioxane and 1,2-dimethoxyethane (DME), nitriles such as acetonitrile and propionitrile, esters such as ethyl acetate and ethyl propionate, aromatic hydrocarbon solvents such as benzene, toluene, xylene and chlorobenzene, amides such as N,N-dimethylformamide (DMF) and N-methylpyrrolidone, dimethylsulfoxide (DMSO), water or mixtures of these. While the reaction temperature is not specially limited, the desired product can be obtained in good yield by carrying out the reaction at a temperature that is determined in the range of 0° C. to 150° C. as required. After completion of the reaction, the desired product can be obtained by ordinary post-treatment procedures. The product can be purified by column chromatography or recrystallization as required.

Production method-5 (step-5) shows a method in which a reaction of a pyrazole derivative (1b) and a compound (6) is carried out in the presence of a base, to produce a pyrazole derivative (1c) of the present invention.

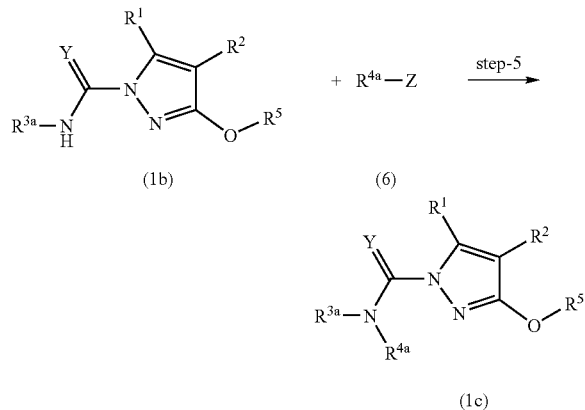

wherein $R^1$, $R^2$, $R^{3a}$, $R^{4a}$, $R^5$, Y and Z are as defined above.

It is essential to carry out the above reaction in the presence of a base. The base can be selected from alkali metal bases such as sodium hydride, sodium amide, sodium carbonate, potassium carbonate, sodium methoxide, sodium ethoxide, potassium-t-butoxide, sodium hydroxide and potassium hydroxide, and organic amines such as triethylamine, tributylamine, N-methylmorpholine, pyridine and dimethylaniline. When the base is used in an amount of one to excess equivalents to the reaction substrate, the desired product can be obtained in good yield.

The reaction is preferably carried out in a solvent, and any solvent can be used so long as it has no adversary effect on the reaction. Examples of the solvent include ether solvents such as diethyl ether, THF, DME and dioxane, nitriles such as acetonitrile and propionitrile, aromatic hydrocarbon solvents such as benzene, toluene, xylene and chlorobenzene, amides such as DMF and N-methylpyrrolidone, DMSO, water or mixtures of these. While the reaction temperature is not specially limited, the desired product can be obtained in good yield by carrying out the reaction at a temperature that is determined in the range of 0° C. to 100° C. as required. After completion of the reaction, the desired product can be obtained by ordinary post-treatment procedures. The product can be purified by column chromatography or recrystallization as required.

Production method-6 (step-6) shows a method in which a reaction of a pyrazole derivative (2) and a carbamic acid chlorides (7) is carried out in the presence of a base, to produce a pyrazole derivative (1d) of the present invention.

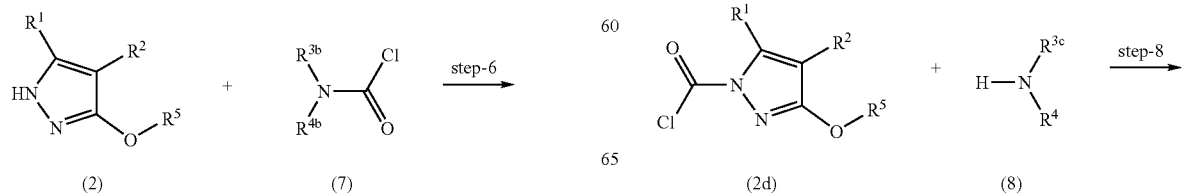

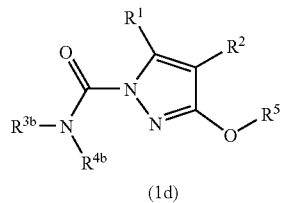

wherein $R^1$, $R^2$, $R^{3b}$, $R^{4b}$ and $R^5$ are as defined above.

It is essential to carry out the above reaction in the presence of a base. The base can be selected from alkali metal bases such as sodium hydride, sodium amide, sodium carbonate, potassium carbonate, sodium methoxide, sodium ethoxide, potassium-t-butoxide, sodium hydroxide and potassium hydroxide, and organic amines such as triethylamine, tributylamine, N-methylmorpholine, pyridine and dimethylaniline. When the base is used in an amount of one to excess equivalents to the reaction substrate, the desired product can be obtained in good yield.

The reaction is preferably carried out in a solvent, and any solvent can be used so long as it has no adversary effect on the reaction. Examples of the solvent include ether solvents such as diethyl ether, THF, DME and dioxane, nitriles such as acetonitrile and propionitrile, aromatic hydrocarbon solvents such as benzene, toluene, xylene and chlorobenzene, amides such as DMF and N-methylpyrrolidone, DMSO, water or mixtures of these. While the reaction temperature is not specially limited, the desired product can be obtained in good yield by carrying out the reaction at a temperature that is determined in the range of 0° C. to 100° C. as required. After completion of the reaction, the desired product can be obtained by ordinary post-treatment procedures. The product can be purified by column chromatography or recrystallization as required.

Production method-7 shows a method in which a pyrazole derivative (2) reacts with phosgene or a phosgene equivalent material such as a phosgene dimer or a phosgene trimer to prepare a pyrazole derivative (2d) of the present invention which is a production intermediate (step-7) and then the pyrazole derivative (2d) reacts with amines (8) in the presence of a base, to produce a pyrazole derivative (1e) of the present invention (step-8).

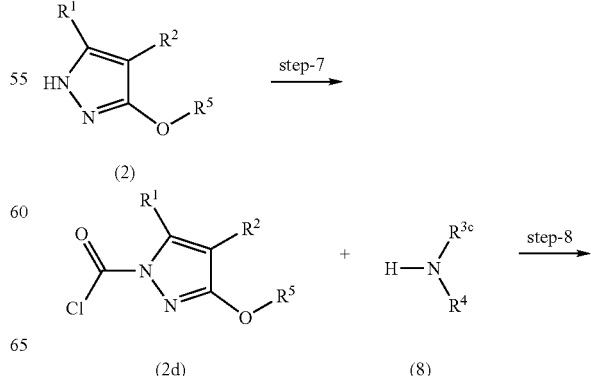

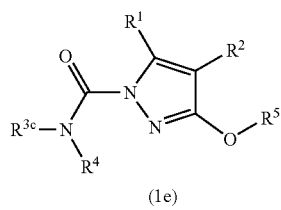

(1e)

wherein $R^1$, $R^2$, $R^{3c}$, $R^4$ and $R^5$ are as defined above.

In the reaction in the step-7, the pyrazole derivative (2) reacts with phosgene or a phosgene equivalent material in a halogen-containing solvent such as dichloromethane, chloroform or carbon tetrachloride, an aromatic hydrocarbon solvent such as benzene, toluene, xylene or chlorobenzene or an ester solvent such as ethyl acetate or propyl acetate, whereby the desired product can be synthesized. While the reaction temperature is not specially limited, the desired product can be obtained in good yield by carrying out the reaction at a temperature that is determined in the range of −30° C. to 150° C. as required. After completion of the reaction, the desired product can be obtained by ordinary post-treatment procedures. The product can be used for the subsequent reaction without its isolation.

It is essential to carry out the react-on in the step-8 in the presence of a base. The base can be selected from alkali metal bases such as sodium hydride, sodium amide, sodium carbonate, potassium carbonate, potassium-t-butoxide, sodium hydroxide and potassium hydroxide, and organic amines such as triethylamine, tributylamine, N-methylmorpholine, pyridine and dimethylaniline. The base is used in an amount of one to excess equivalents to the reaction substrate, whereby the desired product can be obtained in good yield.

The reaction is preferably carried out in an organic solvent, and the solvent can be selected from benzene, toluene, xylene, THF, diethyl ether, chloroform, dichloromethane, methanol, ethanol, propyl alcohol, isopropyl alcohol, tert-butyl alcohol, ethyl acetate, DMF or DMSO. The reaction can be carried out at a temperature that is determined in the range of room temperature to the reflux temperature of a solvent as required. After completion of the reaction, the desired product can be obtained by ordinary post-treatment procedures. The product can be purified by column chromatography or recrystallization as required.

Production method-8 (step 9) shows a method in which a pyrazole derivative (1f) is halogenated to produce a pyrazole derivative (1g) of the present invention.

[Production Method-8]

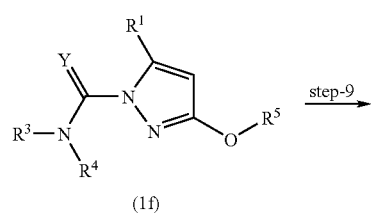

(1f)

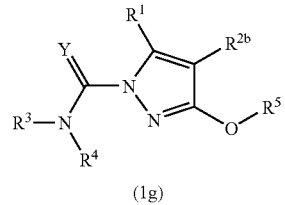

(1g)

wherein $R^1$, $R^{2b}$, $R^3$, $R^4$, $R^5$ and Y are as defined above.

The halogenation can be carried out with a halogenating reagent. The halogenating reagent can be selected from sulfuryl chloride, N-chlorosuccinimide or N-bromosuccinimide.

The reaction is preferably carried out in a solvent, and any solvent can be used so long as it has no adversary effect on the reaction. Examples of the solvent include aliphatic hydrocarbon solvents such as pentane, hexane and octane, ether solvents such as diethyl ether, tetrahydrofuran, dioxane and DME, halogen-containing solvents such as dichloromethane, chloroform and carbon tetrachloride, aromatic hydrocarbon solvents such as chlorobenzene and dichlorobenzene, organic acid solvents such as acetic acid and propionic acid, water and mixtures of these.

While the reaction temperature differs depending upon the halogenating reagent used, it is determined at a temperature in the range of −10° C. to 150° C. The reaction is preferably carried out at a temperature determined in the range of 0° C. to the reflux temperature of a solvent as required, since a good yield is attained. After completion of the reaction, the desired product can be obtained by ordinary post-treatment procedures. The product can be purified by column chromatography or recrystallization as required.

Production method-9 (step-10) shows a method in which a thiocarbonyl group of a pyrazole derivative (1 h) is oxidized to produce a pyrazole derivative (1i) of the present invention.

[Production Method-9]

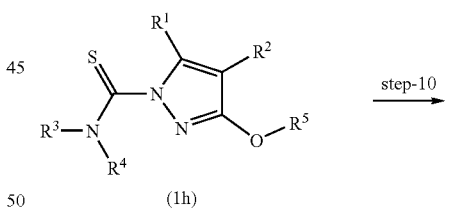

(1h)

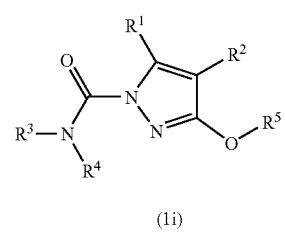

(1i)

wherein $R^1$, $R^2$, $R^3$, $R^4$ and $R^5$ are as defined above.

The thiocarbonyl group can be oxidized with an oxidizing reagent. As an oxidizing reagent, for example, hydrogen peroxide can be used.

The reaction is preferably carried out in an aqueous alcohol with a suitable water-concentration. The alcohol can be selected from methanol, ethanol or propanol. The above reaction is preferably carried out in the presence of a base, and the base can be selected from sodium hydroxide or potassium hydroxide. The reaction can be carried out at a temperature that is determined in the range of −30° C. to 60° C. as required. After completion of the reaction, the desired product can be obtained by ordinary post-treatment procedures. The product can be purified by column chromatography or recrystallization as required.

The present invention will be explained further in detail with reference to Referential Examples and Examples hereinafter, while the present invention shall not be limited thereto.

EXAMPLES

Referential Example 1

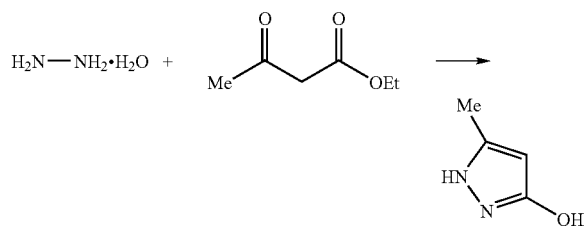

Hydrazine monohydrate (10.0 g, 20.0 mmol) was added to a solution of ethyl 3-oxobutanoate (26.0 g, 20.0 mmol) in ethanol (50 ml) at 0° C., and the mixture was stirred at room temperature for 1 hour. After completion of the reaction, a precipitated solid was filtered and washed with diethyl ether, to give a white solid of 3-hydroxy-5-methylpyrazole (16.9 g, yield: 86.0%). mp: 215-216° C.; $^1$H-NMR (DMSO-$d_6$, DMSO, ppm): δ 2.10 (s, 3H), 5.22 (s, 1H), 8.50-11.90 (br s, 2H).

Referential Examples 2-9

Reactions of hydrazine monohydrate with β-ketoester derivative (Referential Example 2: ethyl 3-oxopentanoate, Referential Example 3: ethyl isobutylylacetate, Referential Example 4: methyl 4,4-dimethyl-3-oxopentanate, Referential Example 5: methyl 4-methoxyacetate, Referential Example 6: diethyl 3-oxoglutarate, Referential Example 7: ethyl 4,4,4-trifluoro-3-oxobutanate, Referential Example 8: ethyl 2-methyl-3-oxobutanate, Referential Example 9: ethyl 2-ethyl-3-oxobutanate) were carried out in the same manner as in Referential Example 1, to give corresponding 3-hydroxypyrazole derivatives. Products/forms/yields/melting points/NMR spectra are described below.

Referential Example 2

5-ethyl-3-hydroxypyrazole/white solid/yield: 74.8%/mp: 191-193° C./$^1$H-NMR (DMSO-$d_6$, DMSO, ppm): δ 1.13 (t, J=7.6 Hz, 3H), 2.46 (q, J=7.6 Hz, 2H), 5.24 (s, 1H), 9.10-11.60 (br s, 1H). (Amino proton was not assigned.).

Referential Example 3

3-hydroxy-5-isopropylpyrazole/white solid/yield: 57.5%/mp: 189-193° C./$^1$H-NMR (DMSO-$d_6$, DMSO, ppm): δ 1.15 (d, J=6.9 Hz, 6H), 2.79 (sep, J=6.9 Hz, 1H), 5.23 (s, 1H), 8.80-12.40 (br s, 1H).

Referential Example 4

5-tert-butyl-3-hydroxypyrazole/white solid/yield: 74.2%/mp: 205-206° C./$^1$H-NMR (DMSO-$d_6$, DMSO, ppm): δ 1.26 (s, 9H), 5.22 (s, 1H), 8.60-12.20 (br s, 2H).

Referential Example 5

3-hydroxy-5-(methoxymethyl)pyrazole/white solid/yield: 80.1%/mp: 123-125° C./$^1$H-NMR (DMSO-$d_6$, DMSO, ppm): δ 3.23 (s, 3H), 4.25 (s, 2H), 5.42 (s, 1H), 9.00-13.00 (m, 2H).

Referential Example 6 ethyl(3-hydroxypyrazol-5-yl)acetate/white solid/yield: 35.4%/mp: 114-117° C./$^1$H-NMR (DMSO-$d_6$, DMSO, ppm): δ 1.20 (t, J=7.1 Hz, 3H), 3.34 (s, 2H), 4.10 (q, J=7.1 Hz, 2H), 5.35 (s, 1H), 8.60-12.20 (m, 2H).

Referential Example 7

3-hydroxy-5-trifluoromethylpyrazole/white solid/yield: 81.5%/mp: 211-215° C./$^1$H-NMR (DMSO-$d_6$, DMSO, ppm): δ 5.69 (s, 1H), 10.70-11.60 (brs, 1H), 12.20-13.40 (br s, 1H).

Referential Example 8

4,5-dimethyl-3-hydroxypyrazole/white solid/yield: 93.7%/mp: 268-270° C./$^1$H-NMR (DMSO-$d_6$, DMSO, TMS, ppm): δ 1.73 (s, 3H), 2.03 (s, 3H), 9.20-12.50 (br s, 2H).

Referential Example 9

4-ethyl-3-hydroxy-5-methylpyrazole/white solid/yield: 86.7%/mp: 232-234° C./$^1$H-NMR (DMSO-$d_6$, DMSO, ppm): δ 1.00 (t, J=7.5 Hz, 3H), 2.05 (s, 3H), 2.21 (q, J=7.5 Hz, 2H), 8.90-11.50 (br s, 2H).

Referential Example 10

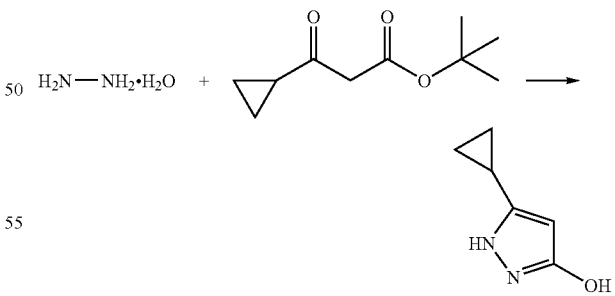

Hydrazine monohydrate (1.80 g, 45.0 mmol) was added to a solution of tert-butyl 4-cyclopropyl-3-oxopropionate (5.53 g, 30.0 mmol) in ethanol (50 ml) at 0° C., and the mixture was stirred at room temperature for 4 hours. After completion of the reaction, a precipitated solid was filtered and washed with diethyl ether, to give a white solid of 5-cyclopropyl-3-hydroxypyrazole (2.08 g, yield: 55.9%). mp: 213-215° C.; $^1$H-NMR (DMSO-$d_6$, DMSO, ppm): δ 0.55-0.65 (m, 2H), 0.75-0.95 (m, 2H), 1.65-1.85 (m, 1H), 5.12 (s, 1H). (Amino proton and hydroxy proton were not assigned.)

Referential Example 11

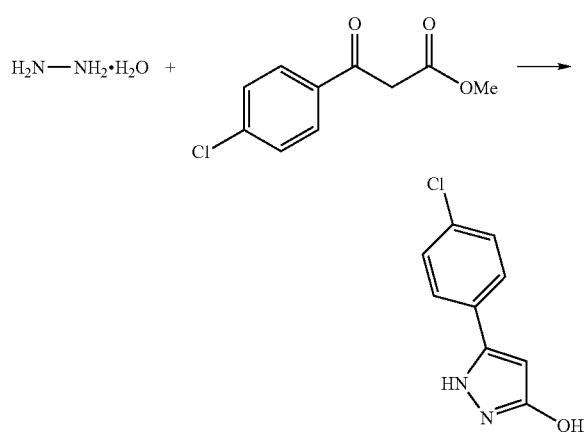

Hydrazine monohydrate (0.80 g, 20 mmol) was added to a solution of methyl 4-chlorobenzoylacetate (3.19 g, 15.0 mmol) in ethanol (40 ml) at 0° C., and the mixture was stirred at room temperature for 2 days. After completion of the reaction, a precipitated solid was filtered and washed with diethyl ether, to give a white solid of 5-(4-chlorophenyl)-3-hydroxypyrazole (2.02 g, yield: 55.1%). mp: 240-241° C.; $^1$H-NMR (DMSO-d$_6$, DMSO, ppm): δ 5.92 (s, 1H), 7.47 (d, J=8.5 Hz, 2H), 7.70 (d, J=8.5 Hz, 2H), 9.30-10.60 (br s, 1H), 11.60-12.70 (br s, 1H).

Referential Example 12

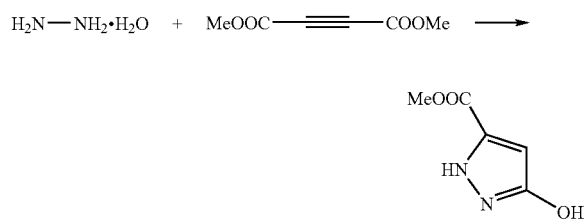

Hydrazine monohydrate (6.7 g, 210 mmol) was added to a solution of dimethyl acetylenedicarboxylate (24.7 g, 175 mmol) in toluene (90 ml) at 0° C., and the thus-obtained mixture was gradually temperature-increased up to room temperature, stirred for 2 hours and further stirred under heating at 130° C. for 4 hours. After completion of the reaction, a precipitated solid was filtered and washed with diethyl ether, to give a white solid of methyl 3-hydroxypyrazole-5-carboxylate (18.2 g, yield: 73.8%). mp: 229-231° C.; $^1$H-NMR (DMSO-d$_6$, DMSO, ppm): δ 3.79 (s, 3H), 5.91 (s, 1H), 10.10-10.45 (br s, 1H). (Hydroxy proton was not assigned.)

Referential Example 13

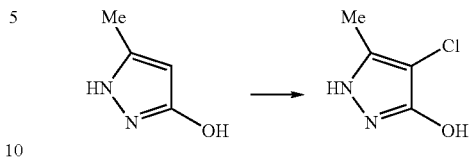

Sulfuryl chloride (4.86 g, 36 mmol) was added to a solution of 3-hydroxy-5-methylpyrazole (2.94 g, 30.0 mmol) in acetic acid (25 ml), and the mixture was stirred at room temperature for 6 hours. After completion of the reaction, the reaction mixture was poured into ice water, and a precipitated solid was filtered and washed with water, to give a yellowish solid of 4-chloro-3-hydroxy-5-methylpyrazole (1.48 g, yield: 37.2%). mp: 235-238° C. (dec.); $^1$H-NMR (CDCl$_3$, TMS, ppm): δ 2.10 (s, 3H), 8.75-9.15 (m, 2H).

Referential Example 14

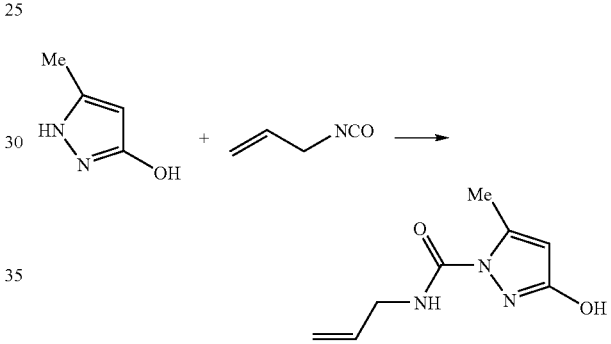

Potassium carbonate (3.52 g, 25.5 mmol) was added to a solution of 3-hydroxy-5-methylpyrazole (5.00 g, 51.0 mmol) in DMF (80 ml). Then, allylisocyanate (4.51 ml, 51.0 mmol) was added, and the mixture was stirred at room temperature for 6 hours. After completion of the reaction, the reaction mixture was poured into 1N hydrochloric acid and extracted with ethyl acetate (50 ml×2). An organic layer was washed with water (50 ml×3), dried over anhydrous magnesium sulfate and then filtered to remove a desiccant, and the solvent was distilled off from a filtrate under reduced pressure. The resultant crude product was purified with a silica gel column (ethyl acetate/hexane=1/3), to give a white solid of N-allyl-3-hydroxy-5-methylpyrazole-1-carboxamide (4.72 g, yield: 51.1%). mp: 80-83° C.; $^1$H-NMR (CDCl$_3$, TMS, ppm): δ 2.55 (d, J=0.8 Hz, 3H), 3.97 (dddt, J=1.6, 1.6, 5.8 and 5.8 Hz, 2H), 5.19 (ddt, J=1.6, 2.7 and 10.3 Hz, 1H), 5.28 (ddt, J=1.6, 2.7 and 17.2 Hz, 1H), 5.63 (d, J=0.8 Hz, 1H), 5.90 (ddt, J=5.8, 10.3 and 17.2 Hz, 1H), 6.70 (m, 1H). (Hydroxy proton was not assigned.)

Referential Example 15

Reaction of 3-hydroxy-5-methylpyrazole with phenyl isocyanate was carried out in the same manner as in Referential Example 14, to give a white solid of N-phenyl-3-hydroxy-5-methylpyrazol-1-carboxamide (yield: 18.9%). mp: 232-234°

C.; $^1$H-NMR (CDCl$_3$, TMS, ppm): δ 2.62 (d, J=0.8 Hz, 3H), 5.72 (d, J=0.8 Hz, 1H), 7.11-7.17 (m, 1H), 7.33-7.39 (m, 2H), 7.53-7.57 (m, 2H), 8.64 (br s, 1H). (Hydroxy proton was not assigned.)

Example 1

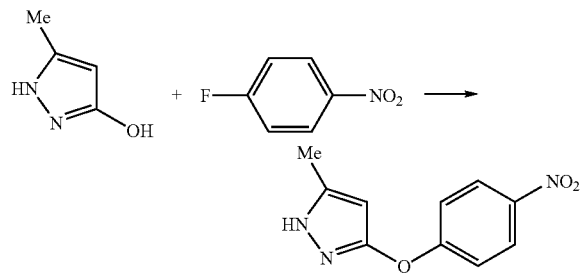

Potassium carbonate (0.5 g, 3.6 mmol) and 4-fluoronitrobenzene (1.6 g, 1.0 mmol) were added to a solution of 3-hydroxy-5-methylpyrazole (0.33 g, 3.4 mmol) in DMF (50 ml) at room temperature, and further, the mixture was stirred at room temperature for 8 hours. After completion of the reaction, the reaction mixture was poured into 2N hydrochloric acid (100 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7→1/3), to give a white solid of 5-methyl-3-(4-nitrophenyloxy)pyrazole (0.4 g, yield: 63.3%) mp: 124-125° C.; $^1$H-NMR (CDCl$_3$, TMS, ppm): δ 2.33 (s, 3H), 5.75 (s, 1H), 7.20 (dd, J=2.2 and 7.1 Hz, 2H), 8.22 (dd, J=2.2 and 7.1 Hz, 2H), 9.30-9.90 (br s, 1H).

Example 2

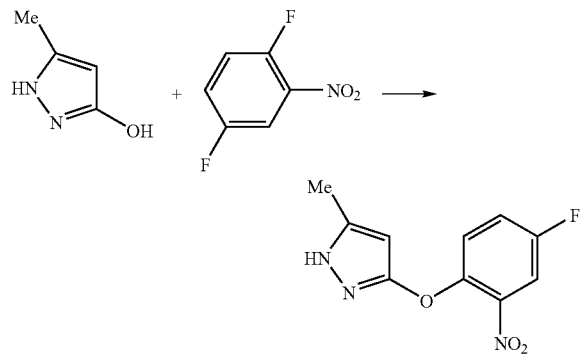

Potassium carbonate (3.19 g, 23.1 mmol) and 2,5-difluoronitrobenzene (7.34 g, 46.1 mmol) were added to a solution of 3-hydroxy-5-methylpyrazole (4.52 g, 46.1 mmol) in DMF (80 ml) at room temperature, and the mixture was stirred at room temperature overnight. After completion of the reaction, the reaction mixture was poured into 1N hydrochloric acid (100 ml) and extracted with ethyl acetate (100 ml×2). An organic layer was washed with water (100 ml×2), dried over anhydrous magnesium sulfate and filtered to remove magnesium sulfate, and the solvent was distilled off from the filtrate under reduced pressure. The resultant crude product was purified with a silica gel column (ethyl acetate/hexane=1/3), to give a yellow solid of 3-(4-fluoro-2-nitrophenyloxy)-5-methylpyrazole (5.33 g, yield: 48.8%). mp: 81-84° C.; $^1$H-NMR (CDCl$_3$, TMS, ppm): δ 2.28 (d, J=0.5 Hz, 3H), 5.71 (d, J=0.5 Hz, 1H), 7.26-7.38 (m, 2H), 7.69 (dd, J=2.8 and 7.9 Hz, 1H), 9.33 (br s, 1H).

Example 3

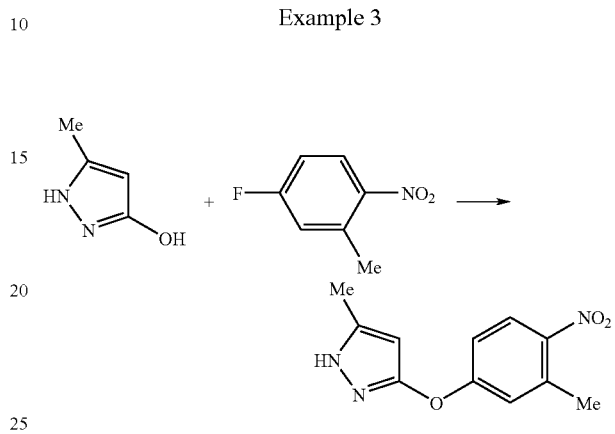

Potassium carbonate (2.23 g, 16.1 mmol) was added to a solution of 3-hydroxy-5-methylpyrazole (3.16 g, 32.2 mmol) and 5-fluoro-2-nitrotoluene (5.00 g, 32.2 mmol) in DMF (50 ml), and the mixture was stirred at 70° C. for 3 hours. After completion of the reaction, a reaction mixture was poured into 2N hydrochloric acid (50 ml) and extracted with ethyl acetate (30 ml×2). An organic layer was washed with water (50 ml×3), dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellowish solid of 5-methyl-3-(4-nitro-3-methylphenyloxy)pyrazole (2.51 g, yield: 27.8%). mp: 114-117° C.; $^1$H-NMR (CDCl$_3$, TMS, ppm): δ 2.30 (d, J=0.5 Hz, 3H), 2.61 (s, 3H), 5.72 (d, J=0.5 Hz, 1H), 6.98-7.04 (m, 2H), 8.05 (d, J=9.8 Hz, 1H), 10.12 (br s, 1H).

Example 4

Reaction of 3-hydroxy-5-methylpyrazole with 5-chloro-2-nitroanisole was carried out in the same manner as Example 3, to give a yellow viscous substance of 5-methyl-3-(3-methoxy-4-nitrophenyloxy)pyrazole (yield: 13.2%). $^1$H-NMR (CDCl$_3$, TMS, ppm): δ 2.34 (s, 3H), 3.93 (s, 3H), 5.74 (s, 1H), 6.70 (dd, J=2.4 and 9.1 Hz, 1H), 6.85 (d, J=2.4 Hz, 1H), 7.95 (d, J=9.1 Hz, 1H), 9.45 (br s, 1H).

Example 5

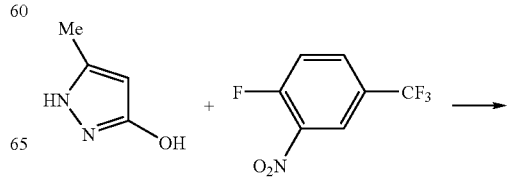

-continued

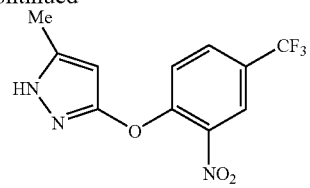

Potassium carbonate (9.12 g, 66.0 mmol) was added to a solution of 3-hydroxy-5-methylpyrazole (5.88 g, 60.0 mmol) and 4-fluoro-3-nitrobenzotrifluoride (12.6 g, 60.0 mmol) in DMF (120 ml), and the mixture was stirred at 50° C. for 4 hours. After completion of the reaction, the reaction mixture was poured into 2N hydrochloric acid (200 ml) and extracted with ethyl acetate (70 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellow solid of 5-methyl-3-(2-nitro-4-trifluoromethylphenyloxy)pyrazole (12.1 g, yield: 69.0%). mp: 89-91° C.; $^1$H-NMR (CDCl$_3$, TMS, ppm): δ 2.28 (s, 3H), 5.77 (s, 1H), 7.40 (d, J=8.8 Hz, 1H), 7.76 (dd, J=2.0 and 8.8 Hz, 1H), 8.21 (d, J=2.0 Hz, 1H), 10.10-11.05 (br s, 1H).

Examples 6-9

Reactions of 4-fluoro-3-nitrobenzotrifluoride with 3-hydroxypyrazole derivative (Example 6: 3-hydroxy-5-trifluoromethylpyrazole, Example 7: 5-ethyl-3-hydroxypyrazole, Example 8: 4,5-dimethyl-3-hydroxypyrazole, Example 9: 4-ethyl-3-hydroxy-5-methylpyrazole) were carried out in the same manner as in Example 5, to give corresponding 3-aryloxypyrazole derivatives. Products/forms/yields/melting points/NMR spectra are described below.

Example 6

3-(2-nitro-4-trifluoromethylphenyloxy)-5-trifluoromethylpyrazole/yellow viscous substance/yield: 28.7%/$^1$H-NMR (CDCl$_3$, TMS, ppm): δ 6.35 (s, 1H), 7.48 (d, J=8.5 Hz, 1H), 7.85 (dd, J=2.0 and 8.8 Hz, 1H), 8.27 (m, 1H), 10.10-10.90 (br s, 1H).

Example 7

5-ethyl-3-(2-nitro-4-trifluoromethylphenyloxy)pyrazole/yellow viscous substance/yield: 77.0%/$^1$H-NMR (CDCl$_3$, TMS, ppm): δ 1.27 (t, J=7.6 Hz, 3H), 2.67 (dq, J=0.4 and 7.6 Hz, 2H), 5.81 (s, 1H), 7.44 (d, J=8.8 Hz, 1H), 7.77 (dd, J=1.9 and 8.8 Hz, 1H), 8.22 (d, J=1.9 Hz, 1H). (Amino proton was not assigned.)

Example 8

4,5-dimethyl-3-(2-nitro-4-trifluoromethylphenyloxy)pyrazole/yellowish solid/yield: 50.8%/mp: 92-95° C./$^1$H-NMR (CDCl$_3$, TMS, ppm): δ 1.89 (s, 3H), 2.23 (s, 3H), 7.38 (d, J=8.8 Hz, 1H), 7.74 (dd, J=1.9 and 8.8 Hz, 1H), 8.22 (d, J=1.9 Hz, 1H), 8.90-10.35 (br s, 1H).

Example 9

4-ethyl-5-methyl-3-(2-nitro-4-trifluoromethylphenyloxy)pyrazole/yellow solid/yield: 49.8%/mp: 92-93° C./$^1$H-NMR (CDCl$_3$, TMS, ppm): δ 1.10 (t, J=7.6 Hz, 3H), 2.24 (s, 3H), 2.36 (q, J=7.6 Hz, 2H), 7.42 (d, J=8.8 Hz, 1H), 7.74 (dd, J=2.0 and 8.8 Hz, 1H), 8.22 (d, J=2.0 Hz, 1H), 9.10-9.75 (brs, 1H).

Example 10

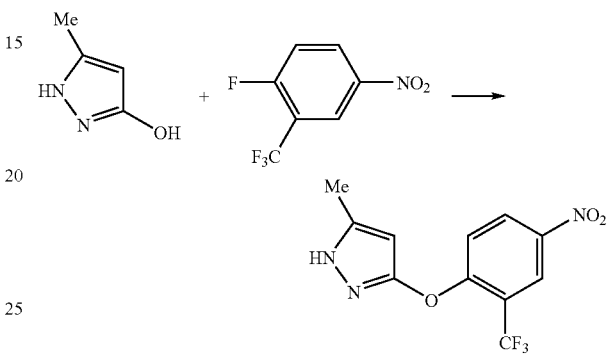

Potassium carbonate (7.60 g, 55.0 mmol) was added to a solution of 3-hydroxy-5-methylpyrazole (4.90 g, 50.0 mmol) and 2-fluoro-5-nitrobenzotrifluoride (10.5 g, 50.0 mmol) in DMF (50 ml), and the mixture was stirred under heating at 60° C. for 4 hours. After completion of the reaction, the reaction mixture was poured into 2N hydrochloric acid (100 ml) and extracted with ethyl acetate (50 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellowish viscous substance of 5-methyl-3-(4-nitro-2-trifluoromethylphenyloxy)pyrazole (8.70 g, yield: 60.6%). $^1$H-NMR (CDCl$_3$, TMS, ppm): δ 2.30 (d, J=0.5 Hz, 3H), 5.78 (d, J=0.5 Hz, 1H), 7.31 (d, J=9.2 Hz, 1H), 8.31 (dd, J=2.7 and 9.2 Hz, 1H), 8.57 (d, J=2.7 Hz, 1H), 10.05-10.50 (br s, 1H).

Examples 11-13

Reactions of 2-fluoro-5-nitrobenzotrifluoride with 3-hydroxypyrazole derivative (Example 11: 5-ethyl-3-hydroxypyrazole, Example 12: 4,5-dimethyl-3-hydroxypyrazole, Example 13: 4-ethyl-3-hydroxy-5-methylpyrazole) were carried out in the same manner as in Example 10, to give corresponding 3-aryloxypyrazole derivatives. Products/forms/yields/melting points/NMR spectra are described below.

Example 11

5-ethyl-3-(4-nitro-2-trifluoromethylphenyloxy)pyrazole/yellow viscous substance/yield: 79.3%/$^1$H-NMR (CDCl$_3$, TMS, ppm): δ 1.29 (t, J=7.6 Hz, 3H), 2.69 (q, J=7.6 Hz, 2H), 5.82 (s, 1H), 7.38 (d, J=9.2 Hz, 1H), 8.35 (dd, J=2.7 and 9.2 Hz, 1H), 8.57 (d, J=2.7 Hz, 1H), 9.45-10.15 (br s, 1H).

Example 12

4,5-dimethyl-3-(4-nitro-2-trifluoromethylphenyloxy) pyrazole/yellow solid/yield: 51.1%/mp: 97-99° C./$^1$H-NMR (CDCl$_3$, TMS, ppm): δ 1.84 (s, 3H), 2.25 (s, 3H), 7.33 (d, J=9.2 Hz, 1H), 8.33 (dd, J=2.7 and 9.2 Hz, 1H), 8.57 (d, J=2.7 Hz, 1H), 9.05~10.20 (br s, 1H).

Example 13

4-ethyl-5-methyl-3-(4-nitro-2-trifluoromethylphenyloxy) pyrazole/orange viscous substance/yield: 50.8%/$^1$H-NMR (CDCl$_3$, TMS, ppm): δ 1.05 (t, J=7.6 Hz, 3H), 2.26 (s, 3H), 2.31 (q, J=7.6 Hz, 2H), 7.36 (d, J=9.2 Hz, 1H), 8.33 (dd, J=2.7 and 9.2 Hz, 1H), 8.57 (d, J=2.7 Hz, 1H). (Amino proton was not assigned.)

Example 14

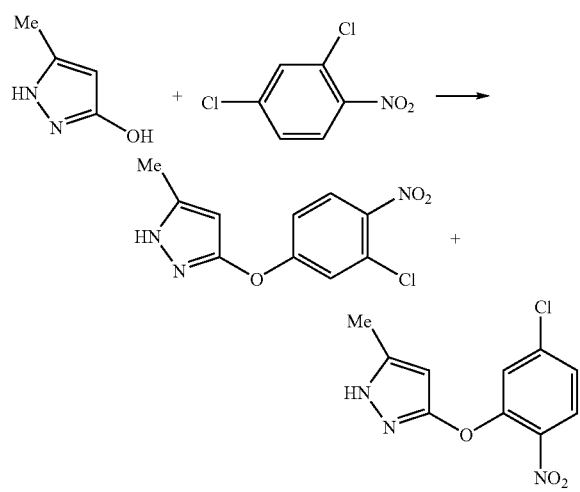

Potassium carbonate (3.52 g, 25.5 mmol) and 2,4-dichloronitrobenzene (9.79 g, 51.0 mmol) were added to a solution of 3-hydroxy-5-methylpyrazole (5.00 g, 51.0 mmol) in DMF (130 ml) at room temperature, and the mixture was stirred at room temperature overnight. After completion of the reaction, the reaction mixture was poured into 1N hydrochloric acid (200 ml) and extracted with ethyl acetate (100 ml×3). An organic layer was washed with water (100 ml×3), dried over anhydrous magnesium sulfate and filtered to remove magnesium sulfate, and the solvent was distilled off from the filtrate under reduced pressure. The resultant crude product was purified with a silica gel column (ethyl acetate/hexane=1/3), to give a yellow solid of 3-(3-chloro-4-nitrophenyloxy)-5-methylpyrazole (6.33 g, yield: 48.9%) [mp: 91-93° C.; $^1$H-NMR (CDCl$_3$, TMS, ppm): δ 2.30 (s, 3H), 5.74 (d, J=0.6 Hz, 1H), 7.10 (dd, J=2.8 and 9.1 Hz, 1H), 7.25 (d, J=2.5 Hz, 1H), 7.97 (d, J=9.1 Hz, 1H), 10.73 (br d, J=8.8 Hz, 1H)] and a yellow solid of 3-(5-chloro-2-nitrophenyloxy)-5-methylpyrazole (2.31 g, yield: 17.9%) [mp: 87-90° C.; $^1$H-NMR (CDCl$_3$, TMS, ppm): δ 2.27 (s, 3H), 5.73 (d, J=0.6 Hz, 1H), 7.17 (dd, J=2.2 and 8.8 Hz, 1H), 7.26 (d, J=2.2 Hz, 1H), 7.91 (d, J=8.8 Hz, 1H), 10.77 (br s, 1H)].

Example 15

Potassium carbonate (3.46 g, 25.0 mmol) and 2,4-difluoronitrobenzene (7.95 g, 50.0 mmol) were added to a solution of 3-hydroxy-5-methylpyrazole (4.91 g, 50.0 mmol) in DMSO (80 ml) at room temperature, and the mixture was stirred at room temperature overnight. After completion of the reaction, the reaction mixture was poured into 1N hydrochloric acid (100 ml) and extracted with ethyl acetate (100 ml×2). An organic layer was washed with water (100 ml×2), dried over anhydrous magnesium sulfate and filtered to remove magnesium sulfate, and the solvent was distilled off from the filtrate under reduced pressure. The resultant crude product was purified with a silica gel column (ethyl acetate/hexane=1/3), to give a yellow solid of 3-(3-fluoro-4-nitrophenyloxy)-5-methylpyrazole (1.52 g, yield: 12.8%) [mp: 80-83° C.; $^1$H-NMR (CDCl$_3$, TMS, ppm): δ 2.33 (d, J=0.5 Hz, 3H), 5.77 (d, J=0.5 Hz, 1H), 6.96-7.03 (m, 2H), 8.06-8.13 (m, 1H), 10.03 (br s, 1H)] and a yellow solid of 3-(5-fluoro-2-nitrophenyloxy)-5-methylpyrazole (0.97 g, yield: 8.2%) [mp: 95-97° C.; $^1$H-NMR (CDCl$_3$, TMS, ppm): δ 2.31 (s, 3H), 5.77 (s, 1H), 6.90 (ddd, J=2.7, 5.8 and 9.1 Hz, 1H), 7.01 (dd, J=2.7 and 9.6 Hz, 1H), 8.03 (dd, J=5.8 and 9.1 Hz, 1H), 9.86 (br s, 1H)].

Example 16

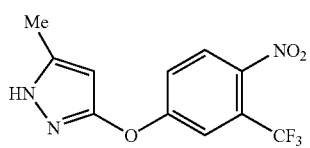

Potassium carbonate (2.49 g, 18.0 mmol) was added to a solution of 3-hydroxy-5-methylpyrazole (1.47 g, 15.0 mmol) and 5-fluoro-2-nitrobenzotrifluoride (3.14 g, 15.0 mmol) in DMF (20 ml), and the mixture was stirred under heating at 70° C. for 3 hours. After completion of the reaction, the reaction mixture was poured into 2N hydrochloric acid (40 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellowish solid of 5-methyl-3-(4-nitro-3-trifluoromethylphenyloxy)pyrazole (2.74 g, yield: 63.6%). mp: 96-98° C.; $^1$H-NMR (CDCl$_3$, TMS, ppm): δ 2.34 (s, 3H), 5.77 (s, 1H), 7.40 (dd, J=2.6 and 8.9 Hz, 1H), 7.56 (d, J=2.6 Hz, 1H), 7.98 (d, J=8.9 Hz, 1H), 9.20-10.15 (br s, 1H).

Example 17

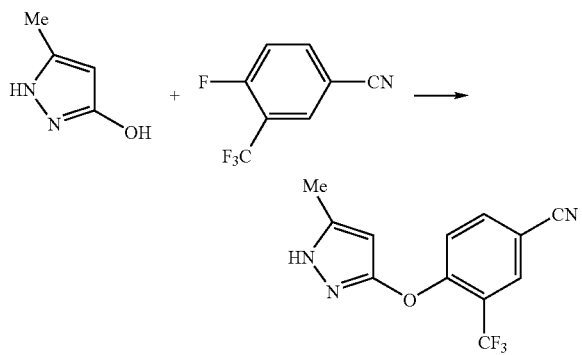

Potassium carbonate (2.8 g, 20.0 mmol) was added to a solution of 3-hydroxy-5-methylpyrazole (1.47 g, 15.0 mmol) and 4-fluoro-3-trifluoromethylbenzonitrile (2.8 g, 15.0 mmol) in DMF (30 ml), and the mixture was stirred under heating at 80° C. for 6 hours. After completion of the reaction, the reaction mixture was poured into 2N hydrochloric acid (70 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a yellowish solid of 3-(4-cyano-2-trifluoromethylphenyloxy)-5-methylpyrazole (1.7 g, yield: 42.4%). mp: 123-125° C.; $^1$H-NMR (CDCl$_3$, TMS, ppm): δ 2.28 (d, J=0.5 Hz, 3H), 5.75 (d, J=0.5 Hz, 1H), 7.30 (d, J=8.8 Hz, 1H), 7.75 (dd, J=2.0 and 8.8 Hz, 1H), 7.96 (d, J=2.0 Hz, 1H), 9.60-11.60 (br s, 1H).

Example 18

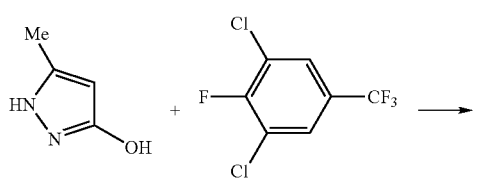

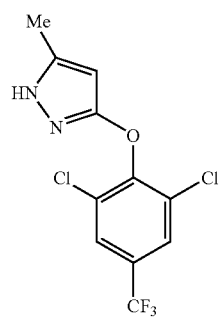

Potassium carbonate (2.8 g, 20.0 mmol) was added to a solution of 3-hydroxy-5-methylpyrazole (1.47 g, 15.0 mmol) and 3,5-dichloro-4-fluorobenzotrifluoride (3.5 g, 15.0 mmol) in DMF (30 ml), and the mixture was stirred under heating at 60° C. for 6 hours. After completion of the reaction, the reaction mixture was poured into 2N hydrochloric acid (70 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10→1/7), to give a white solid of 3-(2,6-dichloro-4-trifluoromethylphenyloxy)-5-methylpyrazole (2.5 g, yield: 54.0%). mp: 153-155° C.; $^1$H-NMR (CDCl$_3$, TMS, ppm): δ 2.27 (s, 3H), 5.68 (s, 1H), 7.64 (s, 2H), 8.75-9.70 (br s, 1H).

Examples 19-29

Reactions of 3,5-dichloro-4-fluorobenzotrifluoride with 3-hydroxypyrazole derivative (Example 19: 5-ethyl-3-hydroxypyrazole, Example 20: 3-hydroxy-5-isopropylpyrazole, Example 21: 5-tert-butyl-3-hydroxypyrazole, Example 22: 5-cyclopropyl-3-hydroxypyrazole, Example 23: 4-ethyl-3-hydroxy-5-methylpyrazole, Example 24: 3-hydroxy-5-(methoxymethyl)pyrazole, Example 25: ethyl(3-hydroxypyrazol-5-yl)acetate, Example 26: methyl 3-hydroxypyrazole-5-carboxylate, Example 27: 4,5-dimethyl-3-hydroxypyrazole, Example 28: 4-ethyl-3-hydroxy-5-methylpyrazole, Example 29: 5-(4-chlorophenyl)-3-hydroxypyrazole) were carried out in the same manner as in Example 18, to give corresponding 3-aryloxypyrazole derivatives. Products/forms/yields/melting points/NMR spectra are described below.

Example 19

3-(2,6-dichloro-4-trifluoromethylphenyloxy)-5-ethylpyrazole/white solid/yield: 35.7%/mp: 118-121° C./$^1$H-NMR (CDCl$_3$, TMS, ppm): δ 1.26 (t, J=7.5 Hz, 3H), 2.62 (q, J=7.5 Hz, 2H), 5.69 (s, 1H), 7.65 (s, 2H), 8.90-9.30 (br s, 1H).

Example 20

3-(2,6-dichloro-4-trifluoromethylphenyloxy)-5-isopropylpyrazole/white solid/yield: 59.7%/mp: 98-101° C./$^1$H-NMR (CDCl$_3$, TMS, ppm): δ 1.26 (d, J=6.9 Hz, 6H), 2.90 (sep, J=6.9 Hz, 1H), 5.68 (d, J=0.2 Hz, 1H), 7.65 (d, J=0.2 Hz, 2H), 9.06 (br s, 1H).

Example 21

5-tert-butyl-3-(2,6-dichloro-4-trifluoromethylphenyloxy)pyrazole/white solid/yield: 68.3%/mp: 170-172° C./$^1$H-NMR (CDCl$_3$, TMS, ppm): δ 1.30 (s, 9H), 5.69 (s, 1H), 7.64 (s, 2H), 8.85-9.15 (m, 1H).

Example 22

5-cyclopropyl-3-(2,6-dichloro-4-trifluoromethylphenyloxy)pyrazole/white solid/yield: 16.8%/mp: 119-121° C./$^1$H-NMR (CDCl$_3$, TMS, ppm): δ 0.65-0.77 (m, 2H), 0.90-1.05 (m, 2H), 1.70-1.85 (m, 1H), 5.54 (s, 1H), 7.65 (s, 2H), 8.80-9.75 (br s, 1H).

Example 23

3-(2,6-dichloro-4-trifluoromethylphenyloxy)-5-(methoxymethyl)pyrazole/white solid/yield: 64.5%/mp: 141-143° C./$^1$H-NMR (CDCl$_3$, TMS, ppm): δ 3.41 (s, 3H), 4.46 (s, 2H), 5.82 (s, 1H), 7.64 (s, 2H), 9.20~9.65 (br s, 1H).

Example 24 methyl 3-(2,6-dichloro-4-trifluoromethylphenyloxy)pyrazole-5-carboxylate/white solid/yield: 43.0%/mp: 114-116° C./$^1$H-NMR (CDCl$_3$, TMS, ppm): δ 3.93 (s, 3H), 6.41 (s, 1H), 7.65 (d, J=0.4 Hz, 2H), 10.10 (br s, 1H).

Example 25 ethyl {3-(2,6-dichloro-4-trifluoromethylphenyloxy)pyrazol-5-yl}acetate/colorless viscous substance/yield: 51.1%/ $^1$H-NMR (CDCl$_3$, TMS, ppm): δ 1.30 (t, J=7.2 Hz, 3H), 3.71 (s, 2H), 4.23 (q, J=7.2 Hz, 2H), 5.79 (s, 1H), 7.65 (s, 2H). (Amino proton was not assigned.)

Example 26

3-(2,6-dichloro-4-trifluoromethylphenyloxy)-4,5-dimethylpyrazole/white solid/yield: 34.0%/mp: 220-223° C./$^1$H-NMR (CDCl$_3$, TMS, ppm): δ 1.90 (s, 3H), 1.93 (s, 3H), 7.71 (s, 2H). (Amino proton was not assigned.)

Example 27

3-(2,6-dichloro-4-trifluoromethylphenyloxy)-4-ethyl-5-methylpyrazole/white solid/yield: 38.3%/mp: 215-218° C./$^1$H-NMR (CDCl$_3$, TMS, ppm): δ 1.10 (t, J=7.5 Hz, 3H), 1.93 (s, 3H), 2.34 (q, J=7.5 Hz, 2H), 7.69 (s, 2H), 9.50-12.50 (br s, 1H).

Example 28

5-(4-chlorophenyl)-3-(2,6-dichloro-4-trifluoromethylphenyloxy)pyrazole/white solid/yield: 55.1%/mp: 181-183° C./$^1$H-NMR (CDCl$_3$, TMS, ppm): δ 5.99 (s, 1H), 7.20-7.40 (m, 4H), 7.51 (s, 2H), 10.35-11.50 (br s, 1H).

Example 29

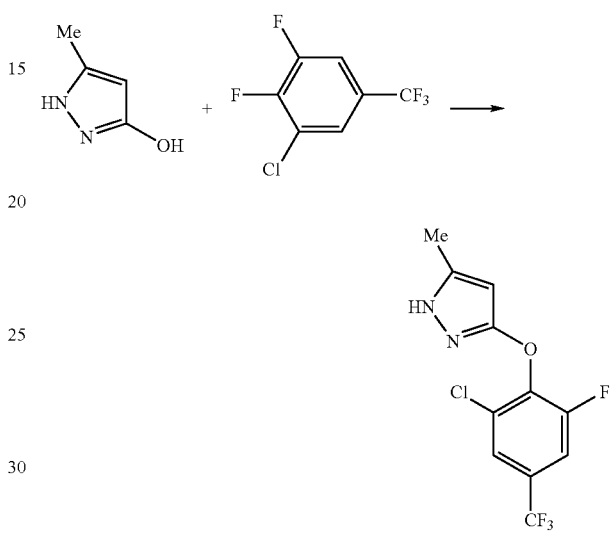

Potassium carbonate (1.66 g, 12 mmol) was added to a solution of 3-hydroxy-5-methylpyrazole (2.45 g, 25.0 mmol) and 3-chloro-4,5-difluorobenzotrifluoride (2.5 g, 25.0 mmol) in DMF (40 ml), and the mixture was stirred under heating at 70° C. for 4 hours. After completion of the reaction, the reaction mixture was poured into 2N hydrochloric acid (100 ml) and extracted with ethyl acetate (50 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of 3-(2-chloro-6-fluoro-4-trifluoromethylphenyloxy)-5-methylpyrazole (2.29 g, yield: 33.8%). mp: 171-174° C.; $^1$H-NMR (CDCl$_3$, TMS, ppm): δ 2.27 (s, 3H), 5.71 (s, 1H), 7.37 (dd, J$_{HF}$=1.8 and 9.4 Hz, 1H), 7.54 (s, 1H), 8.85-9.55 (br s, 1H).

Example 30

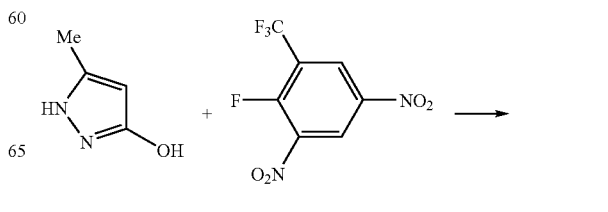

-continued

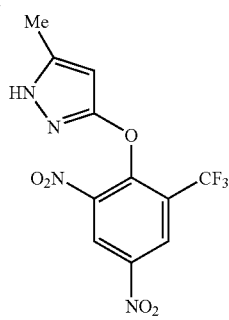

Sodium hydride (60% in oil, 0.2 g, 5.5 mmol) was added to a solution of 3-hydroxy-5-methylpyrazole (0.49 g, 5.0 mmol) and 3,5-dinitro-2-fluorobenzotrifluoride (1.35 g, 5.0 mmol) in DMF (10 ml), and the mixture was stirred under heating at 70° C. for 6 hours. After completion of the reaction, the reaction mixture was poured into 2N hydrochloric acid (30 ml) and extracted with ethyl acetate (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a yellowish solid of 3-(2,4-dinitro-6-trifluoromethylphenyloxy)-5-methylpyrazole (0.58 g, yield: 34.9%). mp: 145-147° C.; $^1$H-NMR (CDCl$_3$, TMS, ppm): δ 2.29 (s, 3H), 5.84 (s, 1H), 8.82 (m, 2H), 9.01 (d, J=2.7 Hz, 1H).

Example 31

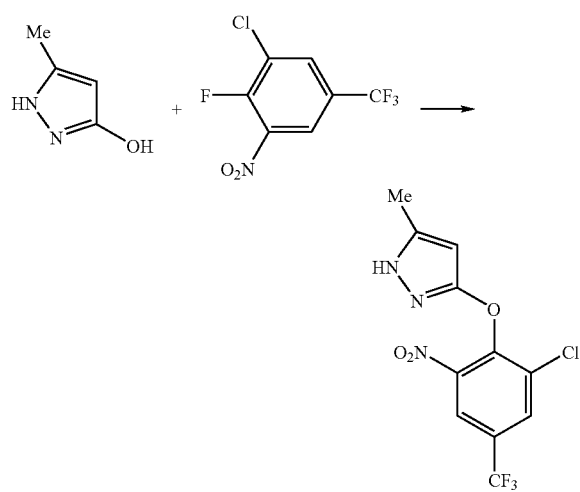

Sodium hydride (60% in oil, 0.44 g, 11.0 mmol) was added to a solution of 3-hydroxy-5-methylpyrazole (0.98 g, 10.0 mmol) and 3-chloro-4-fluoro-5-nitrobenzotrifluoride (1.5 g, 10.0 mmol) in DMF (30 ml), and the mixture was stirred under heating at 60° C. for 7 hours. After completion of the reaction, the reaction mixture was poured into 2N hydrochloric acid (80 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7→1/3), to give a yellowish solid of 3-(2-chloro-6-nitro-4-trifluoromethylphenyloxy)-5-methylpyrazole (1.8 g, yield: 56.6%). mp: 120-123° C.; $^1$H-NMR (CDCl$_3$, TMS, ppm): δ 2.29 (s, 3H), 5.79 (s, 1H), 7.98 (d, J=1.8 Hz, 1H), 8.17 (d, J=1.8 Hz, 1H), 8.65-9.30 (br s, 1H).

Example 32

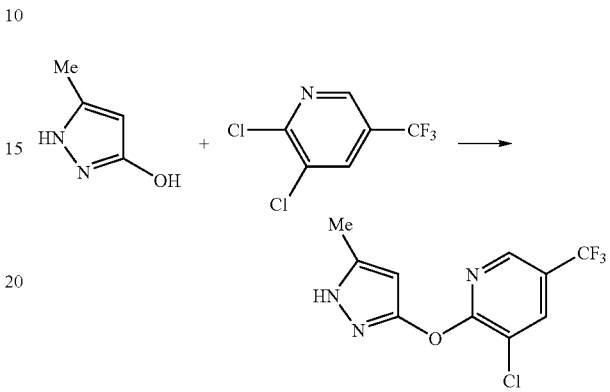

Sodium hydride (60% in oil, 0.2 g, 5.5 mmol) was added to a solution of 3-hydroxy-5-methylpyrazole (0.49 g, 5.0 mmol) in DMF (10 ml) at 0° C., and the mixture was stirred for 30 minutes while it was allowed to have room temperature gradually. Then, 2,3,5-trichloropyridine (0.9 g, 5.0 mmol) was added, and the mixture was stirred under heating at 70° C. for 2 days. After completion of the reaction, the reaction mixture was poured into 2N hydrochloric acid (20 ml) and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7→1/2), to give a white solid of 3-(3,5-dichloropyridin-2-yloxy)-5-methylpyrazole (0.7 g, yield: 57.4%). mp: 109-111° C.; $^1$H-NMR (CDCl$_3$, TMS, ppm): δ 2.32 (s, 3H), 5.86 (s, 1H), 7.77 (d, J=2.3 Hz, 1H), 8.03 (d, J=2.3 Hz, 1H), 9.40-11.50 (br s, 1H).

Examples 34-35

Reactions of 3-hydroxy-5-methylpyrazole with pyridine derivative (Example 34: 2-chloro-6-methoxy-3-nitropyridine, Example 35: 2-chloro-4-methyl-5-nitropyridine) were carried out in the same manner as in Example 33, to give corresponding 3-aryloxypyrazole derivatives. Products/forms/yields/melting points/NMR spectra are described below.

Example 33

5-methyl-3-(6-methoxy-3-nitropyridin-2-yloxy)pyrazole/ yellow solid/yield: 63.6%/mp: 133-136° C./$^1$H-NMR (CDCl$_3$, TMS, ppm): δ 2.32 (d, J=0.6 Hz, 3H), 3.80 (s, 3H), 5.90 (d, J=0.6 Hz, 1H), 6.51 (dd, J=1.7 and 8.8 Hz, 1H), 8.39 (d, J=8.8 Hz, 1H), 10.90 (br s, 1H).

Example 34

5-methyl-3-(4-methyl-5-nitropyridin-2-yloxy)pyrazole/ white solid/yield: 39.8%/mp: 136-139° C./$^1$H-NMR (CDCl$_3$, TMS, ppm): δ 2.35 (d, J=0.5 Hz, 3H), 2.67 (s, 3H), 5.91 (d, J=0.5 Hz, 1H), 6.94 (s, 1H), 8.93 (s, 1H), 9.59 (br s, 1H).

Example 35

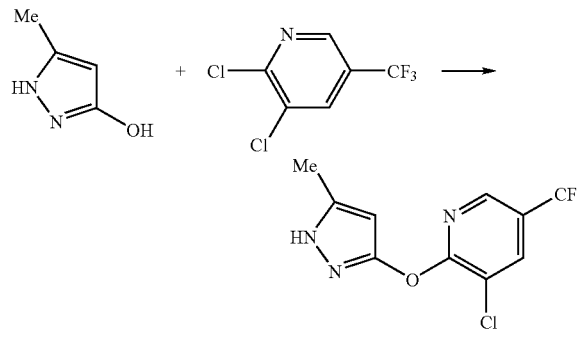

Potassium carbonate (7.60 g, 55.0 mmol) was added to a solution of 3-hydroxy-5-methylpyrazole (4.90 g, 50.0 mmol) and 2,3-dichloro-5-trifluoromethylpyridine (10.8 g, 50.0 mmol) in DMF (50 ml) at room temperature, and the mixture was stirred under heating at 60° C. for 4 hours. After completion of the reaction, the reaction mixture was poured into 2N hydrochloric acid (100 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/2), to give a white solid of 3-(3-chloro-5-trifluoromethylpyridin-2-yloxy)-5-methylpyrazole (10.5 g, yield: 76.0%). mp: 93-95° C.; $^1$H-NMR (CDCl$_3$, TMS, ppm): δ 2.32 (s, 3H), 5.90 (s, 1H), 7.98 (d, J=2.0 Hz, 1H), 8.33 (m, 1H), 10.80-11.60 (br s, 1H).

Examples 36-39

Reactions of 2,3-dichloro-5-trifluoromethylpyridine with 3-hydroxypyrazole derivative (Example 36: 3-hydroxy-5-trifluoromethylpyrazole, Example 37: 5-ethyl-3-hydroxypyrazole, Example 38: 4,5-dimethylpyrazole-3-hydroxy, Example 39: 4-ethyl-3-hydroxy-5-methylpyrazole) were carried out in the same manner as in Example 35, to give corresponding 3-aryloxypyrazole derivatives. Products/forms/yields/melting points/NMR spectra are described below.

Example 36

3-(3-chloro-5-trifluoromethylpyridin-2-yloxy)-5-trifluoromethylpyrazole/colorless viscous substance/yield: 41.5%/$^1$H-NMR (CDCl$_3$, TMS, ppm): δ 6.53 (s, 1H), 8.05 (d, J=2.5 Hz, 1H), 8.38 (m, 1H), 10.90-11.65 (br s, 1H).

Example 37

3-(3-chloro-5-trifluoromethylpyridin-2-yloxy)-5-ethylpyrazole/white solid/yield: 85.2%/mp: 55-57° C./$^1$H-NMR (CDCl$_3$, TMS, ppm): δ 1.27 (t, J=7.5 Hz, 3H), 2.70 (q, J=7.5 Hz, 2H), 5.92 (s, 1H), 7.98 (d, J=2.5 Hz, 1H), 8.34 (m, 1H), 10.15-10.70 (br s, 1H).

Example 38

3-(3-chloro-5-trifluoromethylpyridin-2-yloxy)-4,5-dimethylpyrazole/white solid/yield: 86.9%/mp: 102-103° C./$^1$H-NMR (DMSO-d$_6$, DMSO, ppm): δ 1.68 (s, 3H), 2.17 (s, 3H), 8.53 (m, 1H), 8.57 (m, 1H), 12.05-12.25 (br s, 1H).

Example 39

3-(3-chloro-5-trifluoromethylpyridin-2-yloxy)-4-ethyl-5-methylpyrazole/white solid/yield: 77.6%/mp: 74-75° C./$^1$H-NMR (DMSO-d$_6$, DMSO, ppm): δ 0.93 (t, J=7.6 Hz, 3H), 2.14 (q, J=7.6 Hz, 2H), 2.19 (s, 3H), 8.45-8.65 (m, 2H), 12.00-12.30 (br s, 1H).

Example 40

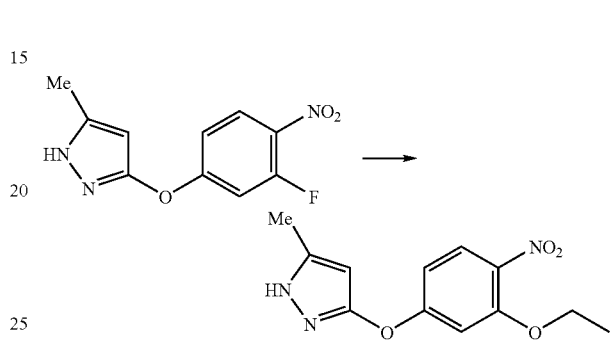

Potassium hydrogencarbonate (0.15 g, 1.5 mmol) was added to a solution of 3-(3-fluoro-4-nitrophenyloxy)-5-methylpyrazole (0.36 g, 1.5 mmol) in ethanol (5 ml), and the mixture was refluxed under heating for 10 hours. After completion of the reaction, the reaction mixture was poured into water (10 ml) and extracted with ethyl acetate (10 ml×2), dried over anhydrous magnesium sulfate and filtered to remove magnesium sulfate, and the solvent was distilled off from the filtrate under reduced pressure. The resultant crude product was purified with a silica gel column (ethyl acetate/hexane=1/5), to give a yellow solid of 3-(3-ethoxy-4-nitrophenyloxy)-5-methylpyrazole (0.17 g, yield: 42.3%). mp: 123-124° C.; $^1$H-NMR (CDCl$_3$, TMS, ppm): δ 1.47 (t, J=7.0 Hz, 3H), 2.33 (d, J=0.5 Hz, 3H), 4.13 (q, J=7.0 Hz, 2H), 5.73 (d, J=0.5 Hz, 1H), 6.68 (dd, J=2.5 and 9.1 Hz, 1H), 6.81 (d, J=2.5 Hz, 1H), 7.91 (d, J=9.1 Hz, 1H), 9.53 (br s, 1H).

Example 41

Reaction of 3-(5-fluoro-2-nitrophenyloxy)-5-methylpyrazole with ethanol was carried out in the presence of potassium hydrogencarbonate in the same manner as in Example 40, to give a yellow viscous substance of 3-(5-ethoxy-2-nitrophenyloxy)-5-methylpyrazole (yield: 59.8%). $^1$H-NMR (CDCl$_3$, TMS, ppm): δ 1.39 (t, J=7.0 Hz, 3H), 2.28 (s, 3H), 4.04 (q, J=7.0 Hz, 2H), 5.72 (s, 1H), 6.68 (dd, J=2.6 and 9.1 Hz, 1H), 6.73 (d, J=2.6 Hz, 1H), 8.04 (d, J=9.1 Hz, 1H), 9.62 (br s, 1H).

Example 42

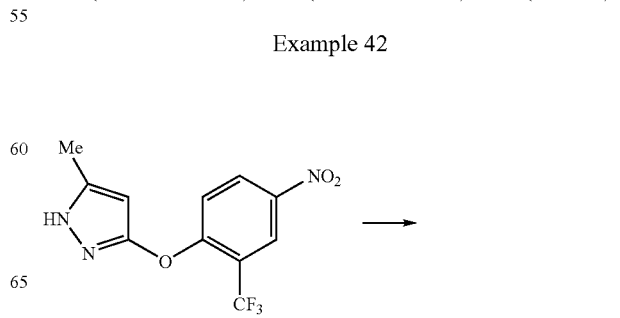

-continued

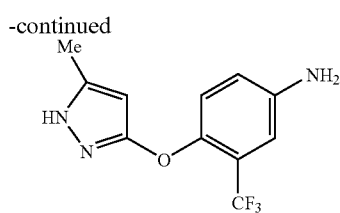

A solution of 5-methyl-3-(4-nitro-2-trifluoromethylphenyloxy)pyrazole (5.3 g, 18.5 mmol) in ethanol (200 ml) was placed in an autoclave, and 10% palladium carbon (2.0 g) was added. An atmosphere in the autoclave was fully replaced with hydrogen gas, and hydrogen gas was filled up to 5 kg/cm$^2$. Then, the reaction solution was stirred at room temperature for 4 hours. After completion of the reaction, the catalyst was separated by filtration using Celite, and the solvent was distilled off from the filtrate under reduced pressure, to give a white solid of 3-(4-amino-2-trifluoromethylphenyloxy)-5-methylpyrazole (3.6 g, yield: 76.1%). mp: 143-145° C.; $^1$H-NMR (DMSO-d$_6$, DMSO, ppm): δ 2.17 (s, 3H), 5.33 (br s, 2H), 5.44 (s, 1H), 6.78 (dd, J=2.6 and 8.8 Hz, 1H), 6.88 (d, J=2.6 Hz, 1H), 6.95 (d, J=8.8 Hz, 1H), 11.80-11.95 (br s, 1H).

Examples 43-45

3-(Substituted phenyloxy)pyrazole derivative having a nitro group (Example 43: 5-methyl-3-(4-nitrophenyloxy)pyrazole, Example 44: 3-(3-chloro-4-nitrophenyloxy)-5-methylpyrazole, Example 45: 5-methyl-(4-nitro-3-trifluoromethylphenyloxy)pyrazole) was reduced in a hydrogen gas atmosphere in the same manner as in Example 42, to give corresponding 3-(substituted phenyloxy)pyrazole derivative having an amino group. Products/forms/yields/melting points/NMR spectra are described below.

Example 43

3-(4-aminophenyloxy)-5-methylpyrazole/brown solid/yield: 49.7%/mp: 170-173° C./$^1$H-NMR (CDCl$_3$, TMS, ppm): δ 1.48-2.13 (br s, 2H), 2.23 (d, J=0.7 Hz, 3H), 5.47 (d, J=0.7 Hz, 1H), 6.64 (dd, J=2.2 and 7.1 Hz, 2H), 6.95 (dd, J=2.2 and 7.1 Hz, 2H). (Amino proton was not assigned.)

Example 44

3-(4-amino-3-chlorophenyloxy)-5-methylpyrazole/brown viscous substance/yield: 27.4%/$^1$H-NMR (CDCl$_3$, TMS, ppm): δ 2.26 (d, J=0.4 Hz, 3H), 3.63 (br s, 2H), 5.60 (d, J=0.4 Hz, 1H), 6.70 (d, J=8.5 Hz, 1H), 6.91 (dd, J=2.3 Hz and 8.5 Hz, 1H), 7.00 (d, J=2.3 Hz, 1H). (Amino proton was not assigned.)

Example 45

3-(4-amino-3-trifluoromethylphenyloxy)-5-methylpyrazole/brown viscous substance/yield: 97.8%/$^1$H-NMR (CDCl$_3$, TMS, ppm): δ 2.24 (s, 3H), 3.85-4.25 (br s, 2H), 5.53 (s, 1H), 6.71 (d, J=8.8 Hz, 1H), 7.14 (dd, J=2.8 and 8.8 Hz, 1H), 7.25 (d, J=2.8 Hz, 1H). (Amino proton was not assigned.)

Example 46

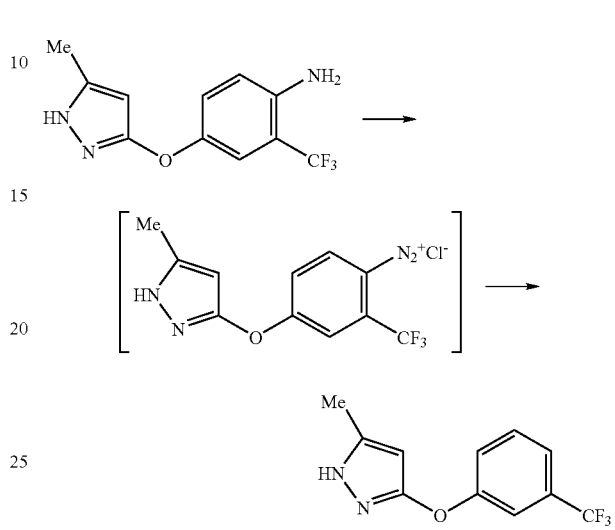

Concentrated hydrochloric acid (3 ml) and water (6 ml) were added to 3-(4-amino-3-trifluoromethylphenyloxy)-5-methylpyrazole, and the mixture was cooled to 0° C. Then, a solution of sodium nitrite (0.54 g, 7.8 mmol) in concentrated hydrochloric acid (2 ml) and water (2 ml) was dropwise added, and the mixture was stirred at an ambient temperature for 1 hour. Then, hypophosphorous acid (2.57 g, 38.9 mmol) was added, and the mixture was stirred at room temperature overnight. After completion of the reaction, the reaction mixture was poured into 1N sodium hydroxide (50 ml) and extracted with ethyl acetate (50 ml×2). An organic layer was washed with water (50 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/4), to give a yellow viscous substance of 5-methyl-3-(3-trifluoromethylphenyloxy)pyrazole (1.47 g, yield: 78.0%). $^1$H-NMR (CDCl$_3$, TMS, ppm): δ 2.2.3 (s, 3H), 5.63 (s, 1H), 7.27~7.46 (m, 4H), 10.91 (br s, 1H).

Examples 47-49

3-(Substituted phenyloxy)pyrazole derivative having an amino group (Example 47: 3-(4-aminophenyloxy)-5-methylpyrazole, Example 48: 3-(4-amino-3-chlorophenyloxy)-5-methylpyrazole, Example 49: 3-(4-amino-2-trifluoromethylphenyloxy)-5-methylpyrazole) was de-aminated via a diazonium salt in the same manner as in Example 46, to give 3-(substituted phenyloxy)pyrazole derivative. Products/forms/yields/melting points/NMR spectra are described below.

Example 47

5-methyl-3-phenyloxypyrazole/brown viscous substance/yield: 72.2%/$^1$H-NMR (CDCl$_3$, TMS, ppm): δ 2.22 (s, 3H), 5.58 (s, 1H), 7.05-7.12 (m, 3H), 7.27-7.35 (m, 2H). (Amino proton was not assigned.)

Example 48

3-(3-chlorophenyloxy)-5-methylpyrazole/yellow viscous substance/yield: 22.4%/$^1$H-NMR (CDCl$_3$, TMS, ppm): δ 2.23 (s, 3H), 5.62 (s, 1H), 6.95-7.13 (m, 3H), 7.21 (d, J=8.1 Hz, 1H), 10.95 (br s, 1H).

Example 49

5-methyl-3-(2-trifluoromethylphenyloxy)pyrazole/yellowish viscous substance/yield: 75.8%/$^1$H-NMR (CDCl$_3$, TMS, ppm): δ 2.20 (d, J=0.4 Hz, 3H), 5.59 (d, J=0.4 Hz, 1H), 7.12-7.20 (m, 2H), 7.42-7.49 (m, 1H), 7.64 (dd, J=0.9 and 7.7 Hz, 1H), 10.70-12.19 (br s, 1H).

Example 50

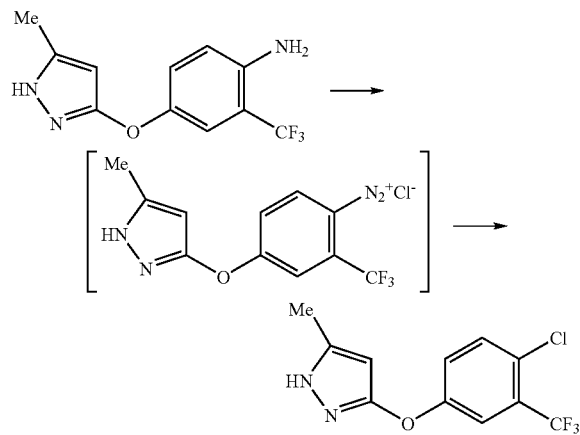

3-(4-Amino-3-trifluoromethylphenyloxy)-5-methylpyrazole (2.00 g, 7.8 mmol) was added to a mixed solution of concentrated hydrochloric acid (2.1 ml) and acetone (20 ml) at room temperature, and the mixture was stirred at room temperature for 20 minutes. After the mixture was cooled below 0° C., a solution of sodium nitrite (0.54 g, 7.8 mmol) in water (3 ml) was dropwise added, and the mixture was stirred at an ambient temperature for 30 minutes. Then, cuprous chloride (0.85 g, 8.6 mmol) was little by little added at 0° C., and the mixture was stirred at room temperature for 1 hour. After completion of the reaction, the reaction mixture was poured into 1N hydrochloric acid (50 ml) and extracted with ethyl acetate (50 ml×2). An organic layer was washed with water (50 ml×3), dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellowish viscous substance of 3-(4-chloro-3-trifluoromethylphenyloxy)-5-methylpyrazole (2.12 g, yield: 98.7%). $^1$H-NMR (CDCl$_3$, TMS, ppm): δ 2.25 (s, 3H), 5.64 (s, 1H), 7.23 (dd, J=3.0 and 8.8 Hz, 1H), 7.31-7.46 (m, 2H), 10.56 (br s, 1H).

Example 51

A diazonium salt was prepared from 3-(4-amino-2-trifluoromethylphenyloxy)-5-methylpyrazole and reacted with cuprous chloride in the same manner as in Example 50, to give a yellowish viscous substance of 3-(4-chloro-2-trifluoromethylphenyloxy)-5-methylpyrazole (yield: 56.0%). $^1$H-NMR (CDCl$_3$, TMS, ppm): δ 2.24 (s, 3H), 5.63 (s, 1H), 7.16 (d, J=8.9 Hz, 1H), 7.41 (dd, J=2.5 and 8.9 Hz, 1H), 7.61 (d, J=2.5 Hz, 1H), 10.93 (br s, 1H).

Example 52

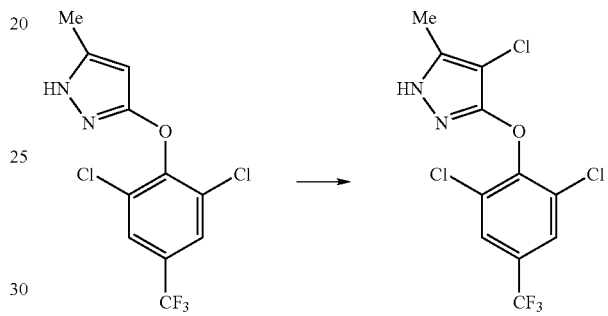

Sulfuryl chloride (0.48 g, 3.6 mmol) was added to a solution of 3-(2,6-dichloro-4-trifluoromethylphenyloxy)-5-methylpyrazole (0.93 g, 3.0 mmol) in acetic acid (10 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of 4-chloro-3-(2,6-dichloro-4-trifluoromethylphenyloxy)-5-methylpyrazole (0.57 g, yield: 55.0%). mp: 156-158° C.; $^1$H-NMR (CDCl$_3$, TMS, ppm): δ 2.28 (s, 3H), 7.65 (s, 2H), 8.75-9.15 (br s, 1H).

Example 53

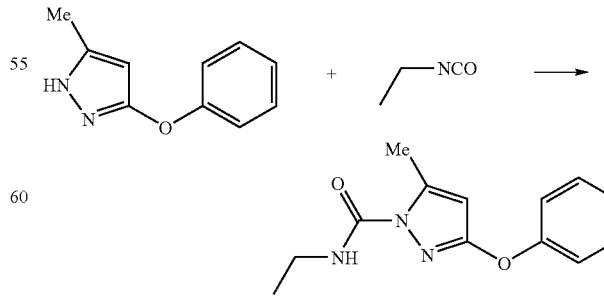

Triethylamine (0.13 g, 1.3 mmol) was added to a solution of 5-methyl-3-phenyloxypyrazole (0.20 g, 1.2 mmol) in ethyl acetate (5 ml), and the mixture cooled to 0° C. Then, ethyl isocyanate (0.09 g, 1.3 mmol) was added, and the mixture was stirred for 30 minutes at an ambient temperature. And, the mixture was stirred for 4 hours while it was allowed to have room temperature gradually. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellow viscous substance of N-ethyl-5-methyl-3-phenyloxypyrazole-1-carboxamide (0.16 g, yield: 56.4%). $^1$H-NMR (CDCl$_3$, TMS, ppm): δ 1.22 (t, J=7.3 Hz, 3H), 2.58 (d, J=0.8 Hz, 3H), 3.38 (dq, J=1.3 and 7.3 Hz, 2H), 5.67 (q, J=0.8 Hz, 1H), 6.99-7.07 (br s, 1H), 7.12-7.19 (m, 3H), 7.33-7.39 (m, 2H).

Example 54

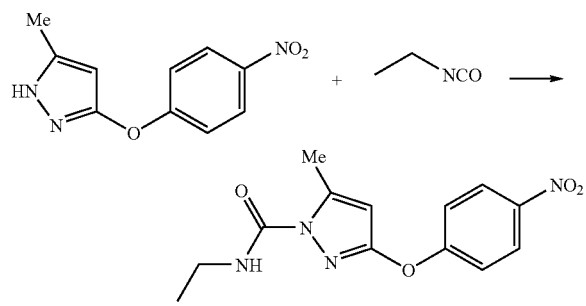

Potassium carbonate (0.19 g, 1.5 mmol) and ethyl isocyanate (0.09 g, 1.3 mmol) were added to a solution of 5-methyl-3-(4-nitrophenyloxy)pyrazole (0.29 g, 1.3 mmol) in ethyl acetate (15 ml), and the mixture was stirred at room temperature for 6 hours. After completion of the reaction, the reaction mixture was poured into 2N hydrochloric acid and extracted with diethyl ether (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/20), to give a white solid of N-ethyl-5-methyl-3-(4-nitrophenyloxy)pyrazole-1-carboxamide (0.38 g, yield: 99.2%). mp: 105-107° C., $^1$H-NMR (CDCl$_3$, TMS, ppm): δ 1.24 (t, J=7.3 Hz, 3H), 2.64 (d, J=0.7 Hz, 3H), 3.40 (dq, J=5.9 and 7.2 Hz, 2H), 5.83 (q, J=0.7 Hz, 1H), 6.75 (m, 1H), 7.20-7.30 (m, 2H), 8.26 (dd, J=2.2 and 7.0 Hz, 2H).

Example 55

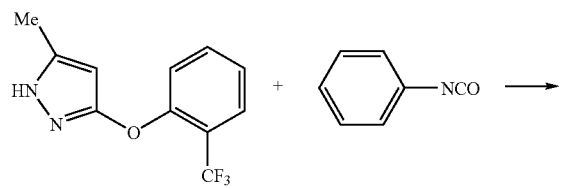

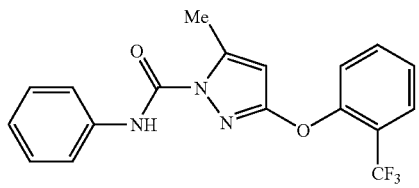

Triethylamine (0.19 g, 1.4 mmol) and phenyl isocyanate (0.17 g, 1.4 mmol) were added to a solution of 5-methyl-3-(2-trifluoromethylphenyloxy)pyrazole (0.30 g, 1.2 mmol) in ethyl acetate (5 ml) at 0° C., and the mixture was allowed to have room temperature gradually and stirred for 6 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give an orange solid of N-phenyl-5-methyl-3-(2-trifluoromethylphenyloxy)pyrazole-1-carboxamide (0.39 g, yield: 87.5%). mp: 87-89° C., $^1$H-NMR (CDCl$_3$, TMS, ppm): δ 2.65 (d, J=0.7 Hz, 3H), 5.78 (d, J=0.7 Hz, 1H), 7.14 (ddd, J=1.2, 2.3 and 7.3 Hz, 1H), 7.28-7.38 (m, 4H), 7.51-7.60 (m, 3H), 7.69-7.73 (m, 1H), 8.90 (br s, 1H).

Example 56

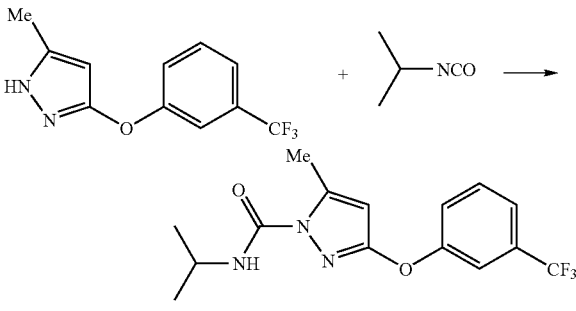

Triethylamine (0.17 g, 1.7 mmol) and isopropyl isocyanate (0.14 g, 1.7 mmol) were added to a solution of 5-methyl-3-(3-trifluoromethylphenyloxy)pyrazole (0.36 g, 1.5 mmol) in ethyl acetate (5 ml), and the mixture was stirred at room temperature for 6 hours. After completion of the reaction, the reaction mixture was poured into 1N hydrochloric acid (10 ml) and extracted with ethyl acetate (10 ml×3). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a colorless viscous substance of N-isopropyl-5-methyl-3-(3-trifluoromethylphenyloxy)pyrazole-1-carboxamide (0.15 g, yield: 30.6%). $^1$H-NMR (CDCl$_3$, TMS, ppm): δ 1.25 (d, J=6.6 Hz, 6H), 2.60

(d, J=0.6 Hz, 3H), 4.05 (sep, J=6.6 and 6.6 Hz, 1H), 5.71 (q, J=0.6 Hz, 1H), 6.81 (br d, J=6.6 Hz, 1H), 7.30-7.35 (m, 1H), 7.40-7.52 (m, 3H).

Examples 57-82

Reactions of 5-methyl-3-(3-trifluoromethylphenyloxy)pyrazole and isocyanates (Example 57: ethyl isocyanate, Example 58: tert-butyl isocyanate, Example 59: hexyl isocyanate, Example 60: cyclohexyl isocyanate, Example 61: allyl isocyanate, Example 62: 2-chloroethyl isocyanate, Example 63: ethyl isocyanatoacetate, Example 64: phenyl isocyanate, Example 65: 2-chlorophenyl isocyanate, Example 66: 3-chlorophenyl isocyanate, Example 67: 3-methylphenyl isocyanate, Example 68: 3-nitrophenyl isocyanate, Example 69: 4-chlorophenyl isocyanate, Example 70: 4-fluorophenyl isocyanate, Example 71: 4-trifluoromethylphenyl isocyanate, Example 72: 2,4-dichlorophenyl isocyanate, Example 73: 2,4-difluorophenyl isocyanate, Example 74: 3,4-dichlorophenyl isocyanate, Example 75: 2,6-dichlorophenyl isocyanate, Example 76: 4-chloro-2-methylphenyl isocyanate, Example 77: 2-methyl-4-nitrophenyl isocyanate, Example 78: 2-chloro-6-methylphenyl isocyanate, Example 79: 2,3,4-trifluorophenyl isocyanate, Example 80: 4-chloro-5-cyclopentyloxy-2-fluorophenyl isocyanate, Example 81: benzyl isocyanate, Example 82: α-phenethyl isocyanate) were carried out in ethyl acetate in the presence of potassium carbonate in the same manner as in Example 56, to give corresponding N-substituted carboxamides. Products/forms/yields/melting points/NMR spectra are described below.

Example 57

N-ethyl-5-methyl-3-(3-trifluoromethylphenyloxy)pyrazole-1-carboxamide/yellow viscous substance/yield: 63.8%/$^1$H-NMR (CDCl$_3$, TMS, ppm): δ 1.23 (t, J=7.3 Hz, 3H), 2.60 (d, J=0.8 Hz, 3H), 3.39 (dq, J=6.0 and 7.3 Hz, 2H), 5.73 (q, J=0.8 Hz, 1H), 6.80-7.05 (m, 1H), 7.25-7.55 (m, 4H).

Example 58

N-tert-butyl-5-methyl-3-(3-trifluoromethylphenyloxy)pyrazole-1-carboxamide/colorless viscous substance/yield: 11.7%/$^1$H-NMR (CDCl$_3$, TMS, ppm): δ 1.43 (s, 9H), 2.59 (d, J=0.6 Hz, 3H), 5.69 (q, J=0.6 Hz, 1H), 6.95 (br s, 1H), 7.29-7.34 (m, 1H), 7.45-7.51 (m, 3H).

Example 59

N-hexyl-5-methyl-3-(3-trifluoromethylphenyloxy)pyrazole-1-carboxamide/yellow viscous substance/yield: 53.1%/$^1$H-NMR (CDCl$_3$, TMS, ppm): δ 0.86-0.91 (m, 3H), 1.26-1.41 (m, 6H), 1.52-1.64 (m, 2H), 2.60 (d, J=0.7 Hz, 3H), 3.29-3.37 (m, 2H), 5.73 (q, J=0.7 Hz, 1H), 6.95 (br s, 1H), 7.32-7.51 (m, 4H).

Example 60

N-cyclohexyl-5-methyl-3-(3-trifluoromethylphenyloxy)pyrazole-1-carboxamide/yellow viscous substance/yield: 26.7%/$^1$H-NMR (CDCl$_3$, TMS, ppm): δ 1.11-1.47 (m, 5H), 1.59-1.80 (m, 3H), 1.94-2.04 (m, 2H), 2.60 (d, J=0.7 Hz, 3H), 3.65-3.80 (m, 1H), 5.71 (q, J=0.7 Hz, 1H), 6.88 (br d, J=7.5 Hz, 1H), 7.30-7.35 (m, 1H), 7.40-7.51 (m, 3H).

Example 61

N-allyl-5-methyl-3-(3-trifluoromethylphenyloxy)pyrazole-1-carboxamide/colorless viscous substance/yield: 83.9%/$^1$H-NMR (CDCl$_3$, TMS, ppm): δ 2.61 (d, J=0.8 Hz, 3H), 3.97 (tt, J=1.5 and 5.8 Hz, 2H), 5.15-5.30 (m, 2H), 5.75 (q, J=0.8 Hz, 1H), 5.80-5.97 (m, 1H), 7.06 (br s, 1H), 7.32-7.36 (m, 1H), 7.40-7.52 (m, 3H).

Example 62

N-(2-chloroethyl)-5-methyl-3-(3-trifluoromethylphenyloxy)pyrazole-1-carboxamide/colorless viscous substance/yield: 71.0%/$^1$H-NMR (CDCl$_3$, TMS, ppm): δ 2.60 (d, J=0.7 Hz, 3H), 3.67-3.70 (m, 4H), 5.76 (q, J=0.7 Hz, 1H), 7.30-7.38 (m, 2H), 7.41-7.49 (m, 3H).

Example 63 ethyl [{3-(3-trifluoromethylphenyloxy)-5-methylpyrazol-1-yl}carbonylamino]acetate/white solid/yield: 73.7%/mp: 66-68° C./$^1$H-NMR (CDCl$_3$, TMS, ppm): δ 1.29 (t, J=7.2 Hz, 3H), 2.60 (d, J=0.8 Hz, 3H), 4.10 (d, J=5.8 Hz, 2H), 4.24 (q, J=7.2 Hz, 2H), 5.76 (q, J=0.8 Hz, 1H), 7.31-7.49 (m, 5H).

Example 64

N-phenyl-5-methyl-3-(3-trifluoromethylphenyloxy)pyrazole-1-carboxamide/yellowish solid/yield: 94.0%/mp: 53-54° C./$^1$H-NMR (CDCl$_3$, TMS, ppm): δ 2.67 (d, J=0.8 Hz, 3H), 5.80 (q, J=0.8 Hz, 1H), 7.15 (ddt, J=1.1, 7.4 and 7.4 Hz, 1H), 7.30-7.60 (m, 8H), 8.89 (br s, 1H).

Example 65

N-2-chlorophenyl-5-methyl-3-(3-trifluoromethylphenyloxy)pyrazole-1-carboxamide/yellowish solid/yield: 70.7%/mp: 84-86° C./$^1$H-NMR (CDCl$_3$, TMS, ppm): δ 2.67 (d, J=0.7 Hz, 3H), 5.85 (q, J=0.7 Hz, 1H), 7.06 (ddt, J=1.5, 7.8 and 7.8 Hz, 1H), 7.20-7.60 (m, 6H), 8.30 (dd, J=1.5 and 8.3 Hz, 1H), 9.56 (br s, 1H).

Example 66

N-3-chlorophenyl-5-methyl-3-(3-trifluoromethylphenyloxy)pyrazole-1-carboxamide/yellow viscous substance/yield: 94.0%/$^1$H-NMR (CDCl$_3$, TMS, ppm): δ 2.66 (d, J=0.9 Hz, 3H), 5.81 (q, J=0.9 Hz, 1H), 7.11 (ddd, J=1.3, 1.9 and 7.5 Hz, 1H), 7.23-7.39 (m, 3H), 7.45-7.55 (m, 3H), 7.70 (t, J=1.9 Hz, 1H), 8.91 (br s, 1H).

Example 67

N-(3-methylphenyl)-5-methyl-3-(3-trifluoromethylphenyloxy)pyrazole-1-carboxamide/yellow solid/yield: 92.2%/mp: 47-49° C./$^1$H-NMR (CDCl$_3$, TMS, ppm): δ 2.36 (s, 3H), 2.66 (d, J=0.7 Hz, 3H), 5.80 (q, J=0.7 Hz, 1H), 6.96 (dd, J=0.4 and 7.3 Hz, 1H), 7.20-7.29 (m, 2H), 7.29-7.41 (m, 2H), 7.43-7.54 (m, 3H), 8.84 (br s, 1H).

Example 68

N-(3-nitrophenyl)-5-methyl-3-(3-trifluoromethylphenyloxy)pyrazole-1-carboxamide/yellow solid/yield: 80.5%/mp: 83-86° C./$^1$H-NMR (CDCl$_3$, TMS, ppm): δ 2.68 (d, J=0.7 Hz, 3H), 5.84 (q, J=0.7 Hz, 1H), 7.36-7.40 (m, 1H), 7.46-7.57 (m, 4H), 7.83 (ddd, J=0.9, 2.2 and 8.2 Hz, 1H), 7.99 (ddd, J=0.9, 2.2 and 8.2 Hz, 1H), 8.52 (dd, J=2.2 and 2.2 Hz, 1H), 9.11 (br s, 1H).

Example 69

N-(4-chlorophenyl)-5-methyl-3-(3-trifluoromethylphenyloxy)pyrazole-1-carboxamide/white solid/yield: 88.9%/mp:

73-74° C./¹H-NMR (CDCl₃, TMS, ppm): δ 2.66 (d, J=0.8 Hz, 3H), 5.81 (q, J=0.8 Hz, 1H), 7.29-7.39 (m, 3H), 7.44-7.55 (m, 5H), 8.88 (br s, 1H).

Example 70

N-(4-fluorophenyl)-5-methyl-3-(3-trifluoromethylphenyloxy)pyrazole-1-carboxamide/yellow solid/yield: 77.0%/mp: 70-72° C./¹H-NMR (CDCl₃, TMS, ppm): δ 2.66 (d, J=0.8 Hz, 3H), 5.80 (q, J=0.8 Hz, 1H), 7.00~7.09 (m, 2H), 7.35-7.39 (m, 1H), 7.43-7.54 (m, 5H), 8.84 (br s, 1H).

Example 71

N-(4-trifluoromethylphenyl)-5-methyl-3-(3-trifluoromethylphenyloxy)pyrazole-1-carboxamide/yellowish solid/yield: 90.8%/mp: 82-84° C./¹H-NMR (CDCl₃, TMS, ppm): δ 2.67 (d, J=0.9 Hz, 3H), 5.83 (q, J=0.9 Hz, 1H), 7.32-7.40 (m, 1H), 7.45-7.56 (m, 3H), 7.64 (dd, J=8.9 and 15.6 Hz, 4H), 9.06 (br s, 1H).

Example 72

N-(2,4-dichlorophenyl)-5-methyl-3-(3-trifluoromethylphenyloxy)pyrazole-1-carboxamide/colorless viscous substance/yield: 63.7%/mp: 113-114° C./¹H-NMR (CDCl₃, TMS, ppm): δ 2.66 (d, J=0.6 Hz, 3H), 5.85 (1H), 7.25-7.30 (m, 1H), 7.39-7.56 (m, 5H), 8.27 (d, J=8.8 Hz, 1H), 9.52 (br s, 1H).

Example 73

N-(2,4-difluorophenyl)-5-methyl-3-(3-trifluoromethylphenyloxy)pyrazole-1-carboxamide/yellowish solid/yield: 45.3%/mp: 84-85° C./¹H-NMR (CDCl₃, TMS, ppm): δ 2.66 (d, J=0.8 Hz, 3H), 5.83 (q, J=0.8 Hz, 1H), 6.80-6.95 (m, 2H), 7.35-7.60 (m, 4H), 8.05-8.20 (m, 1H), 9.00 (br s, 1H).

Example 74

N-(3,4-dichlorophenyl)-5-methyl-3-(3-trifluoromethylphenyloxy)pyrazole-1-carboxamide/white solid/yield: 85.2%/mp: 97-99° C./¹H-NMR (CDCl₃, TMS, ppm): δ 2.65 (d, J=0.7 Hz, 3H), 5.82 (q, J=0.7 Hz, 1H), 7.32 (dd, J=2.5 and 8.8 Hz, 1H), 7.35-7.56 (m, 5H), 7.81 (d, J=2.4 Hz, 1H), 8.90 (br s, 1H).

Example 75

N-(2,6-dichlorophenyl)-5-methyl-3-(3-trifluoromethylphenyloxy)pyrazole-1-carboxamide/yellowish viscous substance/yield: 50.2%/¹H-NMR (CDCl₃, TMS, ppm): δ 2.64 (d, J=0.8 Hz, 3H), 5.84 (q, J=0.8 Hz, 1H), 7.21 (dd, J=7.5 and 8.8 Hz, 1H), 7.39-7.53 (m, 6H), 8.57 (br s, 1H).

Example 76

N-(4-chloro-2-methylphenyl)-5-methyl-3-(3-trifluoromethylphenyloxy)pyrazole-1-carboxamide/white solid/yield: 83.7%/mp: 95-96° C./¹H-NMR (CDCl₃, TMS, ppm): δ 2.21 (s, 3H), 2.65 (d, J=0.8 Hz, 3H), 5.83 (q, J=0.8 Hz, 1H), 7.17-7.23 (m, 2H), 7.37-7.54 (m, 4H), 7.91 (d, J=8.4 Hz, 1H), 8.82 (br s, 1H).

Example 77

N-(2-methyl-4-nitrophenyl)-5-methyl-3-(3-trifluoromethylphenyloxy)pyrazole-1-carboxamide/yellowish solid/yield: 16.7%/mp: 165-166° C./¹H-NMR (CDCl₃, TMS, ppm): δ 2.29 (s, 3H), 2.68 (d, J=0.8 Hz, 3H), 5.88 (q, J=0.8 Hz, 1H), 7.39-7.43 (m, 1H), 7.47-7.57 (m, 3H), 8.08-8.16 (m, 2H), 8.37 (d, J=9.0 Hz, 1H), 9.24 (br s, 1H).

Example 78

N-(2-chloro-6-methylphenyl)-5-methyl-3-(3-trifluoromethylphenyloxy)pyrazole-1-carboxamide/white solid/yield: 66.1%/mp: 55-58° C./¹H-NMR (CDCl₃, TMS, ppm): δ 2.36 (s, 3H), 2.64 (d, J=0.8 Hz, 3H), 5.83 (q, J=0.8 Hz, 1H), 7.12-7.20 (m, 2H), 7.30 (dd, J=2.9 and 6.5 Hz, 1H), 7.39-7.54 (m, 4H), 8.52 (br s, 1H).

Example 79

N-(2,3,4-trifluorophenyl)-5-methyl-3-(3-trifluoromethylphenyloxy)pyrazole-1-carboxamide/white solid/yield: 73.4%/mp: 102-104° C./¹H-NMR (CDCl₃, TMS, ppm): δ 2.65 (d, J=0.8 Hz, 3H), 5.84 (q, J=0.8 Hz, 1H), 6.93-7.05 (m, 1H), 7.38-7.42 (m, 1H), 7.45-7.56 (m, 3H), 7.85~7.92 (m, 1H), 9.30 (br s, 1H).

Example 80

N-(2-fluoro-4-chloro-5-cyclopentyloxyphenyl)-5-methyl-3-(3-trifluoromethylphenyloxy)pyrazole-1-carboxamide/white solid/yield: 52.0%/mp: 81-83° C./¹H-NMR (CDCl₃, TMS, ppm): δ 1.55-1.70 (m, 2H), 1.75-2.00 (m, 6H), 2.66 (d, J=0.8 Hz, 3H), 4.75-4.90 (m, 1H), 5.82 (q, J=0.8 Hz, 1H), 7.14 (d, J=10.2 Hz, 1H), 7.35-7.55 (m, 4H), 7.97 (d, J=7.3 Hz, 1H), 9.00-9.20 (m, 1H).

Example 81

N-benzyl-5-methyl-3-(3-trifluoromethylphenyloxy)pyrazole-1-carboxamide/colorless viscous substance/yield: 56.8%/¹H-NMR (CDCl₃, TMS, ppm): δ 2.62 (d, J=0.8 Hz, 3H), 4.53 (d, J=6.0 Hz, 2H), 5.74 (q, J=0.8 Hz, 1H), 7.20~7.50 (m, 10H).

Example 82

N-α-phenethyl-5-methyl-3-(3-trifluoromethylphenyloxy)pyrazole-1-carboxamide/colorless viscous substance/yield: 63.7%/¹H-NMR (CDCl₃, TMS, ppm): δ 1.57 (d, J=6.9 Hz, 3H), 2.58 (s, 3H), 5.06 (dq, J=7.1 and 7.1 Hz, 1H), 5.71 (s, 1H), 7.26-7.36 (m, 7H), 7.43-7.51 (m, 3H).

Example 83

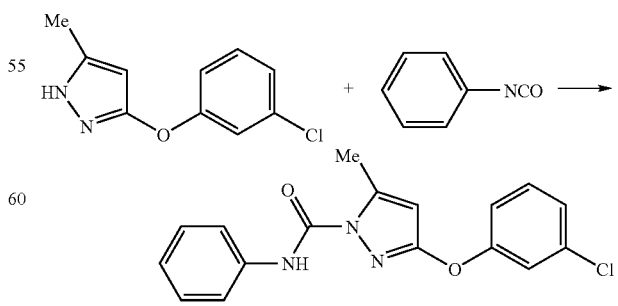

Triethylamine (0.13 g, 1.3 mmol) and phenyl isocyanate (0.15 g, 1.3 mmol) were added to a solution of 3-(3-chlorophenyloxy)-5-methylpyrazole (0.25 g, 1.2 mmol) in ethyl acetate (5 ml) at 0° C., and while the mixture was allowed to have room temperature gradually, it was stirred for 6 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellow viscous substance of N-phenyl-3-(3-chlorophenyloxy)-5-methylpyrazole-1-carboxamide (0.34 g, yield: 84.5%). $^1$H-NMR (CDCl$_3$, TMS, ppm): δ 2.66 (d, J=0.8 Hz, 3H), 5.78 (q, J=0.8 Hz, 1H), 7.05-7.11 (m, 1H), 7.14-7.21 (m, 3H), 7.28-7.39 (m, 3H), 7.52-7.56 (m, 2H), 8.91 (br s, 1H).

Example 84

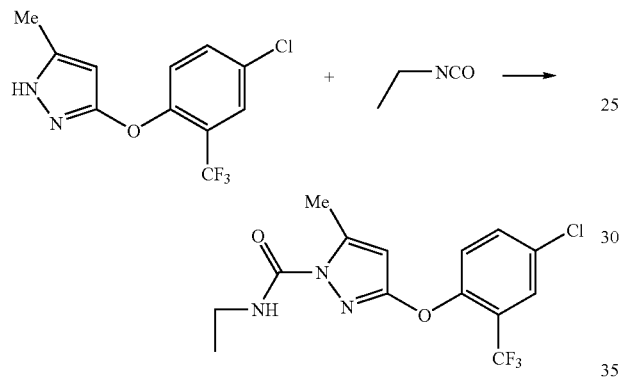

Triethylamine (0.17 g, 1.65 mmol) and ethyl isocyanate (0.31 g, 2.2 mmol) were added to a solution of 3-(4-chloro-2-trifluoromethylphenyloxy)-5-methylpyrazole (0.55 g, 2.0 mmol) in ethyl acetate (5 ml), and the mixture was stirred at room temperature for 6 hours. After completion of the reaction, the reaction mixture was poured into 1N hydrochloric acid (10 ml) and extracted with ethyl acetate (10 ml×3). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a colorless viscous substance of N-ethyl-3-(4-chloro-2-trifluoromethylphenyloxy)-5-methylpyrazole-1-carboxamide (0.53 g, yield: 75.9%). $^1$H-NMR (CDCl$_3$, TMS, ppm): δ 1.22 (t, J=7.3 Hz, 3H), 2.59 (d, J=0.7 Hz, 3H), 3.37 (q, J=7.3 Hz, 2H), 5.73 (q, J=0.7 Hz, 1H), 6.91 (br s, 1H), 7.22 (d, J=8.8 Hz, 1H), 7.49 (dd, J=2.5 and 8.8 Hz, 1H), 7.65 (d, J=2.5 Hz, 1H).

Example 85

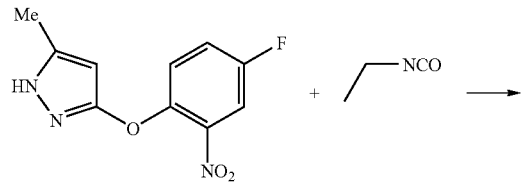

-continued

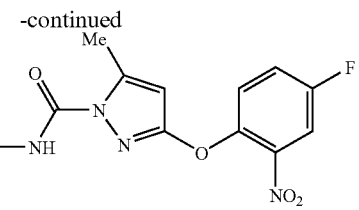

Triethylamine (0.32 g, 3.2 mmol) and ethyl isocyanate (0.23 g, 3.2 mmol) were added to a solution of 3-(4-fluoro-2-nitrophenyloxy)-5-methylpyrazole (0.69 g, 2.9 mmol) in ethyl acetate (10 ml) at 0° C., and the mixture was allowed to have room temperature gradually and stirred for 5 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellow solid of N-ethyl-3-(4-fluoro-2-nitrophenyloxy)-5-methylpyrazole-1-carboxamide (0.72 g, yield: 79.7%). mp: 81-84° C.; $^1$H-NMR (CDCl$_3$, TMS, ppm): δ 1.20 (t, J=7.2 Hz, 3H), 2.59 (d, J=0.8 Hz, 3H), 3.34 (dq, J=1.4 and 7.2 Hz, 2H), 5.78 (q, J=0.8 Hz, 1H), 6.71 (br s, 1H), 7.34-7.37 (m, 2H), 7.73 (ddd, J=1.2, 2.2 and 7.7 Hz, 1H).

Example 86

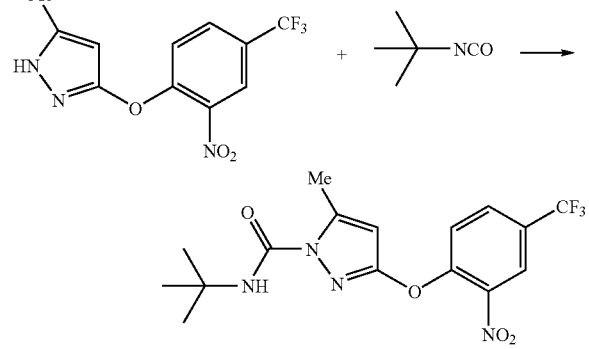

Potassium carbonate (0.83 g, 6.0 mmol) and tert-butyl isocyanate (0.59 g, 6.0 mmol) were added to a solution of 5-methyl-3-(2-nitro-4-trifluoromethylphenyloxy)pyrazole (1.15 g, 4.0 mmol) in DMF (10 ml), and the mixture was stirred at room temperature for 4 hours. After completion of the reaction, the reaction mixture was poured into 2N hydrochloric acid and extracted with ethyl acetate (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of N-tert-butyl-5-methyl-3-(2-nitro-4-trifluoromethylphenyloxy)-pyrazole-1-carboxamide (0.80 g, yield: 51.8%). mp: 104-106° C.; $^1$H-NMR (CDCl$_3$, TMS, ppm): δ 1.41 (s, 9H), 2.61 (s, 3H), 5.82 (s, 1H), 6.65-6.90 (br s, 1H), 7.43 (d, J=8.7 Hz, 1H), 7.82 (dd, J=2.1 and 8.7 Hz, 1H), 8.23 (d, J=2.1 Hz, 1H).

Examples 87-90

Reactions of 5-methyl-3-(2-nitro-4-trifluoromethylphenyloxy)pyrazole and isocyanates (Example 87: methyl isocyanate, Example 88: ethyl isocyanate, Example 89: propyl isocyanate, Example 90: isopropyl isocyanate) were carried out in the same manner as in Example 86, to give corresponding N-substituted carboxamides. Products/forms/yields/melting points/NMR spectra are described below.

Example 87

N-methyl-5-methyl-3-(2-nitro-4-trifluoromethylphenyloxy)pyrazole-1-carboxamide/white solid/yield: 89.0%/mp: 70-72° C./$^1$H-NMR (CDCl$_3$, TMS, ppm): δ 2.62 (d, J=0.8 Hz, 3H), 2.91 (d, J=5.0 Hz, 3H), 5.88 (q, J=0.8 Hz, 1H), 6.55-6.85 (m, 1H), 7.49 (d, J=8.7 Hz, 1H), 7.83 (dd, J=2.0 and 8.7 Hz, 1H), 8.25 (d, J=2.0 Hz, 1H).

Example 88

N-ethyl-5-methyl-3-(2-nitro-4-trifluoromethylphenyloxy)pyrazole-1-carboxamide/yellow viscous substance/yield: 25.2%/$^1$H-NMR (CDCl$_3$, TMS, ppm): δ 1.21 (t, J=7.3 Hz, 3H), 2.62 (d, J=0.7 Hz, 3H), 3.36 (dq, J=6.0 and 7.3 Hz, 2H), 5.87 (q, J=0.7 Hz, 1H), 6.60-6.95 (m, 1H), 7.48 (d, J=8.5 Hz, 1H), 7.85 (d, J=2.0 and 8.5 Hz, 1H), 8.25 (d, J=2.0 Hz, 1H).

Example 89

N-propyl-5-methyl-3-(2-nitro-4-trifluoromethylphenyloxy)pyrazole-1-carboxamide/yellowish solid/yield: 13.6%/mp: 50-51° C./$^1$H-NMR (CDCl$_3$, TMS, ppm): δ 0.95 (t, J=7.4 Hz, 3H), 1.60 (tq, J=7.1 and 7.4 Hz, 2H), 2.62 (d, J=0.7 Hz, 3H), 3.28 (dt, J=6.3 and 7.1 Hz, 2H), 5.87 (q, J=0.7 Hz, 1H), 6.65~6.95 (m, 1H), 7.48 (d, J=8.8 Hz, 1H), 7.85 (dd, J=2.0 and 8.8 Hz, 1H), 8.25 (d, J=2.0 Hz, 1H).

Example 90

N-isopropyl-5-methyl-3-(2-nitro-4-trifluoromethylphenyloxy)pyrazole-1-carboxamide/yellow viscous substance/yield: 70.6%/$^1$H-NMR (CDCl$_3$, TMS, ppm): δ 1.24 (d, J=6.6 Hz, 6H), 2.62 (d, J=0.7 Hz, 3H), 3.90-4.10 (m, 1H), 5.86 (q, J=0.7 Hz, 1H), 6.50-6.80 (m, 1H), 7.46 (d, J=8.6 Hz, 1H), 7.84 (dd, J=2.0 and 8.6 Hz, 1H), 8.25 (d, J=2.0 Hz, 1H).

Example 91

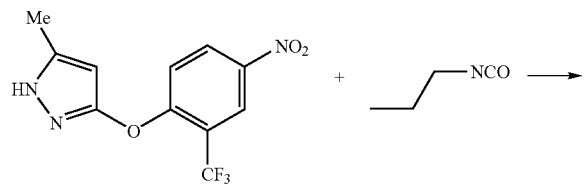

-continued

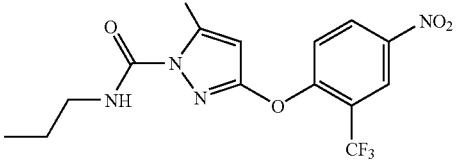

Potassium carbonate (0.61 g, 4.4 mmol) and propyl isocyanate (0.34 g, 4.0 mmol) were added to a solution of 5-methyl-3-(4-nitro-2-trifluoromethylphenyloxy)pyrazole (1.15 g, 4.0 mmol) in ethyl acetate (10 ml), and the mixture was stirred at room temperature for 3 hours. After completion of the reaction, the reaction mixture was poured into 2N hydrochloric acid and extracted with ethyl acetate (20 ml×3). An organic layer was washed with water, dried over anhydrous magnesium sulfate and filtered co remove a desiccant, and the solvent was distilled off from the filtrate under reduced pressure. The resultant crude product was purified with a silica gel column (ethyl acetate/hexane=1/5), to give a yellow viscous substance of N-propyl-5-methyl-3-(4-nitro-2-trifluoromethylphenyloxy)pyrazole-1-carboxamide (1.08 g, yield: 72.5%). $^1$H-NMR (CDCl$_3$, TMS, ppm): δ 0.97 (t, J=7.4 Hz, 3H), 1.62 (tq, J=7.4 and 7.4 Hz, 2H), 2.64 (d, J=0.7 Hz, 3H), 3.25-3.40 (m, 2H), 5.88 (q, J=0.7 Hz, 1H), 6.80-7.05 (m, 1H), 7.42 (d, J=9.2 Hz, 1H), 8.40 (dd, J=2.7 and 9.2 Hz, 1H), 8.59 (d, J=2.7 Hz, 1H).

Examples 93-95

Reactions of 5-methyl-3-(4-nitro-2-trifluoromethylphenyloxy)pyrazole and isocyanates (Example 93: methyl isocyanate, Example 94: ethyl isocyanate, Example 95: isopropyl isocyanate) were carried out in the same manner as in Example 92, to give corresponding N-substituted carboxamides. Products/forms/yields/melting points/NMR spectra are described below.

Example 92

N-methyl-5-methyl-3-(4-nitro-2-trifluoromethylphenyloxy)pyrazole-1-carboxamide/white solid/yield: 79.7%/mp: 142-144° C./$^1$H-NMR (CDCl$_3$, TMS, ppm): δ 2.64 (d, J=0.8 Hz, 3H), 2.95 (d, J=5.0 Hz, 3H), 5.89 (q, J=0.8 Hz, 1H), 6.75-6.95 (m, 1H), 7.43 (d, J=9.2 Hz, 1H), 8.40 (dd, J=2.7 and 9.2 Hz, 1H), 8.59 (d, J=2.7 Hz, 1H).

Example 93

N-ethyl-5-methyl-3-(4-nitro-2-trifluoromethylphenyloxy)pyrazole-1-carboxamide/yellowish solid/yield: 86.5%/mp: 95-97° C./$^1$H-NMR (CDCl$_3$, TMS, ppm): δ 1.24 (t, J=7.3 Hz, 3H), 2.64 (d, J=0.6 Hz, 3H), 3.40 (dq, J=5.9 and 7.3 Hz, 2H), 5.88 (q, J=0.6 Hz, 1H), 6.75-7.00 (m, 1H), 7.42 (d, J=9.2 Hz, 1H), 8.38 (dd, J=2.8 and 9.2 Hz, 1H), 8.59 (d, J=2.8 Hz, 1H).

Example 94

N-isopropyl-5-methyl-3-(4-nitro-2-trifluoromethylphenyloxy)pyrazole-1-carboxamide/white solid/yield: 77.9%/mp: 90-92° C./$^1$H-NMR (CDCl$_3$; TMS, ppm): δ 1.26 (d, J=6.6 Hz, 6H), 2.64 (d, J=0.8 Hz, 3H), 4.05 (dq, J=1.4 and 6.6 Hz, 1H), 5.86 (q, J=0.8 Hz, 1H), 6.60-6.90 (m, 1H), 7.40 (d, J=9.2 Hz, 1H), 8.40 (dd, J=2.7 and 9.2 Hz, 1H), 8.59 (d, J=2.7 Hz, 1H).

Example 95

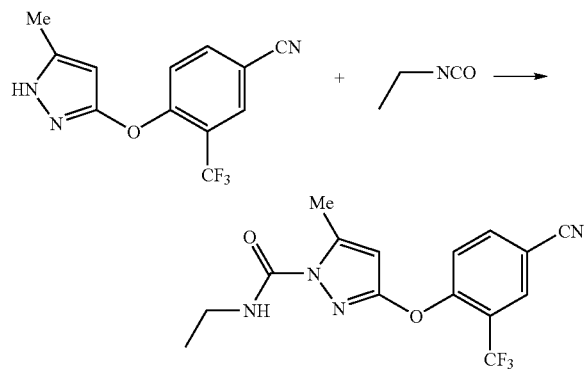

Potassium carbonate (0.23 g, 1.7 mmol) and ethyl isocyanate (0.11 g, 1.5 mmol) were added to a solution of 3-(4-cyano-2-trifluoromethylphenyloxy)-5-methylpyrazole (0.40 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellowish solid of N-ethyl-3-(4-cyano-2-trifluoromethylphenyloxy)-5-methylpyrazole-1-carboxamide (0.35 g, yield: 69.0%). mp: 103-105° C.; $^1$H-NMR (CDCl$_3$, TMS, ppm): δ 1.23 (t, J=7.3 Hz, 3H), 2.63 (d, J=0.7 Hz, 3H), 3.39 (dq, J=5.9 and 7.2 Hz, 2H), 5.85 (q, J=0.7 Hz, 1H), 6.80-7.00 (m, 1H), 7.38 (d, J=8.7 Hz, 1H), 7.81 (dd, J=1.8 and 8.7 Hz, 1H), 7.99 (d, J=1.8 Hz, 1H).

Example 96

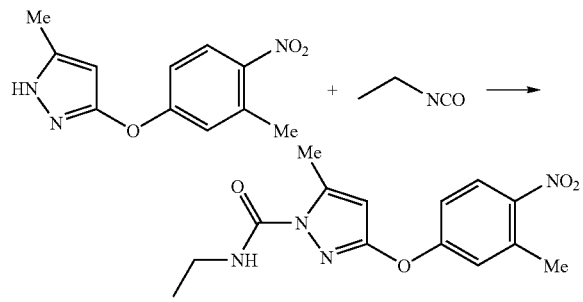

Triethylamine (0.18 g, 1.8 mmol) and ethyl isocyanate (0.13 g, 1.8 mmol) were added to a solution of 5-methyl-3-(3-methyl-4-nitrophenyloxy)pyrazole (0.35 g, 1.5 mmol) in ethyl acetate (10 ml), and the mixture was stirred at room temperature for 8 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a white solid of N-ethyl-5-methyl-3-(3-methyl-4-nitrophenyloxy)pyrazole-1-carboxamide (0.27 g, yield: 59.2%). mp: 67-69° C.; $^1$H-NMR (CDCl$_3$, TMS, ppm): δ 1.24 (t, J=7.3 Hz, 3H), 2.63 (s, 6H), 3.40 (dq, J=5.9 and 7.3 Hz, 2H), 5.79 (q, J=0.8 Hz, 1H), 6.85-7.00 (m, 1H), 7.00-7.15 (m, 2H), 8.07 (d, J=8.6 Hz, 1H).

Example 97

Reaction of 5-methyl-3-(3-methoxy-4-nitrophenyloxy)pyrazole with ethyl isocyanate was carried out in the same manner as in Example 96, to give a yellow viscous substance of N-ethyl-5-methyl-3-(3-methoxy-4-nitrophenyloxy)pyrazole-1-carboxamide (yield: 62.9%). $^1$H-NMR (CDCl$_3$, TMS, ppm): δ 1.24 (t, J=7.2 Hz, 3H), 2.63 (d, J=0.6 Hz, 3H), 3.40 (dq, J=5.9 and 7.2 Hz, 2H), 3.95 (s, 3H), 5.81 (q, J=0.6 Hz, 1H), 6.75 (dd, J=2.4 and 9.0 Hz, 1H), 6.84 (d, J=2.4 Hz, 1H), 6.93 (br s, 1H), 7.96 (d, J=9.0 Hz, 1H).

Example 98

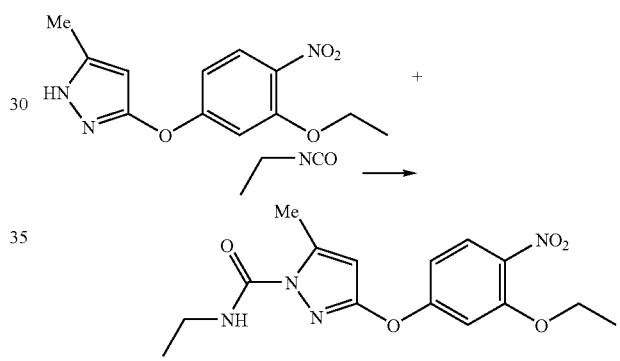

Triethylamine (0.07 g, 0.7 mmol) and ethyl isocyanate (0.12 g, 0.7 mmol) were added to a solution of 3-(3-ethoxy-4-nitrophenyloxy)-5-methylpyrazole (0.16 g, 0.6 mmol) in ethyl acetate (5 ml) at 0° C., and the mixture was allowed to have room temperature gradually and stirred for 5 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellow solid of N-ethyl-3-(3-ethoxy-4-nitrophenyloxy)-5-methylpyrazole-1-carboxamide (0.13 g, yield: 61.8%). mp: 110-112° C.; $^1$H-NMR (CDCl$_3$, TMS, ppm): δ 1.24 (t, J=7.3 Hz, 3H), 1.49 (t, J=7.0 Hz, 3H), 2.63 (d, J=0.5 Hz, 3H), 3.40 (dq, J=6.0 and 7.3 Hz, 2H), 4.14 (q, J=7.0 Hz, 2H), 5.80 (q, J=0.5 Hz, 1H), 6.73 (dd, J=2.4 and 9.0 Hz, 1H), 6.82 (d, J=2.4 Hz, 1H), 6.92 (br s, 1H), 7.92 (d, J=9.0 Hz, 1H).

Example 99

Reaction of 3-(5-ethoxy-2-nitrophenyloxy)-5-methylpyrazole with ethyl isocyanate was carried out in ethyl acetate in the presence of potassium carbonate in the same manner as in Example 99, to give a yellow solid of N-ethyl-3-(5-ethoxy-2-nitrophenyloxy)-5-methylpyrazole-1-carboxamide (yield: 75.9%). mp: 73-75° C.; ¹H-NMR (CDCl₃, TMS, ppm): δ 1.20 (t, J=7.2 Hz, 3H), 1.44 (t, J=7.0 Hz, 3H), 2.59 (d, J=0.7 Hz, 3H), 3.35 (dq, J=5.9 and 7.2 Hz, 2H), 4.09 (q, J=7.0 Hz, 2H), 5.78 (q, J=0.7 Hz, 1H), 6.73 (d, J=2.4 Hz, 1H), 6.77 (dd, J=2.4 and 8.9 Hz, 1H), 6.81 (br s, 1H), 8.06 (d, J=8.9 Hz, 1H).

Example 100

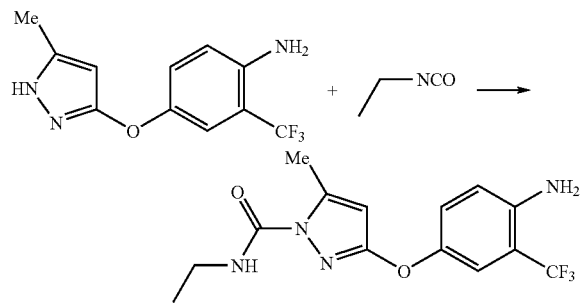

Triethylamine (0.13 g, 1.3 mmol) and ethyl isocyanate (0.09 g, 1.3 mmol) were added to a solution of 3-(4-amino-3-trifluoromethylphenyloxy)-5-methylpyrazole (0.30 g, 1.2 mmol) in ethyl acetate (5 ml) at 0° C., and the mixture was allowed to have room temperature gradually and stirred for 6 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellowish solid of N-ethyl-3-(4-amino-3-trifluoromethylphenyloxy)-5-methylpyrazole-1-carboxamide (0.19 g, yield: 50.5%). mp: 102-104° C.; ¹H-NMR (CDCl₃, TMS, ppm): δ 1.22 (t, J=7.3 Hz, 3H), 2.56 (d, J=0.8 Hz, 3H), 3.37 (dq, J=5.9 and 7.3 Hz, 2H), 4.11 (br s, 2H), 5.61 (q, J=0.8 Hz, 1H), 6.74 (d, J=8.8 Hz, 1H), 6.93 (br s, 1H), 7.14 (dd, J=2.7 and 8.8 Hz, 1H), 7.27 (d, J=2.7 Hz, 1H).

Example 101

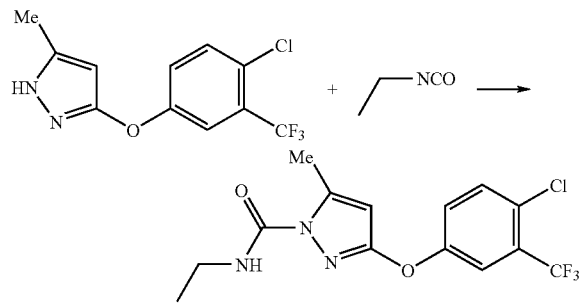

Triethylamine (0.17 g, 1.7 mmol) and ethyl isocyanate (0.12 g, 1.7 mmol) were added to a solution of 3-(4-chloro-3-trifluoromethylphenyloxy)-5-methylpyrazole (0.42 g, 1.5 mmol) in ethyl acetate (5 ml) at 0° C., and the mixture was allowed to have room temperature gradually and stirred for 5 hours. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/15), to give a yellow viscous substance of N-ethyl-3-(4-chloro-3-trifluoromethylphenyloxy)-5-methylpyrazole-1-carboxamide (0.42 g, yield: 80.1%). ¹H-NMR (CDCl₃, TMS, ppm): δ 1.22 (t, J=7.2 Hz, 3H), 2.59 (d, J=0.8 Hz, 3H), 3.38 (dq, J=5.9 and 7.2 Hz, 2H), 5.73 (q, J=0.8 Hz, 1H), 6.91 (br s, 1H), 7.22 (d, J=8.8 Hz, 1H), 7.49 (dd, J=2.4 and 8.8 Hz, 1H), 7.65 (d, J=2.4 Hz, 1H).

Example 102

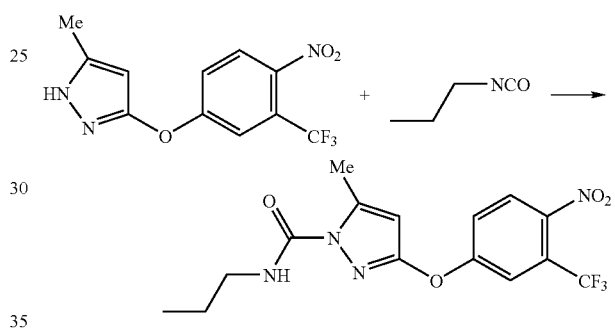

Potassium carbonate (0.30 g, 2.2 mmol) and propyl isocyanate (0.17 g, 2.0 mmol) were added to a solution of 5-methyl-3-(4-nitro-3-trifluoromethylphenyloxy)pyrazole (0.57 g, 2.0 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellow viscous substance of N-propyl-5-methyl-3-(4-nitro-3-trifluoromethylphenyloxy)pyrazole-1-carboxamide (0.64 g, yield: 69.0%). ¹H-NMR (CDCl₃, TMS, ppm): δ 0.97 (t, J=7.3 Hz, 3H), 1.62 (q, J=7.3 Hz, 2H), 2.64 (s, 3H), 3.32 (dt, J=7.3 and 7.3 Hz, 2H), 5.85 (m, 1H), 6.80~7.05 (m, 1H), 7.45 (dd, J=2.6 and 9.0 Hz, 1H), 7.64 (d, J=2.6 Hz, 1H), 8.00 (d, J=9.0 Hz, 1H).

Examples 103-104

Reactions of 5-methyl-3-(4-nitro-3-trifluoromethylphenyloxy)pyrazole with isocyanates (Example 103: methyl isocyanate, Example 104: ethyl isocyanate) were carried out in ethyl acetate in the presence of potassium carbonate in the same manner as in Example 102, to give corresponding N-substituted carboxamides. Products/forms/yields/melting points/NMR spectra are described below.

Example 103

N-methyl-5-methyl-3-(4-nitro-3-trifluoromethylphenyloxy)pyrazole-1-carboxamide/yellow solid/yield: 42.1%/mp: 139-141° C./$^1$H-NMR (CDCl$_3$, TMS, ppm): δ 2.65 (d, J=0.4 Hz, 3H), 2.95 (d, J=5.0 Hz, 3H), 5.86 (m, 1H), 6.65-7.00 (m, 1H), 7.47 (dd, J=2.6 and 8.9 Hz, 1H), 7.61 (d, J=2.6 Hz, 1H), 8.00 (d, J=8.9 Hz, 1H).

Example 104

N-ethyl-5-methyl-3-(4-nitro-3-trifluoromethylphenyloxy)pyrazole-1-carboxamide/yellowish solid/yield: 34.9%/mp: 95-97° C./$^1$H-NMR (CDCl$_3$, TMS, ppm): δ 1.24 (t, J=7.3 Hz, 3H), 2.65 (s, 3H), 3.41 (dq, J=5.9 and 7.2 Hz, 2H), 5.85 (m, 1H), 6.75-7.00 (m, 1H), 7.45 (dd, J=2.6 and 8.9 Hz, 1H), 7.63 (d, J=2.6 Hz, 1H), 8.00 (d, J=8.9 Hz, 1H).

Example 105

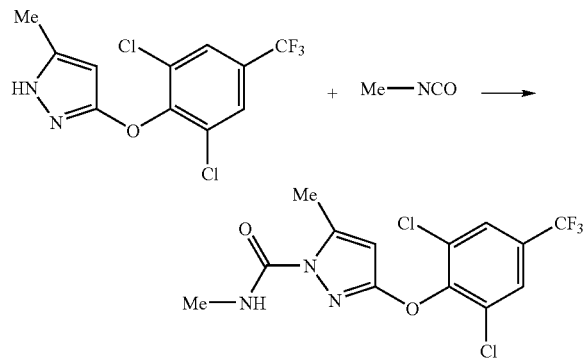

Triethylamine (0.40 g, 4.0 mmol) and methyl isocyanate (0.25 g, 4.4 mmol) were added to a solution of 3-(2,6-dichloro-4-trifluoromethylphenyloxy)-5-methylpyrazole (1.24 g, 4.0 mmol) in ethyl acetate (20 ml), and the mixture was stirred at room temperature for 6 hours. After completion of the reaction, the reaction mixture was poured into 2N hydrochloric acid and extracted with ethyl acetate (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-methyl-3-(2,6-dichloro-4-trifluoromethylphenyloxy)-5-methylpyrazole-1-carboxamide (0.87 g, yield: 59.0%). mp: 113-114° C.; $^1$H-NMR (CDCl$_3$, TMS, ppm): δ 2.60 (d, J=0.7 Hz, 3H), 2.88 (d, J=4.9 Hz, 3H), 5.77 (d, J=0.7 Hz, 1H), 6.50-6.75 (m, 1H), 7.66 (s, 2H).

Example 106

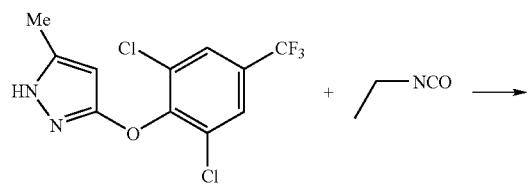

-continued

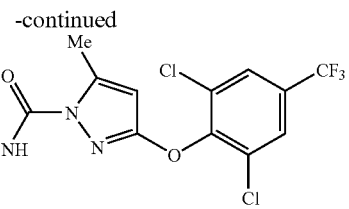

Potassium carbonate (0.30 g, 2.2 mmol) and ethyl isocyanate (0.14 g, 2.0 mmol) were added to a solution of 3-(2,6-dichloro-4-trifluoromethylphenyloxy)-5-methylpyrazole (0.62 g, 2.0 mmol) in ethyl acetate (10 ml), and the mixture was stirred at room temperature for 4 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-ethyl-3-(2,6-dichloro-4-trifluoromethylphenyloxy)-5-methylpyrazole-1-carboxamide (0.48 g, yield: 62.8%). mp: 80-82° C.; $^1$H-NMR (CDCl$_3$, TMS, ppm): δ 1.19 (t, J=7.3 Hz, 3H), 2.59 (s, 3H), 3.34 (dq, J=6.1 and 7.3 Hz, 2H), 5.72 (s, 1H), 6.60-6.85 (m, 1H), 7.67 (s, 2H).

Examples 107-117

Reactions of 3-(2,6-dichloro-4-trifluoromethylphenyloxy)-5-methylpyrazole with isocyanates (Example 107: propyl isocyanate, Example 108: isopropyl isocyanate, Example 109: tert-butyl isocyanate, Example 110: hexyl isocyanate, Example 111: octyl isocyanate, Example 112: allyl isocyanate, Example 113: 2-chloroethyl isocyanate, Example 114: 2-bromoethyl isocyanate, Example 115: benzyl isocyanate, Example 116: ethyl isocyanatoacetate, Example 117: ethyl 3-isocyanatopropionate) were carried out in ethyl acetate in the presence of a base in the same manner as in Example 105 or 106, to give corresponding N-substituted carboxamides. Products/forms/yields/melting points/NMR spectra are described below.

Example 107

N-propyl-3-(2,6-dichloro-4-trifluoromethylphenyloxy)-5-methylpyrazole-1-carboxamide/colorless viscous substance/yield: 68.4%/$^1$H-NMR (CDCl$_3$, TMS, ppm): δ 0.92 (t, J=7.5 Hz, 3H), 1.59 (tq, J=7.5 and 7.8 Hz, 2H), 2.58 (d, J=0.8 Hz, 3H), 3.25 (m, 2H), 5.71 (q, J=0.8 Hz, 1H), 6.70-6.90 (m, 1H), 7.66 (s, 2H).

Example 108

N-isopropyl-3-(2,6-dichloro-4-trifluoromethylphenyloxy)-5-methylpyrazole-1-carboxamide/white solid/yield: 68.4%/mp: 103-105° C./$^1$H-NMR (CDCl$_3$, TMS, ppm): δ 1.22 (d, J=6.5 Hz, 6H), 2.57 (d, J=0.8 Hz, 3H), 3.90-4.10 (m, 1H), 5.62 (q, J=0.8 Hz, 1H), 6.50-6.75 (m, 1H), 7.67 (s, 2H).

Example 109

N-tert-butyl-3-(2,6-dichloro-4-trifluoromethylphenyloxy)-5-methylpyrazole-1-carboxamide/white solid/yield: 54.8%/mp: 116-117° C./$^1$H-NMR (CDCl$_3$, TMS, ppm): δ 1.40 (s, 9H), 2.56 (s, 3H), 5.57 (s, 1H), 6.70-6.85 (m, 1H), 7.67 (s, 2H).

Example 110

N-hexyl-3-(2,6-dichloro-4-trifluoromethylphenyloxy)-5-methylpyrazole-1-carboxamide/colorless viscous substance/yield: 69.5%/$^1$H-NMR (CDCl$_3$, TMS, ppm): δ 0.88 (t, J=6.8 Hz, 3H), 1.15-1.40 (m, 6H), 1.45-1.65 (m, 2H), 2.58 (s, 3H), 3.15-3.40 (m, 2H), 5.71 (s, 1H), 6.65-6.85 (m, 1H), 7.66 (s, 2H).

Example 111

N-octyl-3-(2,6-dichloro-4-trifluoromethylphenyloxy)-5-methylpyrazole-1-carboxamide/white solid/yield: 64.3%/mp: 43-45° C./$^1$H-NMR (CDCl$_3$, TMS, ppm): δ 0.88 (t, J=6.8 Hz, 3H), 1.10-1.45 (m, 10H), 1.45-1.65 (m, 2H), 2.58 (s, 3H), 3.15-3.35 (m, 2H), 5.70 (s, 1H), 6.65-6.85 (m, 1H), 7.66 (s, 2H).

Example 112

N-allyl-3-(2,6-dichloro-4-trifluoromethylphenyloxy)-5-methylpyrazole-1-carboxamide/colorless viscous substance/yield: 83.1%/$^1$H-NMR (CDCl$_3$, TMS, ppm): δ 2.59 (d, J=0.8 Hz, 3H), 3.80-4.00 (m, 2H), 5.05-5.30 (m, 2H), 5.75 (q, J=0.8 Hz, 1H), 5.75-5.95 (m, 1H), 6.70-7.00 (m, 1H), 7.66 (s, 2H).

Example 113

N-(2-chloroethyl)-3-(2,6-dichloro-4-trifluoromethylphenyloxy)-5-methylpyrazole-1-carboxamide/white solid/yield: 62.4%/mp: 116-118° C./$^1$H-NMR (CDCl$_3$, TMS, ppm): δ 2.58 (s, 3H), 3.50-3.75 (m, 4H), 5.76 (s, 1H), 6.95-7.20 (m, 1H), 7.67 (s, 2H).

Example 114

N-(2-bromoethyl)-3-(2,6-dichloro-4-trifluoromethylphenyloxy)-5-methylpyrazole-1-carboxamide/white solid/yield: 58.6%/mp: 106-107° C./$^1$H-NMR (CDCl$_3$, TMS, ppm): δ 2.58 (s, 3H), 3.48 (t, J=6.1 Hz, 2H), 3.69 (dt, J=6.1 and 6.1 Hz, 2H), 5.77 (s, 1H), 6.95-7.20 (m, 1H), 7.67 (s, 2H).

Example 115

N-benzyl-3-(2,6-dichloro-4-trifluoromethylphenyloxy)-5-methylpyrazole-1-carboxamide/white solid/yield: 76.5%/mp: 50-53° C./$^1$H-NMR (CDCl$_3$, TMS, ppm): δ 2.61 (d, J=0.7 Hz, 3H), 4.40 (d, J=6.2 Hz, 2H), 5.74 (q, J=0.7 Hz, 1H), 7.13 (br t, J=6.2 Hz, 1H), 7.25-7.40 (m, 5H), 7.65 (s, 2H).

Example 116 ethyl [{3-(2,6-dichloro-4-trifluoromethylphenyloxy)-5-methylpyrazol-1-yl}carbonylamino]acetate/white solid/yield: 76.5%/mp: 50-53° C./$^1$H-NMR (CDCl$_3$, TMS, ppm): δ 1.27 (t, J=7.1 Hz, 3H), 2.58 (d, J=0.7 Hz, 3H), 4.04 (d, J=5.9 Hz, 2H), 4.21 (q, J=7.2 Hz, 2H), 5.80 (q, J=0.7 Hz, 1H), 7.10 (br t, J=5.9 Hz, 1H), 7.66 (s, 2H).

Example 117 ethyl 3-[{3-(2,6-dichloro-4-trifluoromethylphenyloxy)-5-methylpyrazol-1-yl}carbonylamino]propionate/white solid/yield: 77.2%/mp: 73-74° C./$^1$H-NMR (CDCl$_3$, TMS, ppm): δ 1.20 (t, J=7.5 Hz, 3H), 2.50-2.65 (m, 4H), 3.56 (q, J=7.5 Hz, 2H), 4.00-4.20 (m, 2H), 5.76 (q, J=0.8 Hz, 1H), 7.00-7.20 (m, 2H), 7.66 (s, 2H).

Example 118

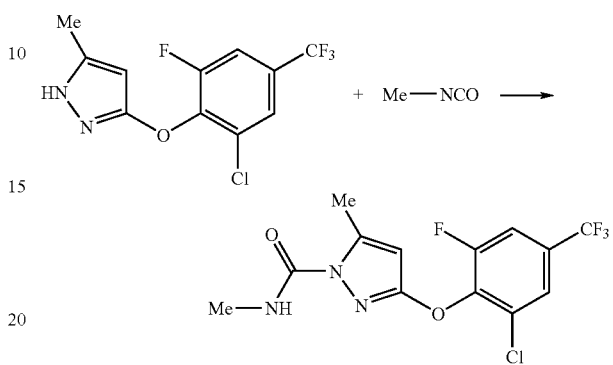

Triethylamine (0.13 g, 1.3 mmol) and methyl isocyanate (0.07 g, 1.2 mmol) were added to a solution of 3-(2-chloro-6-fluoro-4-trifluoromethylphenyloxy)-5-methylpyrazole (0.32 g, 1.1 mmol) in ethyl acetate (10 ml), and the mixture was stirred at room temperature for 4 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-methyl-3-(2-chloro-6-fluoro-4-trifluoromethylphenyloxy)-5-methylpyrazole-1-carboxamide (0.22 g, yield: 56.9%). mp: 87-88° C.; $^1$H-NMR (CDCl$_3$, TMS, ppm): δ 2.59 (s, 3H), 2.88 (d, J=5.0 Hz, 3H), 5.80 (s, 1H), 6.55-6.75 (m, 1H), 7.40 (dd, J$_{HF}$=2.0 and 9.3 Hz, 1H), 7.56 (s, 1H).

Examples 119-123

Reactions of 3-(2-chloro-6-fluoro-4-trifluoromethylphenyloxy)-5-methylpyrazole with isocyanates (Example 119: ethyl isocyanate, Example 120: isopropyl isocyanate, Example 121: propyl isocyanate, Example 122: allyl isocyanate, Example 123: 2-bromoethyl isocyanate) were carried out in the same manner as in Example 118, to give corresponding N-substituted carboxamides. Products/forms/yields/melting points/NMR spectra are described below.

Example 119

N-ethyl-3-(2-chloro-6-fluoro-4-trifluoromethylphenyloxy)-5-methylpyrazole-1-carboxamide/white solid/yield: 42.8%/mp: 58-60° C./$^1$H-NMR (CDCl$_3$, TMS, ppm): δ 1.19 (t, J=7.3 Hz, 3H), 2.59 (d, J=0.7 Hz, 3H), 3.34 (dq, J=6.0 and 7.2 Hz, 2H), 5.76 (q, J=0.7 Hz, 1H), 6.60-6.85 (m, 1H), 7.40 (dd, J$_{HF}$=1.8 and 9.2 Hz, 1H), 7.57 (s, 1H).

Example 120

N-isopropyl-3-(2-chloro-6-fluoro-4-trifluoromethylphenyloxy)-5-methylpyrazole-1-carboxamide/colorless viscous substance/yield: 31.1%/$^1$H-NMR (CDCl$_3$, TMS, ppm): δ 1.22 (d, J=6.6 Hz, 6H), 2.58 (d, J=0.8 Hz, 3H), 4.01 (dsep, J=6.6 and 6.6 Hz, 1H), 5.69 (q, J=0.8 Hz, 1H), 6.60 (br d, J=6.6 Hz, 1H), 7.41 (dd, $J_{HF}$=1.8 and 9.2 Hz, 1H), 7.58 (s, 1H).

Example 121

N-propyl-3-(2-chloro-6-fluoro-4-trifluoromethylphenyloxy)-5-methylpyrazole-1-carboxamide/colorless viscous substrate/yield: 49.5%/$^1$H-NMR (CDCl$_3$, TMS, ppm): δ 0.92 (t, J=7.4 Hz, 3H), 1.58 (tq, J=7.4 and 13.3 Hz, 3H), 2.58 (d, J=0.8 Hz, 3H), 3.25 (dt, J=6.4 and 13.3 Hz, 1H), 5.76 (q, J=0.8 Hz, 1H), 6.65-6.90 (m, 1H), 7.40 (dd, J=2.0 and 9.4 Hz, 1H), 7.57 (s, 1H).

Example 122

N-allyl-3-(2-chloro-6-fluoro-4-trifluoromethylphenyloxy)-5-methylpyrazole-1-carboxamide/colorless viscous substrate/yield: 50.7%/$^1$H-NMR (CDCl$_3$, TMS, ppm): δ 2.59 (d, J=0.8 Hz, 3H), 3.92 (ddt, J=1.6, 5.8 and 5.8 Hz, 2H), 5.10-5.25 (m, 2H), 5.79 (q, J=0.8 Hz, 1H), 5.75-5.95 (m, 1H), 6.70-7.00 (m, 1H), 9.40 (dd, $J_{HF}$=2.1 and 9.5 Hz, 1H), 7.57 (s, 1H).

Example 123

N-(2-bromoethyl)-3-(2-chloro-6-fluoro-4-trifluoromethylphenyloxy)-5-methylpyrazole-1-carboxamide/white solid/yield: 63.7%/mp: 85-86° C./$^1$H-NMR (CDCl$_3$, TMS, ppm): δ 2.58 (d, J=0.8 Hz, 3H), 3.48 (t, J=6.3 Hz, 2H), 3.70 (dt, J=6.3 and 6.3 Hz, 2H), 5.81 (d, J=0.8 Hz, 1H), 7.09 (br t, J=6.3 Hz, 1H), 7.40 (dd, $J_{HF}$=1.8 and 9.3 Hz, 1H), 7.57 (s, 1H).

Example 124

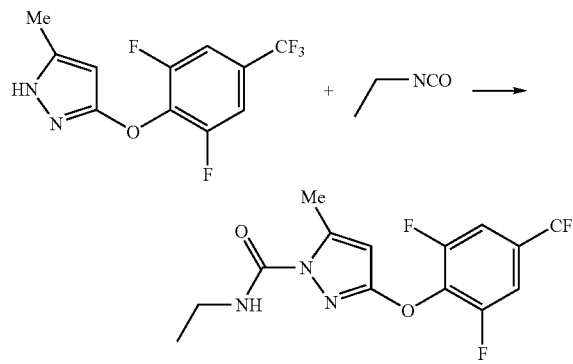

Triethylamine (0.20 g, 2.0 mmol) and ethyl isocyanate (0.14 g, 2.0 mmol) were added to a solution of 3-(2,6-difluoro-4-trifluoromethylphenyloxy)-5-methylpyrazole (0.42 g, 1.5 mmol) in ethyl acetate (10 ml), and the mixture was stirred at room temperature for 12 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (chloroform), to give a white solid of N-ethyl-3-(2,6-difluoro-4-trifluoromethylphenyloxy)-5-methylpyrazole-1-carboxamide (0.11 g, yield: 21.0%). mp: 102-104° C.; $^1$H-NMR (CDCl$_3$, TMS, ppm): δ 1.21 (t, J=7.3 Hz, 3H), 2.19 (s, 3H), 3.32 (dq, J=6.0 and 7.3 Hz, 2H), 5.00-5.25 (m, 1H), 6.25 (s, 1H), 7.36 (d, $J_{HF}$=7.0 Hz, 2H).

Example 125

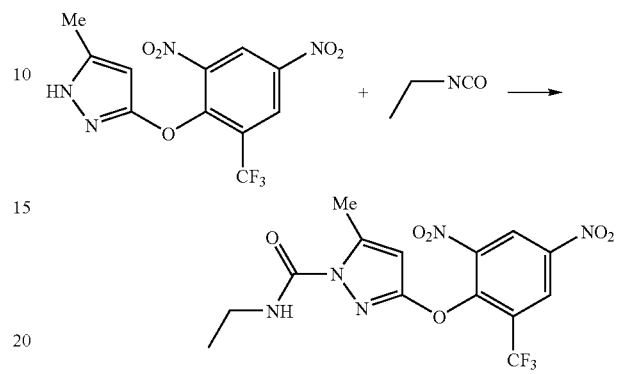

Potassium carbonate (0.15 g, 1.1 mmol) and ethyl isocyanate (0.07 g, 1.0 mmol) were added to a solution of 3-(2,4-dinitro-6-trifluoromethylphenyloxy)-5-methylpyrazole (0.33 g, 1.0 mmol) in ethyl acetate (10 ml), and the mixture was stirred at room temperature for 12 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellowish solid of N-ethyl-3-(2,4-dinitro-6-trifluoromethylphenyloxy)-5-methylpyrazole-1-carboxamide (0.20 g, yield: 49.6%). mp: 169-171° C.; $^1$H-NMR (CDCl$_3$, TMS, ppm): δ 1.18 (t, J=7.2 Hz, 3H), 2.59 (d, J=0.4 Hz, 3H), 3.31 (dq, J=6.0 and 7.2 Hz, 2H), 5.95 (q, J=0.4 Hz, 1H), 6.25-6.50 (m, 1H), 8.85 (d, J=2.7 Hz, 1H), 9.02 (d, J=2.7 Hz, 1H).

Example 126

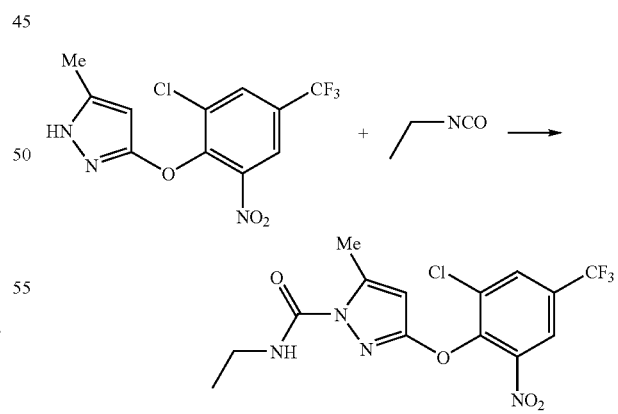

Potassium carbonate (0.30 g, 2.2 mmol) and ethyl isocyanate (0.14 g, 2.0 mmol) were added to a solution of 3-(2-chloro-6-nitro-4-trifluoromethylphenyloxy)-5-methylpyrazole (0.64 g, 2.0 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellowish solid of N-ethyl-3-(2-chloro-6-nitro-4-trifluoromethylphenyloxy)-5-methylpyrazole-1-carboxamide (0.13 g, yield: 16.6%). mp: 98-99° C.; $^1$H-NMR (CDCl$_3$, TMS, ppm): δ 1.18 (t, J=7.2 Hz, 3H), 2.60 (d, J=0.5 Hz, 3H), 3.32 (dq, J=6.0 and 7.2 Hz, 2H), 5.87 (q, J=0.5 Hz, 1H), 6.40-6.65 (m, 1H), 8.01 (d, J=2.0 Hz, 1H), 8.17 (m, 1H).

Examples 127-128

Reactions of 3-(2-chloro-6-nitro-4-trifluoromethylphenyloxy)-5-methylpyrazole and isocyanates (Example 127: methyl isocyanate, Example 128: propyl isocyanate) were carried out in ethyl acetate in the presence of potassium carbonate in the same manner as in Example 126, to give corresponding N-substituted carboxamides. Products/forms/yields/melting points/NMR spectra are described below.

Example 127

N-methyl-3-(2-chloro-6-nitro-4-trifluoromethylphenyloxy)-5-methylpyrazole-1-carboxamide/white solid/yield: 60.9%/mp: 140-142° C./$^1$H-NMR (CDCl$_3$, TMS, ppm): δ 2.60 (d, J=0.6 Hz, 3H), 2.87 (d, J=5.0 Hz, 3H), 5.89 (q, J=0.6 Hz, 1H), 6.40-6.55 (m, 1H), 8.01 (d, J=2.0 Hz, 1H), 8.19 (m, 1H).

Example 128

N-propyl-3-(2-chloro-6-nitro-4-trifluoromethylphenyloxy)-5-methylpyrazole-1-carboxamide/white solid/yield: 34.4%/mp: 111-113° C./$^1$H-NMR (CDCl$_3$, TMS, ppm): δ 0.92 (t, J=7.4 Hz, 3H), 1.57 (m, 2H), 2.19 (s, 3H), 3.23 (dt, J=7.4 and 7.4 Hz, 2H), 5.88 (s, 1H), 6.45-6.70 (m, 1H), 8.01 (d, J=2.1 Hz, 1H), 8.17 (m, 1H).

Example 129

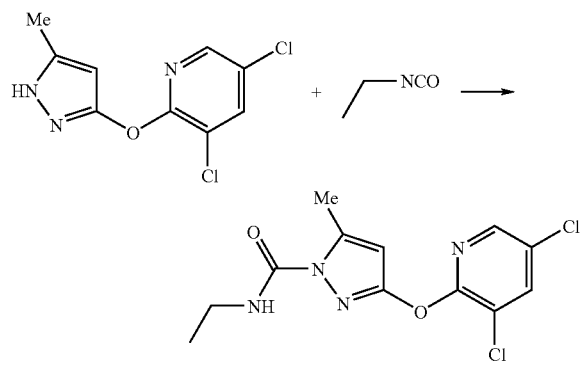

Potassium carbonate (0.30 g, 2.2 mmol) and ethyl isocyanate (0.14 g, 2.0 mmol) were added to a solution of 3-(3,5-dichloropyridin-2-yloxy)-5-methylpyrazole (0.49 g, 2.0 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-ethyl-3-(3,5-dichloropyridin-2-yloxy)-5-methylpyrazole-1-carboxamide (0.44 g, yield: 69.8%). mp: 74-76° C.; $^1$H-NMR (CDCl$_3$, TMS, ppm): δ 1.23 (t, J=7.2 Hz, 3H), 2.64 (s, 3H), 3.39 (dq, J=5.8 and 7.2 Hz, 2H), 6.00 (s, 1H), 6.90-7.15 (m, 1H), 7.80 (d, J=2.3 Hz, 1H), 8.05 (d, 2.3 Hz, 1H).

Example 130

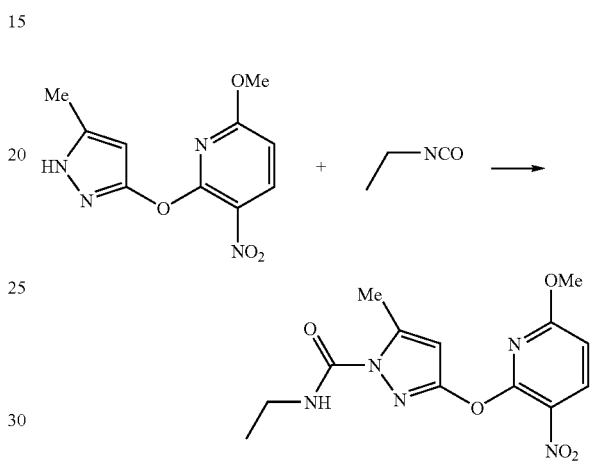

Triethylamine (0.22 g, 2.2 mmol) was added to a solution of 5-methyl-3-(6-methoxy-3-nitropyridin-2-yloxy)pyrazole (0.5 g, 2.0 mmol) in ethyl acetate (10 ml), and the mixture was cooled to 0° C. Ethyl isocyanate (0.16 g, 2.2 mmol) was added, and the mixture was stirred at an ambient temperature for 30 minutes. The mixture was allowed to have room temperature. After completion of the reaction, the reaction mixture was poured into 1N hydrochloric acid (10 ml) and extracted with ethyl acetate (10 ml×2). An organic layer was washed with water (10 ml×2), dried over anhydrous magnesium sulfate and filtered to remove a desiccant, and the solvent was distilled off from the filtrate under reduced pressure. The resultant crude product was purified with a silica gel column (ethyl acetate/hexane=1/6), to give a yellow viscous substance of N-ethyl-5-methyl-3-(6-methoxy-3-nitropyridin-2-yloxy)pyrazole-1-carboxamide (0.38 g, yield: 59.8%). $^1$H-NMR (CDCl$_3$, TMS, ppm): δ 1.24 (t, J=7.3 Hz, 3H), 2.65 (d, J=0.8 Hz, 3H), 3.40 (dq, J=1.4 and 7.3 Hz, 2H), 3.84 (s, 3H), 6.02 (q, J=0.8 Hz, 1H), 6.57 (dd, J=3.5 and 8.8 Hz, 1H), 7.05 (br s, 1H), 8.41 (dd, J=3.5 and 8.8 Hz, 1H).

Example 131

Reaction of 5-methyl-3-(4-methyl-5-nitropyridin-2-yloxy)pyrazole with ethyl isocyanate was carried out in the presence of triethylamine in the same manner as in Example 130, to give a yellow viscous substance of N-ethyl-5-methyl-3-(4-methyl-5-nitropyridin-2-yloxy)pyrazole-1-carboxamide (yield: 19.3%). $^1$H-NMR (CDCl$_3$, TMS, ppm): δ 1.23 (t, J=7.3 Hz, 3H), 2.65 (d, J=0.7 Hz, 3H), 2.70 (s, 3H), 3.40 (dq, J=5.9 and 7.3 Hz, 2H), 6.03 (q, J=0.7 Hz, 1H), 6.95 (s, 1H), 6.99 (br s, 1H), 8.92 (s, 1H).

Example 132

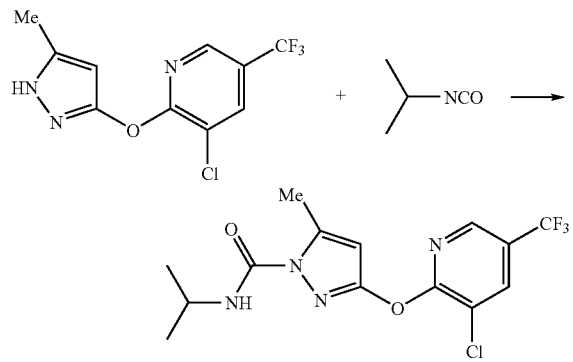

Potassium carbonate (0.75 g, 5.4 mmol) and isopropyl isocyanate (0.46 g, 5.4 mmol) were added to a solution of 3-(3-chloro-5-trifluoromethylpyridin-2-yloxy)-5-methylpyrazole (1.00 g, 3.6 mmol) in ethyl acetate (10 ml), and the mixture was stirred at room temperature for 3 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a colorless viscous substance of N-isopropyl-3-(3-chloro-5-trifluoromethylpyridin-2-yloxy)-5-methylpyrazole-1-carboxamide (0.91 g, yield: 69.7%). $^1$H-NMR (CDCl$_3$, TMS, ppm): δ 1.25 (d, J=6.5 Hz, 6H), 2.65 (d, J=0.8 Hz, 3H), 3.95-4.20 (m, 1H), 6.04 (q, J=0.8 Hz, 1H), 6.80~7.00 (m, 1H), 8.02 (d, J=2.3 Hz, 1H), 8.35 (m, 1H).

Examples 133-150

Reactions of 3-(3-chloro-5-trifluoromethylpyridin-2-yloxy)-5-methylpyrazole and isocyanates (Example 133: methyl isocyanate, Example 134: ethyl isocyanate, Example 135: propyl isocyanate, Example 136: tert-butyl isocyanate, Example 137: pentyl isocyanate, Example 138: hexyl isocyanate, Example 139: heptyl isocyanate, Example 140: octyl isocyanate, Example 141: dodecyl isocyanate, Example 142: cyclohexyl isocyanate, Example 143: allyl isocyanate, Example 144: 2-chloroethyl isocyanate, Example 145: phenyl isocyanate, Example 146: 3-chlorophenyl isocyanate, Example 147: 3,4-dichlorophenyl isocyanate, Example 148: 3-trifluoromethylphenyl isocyanate, Example 149: 4-trifluoromethylphenyl isocyanate, Example 150: 3-nitrophenyl isocyanate) were carried out in the same manner as in Example 132, to give corresponding N-substituted carboxamides. Products/forms/yields/melting points/NMR spectra are described below.

Example 133

N-methyl-3-(3-chloro-5-trifluoromethylpyridin-2-yloxy)-5-methylpyrazole-1-carboxamide/white solid/yield: 81.7%/mp: 85-86° C./$^1$H-NMR (CDCl$_3$, TMS, ppm): δ 2.66 (d, J=0.8 Hz, 3H), 2.95 (d, J=5.0 Hz, 3H), 6.05 (q, J=0.8 Hz, 1H), 6.85-7.15 (m, 1H), 8.01 (d, J=2.0 Hz, 1H), 8.35 (m, 1H).

Example 134

N-ethyl-3-(3-chloro-5-trifluoromethylpyridin-2-yloxy)-5-methylpyrazole-1-carboxamide/white solid/yield: 55.8%/mp: 85-86° C./$^1$H-NMR (CDCl$_3$, TMS, ppm): δ 1.23 (t, J=7.3 Hz, 3H), 2.66 (s, 3H), 3.40 (dq, J=6.0 and 7.3 Hz, 2H), 6.04 (s, 1H), 6.90-7.15 (m, 1H), 8.02 (d, J=2.0 Hz, 1H), 8.35 (m, 1H).

Example 135

N-propyl-3-(3-chloro-5-trifluoromethylpyridin-2-yloxy)-5-methylpyrazole-1-carboxamide/colorless viscous substance/yield: 86.3%/$^1$H-NMR (CDCl$_3$, TMS, ppm): δ 0.97 (t, J=7.3 Hz, 3H), 1.60 (tq, J=7.3 and 7.3 Hz, 2H), 2.66 (d, J=0.8 Hz, 3H), 3.30 (dt, J=6.5 and 7.3 Hz, 2H), 6.05 (q, J=0.8 Hz, 1H), 6.95-7.20 (m, 1H), 8.02 (d, J=2.0 Hz, 1H), 8.35 (m, 1H).

Example 136

N-tert-butyl-3-(3-chloro-5-trifluoromethylpyridin-2-yloxy)-5-methylpyrazole-1-carboxamide/colorless viscous substance/yield: 74.5%/$^1$H-NMR (CDCl$_3$, TMS, ppm): δ 1.44 (s, 9H), 2.64 (d, J=0.7 Hz, 3H), 6.02 (q, J=0.7 Hz, 1H), 6.90-7.15 (br s, 1H), 8.01 (d, J=2.1 Hz, 1H), 8.34 (m, 1H).

Example 137

N-pentyl-3-(3-chloro-5-trifluoromethylpyridin-2-yloxy)-5-methylpyrazole-1-carboxamide/yellowish solid/yield: 73.2%/mp: 142-144° C./$^1$H-NMR (CDCl$_3$, TMS, ppm): δ 0.90 (t, J=7.0 Hz, 3H), 1.20-1.45 (m, 4H), 1.50-1.70 (m, 2H), 2.66 (d, J=0.8 Hz, 3H), 3.25-3.40 (m, 2H), 6.04 (q, J=0.8 Hz, 1H), 6.95-7.15 (m, 1H), 8.02 (d, J=2.3 Hz, 1H), 8.25-8.40 (m, 1H).

Example 138

N-hexyl-3-(3-chloro-5-trifluoromethylpyridin-2-yloxy)-5-methylpyrazole-1-carboxamide/colorless viscous substance/yield: 65.2%/$^1$H-NMR (CDCl$_3$, TMS, ppm): δ 0.89 (t, J=6.8 Hz, 3H), 1.15-1.45 (m, 6H), 1.45-1.70 (m, 2H), 2.65 (d, J=0.8 Hz, 3H), 3.25-3.45 (m, 2H), 6.04 (q, J=0.8H, 1H), 6.95-7.15 (m, 1H), 8.02 (d, J=2.0 Hz, 1H), 8.35 (m, 1H).

Example 139

N-heptyl-3-(3-chloro-5-trifluoromethylpyridin-2-yloxy)-5-methylpyrazole-1-carboxamide/colorless viscous substance/yield: 84.9%/$^1$H-NMR (CDCl$_3$, TMS, ppm): δ 0.75-1.00 (m, 3H), 1.10-1.50 (m, 8H), 1.50-1.70 (m, 2H), 2.65 (s, 3H), 3.20-3.45 (m, 2H), 6.04 (s, 1H), 6.95-7.15 (m, 1H), 8.02 (d, J=2.0 Hz, 1H), 8.36 (m, 1H).

Example 140

N-octyl-3-(3-chloro-5-trifluoromethylpyridin-2-yloxy)-5-methylpyrazole-1-carboxamide/colorless viscous substance/yield: 81.5%/$^1$H-NMR (CDCl$_3$, TMS, ppm): δ 0.88 (t, J=7.0 Hz, 3H), 1.15-1.45 (m, 10H), 1.45-1.75 (m, 2H), 2.66 (d, J=0.5 Hz, 3H), 3.20-3.45 (m, 2H), 6.04 (s, 1H), 6.95-7.15 (m, 1H), 8.02 (d, J=2.0 Hz, 1H), 8.35 (m, 1H).

Example 141

N-dodecyl-3-(3-chloro-5-trifluoromethylpyridin-2-yloxy)-5-methylpyrazole-1-carboxamide/white solid/yield: 80.7%/mp: 56-57° C./$^1$H-NMR (CDCl$_3$, TMS, ppm): δ 0.88 (t, J=6.9 Hz, 3H), 1.20-1.40 (m, 18H), 1.50-1.65 (m, 2H), 2.65 (d, J=0.8 Hz, 3H), 3.25-3.40 (m, 2H), 6.04 (q, J=0.8 Hz, 1H), 6.95-7.15 (m, 1H), 8.03 (d, J=2.1 Hz, 1H), 8.38 (m, 1H).

Example 142

N-cyclohexyl-3-(3-chloro-5-trifluoromethylpyridin-2-yloxy)-5-methylpyrazole-1-carboxamide/white solid/yield: 65.5%/mp: 69-71° C./$^1$H-NMR (CDCl$_3$, TMS, ppm): δ 1.05-1.50 (m, 6H), 1.55-1.85 (m, 2H), 1.90-2.10 (m, 2H), 2.65 (d, J=0.8 Hz, 3H), 3.60-3.85 (m, 1H), 6.03 (q, J=0.8 Hz, 1H), 6.80-7.05 (m, 1H), 8.01 (d, J=2.0 Hz, 1H), 8.35 (m, 1H).

Example 143

N-allyl-3-(3-chloro-5-trifluoromethylpyridin-2-yloxy)-5-methylpyrazole-1-carboxamide/colorless viscous substance/yield: 62.2%/$^1$H-NMR (CDCl$_3$, TMS, ppm): δ 2.66 (d, J=0.8 Hz, 3H), 3.85-4.05 (m, 2H), 5.05-5.35 (m, 2H), 5.75-6.00 (m, 1H), 6.06 (q, J=0.8 Hz, 1H), 7.05-7.25 (m, 1H), 8.02 (d, J=2.3 Hz, 1H), 8.35 (m, 1H).

Example 144

N-(2-chloroethyl)-3-(3-chloro-5-trifluoromethylpyridin-2-yloxy)-5-methylpyrazole-1-carboxamide/white solid/yield: 65.2%/mp: 98-100° C./$^1$H-NMR (CDCl$_3$, TMS, ppm): δ 2.65 (d, J=0.5 Hz, 3H), 3.65-3.75 (m, 4H), 6.08 (q, J=0.5 Hz, 1H), 7.30-7.50 (m, 1H), 8.03 (d, J=1.8 Hz, 1H), 8.36 (m, 1H).

Example 145

N-phenyl-3-(3-chloro-5-trifluoromethylpyridin-2-yloxy)-5-methylpyrazole-1-carboxamide/white solid/yield: 4.9%/mp: 116-118° C./$^1$H-NMR (CDCl$_3$, TMS, ppm): δ 2.72 (d, J=0.8 Hz, 3H), 6.12 (q, J=0.8 Hz, 1H), 7.10-7.20 (m, 1H), 7.30-7.45 (m, 2H), 7.50-7.60 (m, 2H), 8.05 (d, J=2.2 Hz, 1H), 8.40 (m, 1H), 8.85-9.10 (m, 1H).

Example 146

N-(3-chlorophenyl)-3-(3-chloro-5-trifluoromethylpyridin-2-yloxy)-5-methylpyrazole-1-carboxamide/white solid/yield: 36.0%/mp: 129-130° C./$^1$H-NMR (CDCl$_3$, TMS, ppm): δ 2.72 (d, J=0.7 Hz, 3H), 6.15 (q, J=0.7 Hz, 1H), 7.05-7.15 (m, 1H), 7.20-7.30 (m, 1H), 7.30-7.40 (m, 1H), 7.73 (t, J=2.0 Hz, 1H), 8.05 (d, J=1.8 Hz, 1H), 8.30-8.40 (m, 1H), 8.90-9.10 (br s, 1H).

Example 147

N-(3,4-dichlorophenyl)-3-(3-chloro-5-trifluoromethylpyridin-2-yloxy)-5-methylpyrazole-1-carboxamide/white solid/yield: 38.1%/mp: 150-152° C./$^1$H-NMR (CDCl$_3$, TMS, ppm): δ 2.71 (s, 3H), 6.15 (s, 1H), 7.30-7.45 (m, 2H), 7.83 (d, J=2.3 Hz, 1H), 8.00-8.10 (m, 1H), 8.25-8.45 (m, 1H), 9.01 (s, 1H).

Example 148

N-(3-trifluoromethylphenyl)-3-(3-chloro-5-trifluoromethylpyridin-2-yloxy)-5-methylpyrazole-1-carboxamide/white solid/yield: 18.0%/mp: 123-124° C./$^1$H-NMR (CDCl$_3$, TMS, ppm): δ 2.73 (d, J=0.8 Hz, 3H), 6.16 (q, J=0.8 Hz, 1H), 7.45 (dt, J=8.0 and 8.0 Hz, 2H), 7.72 (d, J=8.0 Hz, 1H), 7.93 (s, 1H), 8.05 (d, J=8.0 Hz, 1H), 8.37 (m, 1H), 9.00-9.25 (br s, 1H).

Example 149

N-(4-trifluoromethylphenyl)-3-(3-chloro-5-trifluoromethylpyridin-2-yloxy)-5-methylpyrazole-1-carboxamide/white solid/yield: 24.4%/mp: 164-167° C./$^1$H-NMR (CDCl$_3$, TMS, ppm): δ 2.73 (d, J=0.7 Hz, 3H), 6.16 (q, J=0.7 Hz, 1H), 7.62 (d, J=8.8 Hz, 2H), 7.70 (d, J=8.8 Hz, 2H), 8.05 (d, J=2.1 Hz, 1H), 8.30-8.45 (m, 1H), 9.10-9.25 (br s, 1H).

Example 150

N-(3-nitrophenyl)-3-(3-chloro-5-trifluoromethylpyridin-2-yloxy)-5-methylpyrazole-1-carboxamide/white solid/yield: 13.6%/mp: 172-174° C./$^1$H-NMR (CDCl$_3$, TMS, ppm): δ 2.73 (s, 3H), 6.18 (s, 1H), 7.54 (t, J=8.2 Hz, 1H), 7.88 (dd, J=0.9 and 2.2 Hz, 1H), 8.03 (dd, J=0.9 and 2.2 Hz, 1H), 8.06 (d, J=2.1 Hz, 1H), 8.37 (m, 1H), 8.54 (t, J=2.1 Hz, 1H), 9.15-9.30 (m, 1H).

Example 151

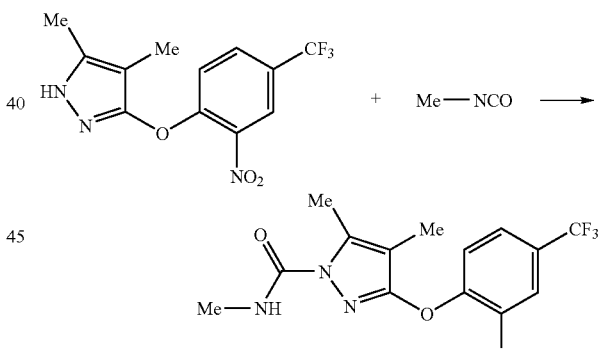

Potassium carbonate (0.50 g, 3.6 mmol) and methyl isocyanate (0.17 g, 3.0 mmol) were added to a solution of 4,5-dimethyl-3-(2-nitro-4-trifluoromethylphenyloxy)pyrazole (1.08 g, 3.6 mmol) in ethyl acetate (20 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellow solid of N-methyl-4,5-dimethyl-3-(2-nitro-4-trifluoromethylphenyloxy)pyrazole-1-carboxamide (0.93 g, yield: 86.5%). mp: 117-119° C.; $^1$H-NMR (CDCl$_3$, TMS, ppm): δ

1.95 (s, 3H), 2.55 (s, 3H), 2.90 (d, J=5.0 Hz, 3H), 6.50-6.80 (m, 1H), 7.49 (d, J=8.7 Hz, 1H), 7.84 (dd, J=2.0 and 8.7 Hz, 1H), 8.25 (d, J=2.0 Hz, 1H).

Example 152

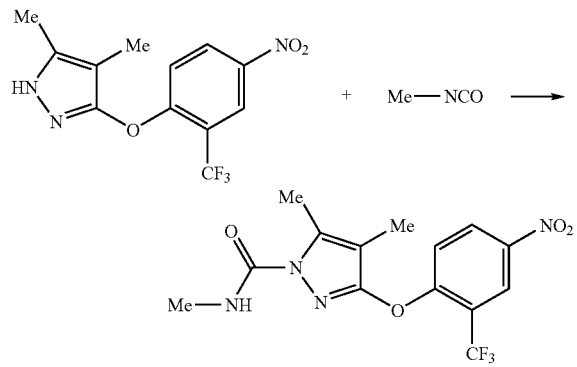

Potassium carbonate (0.50 g, 3.6 mmol) and methyl isocyanate (0.17 g, 3.0 mmol) were added to a solution of 4,5-dimethyl-3-(4-nitro-2-trifluoromethylphenyloxy)pyrazole (1.08 g, 3.6 mmol) in ethyl acetate (20 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a white solid of N-methyl-4,5-dimethyl-3-(4-nitro-2-trifluoromethylphenyloxy)pyrazole-1-carboxamide (0.88 g, yield: 81.9%). mp: 113-115° C.; $^1$H-NMR (CDCl$_3$, TMS, ppm): δ 1.88 (s, 3H), 2.57 (s, 3H), 2.94 (d, J=5.0 Hz, 3H), 6.70-6.95 (m, 1H), 7.44 (d, J=9.2 Hz, 1H), 8.39 (dd, J=2.7 and 9.2 Hz, 1H), 8.60 (d, J=2.7 Hz, 1H).

Example 153

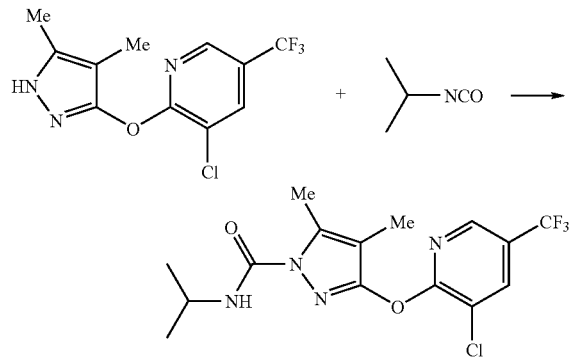

Potassium carbonate (0.62 g, 4.5 mmol) and isopropyl isocyanate (0.26 g, 3.0 mmol) were added to a solution of 3-(3-chloro-5-trifluoromethylpyridin-2-yloxy)-4,5-dimethylpyrazole (0.88 g, 3.0 mmol) in DMF (10 ml), and the mixture was stirred at room temperature for 6 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of N-isopropyl-3-(3-chloro-5-trifluoromethylpyridin-2-yloxy)-4,5-dimethylpyrazole-1-carboxamide (0.55 g, yield: 48.7%) mp: 78-80° C.; $^1$H-NMR (CDCl$_3$, TMS, ppm): δ 1.24 (d, J=6.6 Hz, 6H), 1.78 (s, 3H), 2.58 (s, 3H), 3.95-4.15 (m, 1H), 6.70-6.95 (m, 1H), 8.02 (d, J=2.1 Hz, 1H), 8.32 (m, 1H).

Examples 154-155

Reactions of 3-(3-chloro-5-trifluoromethylpyridin-2-yloxy)-4,5-dimethylpyrazole and isocyanates (Example 154: methyl isocyanate, Example 155: ethyl isocyanate) were carried out in the same manner as in Example 153, to give corresponding N-substituted carboxamides. Products/forms/yields/melting points/NMR spectra are described below.

Example 154

N-methyl-3-(3-chloro-5-trifluoromethylpyridin-2-yloxy)-4,5-dimethylpyrazole-1-carboxamide/white solid/yield: 92.3%/mp: 117-118° C./$^1$H-NMR (CDCl$_3$, TMS, ppm): δ 1.80 (s, 3H), 2.58 (s, 3H), 2.93 (d, J=4.9 Hz, 3H), 6.80-7.10 (m, 1H), 8.02 (d, J=2.0 Hz, 1H), 8.32 (m, 1H).

Example 155

N-ethyl-3-(3-chloro-5-trifluoromethylpyridin-2-yloxy)-4,5-dimethylpyrazole-1-carboxamide/white solid/yield: 38.6%/mp: 124-125° C./$^1$H-NMR (CDCl$_3$, TMS, ppm): δ 1.21 (t, J=7.3 Hz, 3H), 1.79 (s, 3H), 2.58 (s, 3H), 3.38 (dq, J=6.0 and 7.2 Hz, 2H), 6.85-7.10 (m, 1H), 8.02 (d, J=2.1 Hz, 1H), 8.32 (m, 1H).

Example 156

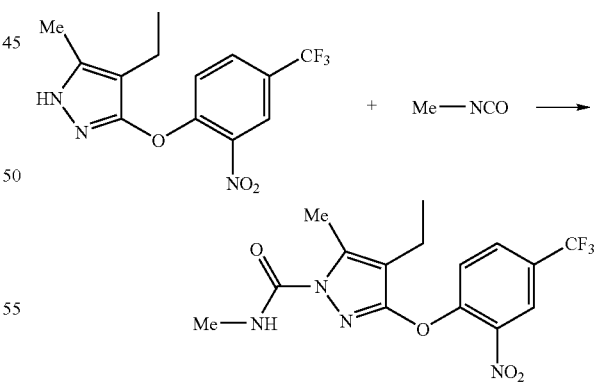

Potassium carbonate (0.50 g, 3.6 mmol) and methyl isocyanate (0.17 g, 3.0 mmol) were added to a solution of 4-ethyl-5-methyl-3-(2-nitro-4-trifluoromethylphenyloxy)pyrazole (1.13 g, 3.6 mmol) in ethyl acetate (20 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellow solid of N-methyl-4-ethyl-5-methyl-3-(2-nitro-4-trifluoromethylphenyloxy)pyrazole-1-carboxamide (0.62 g, yield: 55.5%). mp: 81-82° C.; $^1$H-NMR (CDCl$_3$, TMS, ppm): δ 1.14 (t, J=7.6 Hz, 3H), 2.41 (q, J=7.6 Hz, 2H), 2.56 (s, 3H), 2.90 (d, J=5.0 Hz, 3H), 6.50-6.75 (m, 1H), 7.51 (d, J=8.7 Hz, 1H), 7.84 (dd, J=2.1 and 8.7 Hz, 1H), 8.26 (d, J=2.1 Hz, 1H).

Example 157

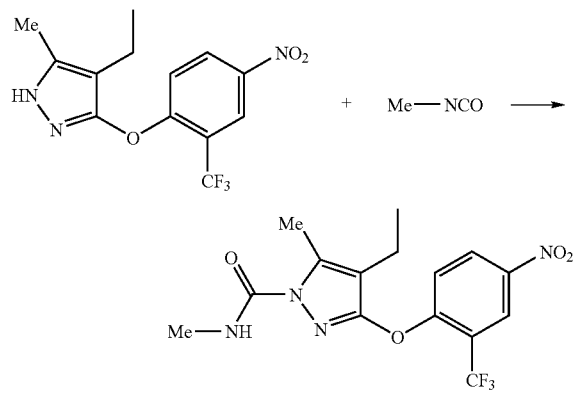

Potassium carbonate (0.50 g, 3.6 mmol) and methyl isocyanate (0.17 g, 3.0 mmol) were added to a solution of 4-ethyl-5-methyl-3-(4-nitro-2-trifluoromethylphenyloxy)pyrazole (1.13 g, 3.6 mmol) in ethyl acetate (15 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/3), to give a yellow solid of N-methyl-4-ethyl-5-methyl-3-(4-nitro-2-trifluoromethylphenyloxy)pyrazole-1-carboxamide (0.71 g, yield: 63.6%). mp: 96-97° C.; $^1$H-NMR (CDCl$_3$, TMS, ppm): δ 1.08 (t, J=7.6 Hz, 3H), 2.35 (q, J=7.6 Hz, 2H), 2.59 (s, 3H), 2.94 (d, J=5.0 Hz, 3H), 6.70-6.90 (m, 1H), 7.48 (d, J=9.2 Hz, 1H), 8.40 (dd, J=2.7 and 9.2 Hz, 1H), 8.60 (d, J=2.7 Hz, 1H).

Example 158

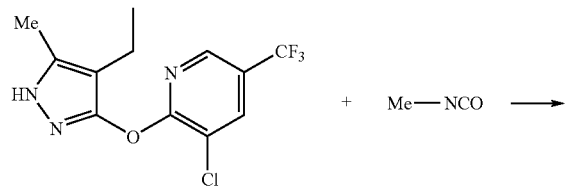

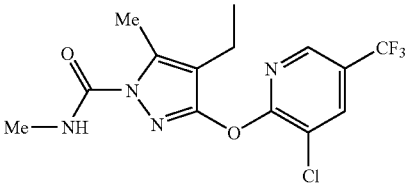

Potassium carbonate (0.83 g, 6.0 mmol) and methyl isocyanate (0.29 g, 5.0 mmol) were added to a solution of 3-(3-chloro-5-trifluoromethylpyridin-2-yloxy)-4-ethyl-5-methylpyrazole (1.83 g, 6.0 mmol) in ethyl acetate (25 ml), and the mixture was stirred at room temperature overnight. After completion of the reaction, the reaction mixture was poured into 2N hydrochloric acid and extracted with diethyl ether (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of N-methyl-3-(3-chloro-5-trifluoromethylpyridin-2-yloxy)-4-ethyl-5-methylpyrazole-1-carboxamide (1.14 g, yield: 62.9%). mp: 84-86° C.; $^1$H-NMR (CDCl$_3$, TMS, ppm): δ 1.04 (t, J=7.6 Hz, 3H), 2.26 (q, J=7.6 Hz, 2H), 2.59 (s, 3H), 2.93 (d, J=5.0 Hz, 3H), 6.80-7.05 (m, 1H), 8.02 (d, J=2.0 Hz, 1H), 8.32 (m, 1H).

Example 159

Reaction of 3-(3-chloro-5-trifluoromethylpyridin-2-yloxy)-4-ethyl-5-methylpyrazole with ethyl isocyanate was carried out in the same manner as in Example 158, to give a white solid of N-ethyl-3-(3-chloro-5-trifluoromethylpyridin-2-yloxy)-4-ethyl-5-methylpyrazole-1-carboxamide (0.36 g, yield: 31.9%). mp: 101-102° C.; $^1$H-NMR (CDCl$_3$, TMS, ppm): δ 1.03 (t, J=7.6 Hz, 3H), 1.21 (t, J=7.3 Hz, 3H), 2.25 (q, J=7.6 Hz, 2H), 2.59 (s, 3H), 3.38 (dq, J=5.9 and 7.3 Hz, 2H), 6.85-7.05 (m, 1H), 8.02 (d, J=2.0 Hz, 1H), 8.32 (m, 1H).

Example 160

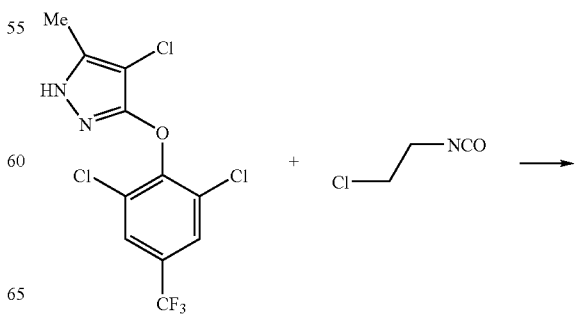

-continued

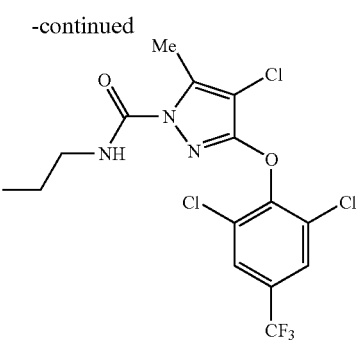

Triethylamine (0.10 g, 1.0 mmol) and 2-chloroethyl isocyanate (0.12 g, 1.1 mmol) were added to a solution of 4-chloro-3-(2,6-dichloro-4-trifluoromethylphenyloxy)-5-methylpyrazole (0.35 g, 1.0 mmol) in ethyl acetate (10 ml), and the mixture was stirred at room temperature for 8 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-(2-chloroethyl)-4-chloro-3-(2,6-dichloro-4-trifluoromethylphenyloxy)-5-methylpyrazole-1-carboxamide (0.44 g, yield: 97.6%). mp: 141-143° C.; $^1$H-NMR (CDCl$_3$, TMS, ppm): δ 2.62 (s, 3H), 3.55-3.65 (m, 4H), 6.80-7.05 (m, 1H), 7.67 (s, 2H).

Example 161

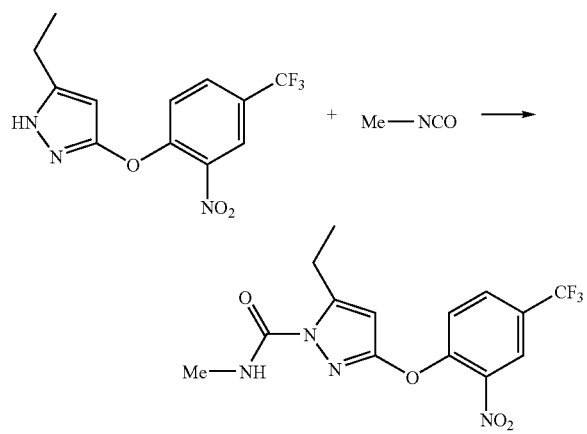

Potassium carbonate (0.72 g, 5.2 mmol) and methyl isocyanate (0.29 g, 5.0 mmol) were added to a solution of 5-ethyl-3-(2-nitro-4-trifluoromethylphenyloxy)pyrazole (1.58 g, 5.2 mmol) in ethyl acetate (20 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellow solid of N-methyl-5-ethyl-3-(2-nitro-4-trifluoromethylphenyloxy)pyrazole-1-carboxamide (0.68 g, yield: 38.0%). mp: 89-91° C.; $^1$H-NMR (CDCl$_3$, TMS, ppm): δ 1.29 (t, J=7.4 Hz, 3H), 2.91 (d, J=5.0 Hz, 3H), 3.09 (q, J=7.4 Hz, 2H), 5.92 (s, 1H), 6.55-6.85 (m, 1H), 7.50 (d, J=8.7 Hz, 1H), 7.85 (dd, J=2.1 and 8.7 Hz, 1H), 8.26 (d, J=2.1 Hz, 1H).

Example 162

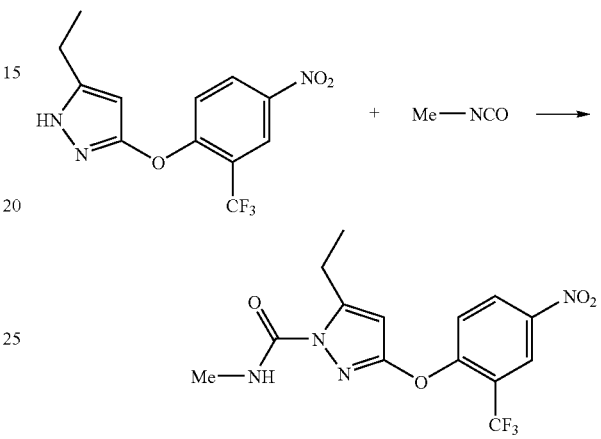

Potassium carbonate (0.83 g, 6.0 mmol) and methyl isocyanate (0.29 g, 5.0 mmol) were added to a solution of 5-ethyl-3-(4-nitro-2-trifluoromethylphenyloxy)pyrazole (1.81 g, 6.0 mmol) in ethyl acetate (15 ml), and the mixture was stirred at room temperature overnight. After completion of the reaction, the reaction mixture was poured into 2N hydrochloric acid and extracted with diethyl ether (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a yellow solid of N-methyl-5-ethyl-3-(4-nitro-2-trifluoromethylphenyloxy)pyrazole-1-carboxamide (1.42 g, yield: 79.3%). mp: 97-100° C.; $^1$H-NMR (CDCl$_3$, TMS, ppm): δ 1.30 (t, J=7.5 Hz, 3H), 2.95 (d, J=5.0 Hz, 3H), 3.12 (q, J=7.5H, 2H), 5.93 (s, 1H), 6.75-7.00 (m, 1H), 7.45 (d, J=9.2 Hz, 1H), 8.41 (dd, J=2.7 and 9.2 Hz, 1H), 8.60 (d, J=2.7 Hz, 1H).

Example 163

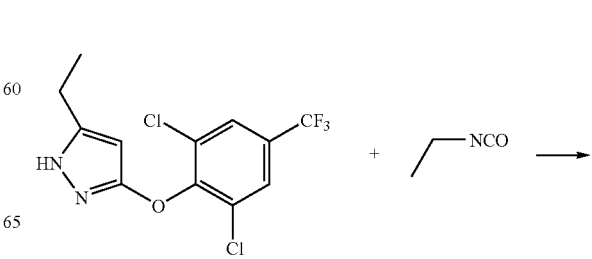

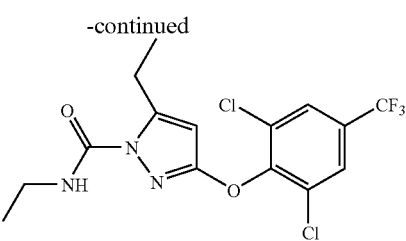

Potassium carbonate (0.46 g, 3.3 mmol) and ethyl isocyanate (0.21 g, 3.0 mmol) were added to a solution of 3-(2,6-dichloro-4-trifluoromethylphenyloxy)-5-ethylpyrazole (0.98 g, 3.0 mmol) in ethyl acetate (10 ml), and the mixture was stirred at room temperature for 6 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-ethyl-3-(2,6-dichloro-4-trifluoromethylphenyloxy)-5-ethylpyrazole-1-carboxamide (0.79 g, yield: 66.5%). mp: 86-89° C.; $^1$H-NMR (CDCl$_3$, TMS, ppm): δ 1.19 (t, J=7.3 Hz, 3H), 1.27 (t, J=7.5 Hz, 3H), 3.06 (q, J=7.5 Hz, 2H), 3.34 (dq, J=6.1 and 7.3 Hz, 2H), 5.75 (s, 1H), 6.60-6.85 (m, 1H), 7.68 (s, 2H).

Example 164

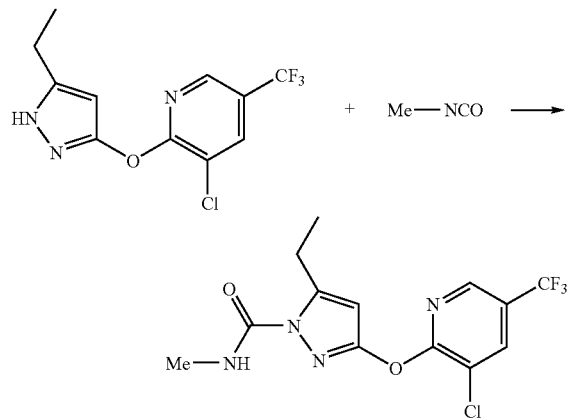

Potassium carbonate (1.16 g, 8.4 mmol) and methyl isocyanate (0.40 g, 7.0 mmol) were added to a solution of 3-(3-chloro-5-trifluoromethylpyridin-2-yloxy)-5-ethylpyrazole (2.45 g, 8.4 mmol) in ethyl acetate (30 ml), and the mixture was stirred at room temperature overnight. After completion of the reaction, the reaction mixture was poured into 2N hydrochloric acid and extracted with diethyl ether (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of N-methyl-3-(3-chloro-5-trifluoromethylpyridin-2-yloxy)-5-ethylpyrazole-1-carboxamide (1.97 g, yield: 80.7%). mp: 85-87° C.; $^1$H-NMR (CDCl$_3$, TMS, ppm): δ 1.31 (t, J=7.5 Hz, 3H), 2.95 (d, J=5.0 Hz, 3H), 3.13 (dq, J=6.0 and 7.5 Hz, 2H), 6.08 (s, 1H), 6.85-7.15 (m, 1H), 8.02 (d, J=2.1 Hz, 1H), 8.36 (m, 1H).

Example 165

Reaction of 3-(3-chloro-5-trifluoromethylpyridin-2-yloxy)-5-ethylpyrazole with ethyl isocyanate was carried out in the same manner as in Example 164, to give a white solid of N-ethyl-3-(3-chloro-5-trifluoromethylpyridin-2-yloxy)-5-ethylpyrazole-1-carboxamide (0.25 g, yield: 23.0%). mp: 85-86° C.; $^1$H-NMR (CDCl$_3$, TMS, ppm): δ 1.23 (t, J=7.3 Hz, 3H), 1.30 (t, J=7.5 Hz, 3H), 3.13 (q, J=7.5 Hz, 2H), 3.40 (dq, J=5.9 and 7.3 Hz, 2H), 6.08 (s, 1H), 6.90-7.15 (m, 1H), 8.02 (d, J=2.1 Hz, 1H), 8.37 (m, 1H).

Example 166

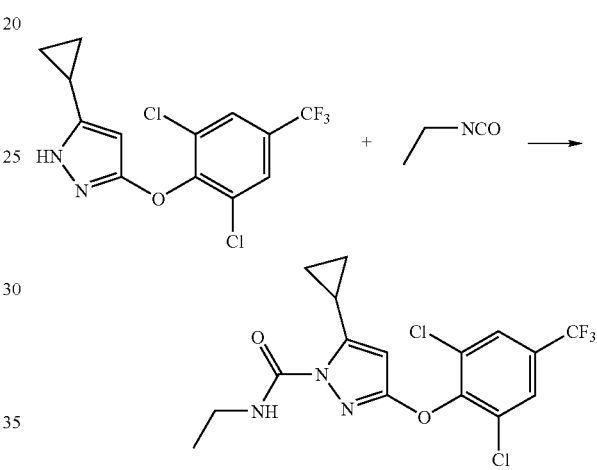

Potassium carbonate (0.23 g, 1.7 mmol) and ethyl isocyanate (0.11 g, 1.5 mmol) were added to a solution of 5-cyclopropyl-3-(2,6-dichloro-4-trifluoromethylphenyloxy)pyrazole (0.51 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a colorless viscous substance of N-ethyl-5-cyclopropyl-3-(2,6-dichloro-4-trifluoromethylpheyloxy)pyrazole-1-carboxamide (0.54 g, yield: 88.2%). $^1$H-NMR (CDCl$_3$, TMS, ppm): δ 0.70 (m, 2H), 1.07 (m, 2H), 1.20 (t, J=7.3 Hz, 3H), 2.81 (m, 1H), 3.36 (dq, J=6.0 and 7.3 Hz, 2H), 5.45 (s, 1H), 6.60-6.85 (m, 1H), 7.66 (s, 2H).

Examples 167-171

Reactions of 3-(substituted phenyloxy)pyrazole derivatives (Example 167: 3-(2,6-dichloro-4-trifluoromethylphenyloxy)-5-isopropylpyrazole, Example 168: 5-tert-butyl-3-(2,6-dichloro-4-trifluoromethylphenyloxy)pyrazole, Example 169: 3-(2,6-dichloro-4-trifluoromethylphenyloxy)-4-ethyl-5-methylpyrazole, Example 170: 3-(2,6-dichloro-4-trifluoromethylphenyloxy)-5-methoxymethylpyrazole, Example 171: {3-(2,6-dichloro-4-trifluoromethylphenyloxy)pyrazol-5-yl}acetate) with ethyl isocyanate were carried out in the presence of a base in the same manner as in Example 166, to give corresponding N-substituted carboxamides. Products/forms/yields/melting points/NMR spectra are described below.

Example 167

N-ethyl-3-(2,6-dichloro-4-trifluoromethylphenyloxy)-5-isopropylpyrazole-1-carboxamide/white solid/yield: 21.9%/mp: 74-76° C./$^1$H-NMR (CDCl$_3$, TMS, ppm): δ 1.19 (t, J=7.3 Hz, 3H), 1.28 (d, J=6.8 Hz, 6H), 3.34 (dq, J=6.0 and 7.3 Hz, 2H), 3.85 (sep, J=6.8 Hz, 1H), 5.77 (m, 1H), 6.77 (br t, J=6.0 Hz, 1H), 7.67 (d, 0.4 Hz, 2H).

Example 168

N-ethyl-5-tert-butyl-3-(2,6-dichloro-4-trifluoromethylphenyloxy)pyrazole-1-carboxamide/colorless viscous substance/yield: 31.4%/$^1$H-NMR (CDCl$_3$, TMS, ppm): δ 1.18 (t, J=7.2 Hz, 3H), 1.46 (s, 9H), 3.33 (dq, J=5.9 and 7.2 Hz, 2H), 5.79 (s, 1H), 6.80-6.95 (m, 1H), 7.67 (d, J=0.4 Hz, 2H).

Example 169

N-ethyl-3-(2,6-dichloro-4-trifluoromethylphenyloxy)-4-ethyl-5-methylpyrazole-1-carboxamide/white solid/yield: 27.6%/mp: 120-123° C./$^1$H-NMR (CDCl$_3$, TMS, ppm): δ 1.15 (t, J=7.5 Hz, 3H), 1.19 (t, J=6.3 Hz, 3H), 1.93 (s, 3H), 2.39 (q, J=7.5 Hz, 2H), 3.29 (dq, J=6.0 and 6.3 Hz, 2H), 7.63 (s, 2H), 8.85 (br t, J=6.0 Hz, 1H).

Example 170

N-ethyl-3-(2,6-dichloro-4-trifluoromethylphenyloxy)-5-methoxymethylpyrazole-1-carboxamide/white solid/yield: 76.0%/mp: 106-108° C./$^1$H-NMR (CDCl$_3$, TMS, ppm): δ 1.20 (t, J=7.2 Hz, 3H), 3.35 (dq, J=6.0 and 7.2 Hz, 2H), 3.49 (s, 3H), 4.83 (d, J=1.0 Hz, 2H), 5.99 (t, J=1.0 Hz, 1H), 6.60-6.80 (m, 1H), 7.67 (d, J=0.4 Hz, 2H).

Example 171

N-ethyl-3-(2,6-dichloro-4-trifluoromethylphenyloxy)-5-ethoxycarbonylmethylpyrazole-1-carboxamide/white solid/yield: 26.9%/mp: 100-102° C./$^1$H-NMR (CDCl$_3$, TMS, ppm): δ 1.18 (t, J=7.3 Hz, 3H), 1.27 (t, J=7.2 Hz, 3H), 3.33 (dq, J=6.0 and 7.3 Hz, 2H), 4.04 (s, 2H), 4.20 (q, J=7.2 Hz, 2H), 5.94 (s, 1H), 6.60-6.80 (m, 1H), 7.67 (d, J=0.5 Hz, 2H).

Example 172

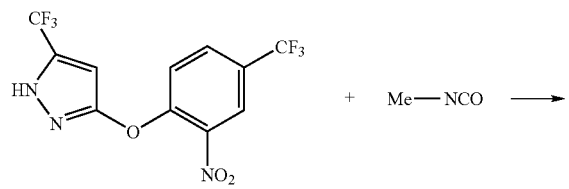

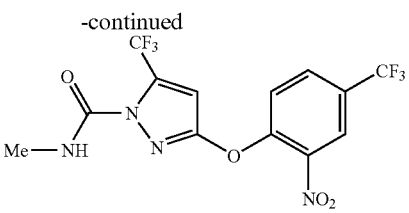

Potassium carbonate (0.58 g, 4.2 mmol) and methyl isocyanate (0.20 g, 3.5 mmol) were added to a solution of 3-(2-nitro-4-trifluoromethylphenyloxy)-5-trifluoromethylpyrazole (1.43 g, 4.2 mmol) in ethyl acetate (15 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5→1/1), to give a yellowish solid of N-methyl-3-(2-nitro-4-trifluoromethylphenyloxy)-5-trifluoromethylpyrazole-1-carboxamide (0.70 g, yield: 50.4%). mp: 102-104° C./$^1$H-NMR (CDCl$_3$, TMS, ppm): δ 3.53 (s, 3H), 5.63 (s, 1H), 7.56 (d, J=8.3 Hz, 1H), 7.95 (d, J=8.3 Hz, 1H), 8.39 (s, 1H), 10.05-10.75 (m, 1H).

Example 173

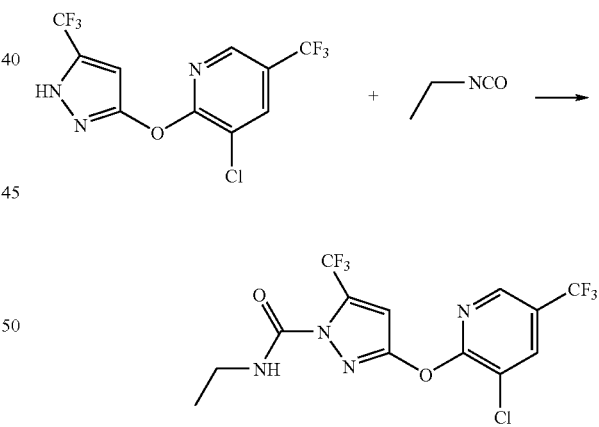

Potassium carbonate (0.69 g, 5.0 mmol) and ethyl isocyanate (0.28 g, 5.0 mmol) were added to a solution of 3-(3-chloro-5-trifluoromethylpyridin-2-yloxy)-5-trifluoromethylpyrazole (1.66 g, 5.0 mmol) in ethyl acetate (20 ml), and the mixture was stirred at room temperature for 3 hours. After completion of the reaction, the reaction mixture was poured into 2N hydrochloric acid and extracted with ethyl acetate (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5→1/1), to give a white solid of N-ethyl-3-(3-chloro-5-trifluoromethylpyridin-2-yloxy)-5-trifluoromethylpyrazole-1-carboxamide (0.83 g, yield: 51.6%). mp: 52-54° C./¹H-NMR (CDCl₃, TMS, ppm): δ 1.34 (t, J=7.1 Hz, 3H), 3.75-4.30 (m, 2H), 5.66 (s, 1H), 7.98 (d, J=1.5 Hz, 1H), 8.64 (m, 1H), 10.20-10.40 (m, 1H).

Example 174

Reaction of 3-(3-chloro-5-trifluoromethylpyridin-2-yloxy)-5-trifluoromethylpyrazole with methyl isocyanate was carried out in the same manner as in Example 173, to give a white solid of N-methyl-3-(3-chloro-5-trifluoromethylpyridin-2-yloxy)-5-trifluoromethylpyrazole-1-carboxamide (0.39 g, yield: 20.1%). mp: 61-63° C.; ¹H-NMR (CDCl₃, TMS, ppm): δ 3.52 (s, 3H), 5.66 (s, 1H), 8.00 (d, J=11.8 Hz, 1H), 8.61 (d, J=1.8 Hz, 1H), 10.10-10.40 (m, 1H).

Example 175

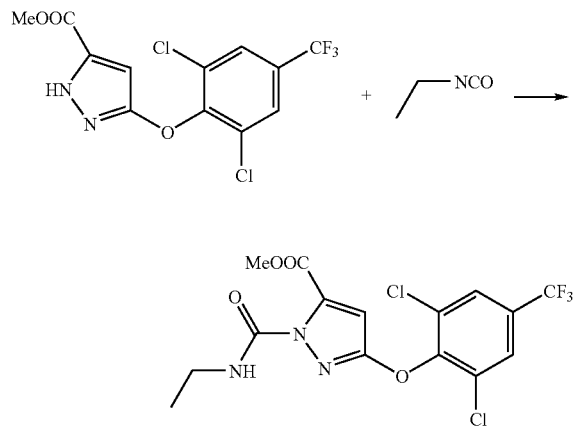

Triethylamine (0.20 g, 2.0 mmol) and ethyl isocyanate (0.14 g, 2.0 mmol) were added to a solution of methyl 3-(2,6-dichloro-4-trifluoromethylphenyloxy)pyrazole-5-carboxylate (0.53 g, 1.5 mmol) in ethyl acetate (10 ml), and the mixture was stirred at room temperature for 6 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (chloroform), to give a white solid of methyl 3-(2,6-dichloro-4-trifluoromethylphenyloxy)-1-(N-ethylcarbamoyl)pyrazole-5-carboxylate (0.15 g, yield: 23.5%). mp: 88-90° C.; ¹H-NMR (CDCl₃, TMS, ppm): δ 1.20 (t, J=7.3 Hz, 3H), 3.37 (dq, J=6.0 and 7.3 Hz, 2H), 3.95 (s, 3H), 6.21 (s, 1H), 6.40-6.60 (m, 1H), 7.68 (d, J=0.5 Hz, 2H).

Example 176

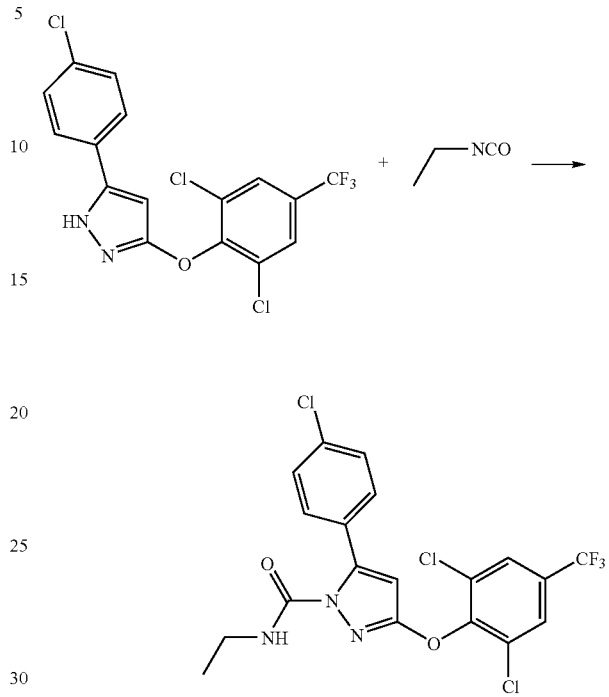

Potassium carbonate (0.25 g, 1.8 mmol) and ethyl isocyanate (0.11 g, 1.5 mmol) were added to a solution of 5-(4-chlorophenyl)-3-(2,6-dichloro-4-trifluoromethylphenyloxy)pyrazole (0.61 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a white solid of N-ethyl-5-(4-chlorophenyl)-3-(2,6-dichloro-4-trifluoromethylphenyloxy)pyrazole-1-carboxamide (0.39 g, yield: 54.3%). mp: 88-89° C.; ¹H-NMR (CDCl₃, TMS, ppm): δ 1.17 (t, J=7.3 Hz, 3H), 3.30 (dq, J=6.1 and 7.3 Hz, 2H), 5.96 (s, 1H), 6.65-6.85 (m, 1H), 7.30-7.50 (m, 4H), 7.70 (s, 2H).

Example 177

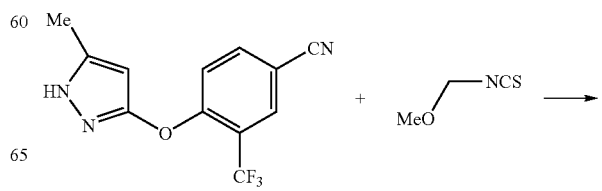

-continued

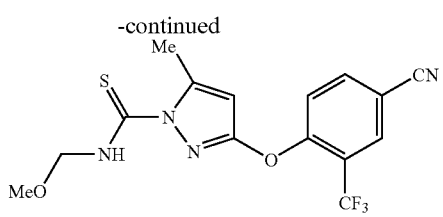

Potassium carbonate (0.23 g, 1.7 mmol) and methoxymethyl isothiocyanate (0.15 g, 1.5 mmol) were added to a solution of 3-(4-cyano-2-trifluoromethylphenyloxy)-5-methylpyrazole (0.40 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-methoxymethyl-3-(4-cyano-2-trifluoromethylphenyloxy)-5-methylpyrazole-1-carbothioamide (0.18 g, yield: 32.4%) mp: 89-90° C.; $^1$H-NMR (CDCl$_3$, TMS, ppm): δ 2.84 (s, 3H), 3.44 (s, 3H), 5.13 (d, J=6.2 Hz, 2H), 5.98 (m, 1H), 7.44 (d, J=8.7 Hz, 1H), 7.84 (dd, J=2.0 and 8.7 Hz, 1H), 8.01 (d, J=2.0 Hz, 1H), 8.95-9.30 (m, 1H).

Example 178

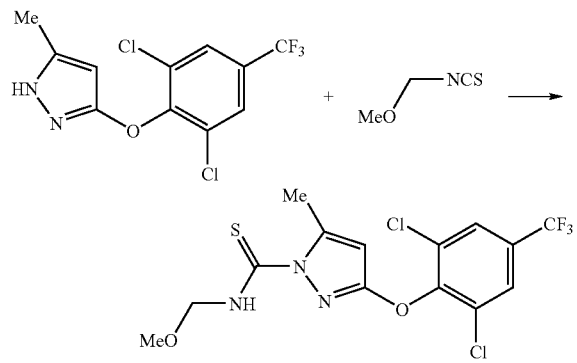

Potassium carbonate (0.23 g, 1.7 mmol) and methoxymethyl isothiocyanate (0.16 g, 1.5 mmol) were added to a solution of 3-(2,6-dichloro-4-trifluoromethylphenyloxy)-5-methylpyrazole (0.47 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-methoxymethyl-3-(2,6-dichloro-4-trifluoromethylphenyloxy)-5-methylpyrazole-1-carbothioamide (0.29 g, yield: 46.7%). mp: 95-96° C.; $^1$H-NMR (CDCl$_3$, TMS, ppm): δ 2.82 (d, J=0.6 Hz, 3H), 3.41 (s, 3H), 5.10 (d, J=6.3 Hz, 2H), 5.91 (q, J=0.6 Hz, 1H), 7.68 (s, 2H), 8.80-9.20 (m, 1H).

Examples 179-185

Reactions of 3-(2,6-dichloro-4-trifluoromethylphenyloxy)-5-methylpyrazole with isothiocyanates (Examples 179: methyl isothiocyanate, Example 180: ethyl isothiocyanate, Example 181: propyl isothiocyanate, Example 182: isopropyl isothiocyanate, Example 183: butyl isothiocyanate, Example 184: 2-methoxyethyl isothiocyanate, Example 185: tetrahydrofurfuryl isothiocyanate) were carried out in the same manner as in Example 178, to give corresponding N-substituted carbothioamides. Products/forms/yields/melting points/NMR spectra are described below.

Example 179

N-methyl-3-(2,6-dichloro-4-trifluoromethylphenyloxy)-5-methylpyrazole-1-carbothioamide/white solid/yield: 39.9%/mp: 121-123° C./$^1$H-NMR (CDCl$_3$, TMS, ppm): δ 2.82 (d, J=0.8 Hz, 3H), 3.15 (d, J=5.0 Hz, 3H), 5.86 (q, J=0.8 Hz, 1H), 7.67 (s, 2H), 8.40-8.70 (m, 1H).

Example 180

N-ethyl-3-(2,6-dichloro-4-trifluoromethylphenyloxy)-5-methylpyrazole-1-carbothioamide/white solid/yield: 29.8%/mp: 94-96° C./$^1$H-NMR (CDCl$_3$, TMS, ppm): δ 1.25 (t, J=7.5 Hz, 3H), 2.81 (s, 3H), 3.67 (dq, J=6.3 and 7.5 Hz, 2H), 5.78 (s, 1H), 7.67 (s, 2H), 8.40-8.70 (m, 1H).

Example 181

N-propyl-3-(2,6-dichloro-4-trifluoromethylphenyloxy)-5-methylpyrazole-1-carbothioamide/white solid/yield: 22.7%/mp: 71-73° C./$^1$H-NMR (CDCl$_3$, TMS, ppm): δ 0.93 (t, J=7.3 Hz, 3H), 1.66 (tq, J=7.3 and 7.3 Hz, 2H), 2.81 (s, 3H), 3.57 (dt, J=6.0 and 7.3 Hz, 2H), 5.79 (s, 1H), 7.67 (s, 2H), 8.45-8.75 (m, 1H).

Example 182

N-isopropyl-3-(2,6-dichloro-4-trifluoromethylphenyloxy)-5-methylpyrazole-1-carbothioamide/white solid/yield: 9.7%/mp: 92-94° C./$^1$H-NMR (CDCl$_3$, TMS, ppm): δ 1.27 (d, J=6.5 Hz, 6H), 2.80 (s, 3H), 4.52 (m, 1H), 5.69 (s, 1H), 7.68 (s, 2H), 8.20-8.70 (m, 1H).

Example 183

N-butyl-3-(2,6-dichloro-4-trifluoromethylphenyloxy)-5-methylpyrazole-1-carbothioamide/colorless viscous substance/yield: 20.3%/$^1$H-NMR (CDCl$_3$, TMS, ppm): δ 0.92 (t, J=7.3 Hz, 3H), 1.25-1.80 (m, 4H), 2.81 (d, J=0.6 Hz, 3H), 3.61 (dt, J=5.7 and 7.2 Hz, 2H), 5.80 (q, J=0.6 Hz, 1H), 7.67 (s, 2H), 8.45-8.75 (m, 1H).

Example 184

N-(2-methoxyethyl)-3-(2,6-dichloro-4-trifluoromethylphenyloxy)-5-methylpyrazole-1-carbothioamide/white solid/yield: 46.7%/mp: 83-86° C./$^1$H-NMR (CDCl$_3$, TMS, ppm): δ 2.81 (d, J=0.5 Hz, 3H), 3.29 (s, 3H), 3.56 (t, J=5.3 Hz, 2H), 3.81 (dt, J=5.3 and 5.3 Hz, 2H), 5.84 (q, J=0.5 Hz, 1H), 7.67 (d, J=0.3 Hz, 2H), 8.65-9.00 (m, 1H).

Example 185

N-tetrahydrofurfuryl-3-(2,6-dichloro-4-trifluoromethylphenyloxy)-5-methylpyrazole-1-carbothioamide/white solid/yield: 16.5%/mp: 69-71° C./$^1$H-NMR (CDCl$_3$, TMS, ppm): δ 1.50-1.65 (m, 1H), 1.65-2.05 (m, 3H), (s, 3H), 3.55-3.70 (m, 2H), 3.70-3.80 (m, 2H), 4.05-4.20 (m, 1H), 5.86 (q, J=0.8 Hz, 1H), 7.66 (d, J=0.5 Hz, 2H), 8.77 (br s, 1H).

Example 186

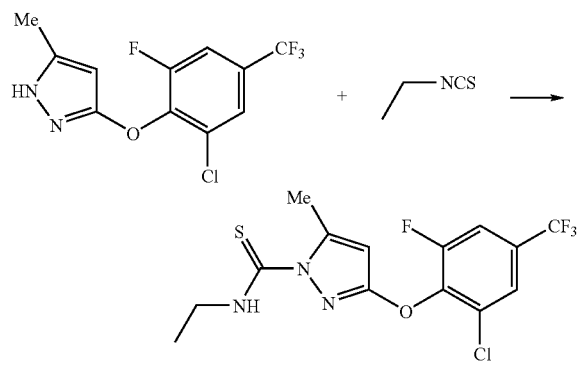

Potassium carbonate (0.22 g, 1.6 mmol) and ethyl isothiocyanate (0.13 g, 1.8 mmol) were added to a solution of 3-(2-chloro-6-fluoro-4-trifluoromethylphenyloxy)-5-methylpyrazole (0.44 g, 1.5 mmol) in ethyl acetate (10 ml), and the mixture was stirred at room temperature overnight. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-ethyl-3-(2-chloro-6-fluoro-4-trifluoromethylphenyloxy)-5-methylpyrazole-1-carbothioamide (0.05 g, yield: 9.4%). mp: 114-115° C.; $^1$H-NMR (CDCl$_3$, TMS, ppm): δ 1.25 (t, J=7.3 Hz, 3H), 2.81 (d, J=0.6 Hz, 3H), 3.67 (dq, J=5.7 and 7.3 Hz, 2H), 5.84 (q, J=0.6 Hz, 1H), 7.41 (dd, J$_{HF}$=2.1 and 9.4 Hz, 1H), 7.62 (s, 1H), 8.54 (br s, 1H).

Example 187

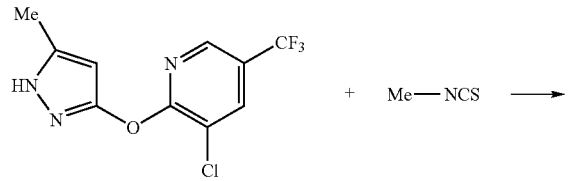

-continued

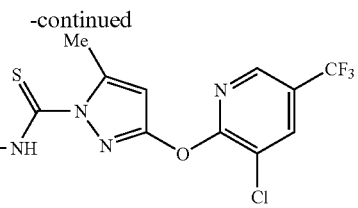

Potassium carbonate (0.75 g, 5.4 mmol) and methyl isothiocyanate (0.39 g, 5.4 mmol) were added to a solution of 3-(3-chloro-5-trifluoromethylpyridin-2-yloxy)-5-methylpyrazole (1.00 g, 3.6 mmol) in DMF (10 ml), and the mixture was stirred at room temperature for 8 hours. After completion of the reaction, the reaction mixture was poured into 2N hydrochloric acid and extracted with ethyl acetate (10 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a white solid of N-methyl-3-(3-chloro-5-trifluoromethylpyridin-2-yloxy)-5-methylpyrazole-1-carbothioamide (0.35 g, yield: 37.7%) mp: 63-65° C.; $^1$H-NMR (CDCl$_3$, TMS, ppm): δ 2.87 (d, J=0.6 Hz, 3H), 3.21 (d, J=4.9 Hz, 3H), 6.14 (q, J=0.6 Hz, 1H), 8.02 (d, J=2.1 Hz, 1H), 8.36 (m, 1H), 8.80-9.05 (m, 1H).

Examples 188-196

Reactions of 3-(3-chloro-5-trifluoromethylpyridin-2-yloxy)-5-methylpyrazole with isothiocyanates (Example 188: ethyl isothiocyanate, Example 189: propyl isothiocyanate, Example 190: isopropyl isothiocyanate, Example 191: butyl isothiocyanate, Example 192: allyl isothiocyanate, Example 193: 2-methoxymethyl isothiocyanate, Example 194: 2-methoxyethyl isothiocyanate, Example 195: methyl 2-isothiocyanato-3-methylbutanoate, Example 196: 4-chlorobenzyl isothiocyanate) were carried out in the same manner as in Example 187, to give corresponding N-substituted carbothioamides. Products/forms/yields/melting points/NMR spectra are described below.

Example 188

N-ethyl-3-(3-chloro-5-trifluoromethylpyridin-2-yloxy)-5-methylpyrazole-1-carbothioamide/white solid/yield: 11.2%/mp: 74-75° C./$^1$H-NMR (CDCl$_3$, TMS, ppm): δ 1.31 (t, J=7.3 Hz, 3H), 2.87 (s, 3H), 3.72 (dq, J=5.5 and 7.3 Hz, 2H), 6.13 (s, 1H), 8.03 (d, J=2.0 Hz, 1H), 8.36 (m, 1H), 8.70-9.05 (m, 1H).

Example 189

N-propyl-3-(3-chloro-5-trifluoromethylpyridin-2-yloxy)-5-methylpyrazole-1-carbothioamide/white solid/yield: 6.4%/mp: 51-53° C./$^1$H-NMR (CDCl$_3$, TMS, ppm): δ 1.00 (t, J=7.3 Hz, 3H), 1.71 (tq, J=7.3 and 7.3 Hz, 2H), 2.87 (d, J=0.8 Hz, 3H), 3.64 (dt, J=5.8 and 7.3 Hz, 2H), 6.13 (q, J=0.8 Hz, 1H), 8.02 (d, J=2.0 Hz, 1H), 8.36 (m, 1H), 8.80-9.05 (m, 1H).

Example 190

N-isopropyl-3-(3-chloro-5-trifluoromethylpyridin-2-yloxy)-5-methylpyrazole-1-carbothioamide/colorless viscous substance/yield: 5.4%/$^1$H-NMR (CDCl$_3$, TMS, ppm): δ

1.32 (d, J=6.6 Hz, 6H), 2.87 (d, J=0.5 Hz, 3H), 4.50-4.70 (m, 1H), 6.12 (m, 1H), 8.03 (d, J=2.0 Hz, 1H), 8.36 (m, 1H), 8.60-8.85 (m, 1H).

Example 191

N-butyl-3-(3-chloro-5-trifluoromethylpyridin-2-yloxy)-5-methylpyrazole-1-carbothioamide/colorless viscous substance/yield: 29.7%/$^1$H-NMR (CDCl$_3$, TMS, ppm): δ 0.96 (t, J=7.3 Hz, 3H), 1.30-1.55 (m, 2H), 1.68-1.80 (m, 2H), 2.87 (s, 3H), 3.60-3.85 (m, 2H), 6.12 (s, 1H), 8.02 (d, J=1.8 Hz, 1H), 8.36 (m, 1H), 8.75-9.05 (m, 1H).

Example 192

N-allyl-3-(3-chloro-5-trifluoromethylpyridin-2-yloxy)-5-methylpyrazole-1-carbothioamide/white solid/yield: 5.9%/mp: 46-48° C./$^1$H-NMR (CDCl$_3$, TMS, ppm): δ 2.87 (s, 3H), 4.25-4.40 (m, 2H), 5.25-5.35 (m, 2H), 5.80-6.10 (m, 1H), 6.15 (q, J=0.5 Hz, 1H), 8.02 (d, J=2.0 Hz, 1H), 8.36 (m, 1H), 8.85-9.10 (m, 1H).

Example 193

N-(2-methoxymethyl)-3-(3-chloro-5-trifluoromethylpyridin-2-yloxy)-5-methylpyrazole-1-carbothioamide/white solid/yield: 31.3%/mp: 102-104° C./$^1$H-NMR (CDCl$_3$, TMS, ppm): δ 2.87 (s, 3H), 3.44 (s, 3H), 5.16 (d, J=6.2 Hz, 2H), 6.18 (d, J=0.4 Hz, 1H), 8.04 (d, J=2.1 Hz, 1H), 8.37 (m, 1H), 9.15-9.55 (m, 1H).

Example 194

N-(2-methoxyethyl)-3-(3-chloro-5-trifluoromethylpyridin-2-yloxy)-5-methylpyrazole-1-carbothioamide/white solid/yield: 16.1%/mp: 108-109° C./$^1$H-NMR (CDCl$_3$, TMS, ppm): δ 2.86 (d, J=0.6 Hz, 3H), 3.38 (s, 3H), 3.63 (t, J=5.4 Hz, 2H), 3.90 (dt, J=5.2 and 5.4 Hz, 2H), 6.12 (q, J=0.6 Hz, 1H), 8.03 (d, J=1.8 Hz, 1H), 8.36 (m, 1H), 9.00-9.25 (m, 1H).

Example 195 methyl 2-[{3-(3-chloro-5-trifluoromethylpyridin-2-yloxy)-5-methylpyrazol-1-yl}thiocarbonylamino]-3-methylbutanoate/white solid/yield: 7.1%/mp: 109-110° C./$^1$H-NMR (CDCl$_3$, TMS, ppm): δ 0.95-1.15 (m, 6H), 2.25-2.55 (m, 1H), 2.84 (m, 3H), 3.78 (s, 3H), 5.01 (dd, J=5.2 and 8.3 Hz, 1H), 6.14 (q, J=0.5 Hz, 1H), 8.03 (d, J=2.1 Hz, 1H), 8.36 (m, 1H), 9.10-9.40 (m, 1H).

Example 196

N-(4-chlorobenzyl)-3-(3-chloro-5-trifluoromethylpyridin-2-yloxy)-5-methylpyrazole-1-carbothioamide/white solid/yield: 12.2%/mp: 119-121° C./$^1$H-NMR (CDCl$_3$, TMS, ppm): δ 2.88 (d, J=0.5 Hz, 3H), 4.86 (d, J=5.3 Hz, 2H), 6.16 (s, 1H), 7.25-7.35 (m, 4H), 8.01 (d, J=2.0 Hz, 1H), 8.34 (m, 1H), 9.05-9.30 (m, 1H).

Example 197

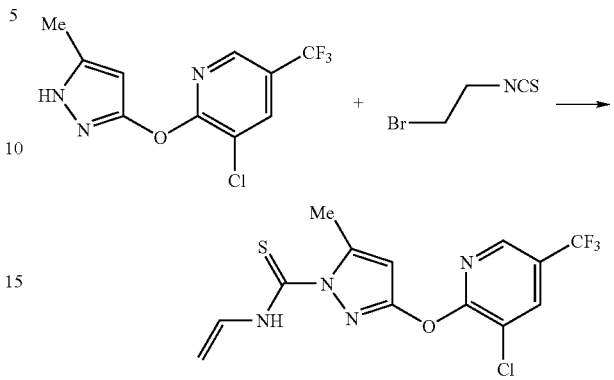

Potassium carbonate (0.76 g, 5.5 mmol) and 2-bromoethyl isothiocyanate (0.83 g, 5 mmol) were added to a solution of 3-(3-chloro-5-trifluoromethylpyridin-2-yloxy)-5-methylpyrazole (1.39 g, 5.0 mmol) in DMF (15 ml), and the mixture was stirred at room temperature for 3 hours. After completion of the reaction, the reaction mixture was poured into 2N hydrochloric acid (30 ml) and extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/20→1/10), to give a white solid of N-vinyl-3-(3-chloro-5-trifluoromethylpyridin-2-yloxy)-5-methylpyrazole-1-carbothioamide (0.11 g, yield: 5.0%). mp: 90-92° C.; $^1$H-NMR (CDCl$_3$, TMS, ppm): δ 2.87 (d, J=0.8 Hz, 3H), 4.79 (d, J=8.6 Hz, 1H), 5.00 (dd, J=0.9 and 15.7 Hz, 1H), 6.19 (q, J=0.8 Hz, 1H), 7.45 (ddd, J=0.9, 8.6 and 15.7 Hz, 1H), 8.04 (d, J=2.1 Hz, 1H), 8.36 (m, 1H), 10.15-10.55 (m, 1H).

Example 198

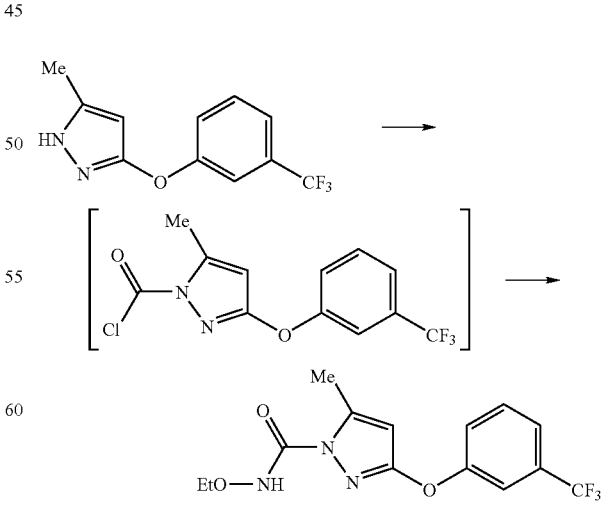

Trichloromethyl chloroformate (0.59 g, 3.0 mmol) was added to a solution of 5-methyl-3-(3-trifluoromethylphenyloxy)pyrazole (0.48 g, 2.0 mmol) in ethyl acetate (10 ml) at 0° C., and while the mixture was allowed to have room temperature gradually, the mixture was further stirred at room temperature for 3 hours. To the reaction mixture were added O-ethylhydroxylamine hydrochloride (0.98 g, 10.0 mmol) and triethylamine (0.61 g, 6.0 mmol), and the resulting mixture was refluxed under heating. After completion of the reaction, the reaction mixture was poured into ice water, and the mixture was extracted with ethyl acetate (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a yellowish viscous substance of N-ethoxy-5-methyl-3-(3-trifluoromethylphenyloxy)pyrazole-1-carboxamide (0.30 g, yield: 45.4%). $^1$H-NMR (CDCl$_3$, TMS, ppm): δ 1.31 (t, J=7.0 Hz, 3H), 2.61 (d, J=0.8 Hz, 3H), 4.05 (q, J=7.0 Hz, 2H), 5.78 (q, J=0.8 Hz, 1H), 7.33-7.37 (m, 1H), 7.42-7.50 (m, 3H), 9.25 (br s, 1H).

Example 199

5-Methyl-3-(3-trifluoromethylphenyloxy)pyrazole reacted with trichloromethyl chloroformate in the same manner as in Example 198 and then reacted with tetrahydrofurfurylamine to give a white solid of N-tetrahydrofurfuryl-5-methyl-3-(3-trifluoromethylphenyloxy)pyrazole-1-carboxamide (yield: 70.3%). mp: 101-102° C.; $^1$H-NMR (CDCl$_3$, TMS, ppm): δ 1.56-1.67 (m, 1H), 1.84-2.05 (m, 3H), 2.60 (s, 3H), 3.29-3.39 (m, 1H), 3.55 (ddd, J=3.8, 6.1 and 13.8 Hz, 1H), 3.70-3.90 (m, 2H), 4.00-4.10 (m, 1H), 5.74 (s, 1H), 7.21 (br s, 1H), 7.33-7.37 (m, 1H), 7.40-7.51 (m, 3H).

Example 200

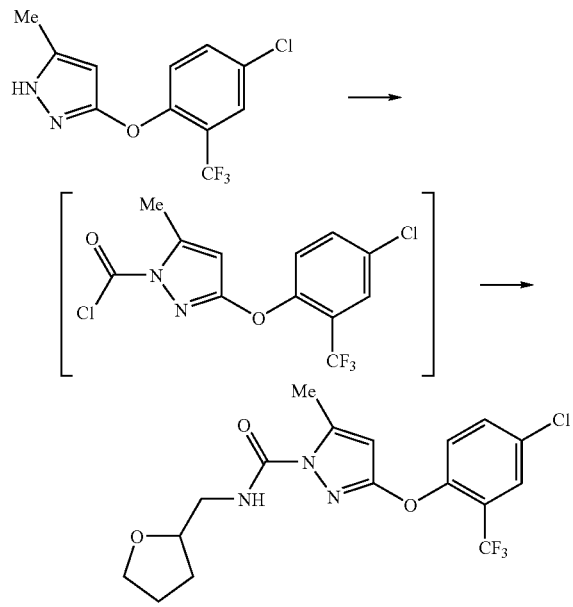

Trichloromethyl chloroformate (0.58 g, 3.0 mmol) was added to a solution of 3-(4-chloro-2-trifluoromethylphenyloxy)-5-methylpyrazole (0.55 g, 2.0 mmol) in ethyl acetate (10 ml) at 0° C., and the mixture was further stirred at an ambient temperature for 30 minutes. Then, the mixture was refluxed under heating for 1 hour. The solvent was distilled off from the reaction mixture and then the reaction mixture was cooled to 0° C. and dissolved in toluene (10 ml). Triethylamine (0.61 g, 6.0 mmol) and tetrahydrofurfurylamine (1.01 g, 10.0 mmol) were added, and while the mixture was allowed to have room temperature gradually, it was stirred for 1 hour. Then, the mixture was refluxed under heating for 2 hours. After completion of the reaction, the reaction mixture was poured into 1N hydrochloric acid (10 ml), and the mixture was extracted with ethyl acetate (10 ml×2). An organic layer was washed with water (10 ml×3), dried over anhydrous magnesium sulfate and filtered to remove a desiccant, and the solvent was distilled off from the filtrate under reduced pressure. The resultant crude product was purified with a silica gel column (ethyl acetate/hexane=1/10), to give a colorless viscous substance of N-tetrahydrofurfuryl-3-(4-chloro-2-trifluoromethylphenyloxy)-5-methylpyrazole-1-carboxamide (0.40 g, yield: 48.9%). $^1$H-NMR (CDCl$_3$, TMS, ppm): δ 1.55-1.66 (m, 1H), 1.84-2.02 (m, 3H), 2.59 (d, J=0.8 Hz, 3H), 3.26-3.37 (m, 1H), 3.54 (ddd, J=3.7, 6.2 and 13.8 Hz, 1H), 3.71-3.90 (m, 2H), 4.00-4.16 (m, 1H), 5.74 (q, J=0.8 Hz, 1H), 7.18 (br s, 1H), 7.25 (d, J=8.7 Hz, 1H), 7.48 (dd, J=2.5 and 8.7 Hz, 1H), 7.64 (d, J=2.5 Hz, 1H).

Example 201

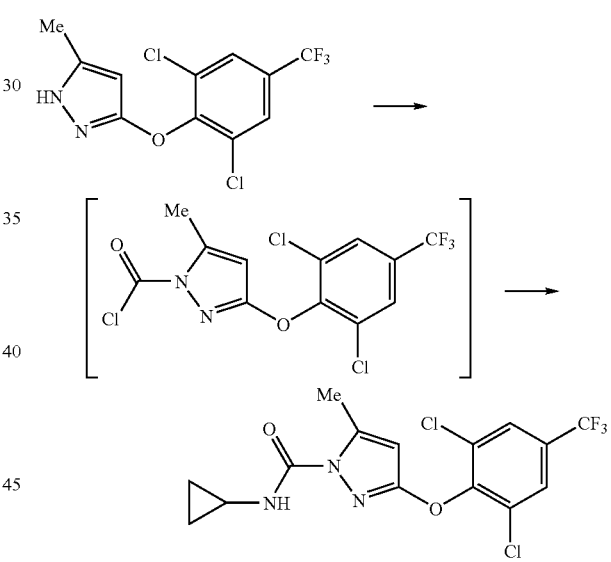

Trichloromethyl chloroformate (0.59 g, 3.0 mmol) was added to a solution of 3-(2,6-dichloro-4-trifluoromethylphenyloxy)-5-methylpyrazole (0.83 g, 3.0 mmol) in chloroform (10 ml) at 0° C., and while the mixture was allowed to have room temperature gradually, it was further stirred at room temperature for 3 hours. Cyclopropylamine (0.17 g, 3.0 mmol) and potassium carbonate (0.50 g, 3.6 mmol) were added to the reaction mixture, and the reaction mixture was refluxed under heating for 5 hours. After completion of the reaction, the reaction mixture was poured into ice water and extracted with chloroform (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a colorless viscous substance of N-cyclopropyl-3-(2,6-dichloro-4-trifluoromethylphenyloxy)-5-methylpyrazole-1-carboxamide (0.27 g, yield:

22.8%). $^1$H-NMR (CDCl$_3$, TMS, ppm): δ 0.55-0.65 (m, 2H), 0.75-0.85 (m, 2H), 2.59 (d, J=0.4 Hz, 3H), 2.60-2.75 (m, 1H), 5.71 (m, 1H), 6.75-6.90 (m, 1H), 7.67 (s, 2H).

Examples 202-216

3-(2,6-Dichloro-4-trifluoromethylphenyloxy)-5-methylpyrazole reacted with trichloromethyl chloroformate, and then reacted with amines (Example 202: s-butylamine, Example 203: 3-aminopentane, Example 204: cyclopentylamine, Example 205: propargylamine, Example 206: O-ethylhydroxylamine hydrochloride, Example 207: O-tert-butylhydroxylamine, Example 208: O-allylhydroxylamine, Example 209: O-benzylhydroxylamine, Example 210: ethanolamine, Example 211: 2,2,2-trifluoroethylamine, Example 212: tetrahydrofurfurylamine, Example 213: furfurylamine, Example 214: 2-morpholinoethylamine, Example 215: 2-picolylamine, Example 216: 2-thienylmethylamine) in the same manner as in Example 201, to give N-substituted carboxamides. Products/forms/yields/melting points/NMR spectra are described below.

Example 202

N-s-butyl-3-(2,6-dichloro-4-trifluoromethylphenyloxy)-5-methylpyrazole-1-carboxamide/white solid/yield: 48.8%/mp: 73-75° C./$^1$H-NMR (CDCl$_3$, TMS, ppm): δ 0.92 (t, J=7.5 Hz, 3H), 1.19 (d, J=6.7 Hz, 3H), 1.45-1.60 (m, 2H), 2.57 (d, J=0.7 Hz, 3H), 3.82 (dq, J=6.7 and 8.4 Hz, 1H), 5.62 (d, J=0.7 Hz, 1H), 6.62 (br d, J=8.4 Hz, 1H), 7.57 (s, 2H).

Example 203

N-(3-pentyl)-3-(2,6-dichloro-4-trifluoromethylphenyloxy)-5-methylpyrazole-1-carboxamide/white solid/yield: 43.6%/mp: 65-67° C./$^1$H-NMR (CDCl$_3$, TMS, ppm): δ 0.91 (t, J=7.4 Hz, 6H), 1.53 (m, 4H), 2.58 (s, 3H), 3.67 (m, 1H), 5.63 (s, 1H), 6.58 (br d, J=9.0 Hz, 1H), 7.67 (s, 2H).

Example 204

N-cyclopentyl-3-(2,6-dichloro-4-trifluoromethylphenyloxy)-5-methylpyrazole-1-carboxamide/white solid/yield: 47.4%/mp: 90-92° C./$^1$H-NMR (CDCl$_3$, TMS, ppm): δ 1.35-1.80 (m, 6H), 1.90-2.10 (m, 2H), 2.57 (d, J=0.4 Hz, 3H), 4.13 (dt, J=7.0 and 7.0 Hz, 1H), 5.61 (d, J=0.6 Hz, 1H), 6.72 (br d, J=7.0 Hz, 1H), 7.67 (s, 2H).

Example 205

N-propargyl-3-(2,6-dichloro-4-trifluoromethylphenyloxy)-5-methylpyrazole-1-carboxamide/colorless viscous substance/yield: 21.7%/$^1$H-NMR (CDCl$_3$, TMS, ppm): δ 2.25 (t, J=2.5 Hz, 1H), 2.59 (s, 3H), 4.09 (dd, J=2.5 and 6.0 Hz, 2H), 5.78 (s, 1H), 6.85-7.00 (m, 1H), 7.67 (s, 2H).

Example 206

N-ethoxy-3-(2,6-dichloro-4-trifluoromethylphenyloxy)-5-methylpyrazole-1-carboxamide/white solid/yield: 5.0%/mp: 105-107° C./$^1$H-NMR (CDCl$_3$, TMS, ppm): δ 1.28 (t, J=7.1 Hz, 3H), 2.59 (s, 3H), 4.03 (q, J=7.1 Hz, 2H), 5.82 (s, 1H), 7.67 (s, 2H), 9.05 (s, 1H).

Example 207

N-t-butoxy-3-(2,6-dichloro-4-trifluoromethylphenyloxy)-5-methylpyrazole-1-carboxamide/white solid/yield: 40.7%/mp: 92-94° C./$^1$H-NMR (CDCl$_3$, TMS, ppm): δ 1.29 (s, 9H), 2.58 (d, J=0.8 Hz, 3H), 5.76 (q, J=0.8 Hz, 1H), 7.67 (s, 2H), 8.73 (s, 1H).

Example 208

N-allyloxy-3-(2,6-dichloro-4-trifluoromethylphenyloxy)-5-methylpyrazole-1-carboxamide/white solid/yield: 37.8%/mp: 68-70° C./$^1$H-NMR (CDCl$_3$, TMS, ppm): δ 2.59 (d, J=0.8 Hz, 3H), 4.35-4.50 (m, 2H), 5.20-5.45 (m, 2H), 5.82 (d, J=0.8 Hz, 1H), 5.85-6.10 (m, 1H), 7.67 (d, J=0.4 Hz, 2H), 9.06 (br s, 1H).

Example 209

N-benzyloxy-3-(2,6-dichloro-4-trifluoromethylphenyloxy)-5-methylpyrazole-1-carboxamide/white solid/yield: 26.1%/mp: 98-100° C./$^1$H-NMR (CDCl$_3$, TMS, ppm): δ 2.61 (d, J=0.7 Hz, 3H), 4.95 (s, 2H), 5.83 (q, J=0.9 Hz, 1H), 7.30-7.45 (m, 5H), 7.63 (d, J=0.5 Hz, 2H), 9.00 (br s, 1H).

Example 210

N-(2-hydroxyethyl)-3-(2,6-dichloro-4-trifluoromethylphenyloxy)-5-methylpyrazole-1-carboxamide/white solid/yield: 20.1%/mp: 124-126° C./$^1$H-NMR (CDCl$_3$, TMS, ppm): δ 2.25 (m, 1H), 2.58 (s, 3H), 3.40-3.55 (m, 2H), 3.70-3.85 (m, 2H), 5.76 (q, J=0.5 Hz, 1H), 6.90-7.15 (m, 1H), 7.66 (s, 2H).

Example 211

N-2,2,2-trifluoroethyl-3-(2,6-dichloro-4-trifluoromethylphenyloxy)-5-methylpyrazole-1-carboxamide/white solid/yield: 51.6%/mp: 104-106° C./$^1$H-NMR (CDCl$_3$, TMS, ppm): δ 2.60 (d, J=0.5 Hz, 3H), 3.93 (dq, J=6.8 and 8.8 Hz, 2H), 5.80 (q, J=0.7 Hz, 1H), 7.05 (br t, J=6.8 Hz, 1H), 7.68 (s, 2H).

Example 212

N-tetrahydrofurfuryl-3-(2,6-dichloro-4-trifluoromethylphenyloxy)-5-methylpyrazole-1-carboxamide/white solid/yield: 13.7%/mp: 74-76° C./$^1$H-NMR (CDCl$_3$, TMS, ppm): δ 1.45-1.65 (m, 1H), 1.75-2.05 (m, 3H), 2.58 (d, J=0.8 Hz, 3H), 3.32 (dt, J=6.2 and 13.9 Hz, 1H), 3.47 (ddd, J=3.7, 5.6 and 13.9 Hz, 1H), 3.60-3.85 (m, 2H), 3.95-4.15 (m, 1H), 5.75 (q, J=0.8 Hz, 1H), 6.85-7.15 (m, 1H), 7.66 (s, 2H).

Example 213

N-furfuryl-3-(2,6-dichloro-4-trifluoromethylphenyloxy)-5-methylpyrazole-1-carboxamide/orange viscous substance/yield: 24.0%/$^1$H-NMR (CDCl$_3$, TMS, ppm): δ 2.59 (d, J=0.6 Hz, 3H), 4.47 (d, J=6.0 Hz, 2H), 5.73 (q, J=0.8 Hz, 1H), 6.25 (m, 1H), 6.32 (dd, J=1.8 and 3.2 Hz, 1H), 7.07 (br t, J=6.0 Hz, 1H), 7.35 (dd, J=0.8 and 1.8 Hz, 1H), 7.66 (s, 2H).

Example 214

N-(2-morpholinoethyl)-3-(2,6-dichloro-4-trifluoromethylphenyloxy)-5-methylpyrazole-1-carboxamide/white solid/yield: 25.7%/mp: 99-101° C./$^1$H-NMR (CDCl$_3$, TMS, ppm): δ 2.40 (t, J=4.7 Hz, 4H), 2.50 (t, J=6.2 Hz, 2H), 2.59 (d, J=0.8 Hz, 3H), 3.37 (dt, J=5.4 and 6.1 Hz, 2H), 3.57 (t, J=4.7 Hz, 4H), 5.80 (q, J=0.8 Hz, 1H), 7.10-7.25 (m, 1H), 7.67 (s, 2H).

Example 215

N-2-picolyl-3-(2,6-dichloro-4-trifluoromethylphenyloxy)-5-methylpyrazole-1-carboxamide/white solid/yield:

27.0%/mp: 121-123° C./$^1$H-NMR (CDCl$_3$, TMS, ppm): δ 2.60 (d, J=0.8 Hz, 3H), 4.59 (d, J=5.8 Hz, 2H), 5.77 (q, J=0.8 Hz, 1H), 7.19 (dd, J=5.8 and 7.8 Hz, 1H), 7.31 (d, J=7.8 Hz, 1H), 7.55-7.70 (m, 4H), 8.50 (d, J=4.2 Hz, 1H).

Example 216

N-(2-thienylmethyl)-3-(2,6-dichloro-4-trifluoromethylphenyloxy)-5-methylpyrazole-1-carboxamide/yellow viscous substance/yield: 34.1%/$^1$H-NMR (CDCl$_3$, TMS, ppm): δ 2.61 (d, J=0.8 Hz, 3H), 4.65 (d, J=5.9 Hz, 2H), 5.74 (q, J=0.8 Hz, 1H), 6.90-7.05 (m, 2H), 7.05-7.20 (m, 1H), 7.20-7.30 (m, 1H), 7.66 (s, 2H).

Example 217

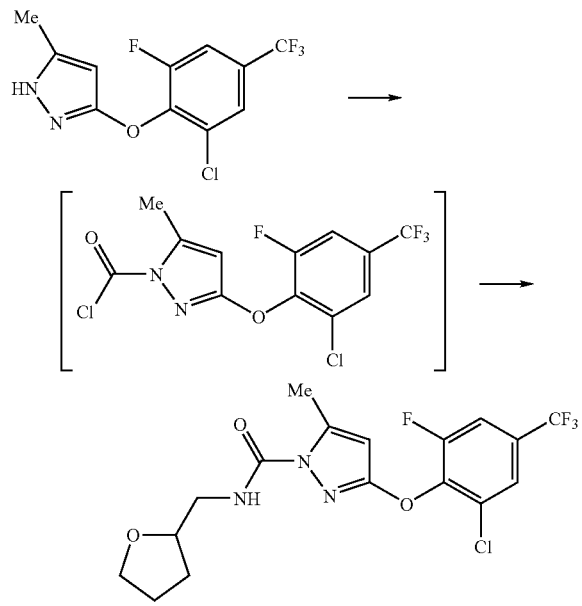

Trichloromethyl chloroformate (0.39 g, 2.0 mmol) was added to a solution of 3-(2-chloro-6-fluoro-4-trifluoromethylphenyloxy)-5-methylpyrazole (0.59 g, 2.0 mmol) in chloroform (10 ml) at 0° C., and while the mixture was allowed to have room temperature gradually, it was further stirred at room temperature for 3 hours. Tetrahydrofurfurylamine (0.61 g, 6.0 mmol) and triethylamine (0.4 g, 4.0 mmol) were added to the reaction mixture, the reaction mixture was refluxed under heating for 5 hours. After completion of the reaction, the reaction mixture was poured into ice water and extracted with chloroform (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/10→1/5), to give a colorless viscous substance of N-tetrahydrofurfuryl-3-(2-chloro-6-fluoro-4-trifluoromethylphenyloxy)-5-methylpyrazole-1-carboxamide (0.25 g, yield: 29.6%). $^1$H-NMR (CDCl$_3$, TMS, ppm): δ 1.50-1.65 (m, 1H), 1.75-2.05 (m, 3H), 2.58 (s, 3H), 3.32 (dt, J=6.3 and 13.9 Hz, 1H), 3.48 (ddd, J=3.7, 5.7 and 13.9 Hz, 1H), 3.74 (dq, J=7.0 and 8.6 Hz, 2H), 4.03 (dq, J=3.7 and 7.0 Hz, 1H), 5.79 (s, 1H), 6.85-7.10 (m, 1H), 7.39 (dd, J$_{HF}$=1.9 and 9.3 Hz, 1H), 7.56 (s, 1H).

Example 218

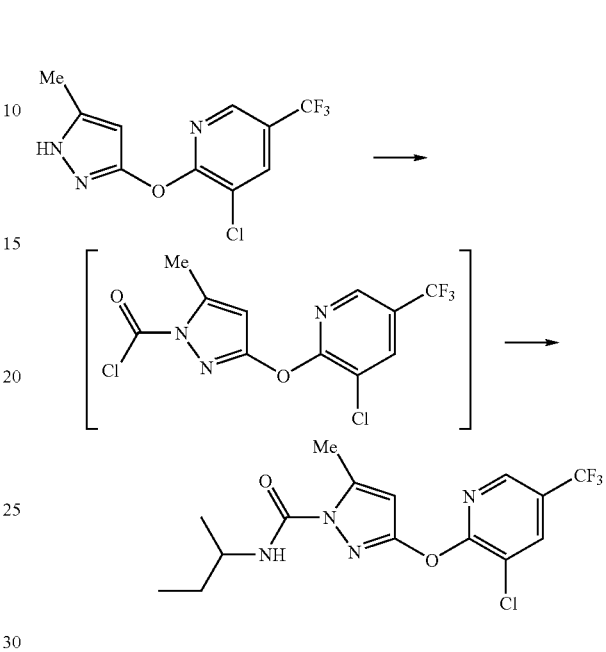

Trichloromethyl chloroformate (0.49 g, 2.5 mmol) was added to a solution of 3-(3-chloro-5-trifluoromethylpyridin-2-yloxy)-5-methylpyrazole (0.69 g, 2.5 mmol) in chloroform (10 ml) at 0° C., and while the mixture was allowed to have room temperature gradually, it was further stirred at room temperature for 3 hours. Sec-butylamine (0.22 g, 3.0 mmol) and potassium carbonate (0.42 g, 3.0 mmol) were added to the reaction mixture, and the mixture was stirred at 50° C. for 8 hours. After completion of the reaction, the reaction mixture was poured into ice water and extracted with chloroform (20 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a colorless viscous substance of N-s-butyl-3-(3-chloro-5-trifluoromethylpyridin-2-yloxy)-5-methylpyrazole-1-carboxamide (0.24 g, yield: 25.5%). $^1$H-NMR (CDCl$_3$, TMS, ppm): δ 0.96 (t, J=7.5 Hz, 3H), 1.22 (d, J=6.6 Hz, 3H), 1.45-1.65 (m, 2H), 2.65 (s, 3H), 3.75-4.00 (m, 1H), 6.04 (s, 1H), 6.75-7.05 (m, 1H), 8.02 (d, J=1.8 Hz, 1H), 8.30-8.40 (m, 1H).

Examples 219-222

3-(3-Chloro-5-trifluoromethylpyridin-2-yloxy)-5-methylpyrazole reacted with trichloromethyl chloroformate, and then reacted with amines (Example 219: cyclopropylamine, Example 220: isobutylamine, Example 221: O-methylhydroxylamine hydrochloride, Example 223: O-ethylhydroxylamine hydrochloride) in the same manner as in Example 218, to give corresponding carboxamides. Products/forms/yields/melting points/NMR spectra are described below.

Example 219

N-cyclopropyl-3-(3-chloro-5-trifluoromethylpyridin-2-yloxy)-5-methylpyrazole-1-carboxamide/white solid/yield:

37.9%/mp: 98-99° C./$^1$H-NMR (CDCl$_3$, TMS, ppm): δ 0.55-0.70 (m, 2H), 0.75-0.90 (m, 2H), 2.66 (s, 3H), 2.70-2.85 (m, 1H), 6.05 (s, 1H), 7.05-7.20 (m, 1H), 8.02 (d, J=2.1 Hz, 1H), 8.35 (d, J=2.1 Hz, 1H).

Example 220

N-isobutyl-3-(3-chloro-5-trifluoromethylpyridin-2-yloxy)-5-methylpyrazole-1-carboxamide/white solid/yield: 29.7%/mp: 45-47° C./$^1$H-NMR (CDCl$_3$, TMS, ppm): δ 0.96 (d, J=6.7 Hz, 6H), 1.87 (sep, J=6.7 Hz, 1H), 2.65 (d, J=0.6 Hz, 3H), 3.18 (t, J=6.5 Hz, 2H), 6.04 (q, J=0.6 Hz, 1H), 7.00-7.20 (m, 1H), 8.02 (d, J=2.1 Hz, 1H), 8.35 (m, 1H).

Example 221

N-methoxy-3-(3-chloro-5-trifluoromethylpyridin-2-yloxy)-5-methylpyrazole-1-carboxamide/colorless viscous substance/yield: 19.4%/$^1$H-NMR (CDCl$_3$, TMS, ppm): δ 2.66 (d, J=0.7 Hz, 3H), 3.86 (s, 3H), 6.10 (q, J=0.7 Hz, 1H), 8.03 (d, J=2.1 Hz, 1H), 8.35 (m, 1H), 9.35-9.55 (m, 1H).

Example 222

N-ethoxy-3-(3-chloro-5-trifluoromethylpyridin-2-yloxy)-5-methylpyrazole-1-carboxamide/yellow viscous substance/yield: 38.5%/$^1$H-NMR (CDCl$_3$, TMS, ppm): δ 1.32 (t, J=7.0 Hz, 3H), 2.66 (s, 3H), 4.07 (q, J=7.0 Hz, 2H), 6.10 (s, 1H), 8.03 (d, J=2.1 Hz, 1H), 8.35 (m, 1H), 9.38 (br s, 1H).

Example 223

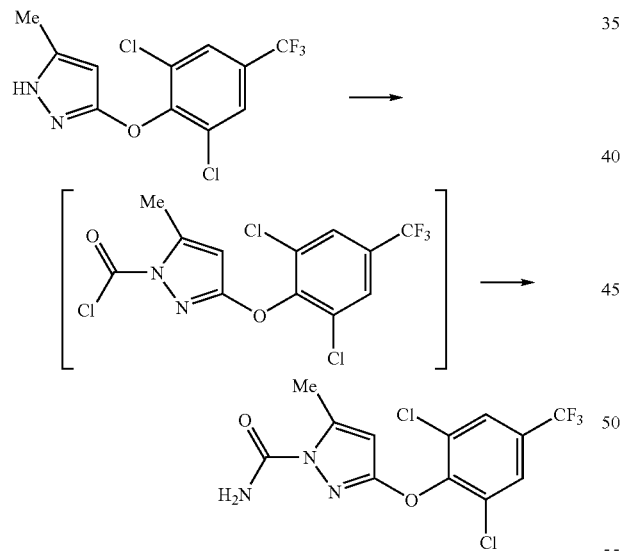

Trichloromethyl chloroformate (3.0 g, 15.0 mmol) was added to a solution of 3-(2,6-dichloro-4-trifluoromethylphenyloxy)-5-methylpyrazole (4.67 g, 15.0 mmol) in chloroform (50 ml) at 0° C., and while the mixture was allowed to have room temperature gradually, it was further stirred at room temperature for 4 hours. 30% ammonia solution (10 ml) was added to the reaction mixture, and the mixture was further stirred at room temperature for 1 hour. After completion of the reaction, water was added to the reaction mixture, and the mixture was extracted with ethyl acetate (30 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/7), to give a white solid of 3-(2,6-dichloro-4-trifluoromethylphenyloxy)-5-methylpyrazole-1-carboxamide (2.82 g, yield: 53.1%). mp: 152-154° C.; $^1$H-NMR (CDCl$_3$, TMS, ppm): δ 2.58 (d, J=0.4 Hz, 3H), 4.80-5.15 (br s, 1H), 5.80 (q, J=0.4 Hz, 1H), 6.45-6.80 (br s, 1H), 7.66 (s, 2H).

Examples 224-226

3-(Substituted phenyloxy)-5-methylpyrazoles (Example 224: 3-(3-chloro-5-trifluoromethylpyridin-2-yloxy)-5-methylpyrazole, Example 225: 3-(3-chloro-5-trifluoromethylpyridin-2-yloxy)-5-methylpyrazole, Example 226: 5-methyl-3-(3-trifluoromethylphenyloxy)pyrazole) reacted with trichloromethyl chloroformate, and then reacted with ammonia solution in the same manner as in Example 223, to give corresponding carboxamide derivatives. Products/forms/yields/melting points/NMR spectra are described below.

Example 224

3-(2-chloro-6-fluoro-4-trifluoromethylphenyloxy)-5-methylpyrazole-1-carboxamide/white solid/yield: 35.5%/mp: 132-135° C./$^1$H-NMR (CDCl$_3$, TMS, ppm): δ 2.59 (d, J=0.8 Hz, 3H), 4.75-5.20 (br s, 1H), 5.84 (q, J=0.8 Hz, 1H), 6.45-6.80 (br s, 1H), 7.39 (dd, $J_{HF}$=2.0 and 9.3 Hz: 1H), 7.56 (s, 1H).

Example 225

3-(3-chloro-5-trifluoromethylpyridin-2-yloxy)-5-methylpyrazole-1-carboxamide/white solid/yield: 76.7%/mp: 101-104° C./$^1$H-NMR (CDCl$_3$, TMS, ppm): δ 2.65 (d, J=0.6 Hz, 3H), 5.00-5.40 (br s, 1H), 6.08 (m, 1H), 6.75-7.15 (br s, 1H), 8.03 (d, J=2.1 Hz, 1H), 8.36 (m, 1H).

Example 226

5-methyl-3-(3-trifluoromethylphenyloxy)pyrazole-1-carboxamide/white solid/yield: 35.8%/mp: 76-77° C./$^1$H-NMR (CDCl$_3$, TMS, ppm): δ 2.60 (d, J=0.8 Hz, 3H), 5.09 (br s, 2H), 5.77 (q, J=0.8 Hz, 1H), 7.33-7.38 (m, 1H), 7.41-7.52 (m, 3H).

Example 227

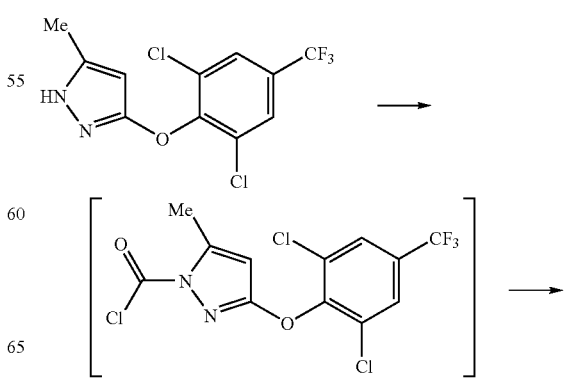

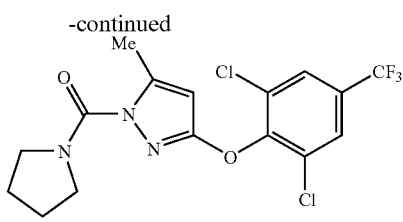

Trichloromethyl chloroformate (0.46 g, 2.3 mmol) was added to a solution of 3-(2,6-dichloro-4-trifluoromethylphenyloxy)-5-methylpyrazole (0.47 g, 1.5 mmol) in ethyl acetate (10 ml) at 0° C., and while the mixture was allowed to have room temperature gradually, it was further stirred under reflux for 4 hours. The reaction mixture was concentrated, and further, toluene (10 ml), triethylamine (0.46 g, 4.5 mmol) and pyrrolidine (0.43 g, 6.0 mmol) were added. Further, the mixture was refluxed under heating for 3 hours. After completion of the reaction, water was added to the reaction mixture, and the mixture was extracted with ethyl acetate (50 ml×3). An organic layer was washed with water, dried over anhydrous magnesium sulfate and filtered to remove a desiccant, and the solvent was distilled off from the filtrate under reduced pressure. The resultant crude product was purified with a silica gel column (ethyl acetate/hexane=1/5), to give a white solid of N,N-tetramethylene-3-(2,6-dichloro-4-trifluoromethylphenyloxy)-5-methylpyrazole-1-carboxamide (0.11 g, yield: 18.0%). mp: 102-104° C.; $^1$H-NMR (CDCl$_3$, TMS, ppm): δ 1.70-1.95 (m, 4H), 2.50 (d, J=0.6 Hz, 3H), 3.40-3.60 (m, 4H), 5.78 (q, J=0.6 Hz, 1H), 7.64 (s, 2H).

Example 228

3-(2,6-Dichloro-4-trifluoromethylphenyloxy)-5-methylpyrazole reacted with trichloromethyl chloroformate to obtain an intermediate, and further, the intermediate reacted with 2,6-dimethylmorpholine, in the same manner as in Example 228, to give a white solid of 3-(2,6-dichloro-4-trifluoromethylphenyloxy-1-(2,6-dimethylmorpholino)carbonyl-5-methylpyrazole (0.14 g, yield: 20.6%). mp: 87~89° C.; $^1$H-NMR (CDCl$_3$, TMS, ppm): δ 0.90-1.30 (m, 6H), 2.46 (d, J=0.7 Hz, 3H), 2.50-2.65 (m, 2H), 3.20-3.75 (m, 2H), 3.80-4.25 (m, 2H), 5.85 (q, J=0.7 Hz, 1H), 7.64 (s, 2H).

Example 229

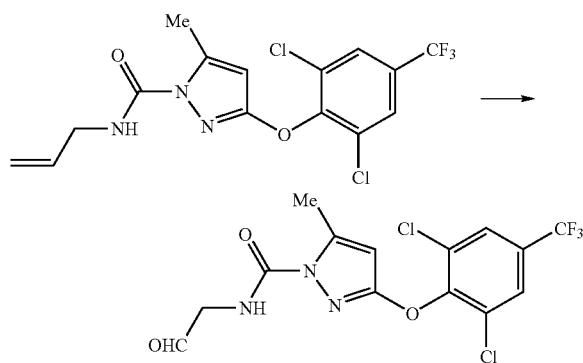

N-allyl-3-(2,6-dichloro-4-trifluoromethylphenyloxy)-5-methylpyrazole-1-carboxamide (4.3 g, 10.9 mmol) was dissolved in a solution mixture of ether (50 ml) and water (50 ml), an aqueous solution (60 ml) of osmium tetraoxide (254 mg, 1.0 mmol) and sodium periodate (4.7 g, 21.8 mmol) were added, and the mixture was stirred at room temperature overnight. After completion of the reaction, a 10% sodium thiosulfate aqueous solution (100 ml) and ethyl acetate (100 ml) were added to the reaction solution, and an organic layer was separated and an aqueous layer was extracted with ethyl acetate (50 ml×2). These organic layers combined were washed with a saturated sodium chloride aqueous solution, dried over anhydrous magnesium sulfate and filtered to remove a desiccant. The solvent was distilled off from the filtrate under reduced pressure. The resultant crude product was purified with a silica gel column (ethyl acetate/hexane=1/7→1/5), to give a white solid of N-formylmethyl-3-(2,6-dichloro-4-trifluoromethylphenyloxy)-5-methylpyrazole-1-carboxamide (2.12 g, yield: 49.1%). mp: 111-113° C.; $^1$H-NMR (CDCl$_3$, TMS, ppm): δ 2.59 (d, J=0.8 Hz, 3H), 4.17 (d, J=5.5 Hz, 2H), 5.81 (q, J=0.8 Hz, 1H), 7.21 (br t, J=5.5 Hz, 1H), 7.67 (s, 2H), 9.66 (s, 1H).

Example 230

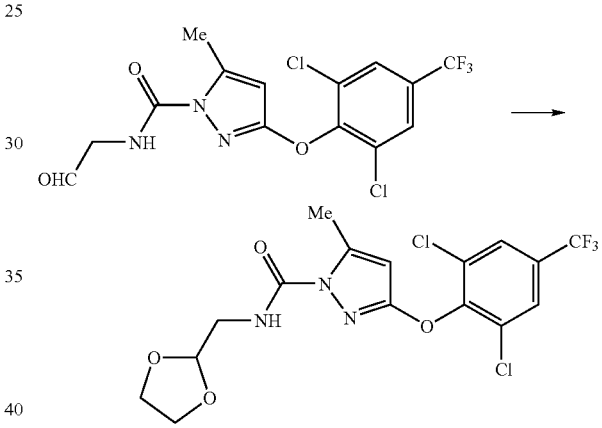

p-Toluenesulfonic acid monohydrate (20 mg, 0.1 mmol) and ethylene glycol (0.31 g, 5 mmol) were added to a solution of N-formylmethyl-3-(2,6-dichloro-4-trifluoromethylphenyloxy)-5-methylpyrazole-1-carboxamide (0.40 g, 1.0 mmol) in benzene (10 ml), and the mixture was refluxed under heating for 5 hours. After completion of the reaction, the solvent was distilled off from the reaction mixture, water (30 ml) was added to the residue, and the mixture was extracted with ethyl acetate (30 ml×3). An organic layer was washed with a saturated sodium chloride aqueous solution, dried over anhydrous magnesium sulfate and filtered to remove a desiccant. The solvent was distilled off from the filtrate under reduced pressure. The resultant crude product was purified with a silica gel column (ethyl acetate/hexane=1/7→chloroform), to give a white solid of N,N-(1,3-dioxa-2-cyclopentyl)methyl-3-(2,6-dichloro-4-trifluoromethylphenyloxy)-5-methylpyrazole-1-carboxamide (0.33 g, yield: 75.0%). mp: 80-81° C.; $^1$H-NMR (CDCl$_3$, TMS, ppm): δ 2.59 (d, J=0.8 Hz, 3H), 3.53 (dd, J=3.3 and 6.1 Hz, 2H), 3.80-3.95 (m, 4H), 5.03 (t, J=3.3 Hz, 1H), 5.76 (q, J=0.8 Hz, 1H), 6.92 (br t, J=6.1 Hz, 1H), 7.66 (s, 2H).

Examples 231-232

N-Formylmethyl-3-(2,6-dichloro-4-trifluoromethylphenyloxy)-5-methylpyrazole-1-carboxamide reacted with alcohols (Example 231: 1,3-propanediol, Example 232: methanol) in the same manner as in Example 230, to give corresponding carboxamides. Products/forms/yields/melting points/NMR spectra are described below.

Example 231

N,N-(1,3-dioxa-2-cyclohexyl)methyl-3-(2,6-dichloro-4-trifluoromethylphenyloxy)-5-methylpyrazole-1-carboxamide/white solid/yield: 74.9%/mp: 87-89° C./$^1$H-NMR (CDCl$_3$, TMS, ppm): δ 1.25-1.45 (m, 1H), 1.95-2.15 (m, 1H), 2.58 (d, J=0.8 Hz, 3H), 3.41 (dd, J=4.7 and 6.1 Hz, 2H), 3.65-3.85 (m, 1H), 4.00-4.15 (m, 1H), 4.67 (t, 4.7 Hz, 1H), 5.73 (q, J=0.8 Hz, 1H), 6.90-7.10 (br t, J=6.1 Hz, 1H), 7.67 (s, 2H).

Example 232

N,N-2,2-dimethoxyethyl-3-(2,6-dichloro-4-trifluoromethylphenyloxy)-5-methylpyrazole-1-carboxamide/white solid/mp: 57-59° C./$^1$H-NMR (CDCl$_3$, TMS, ppm): δ 2.58 (d, J=0.7 Hz, 3H), 3.38 (s, 6H), 3.35-3.45 (m, 2H), 4.41 (t, J=5.4 Hz, 1H), 5.75 (q, J=0.8 Hz, 1H), 6.80-7.00 (m, 1H), 7.66 (d, J=0.4 Hz, 2H).

Example 233

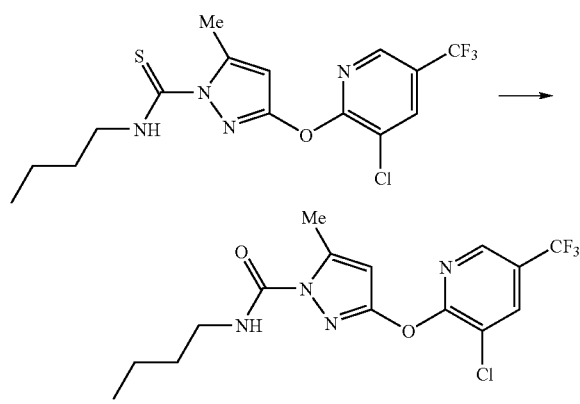

Potassium hydroxide (0.42 g, 7.5 mmol) and 30% hydrogen peroxide (2.7 ml) were added to a solution of N-butyl-3-(3-chloro-5-trifluoromethylpyridin-2-yloxy)-5-methylpyrazole-1-carbothioamide (0.98 g, 2.5 mmol) in methanol (10 ml), and the mixture was stirred at room temperature for 3 hours. Concentrated hydrochloric acid was added to the reaction mixture up to a pH of 1, and the mixture was further stirred at room temperature for 2 hours. After completion of the reaction, the reaction mixture was extracted with ethyl acetate (15 ml×3), and the organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/10→1/1), to give a colorless viscous substance of N-butyl-3-(3-chloro-5-trifluoromethylpyridin-2-yloxy)-5-methylpyrazole-1-carboxamide (0.17 g, yield: 18.1%). $^1$H-NMR (CDCl$_3$, TMS, ppm): δ 0.94 (t, J=7.3 Hz, 3H), 1.30-1.50 (m, 2H), 1.50-1.70 (m, 2H), 2.65 (s, 3H), 3.35 (dt, J=6.3 and 6.3 Hz, 2H), 6.04 (s, 1H), 6.90-7.20 (m, 1H), 8.02 (d, J=2.0 Hz, 1H), 8.35 (m, 1H).

Example 234

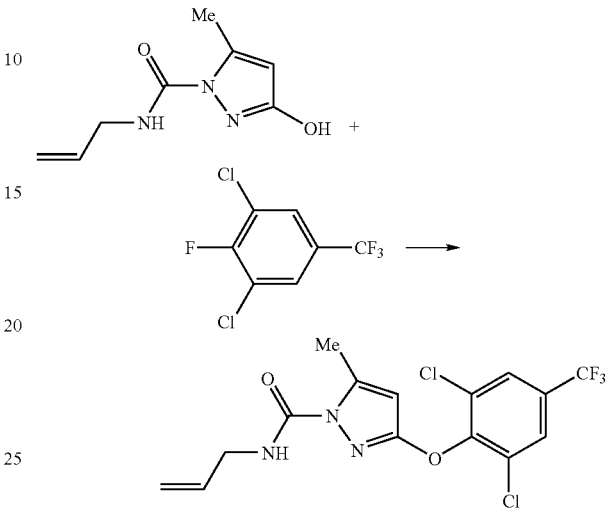

Potassium carbonate (0.07 g, 0.50 mmol) was added to a solution of N-allyl-3-hydroxy-5-methylpyrazole-1-carboxamide (0.18 g, 1.0 mmol) in DMF (5 ml), then, 3,5-dichloro-4-fluorotrifluoromethylbenzene (0.23 g, 1.0 mmol) was added, and the mixture was stirred at room temperature for 5 hours. After completion of the reaction, the reaction mixture was poured into 1N hydrochloric acid (10 ml), and the mixture was extracted with ethyl acetate (10 ml×2). An organic layer was washed with water (10 ml×3) and dried over anhydrous magnesium sulfate, and a desiccant was removed from a filtrate. The solvent was distilled off from the filtrate under reduced pressure. The resultant crude product was purified with a silica gel column (ethyl acetate/hexane=1/10), to give a yellow viscous substance of N-allyl-3-(2,6-dichloro-4-trifluoromethyloxy)-5-methylpyrazole-1-carboxamide (0.18 g, yield: 45.7%). The product had NMR spectrum as shown in Example 112.

Example 235

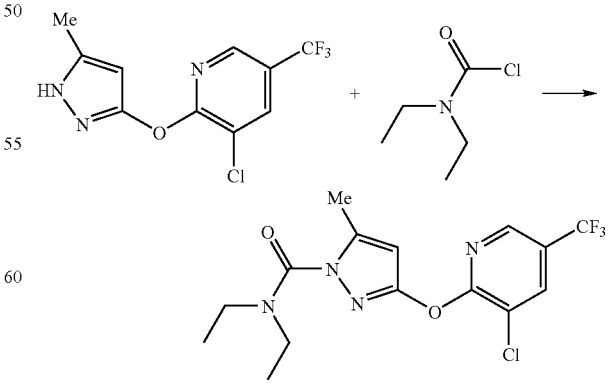

Diethylcarbamoyl chloride (1.52 g, 7.8 mmol) was added to a solution of 3-(3-chloro-5-trifluoromethylpyridin-2- yloxy)-5-methylpyrazole (1.39 g, 5.0 mmol) and potassium carbonate (1.98 g, 14.3 mmol) in DMF (15 ml), the mixture was stirred at 70° C. for 9 hours and further stirred at room temperature for 2 days. After completion of the reaction, the reaction mixture was poured into 2N hydrochloric acid, and the mixture was extracted with ethyl acetate (20 ml×3). An organic-layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/5), to give a colorless viscous substance of N,N-diethyl-3-(3-chloro-5-trifluoromethylpyridin-2-yloxy)-5-methylpyrazole-1-carboxamide (0.21 g, yield: 11.2%). $^1$H-NMR (CDCl$_3$, TMS, ppm): δ 1.21 (t, J=7.0 Hz, 6H), 2.48 (d, J=0.6 Hz, 3H), 3.47 (q, J=7.0 Hz, 4H), 6.00 (q, J=0.6 Hz, 1H), 7.99 (d, J=2.1 Hz, 1H), 8.33 (m, 1H).

Example 236

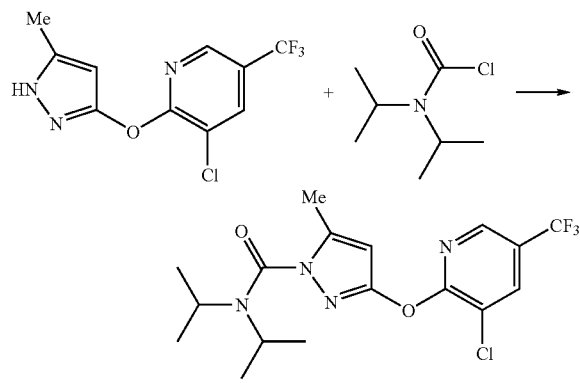

A solution of diisopropylcarbamoyl chloride (1.47 g, 9.0 mmol) in pyridine (5 ml) was added to a solution of 3-(3-chloro-5-trifluoromethylpyridin-2-yloxy)-5-methylpyrazole (1.67 g, 6.0 mmol) in pyridine (10 ml), and the mixture was stirred under heating at 80° C. for 20 hours. After completion of the reaction, the reaction mixture was poured into 2N hydrochloric acid, and the mixture was extracted with ethyl acetate (20 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/5), to give a white solid of N,N-diisopropyl-3-(3-chloro-5-trifluoromethylpyridin-2-yloxy)-5-methylpyrazole-1-carboxamide (2.1 g, yield: 86.7%). mp: 58-60° C.; $^1$H-NMR (CDCl$_3$, TMS, ppm): δ 1.28 (d, J=7.5 Hz, 12H), 2.29 (s, 3H), 3.50-4.10 (m, 2H), 6.00 (s, 1H), 7.98 (d, J=2.5 Hz, 1H), 8.31 (m, 1H).

Example 237

N,N-Dimethyl-3-(3-chloro-5-trifluoromethylpyridin-2-yloxy)-5-methylpyrazole-1-carboxamide was obtained in the same manner as in Example 235. White solid/yield: 30.6%/mp: 102-104° C./$^1$H-NMR (CDCl$_3$, TMS, ppm): δ 2.32 (s, 3H), 2.85-3.30 (br s, 6H), 6.01 (s, 1H), 7.99 (d, J=2.0 Hz, 1H), 8.30 (m, 1H).

Examples 238-240

3-(3-Chloro-5-trifluoromethylpyridin-2-yloxy)-5-trifluoromethylpyrazole reacted with carbamoyl chloride derivatives (Example 238: dimethylcarbamoyl chloride, Example 240 diethylcarbamoyl chloride, Example 241: diisopropylcarbamoyl chloride) in the same manner as in Example 236, to give corresponding carboxamides. Products/forms/yields/melting points/NMR spectra are described below.

Example 238

N,N-dimethyl-3-(3-chloro-5-trifluoromethylpyridin-2-yloxy)-5-trifluoromethylpyrazole-1-carboxamide/orange viscous substance/yield: 25.0%/$^1$H-NMR (CDCl$_3$, TMS, ppm): δ 3.13 (s, 6H), 6.51 (s, 1H), 8.00-8.10 (m, 1H), 8.25-8.35 (m, 1H).

Example 239

N,N-diethyl-3-(3-chloro-5-trifluoromethylpyridin-2-yloxy)-5-trifluoromethylpyrazole-1-carboxamide/white solid/yield: 58.1%/mp: 58-60° C./$^1$H-NMR (CDCl$_3$, TMS, ppm): δ 1.27 (m, 6H), 3.40 (q, J=6.9 Hz, 4H), 6.51 (s, 1H), 8.03 (d, J=2.1 Hz, 1H), 8.30 (m, 1H).

Example 240

N,N-diisopropyl-3-(3-chloro-5-trifluoromethylpyridin-2-yloxy)-5-trifluoromethylpyrazole-1-carboxamide/colorless viscous substance/yield: 50.9%/$^1$H-NMR (CDCl$_3$, TMS, ppm): δ 1.10-1.55 (m, 12H), 3.35-4.05 (m, 2H), 6.53 (s, 1H), 8.04 (d, J=2.2 Hz, 1H), 8.34 (m, 1H).

Example 241

N,N-Diisopropyl-3-(2-nitro-4-trifluoromethylphenyloxy)-5-trifluoromethylpyrazole-1-carboxamide was obtained in the same manner as in Example 236. White solid/yield: 22.9%/mp: 118-120° C./$^1$H-NMR (CDCl$_3$, TMS, ppm): δ 1.33 (d, J=5.9 Hz, 12H), 2.27 (s, 3H), 3.30-4.25 (m, 2H), 5.70 (s, 1H), 7.43 (d, J=8.8 Hz, 1H), 7.78 (dd, J=2.0 and 8.8 Hz, 1H), 8.24 (d, J=2.0 Hz, 1H).

Example 242

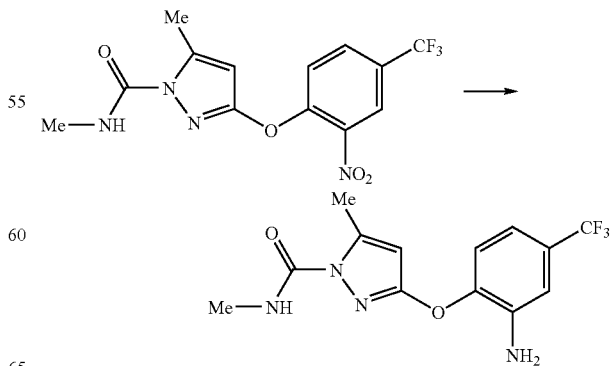

A solution of N-methyl-5-methyl-3-(2-nitro-4-trifluoromethylphenyloxy)pyrazole-1-carboxamide (2.1 g, 6.0 mmol) in ethanol (50 ml) was placed in an autoclave, and 10% palladium carbon (0.7 g) was added. An atmosphere in the autoclave was fully replaced with hydrogen gas, and hydrogen gas was charged up to 5 kg/cm². Then, the reaction solution was stirred at room temperature for 5 hours. After completion of the reaction, the catalyst was removed by filtration using Celite, and the solvent was distilled off from the filtrate under reduced pressure, to give a yellowish solid of N-methyl-3-(2-amino-4-trifluoromethylphenyloxy)-5-methylpyrazole-1-carboxamide (1.6 g, yield: 82.2%). mp: 93-94; ¹H-NMR (CDCl₃, TMS, ppm): δ 2.59 (d, J=0.7 Hz, 3H), 2.93 (d, J=5.0 Hz, 1H), 3.90-4.15 (br s, 2H), 5.71 (q, J=0.7 Hz, 1H), 6.80-6.95 (m, 1H), 6.97 (dd, J=1.7 and 8.4 Hz, 1H), 7.11 (d, J=8.4 Hz, 1H).

Example 243

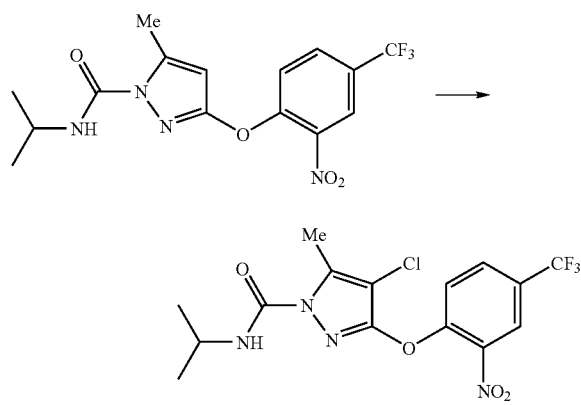

Sulfuryl chloride (0.24 g, 1.8 mmol) was added to a solution of N-isopropyl-5-methyl-3-(2-nitro-4-trifluoromethylphenyloxy)pyrazole-1-carboxamide (0.56 g, 1.5 mmol) in acetic acid (5 ml), and the mixture was stirred at room temperature for 4 hours. After completion of the reaction, the reaction mixture was poured into ice water and extracted with ethyl acetate (20 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/10), to give a yellowish solid of N-isopropyl-4-chloro-5-methyl-3-(2-nitro-4-trifluoromethylphenyloxy)pyrazole-1-carboxamide (0.60 g, yield: 98.4%). mp: 89-91° C.; ¹H-NMR (CDCl₃, TMS, ppm): δ 1.24 (d, J=6.6 Hz, 6H), 2.63 (s, 3H), 3.90-4.10 (m, 1H), 6.40-6.65 (m, 1H), 7.38 (d, J=8.7 Hz, 1H), 7.85 (dd, J=2.0 and 8.7 Hz, 1H), 8.29 (d, J=2.0 Hz, 1H).

Example 244

A white solid of N-methyl-4-chloro-5-methyl-3-(2-nitro-4-trifluoromethylphenyloxy)pyrazole-1-carboxamide was obtained in the same manner as in Example 243 (0.36 g, yield: 79.3%). mp: 107-108° C.; ¹H-NMR (CDCl₃, TMS, ppm): δ 2.63 (s, 3H), 2.91 (d, J=5.0 Hz, 3H), 6.50-6.75 (m, 1H), 7.46 (d, J=8.7 Hz, 1H), 7.88 (dd, J=2.0 and 8.7 Hz, 1H), 8.30 (d, J=2.0 Hz, 1H).

Example 245

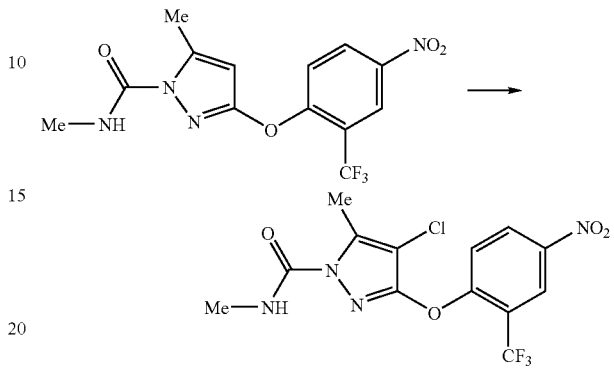

Sulfuryl chloride (0.16 g, 1.2 mmol) was added to a solution of N-methyl-5-methyl-3-(4-nitro-2-trifluoromethylphenyloxy)pyrazole-1-carboxamide (0.34 g, 1.0 mmol) in acetic acid (5 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/10), to give a white solid of N-methyl-4-chloro-5-methyl-3-(4-nitro-2-trifluoromethylphenyloxy)pyrazole-1-carboxamide (0.27 g, yield: 71.2%). mp: 157-158° C.; ¹H-NMR (CDCl₃, TMS, ppm): δ 2.66 (s, 3H), 2.96 (d, J=5.0 Hz, 3H), 6.70-6.95 (m, 1H), 7.31 (d, J=9.2 Hz, 1H), 8.41 (dd, J=2.7 and 9.2 Hz, 1H), 8.62 (d, J=2.7 Hz, 1H).

Example 246

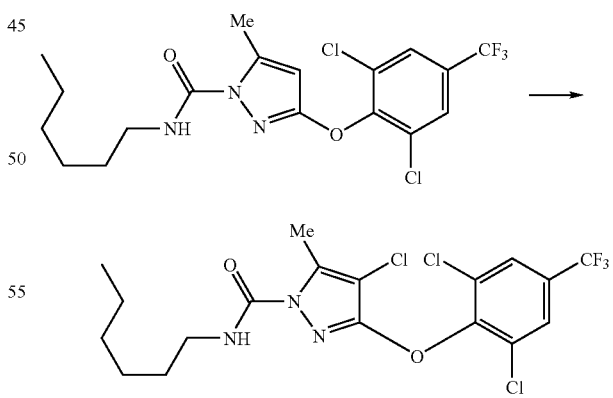

Sulfuryl chloride (0.16 g, 1.2 mmol) was added to a solution of N-hexyl-3-(2,6-dichloro-4-trifluoromethylphenyloxy)-5-methylpyrazole-1-carboxamide (0.44 g, 1.0 mmol) in acetic acid (5 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane 1/10), to give a white solid of N-hexyl-4-chloro-3-(2,6-dichloro-4-trifluoromethylphenyloxy)-5-methylpyrazole-1-carboxamide (0.40 g, yield: 84.8%). mp: 86-88° C.; $^1$H-NMR (CDCl$_3$, TMS, ppm): δ 0.88 (t, J=6.8 Hz, 3H), 1.26 (m, 6H), 1.40-1.60 (m, 2H), 2.62 (s, 3H), 3.15-3.35 (m, 2H), 6.50-6.70 (m, 1H), 7.67 (s, 2H).

Examples 247-248

N-Substituted-3-(3-chloro-5-trifluoromethylpyridin-2-yloxy)-5-methylpyrazole-1-carboxamide derivatives (Example 247: N-methyl compound, Example 248: N-ethyl compound) reacted with sulfuryl chloride in the same manner as in Example 246, to give corresponding 4-chloro derivatives. Products/forms/yields/melting points/NMR spectra are described below.

Example 247

N-methyl-4-chloro-3-(2,6-dichloro-4-trifluoromethylphenyloxy)-5-methylpyrazole-1-carboxamide/white solid/ yield: 66.5%/mp: 125-127° C./$^1$H-NMR (CDCl$_3$, TMS, ppm): δ 2.62 (s, 3H), 2.87 (d, J=5.0 Hz, 3H), 6.35-6.70 (m, 1H), 7.67 (s, 2H).

Example 248

N-ethyl-4-chloro-3-(2,6-dichloro-4-trifluoromethylphenyloxy)-5-methylpyrazole-1-carboxamide/white solid/yield: 48.0%/mp: 85-86° C./$^1$H-NMR (CDCl$_3$, TMS, ppm): δ 1.17 (t, J=7.2 Hz, 3H), 2.62 (s, 3H), 3.32 (dq, J=6.1 and 7.2 Hz, 2H), 6.40-6.70 (m, 1H), 7.67 (m, 2H).

Example 249

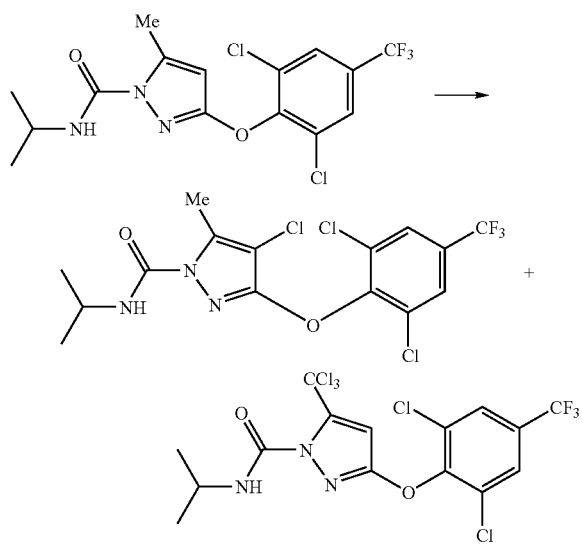

Sulfuryl chloride (0.16 g, 1.2 mmol) was added to a solution of N-isopropyl-3-(2,6-dichloro-4-trifluoromethylphenyloxy)-5-methylpyrazole-1-carboxamide (0.40 g, 1.0 mmol) in acetic acid (5 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/20), to give a white solid of N-isopropyl-4-chloro-3-(2,6-dichloro-4-trifluoromethylphenyloxy)-5-methylpyrazole-1-carboxamide (0.19 g, yield: 44.1%) [mp: 109-111° C.; $^1$H-NMR (CDCl$_3$, TMS, ppm): δ 1.20 (d, J=7.5 Hz, 6H), 2.61 (s, 3H), 3.85-4.10 (m, 1H), 6.25-6.50 (m, 1H), 7.67 (s, 2H).] and a white solid of N-isopropyl-3-(2,6-dichloro-4-trifluoromethylphenyloxy)-5-trichloromethylpyrazole-1-carboxamide (0.04 g, yield: 8.0%) [mp: 105-106° C.; $^1$H-NMR (CDCl$_3$, TMS, ppm): δ 1.22 (d, J=6.5 Hz, 6H), 3.85-4.15 (m, 1H), 6.25-6.55 (m, 1H), 7.69 (s, 2H), 8.24 (s, 1H)].

Example 250

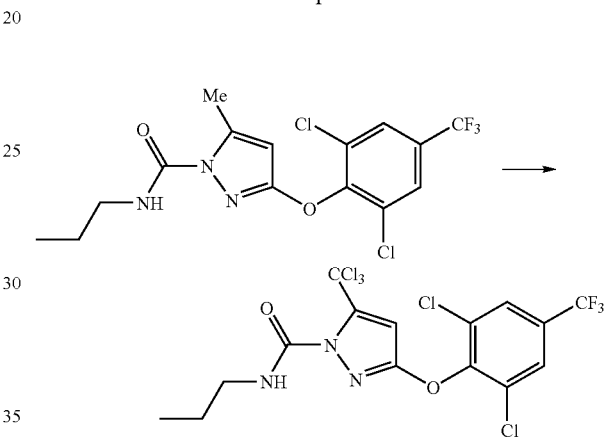

Sulfuryl chloride (0.09 g, 0.7 mmol) was added to a solution of N-propyl-3-(2,6-dichloro-4-trifluoromethylphenyloxy)-5-methylpyrazole-1-carboxamide (0.24 g, 0.6 mmol) in acetic acid (5 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/20), to give a white solid of N-propyl-3-(2,6-dichloro-4-trifluoromethylphenyloxy)-5-trichloromethylpyrazole-1-carboxamide (0.11 g, yield: 36.7%). mp: 89-91° C.; 1H-NMR (CDCl$_3$, TMS, ppm): δ 0.90 (t, J=7.3 Hz, 3H), 1.56 (tq, J=7.3 and 8.0 Hz, 2H), 3.25 (dt, J=6.3 and 8.0 Hz, 2H), 6.50-6.80 (m, 1H), 7.69 (s, 2H), 8.23 (s, 1H).

Example 251

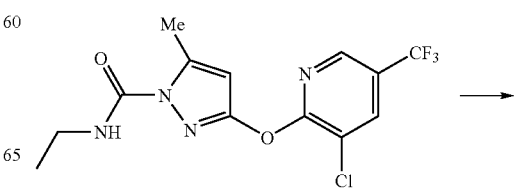

-continued

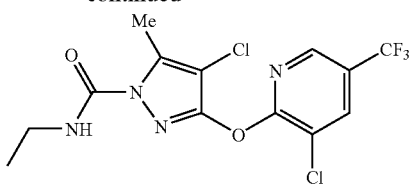

Sulfuryl chloride (0.16 g, 1.2 mmol) was added to a solution of N-ethyl-3-(3-chloro-5-trifluoromethylpyridin-2-yloxy)-5-methylpyrazole-1-carboxamide (0.35 g, 1.0 mmol) in acetic acid (5 ml), and the mixture was stirred at room temperature for 4 hours. After completion of the reaction, the reaction mixture was poured into ice water and extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/10), to give a white solid of N-ethyl-4-chloro-3-(3-chloro-5-trifluoromethylpyridin-2-yloxy)-5-methylpyrazole-1-carboxamide (0.35 g, yield: 92.1%). mp: 111-112° C.; $^1$H-NMR (CDCl$_3$, TMS, ppm): δ 1.23 (t, J=7.3 Hz, 3H), 2.66 (s, 3H), 3.41 (dq, J=5.8 and 7.3 Hz, 2H), 6.85-7.10 (m, 1H), 8.03 (d, J=2.0 Hz, 1H), 8.31 (m, 1H).

Examples 252-260

N-Substituted-3-(3-chloro-5-trifluoromethylpyridin-2-yloxy)-5-methylpyrazole-1-carboxamide derivatives reacted with sulfuryl chloride in the same manner as in Example 251, to give corresponding 4-chloro derivatives. Products/forms/yields/melting points/NMR spectra are described below.

Example 252

N-methyl-4-chloro-3-(3-chloro-5-trifluoromethylpyridin-2-yloxy)-5-methylpyrazole-1-carboxamide/white solid/yield: 97.1%/mp: 81-83° C./$^1$H-NMR (CDCl$_3$, TMS, ppm): δ 2.66 (s, 3H), 2.96 (d, J=5.0 Hz, 3H), 6.80-7.15 (m, 1H), 8.04 (d, J=2.1 Hz, 1H), 8.32 (m, 1H).

Example 253

N-propyl-4-chloro-3-(3-chloro-5-trifluoromethylpyridin-2-yloxy)-5-methylpyrazole-1-carboxamide/white solid/yield: 90.4%/mp: 54-56° C./$^1$H-NMR (CDCl$_3$, TMS, ppm): δ 0.97 (t, J=7.3 Hz, 3H), 1.62 (tq, J=7.0 and 7.3 Hz, 2H), 2.65 (s, 3H), 3.32 (dt, J=7.0 and 7.3 Hz, 2H), 6.90-7.15 (m, 1H), 8.03 (d, J=2.1 Hz, 1H), 8.31 (m, 1H).

Example 254

N-isopropyl-4-chloro-3-(3-chloro-5-trifluoromethylpyridin-2-yloxy)-5-methylpyrazole-1-carboxamide/white solid/yield: 89.2%/mp: 57-59° C./$^1$H-NMR (CDCl$_3$, TMS, ppm): δ 1.25 (d, J=6.5 Hz, 6H), 2.65 (s, 3H), 3.95-4.20 (m, 1H), 6.75-6.95 (m, 1H), 8.04 (d, J=2.0 Hz, 1H), 8.32 (m, 1H).

Example 255

N-pentyl-4-chloro-3-(3-chloro-5-trifluoromethylpyridin-2-yloxy)-5-methylpyrazole-1-carboxamide/white solid/yield: 80.0%/mp: 76-78° C./$^1$H-NMR (CDCl$_3$, TMS, ppm): δ 0.90 (t, J=6.9 Hz, 3H), 1.20-1.45 (m, 4H), 1.50-1.70 (m, 2H), 2.65 (s, 3H), 3.25-3.45 (m, 2H), 6.85-7.10 (m, 1H), 8.03 (d, J=2.0 Hz, 1H), 8.32 (m, 1H).

Example 256

N-hexyl-4-chloro-3-(3-chloro-5-trifluoromethylpyridin-2-yloxy)-5-methylpyrazole-1-carboxamide/white solid/yield: 70.6%/mp: 57-59° C./$^1$H-NMR (CDCl$_3$, TMS, ppm): δ 0.88 (t, J=6.9 Hz, 3H), 1.15-1.45 (m, 6H), 1.45-1.70 (m, 2H), 2.65 (s, 3H), 3.20-3.45 (m, 2H), 6.90-7.05 (m, 1H), 8.04 (d, J=2.5 Hz, 1H), 8.32 (m, 1H).

Example 257

N-heptyl-4-chloro-3-(3-chloro-5-trifluoromethylpyridin-2-yloxy)-5-methylpyrazole-1-carboxamide/white solid/yield: 80.0%/mp: 67-68° C./$^1$H-NMR (CDCl$_3$, TMS, ppm): δ 0.88 (t, J=7.0 Hz, 3H), 1.10-1.45 (m, 8H), 1.45-1.70 (m, 2H), 2.65 (s, 3H), 3.20-3.50 (m, 2H), 6.80-7.10 (m, 1H), 8.03 (d, J=2.0 Hz, 1H), 8.32 (m, 1H).

Example 258

N-octyl-4-chloro-3-(3-chloro-5-trifluoromethylpyridin-2-yloxy)-5-methylpyrazole-1-carboxamide/white solid/yield: 88.6%/mp: 61-62° C./$^1$H-NMR (CDCl$_3$, TMS, ppm): δ 0.87 (t, J=6.3 Hz, 3H), 1.15-1.45 (m, 10H), 1.45-1.70 (m, 2H), 2.65 (s, 3H), 3.25-3.45 (m, 2H), 6.90-7.10 (m, 1H), 8.03 (d, J=1.8 Hz, 1H), 8.32 (m, 1H).

Example 259

N-dodecyl-4-chloro-3-(3-chloro-5-trifluoromethylpyridin-2-yloxy)-5-methylpyrazole-1-carboxamide/white solid/yield: 89.9%/mp: 68-70° C./$^1$H-NMR (CDCl$_3$, TMS, ppm): δ 0.88 (t, J=6.9 Hz, 3H), 1.15-1.40 (m, 18H), 1.50-1.65 (m, 2H), 2.65 (s, 3H), 3.25 (m, 2H), 6.90-7.10 (m, 1H), 8.04 (d, J=1.9 Hz, 1H), 8.25-8.35 (m, 1H).

Example 260

N-cyclohexyl-4-chloro-3-(3-chloro-5-trifluoromethylpyridin-2-yloxy)-5-methylpyrazole-1-carboxamide/white solid/yield: 85.7%/mp: 94-96° C./$^1$H-NMR (CDCl$_3$, TMS, ppm): δ 1.05-1.50 (m, 6H), 1.55-1.90 (m, 2H), 1.90-2.10 (m, 2H), 2.65 (s, 3H), 3.60-3.85 (m, 1H), 6.75-7.00 (m, 1H), 8.03 (d, J=1.8 Hz, 1H), 8.32 (m, 1H).

Example 261

N-(2-chloroethyl)-4-chloro-3-(3-chloro-5-trifluoromethylpyridin-2-yloxy)-5-methylpyrazole-1-carboxamide/white solid/yield: 86.2%/mp: 112-114° C./$^1$H-NMR (CDCl$_3$, TMS, ppm): δ 2.65 (s, 3H), 3.60-3.80 (m, 4H), 7.30-7.45 (m, 1H), 8.04 (d, J=2.1 Hz, 1H), 8.32 (m, 1H).

Example 262

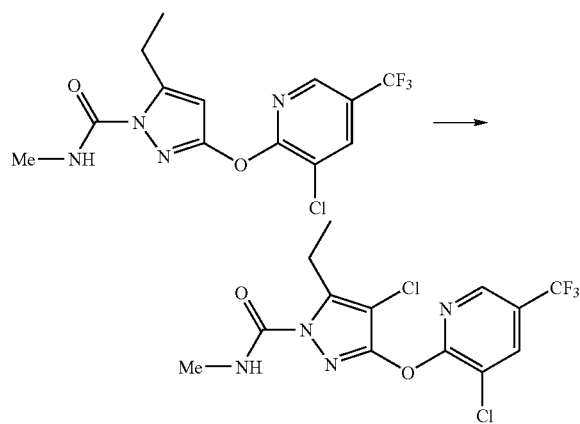

Sulfuryl chloride (0.17 g, 1.2 mmol) was added to a solution of N-methyl-3-(3-chloro-5-trifluoromethylpyridin-2-yloxy)-5-ethylpyrazole-1-carboxamide (0.35 g, 1.0 mmol) in acetic acid (5 ml), and the mixture was stirred at room temperature for 5 hours. After completion of the reaction, the reaction mixture was poured into ice water and extracted with ethyl acetate (10 ml×3). The organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/10), to give a white solid of N-methyl-4-chloro-3-(3-chloro-5-trifluoromethylpyridin-2-yloxy)-5-ethylpyrazole-1-carboxamide (0.31 g, yield: 80.9%). mp: 88-89° C.; $^1$H-NMR (CDCl$_3$, TMS, ppm): δ 1.30 (t, J=7.4 Hz, 3H), 2.96 (d, J=5.0 Hz, 3H), 3.14 (q, J=7.4 Hz, 2H), 6.90-7.10 (m, 1H), 8.04 (d, J=2.0 Hz, 1H), 8.32 (m, 1H).

Example 263

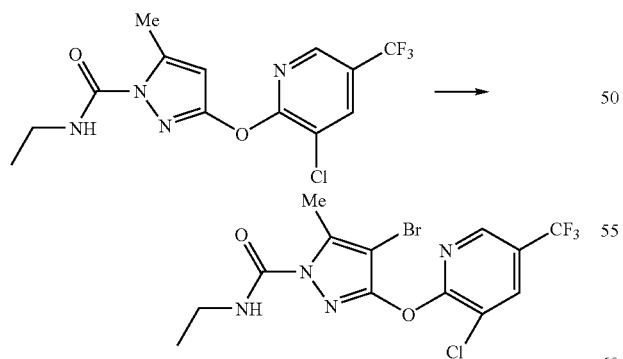

N-Bromosuccinimide (0.64 g, 3.6 mmol) was added to a solution of N-ethyl-3-(3-chloro-5-trifluoromethylpyridin-2-yloxy)-5-methylpyrazole-1-carboxamide (1.05 g, 3.0 mmol) in dichloromethane (20 ml), and the mixture was stirred at room temperature for 6 hours. After completion of the reaction, water was added to the reaction mixture, and the mixture was extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/7), to give a white solid of N-ethyl-4-bromo-3-(3-chloro-5-trifluoromethylpyridin-2-yloxy)-5-methylpyrazole-1-carboxamide (0.86 g, yield: 67.0%). mp: 123-125° C.; $^1$H-NMR (CDCl$_3$, TMS, ppm): δ 1.23 (t, J=7.3 Hz, 3H), 2.67 (s, 3H), 3.40 (dq, J=5.9 and 7.3 Hz, 2H), 6.90-7.10 (m, 1H), 8.04 (d, J=2.0 Hz, 1H), 8.32 (m, 1H).

Example 264

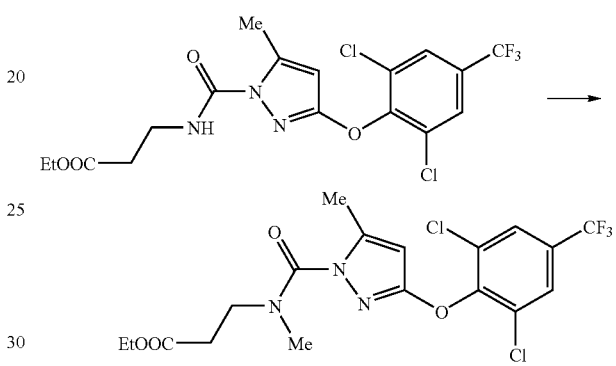

Sodium hydride (60% in oil, 0.03 g, 0.7 mmol) was added to a solution of ethyl 3-[{3-(2,6-dichloro-4-trifluoromethylphenyloxy)-5-methylpyrazol-1-yl}carbonylamino]propionate (0.30 g, 0.7 mmol) in DMF (5 ml) at 0° C., and the mixture was stirred at an ambient temperature for 30 minutes. Then, methyl iodide (0.10 g, 0.7 mmol) was added, and the mixture was allowed to have room temperature gradually and stirred overnight. After completion of the reaction, the reaction mixture was poured into water (10 ml) and extracted with ethyl acetate (10 ml×2). An organic layer was washed with water (10 ml×3), dried over anhydrous magnesium sulfate and filtered to remove a desiccant. The solvent was distilled off from the filtrate under reduced pressure. The resultant crude product was purified with a silica gel column (ethyl acetate/hexane=1/15), to give a colorless viscous substance of ethyl 3-[{3-(2,6-dichloro-4-trifluoromethylphenyloxy)-5-methylpyrazol-1-yl}carbonyl]methylamino]propionate (0.23 g, yield: 74.4%). $^1$H-NMR (CDCl$_3$, TMS, ppm): δ 1.28 (t, J=7.1 Hz, 3H), 2.22-2.40 (m, 2H), 2.45 (s, 3H), 2.96 (s, 3H), 3.57 (m, 2H), 4.12 (q, J=7.1 Hz, 2H), 5.83 (s, 1H), 7.63 (s, 2H).

Example 265

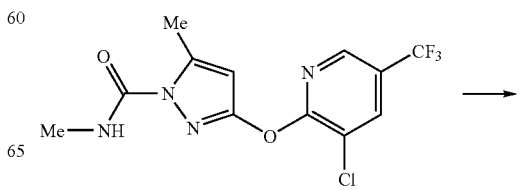

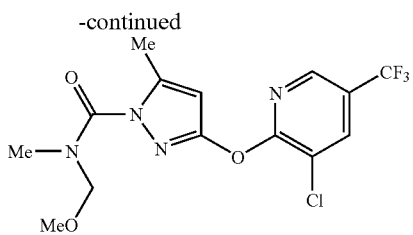

Chloromethyl methyl ether (0.16 g, 2.0 mmol) was added to a solution of sodium hydride (60% in oil, 0.09 g, 2.2 mmol) and N-methyl-3-(3-chloro-5-trifluoromethylpyridin-2-yloxy)-5-methylpyrazole-1-carboxamide (0.67 g, 2.0 mmol) in DMF (10 ml) at 0° C., and while the mixture was allowed to have room temperature gradually, the mixture was stirred overnight. After completion of the reaction, water was added to the reaction mixture, and the mixture was extracted with ethyl acetate (10 ml×3). An organic layer was washed with water, dried over anhydrous magnesium sulfate and filtered to remove a desiccant. The solvent was distilled off from the filtrate under reduced pressure. The resultant crude product was purified with a silica gel column (ethyl acetate/hexane=1/5), to give a colorless viscous substance of N-methyl-N-methoxymethyl-3-(3-chloro-5-trifluoromethylpyridin-2-yloxy)-5-methylpyrazole-1-carboxamide (0.18 g, yield: 23.8%). $^1$H-NMR (CDCl$_3$, TMS, ppm): δ 1.87 (s, 3H), 3.52 (s, 3H), 3.53 (s, 3H), 5.18 (s, 2H), 5.46 (s, 1H), 7.80-7.95 (m, 1H), 8.50-8.65 (m, 1H).

The following Tables 1 to 4 show compounds of the present invention that can be synthesized by those processes shown in the above Production Examples, Referential Examples and Examples. The present invention shall not be limited to these compounds. Abbreviations in Tables have the following meanings. Me: methyl; Et: ethyl, Pr: propyl; i-Pr: isopropyl; c-Pr: cyclopropyl, Bu: butyl; i-Bu: isobutyl; s-Bu: secondary butyl; t-Bu: tertiary butyl; Pent: pentyl; c-Pent: cyclopentyl; Hex: hexyl; c-Hex: cyclohexyl; Hep: heptyl; Oct: octyl; Dod: dodecyl;

*1): tetrahydrofurfuryl;

*2): (1,3-dioxa-2-cyclopentyl)methyl;

*3): (1,3-dioxa-2-cyclohexyl)methyl;

*4): furfuryl;

*5): 2-morpholinoethyl;

*6): 2-picolyl;

*7): 2-thienylmethyl;

*8): (4-chloro-5-cyclopentyloxy-2-fluoro)phenyl;

TABLE 1

3-(Substituted phenyloxy)pyrazole derivatives

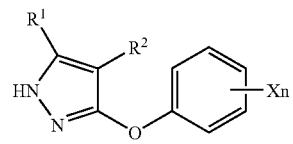

| Compound No. | Example No. | R$^1$ | R$^2$ | Xn |
| --- | --- | --- | --- | --- |
| 1-1 | | H | H | 2,6-Cl$_2$-4-CF$_3$ |
| 1-2 | | H | H | 2-Cl-6-F-4-CF$_3$ |
| 1-3 | 47 | Me | H | H |
| 1-4 | 3 | Me | H | 3-Me-4-NO$_2$ |
| 1-5 | 4 | Me | H | 3-MeO-4-NO$_2$ |
| 1-6 | 40 | Me | H | 3-EtO-4-NO$_2$ |
| 1-7 | 41 | Me | H | 5-EtO-2-NO$_2$ |
| 1-8 | 48 | Me | H | 3-Cl |
| 1-9 | | Me | Cl | 3-Cl |
| 1-10 | | Me | H | 2-Cl-4-CF$_3$ |
| 1-11 | | Me | Cl | 2-Cl-4-CF$_3$ |
| 1-12 | 51 | Me | H | 4-Cl-2-CF$_3$ |
| 1-13 | | Me | Cl | 4-Cl-2-CF$_3$ |
| 1-14 | 50 | Me | H | 4-Cl-3-CF$_3$ |
| 1-15 | | Me | Cl | 4-Cl-3-CF$_3$ |
| 1-16 | | Me | H | 4-F-3-CF$_3$ |
| 1-17 | 18 | Me | H | 2,6-Cl$_2$-4-CF$_3$ |
| 1-18 | 52 | Me | Cl | 2, 6-Cl$_2$-4-CF$_3$ |
| 1-19 | 29 | Me | H | 2-Cl-6-F-4-CF$_3$ |
| 1-20 | | Me | Cl | 2-Cl-6-F-4-CF$_3$ |
| 1-21 | 31 | Me | H | 2-Cl-6-NO$_2$-4-CF$_3$ |
| 1-22 | 44 | Me | H | 3-Cl-4-NH$_2$ |
| 1-23 | 14 | Me | H | 3-Cl-4-NO$_2$ |
| 1-24 | | Me | Cl | 3-Cl-4-NO$_2$ |
| 1-25 | 14 | Me | H | 5-Cl-2-NO$_2$ |
| 1-26 | 15 | Me | H | 3-F-4-NO$_2$ |
| 1-27 | | Me | Cl | 3-F-4-NO$_2$ |
| 1-28 | 15 | Me | H | 5-F-2-NO$_2$ |
| 1-29 | 2 | Me | H | 4-F-2-NO$_2$ |
| 1-30 | 17 | Me | H | 4-CN-2-CF$_3$ |
| 1-31 | 49 | Me | H | 2-CF$_3$ |
| 1-32 | 46 | Me | H | 3-CF$_3$ |
| 1-33 | | Me | Cl | 3-CF$_3$ |
| 1-34 | | Me | H | 2,4-(CF$_3$)$_2$ |
| 1-35 | | Me | Cl | 2,4-(CF$_3$)$_2$ |
| 1-36 | 43 | Me | H | 4-NH$_2$ |
| 1-37 | 42 | Me | H | 4-NH$_2$-2-CF$_3$ |
| 1-38 | 45 | Me | H | 4-NH$_2$-3-CF$_3$ |
| 1-39 | | Me | H | 2-NH$_2$-4-CF$_3$ |
| 1-40 | 10 | Me | H | 4-NO$_2$-2-CF$_3$ |
| 1-41 | | Me | Cl | 4-NO$_2$-2-CF$_3$ |
| 1-42 | 16 | Me | H | 4-NO$_2$-3-CF$_3$ |
| 1-43 | | Me | Cl | 4-NO$_2$-3-CF$_3$ |
| 1-44 | 5 | Me | H | 2-NO$_2$-4-CF$_3$ |
| 1-45 | | Me | Cl | 2-NO$_2$-4-CF$_3$ |
| 1-46 | 30 | Me | H | 2,4-(NO$_2$)$_2$-6-CF$_3$ |
| 1-47 | 1 | Me | H | 4-NO$_2$ |
| 1-48 | 26 | Me | Me | 2,6-Cl$_2$-4-CF$_3$ |
| 1-49 | | Me | Me | 2-Cl-6-F-4-CF$_3$ |
| 1-50 | 12 | Me | Me | 4-NO$_2$-2-CF$_3$ |
| 1-51 | 8 | Me | Me | 2-NO$_2$-4-CF$_3$ |
| 1-52 | 27 | Me | Et | 2,6-Cl$_2$-4-CF$_3$ |
| 1-53 | | Me | Et | 2-Cl-6-F-4-CF$_3$ |
| 1-54 | 13 | Me | Et | 4-NO$_2$-2-CF$_3$ |
| 1-55 | 9 | Me | Et | 2-NO$_2$-4-CF$_3$ |
| 1-56 | 19 | Et | H | 2,6-Cl$_2$-4-CF$_3$ |
| 1-57 | | Et | Cl | 2,6-Cl$_2$-4-CF$_3$ |
| 1-58 | | Et | H | 2-Cl-6-F-4-CF$_3$ |
| 1-59 | | Et | Cl | 2-Cl-6-F-4-CF$_3$ |
| 1-60 | 11 | Et | H | 4-NO$_2$-2-CF$_3$ |
| 1-61 | | Et | Cl | 4-NO$_2$-2-CF$_3$ |
| 1-62 | 7 | Et | H | 2-NO$_2$-4-CF$_3$ |
| 1-63 | | Et | Cl | 2-NO$_2$-4-CF$_3$ |
| 1-64 | | Pr | H | 2,6-Cl$_2$-4-CF$_3$ |
| 1-65 | | Pr | H | 2-Cl-6-F-4-CF$_3$ |
| 1-66 | 20 | i-Pr | H | 2,6-Cl$_2$-4-CF$_3$ |
| 1-67 | | i-Pr | H | 2-Cl-6-F-4-CF$_3$ |
| 1-68 | 22 | c-Pr | H | 2,6-Cl$_2$-4-CF$_3$ |
| 1-69 | | c-Pr | H | 2-Cl-6-F-4-CF$_3$ |

TABLE 1-continued

3-(Substituted phenyloxy)pyrazole derivatives

| Compound No. | Example No. | $R^1$ | $R^2$ | Xn |
|---|---|---|---|---|
| 1-70 | 21 | t-Bu | H | 2,6-Cl$_2$-4-CF$_3$ |
| 1-71 | | t-Bu | H | 2-Cl-6-F-4-CF$_3$ |
| 1-72 | 23 | MeOCH$_2$ | H | 2,6-Cl$_2$-4-CF$_3$ |
| 1-73 | | MeOCH$_2$ | H | 2-Cl-6-F-4-CF$_3$ |
| 1-74 | 25 | MeO$_2$CCH$_2$ | H | 2,6-Cl$_2$-4-CF$_3$ |
| 1-75 | | MeO$_2$CCH$_2$ | H | 2-Cl-6-F-4-CF$_3$ |
| 1-76 | | CF$_3$ | H | 2,6-Cl$_2$-4-CF$_3$ |
| 1-77 | 6 | CF$_3$ | H | 2-NO$_2$-4-CF$_3$ |
| 1-78 | | CF$_3$ | H | 2-Cl-6-F-4-CF$_3$ |
| 1-79 | 24 | MeO$_2$C | H | 2,6-Cl$_2$-4-CF$_3$ |
| 1-80 | | MeO$_2$C | H | 2-Cl-6-F-4-CF$_3$ |
| 1-81 | | EtO$_2$C | H | 2,6-Cl$_2$-4-CF$_3$ |
| 1-82 | | EtO$_2$C | H | 2-Cl-6-F-4-CF$_3$ |
| 1-83 | 28 | 4-Cl-C$_6$H$_4$ | H | 2,6-Cl$_2$-4-CF$_3$ |
| 1-84 | | 4-Cl-C$_6$H$_4$ | H | 2-Cl-6-F-4-CF$_3$ |

TABLE 2

3-(Substituted pyridyloxy)pyrazole derivatives

| Compound No. | Example No. | $R^1$ | $R^2$ | Xn |
|---|---|---|---|---|
| 2-1 | | H | H | 3-Cl-5-CF$_3$ |
| 2-2 | 34 | Me | H | 4-Me-5-NO$_2$ |
| 2-3 | 33 | Me | H | 6-MeO-3-NO$_2$ |
| 2-4 | 32 | Me | H | 3,5-Cl$_2$ |
| 2-5 | 35 | Me | H | 3-Cl-5-CF$_3$ |
| 2-6 | | Me | Cl | 3-Cl-5-CF$_3$ |
| 2-7 | | Me | H | 5-CF$_3$ |
| 2-8 | | Me | H | 3,5-(NO$_2$)$_2$ |
| 2-9 | 38 | Me | Me | 3-Cl-5-CF$_3$ |
| 2-10 | 39 | Me | Et | 3-Cl-5-CF$_3$ |
| 2-11 | 37 | Et | H | 3-Cl-5-CF$_3$ |
| 2-12 | | Et | Cl | 3-Cl-5-CF$_3$ |
| 2-13 | | Pr | H | 3-Cl-5-CF$_3$ |
| 2-14 | | i-Pr | H | 3-Cl-5-CF$_3$ |
| 2-15 | | c-Pr | H | 3-Cl-5-CF$_3$ |
| 2-16 | | t-Bu | H | 3-Cl-5-CF$_3$ |
| 2-17 | | MeOCH$_2$ | H | 3-Cl-5-CF$_3$ |
| 2-18 | | MeO$_2$CCH$_2$ | H | 3-Cl-5-CF$_3$ |
| 2-19 | 36 | CF$_3$ | H | 3-Cl-5-CF$_3$ |
| 2-20 | | MeO$_2$C | H | 3-Cl-5-CF$_3$ |
| 2-21 | | 4-Cl-C$_6$H$_4$ | H | 3-Cl-5-CF$_3$ |

TABLE 3

Synthesis of 3-(substituted Phenyloxy)pyrazole derivatives

| Compound No. | Example No. | $R^1$ | $R^2$ | $R^3$ | $R^4$ | Xn | Y |
|---|---|---|---|---|---|---|---|
| 3-1 | | H | H | H | H | 2,6-Cl$_2$-4-CF$_3$ | O |
| 3-2 | | H | H | H | H | 2-Cl-6-F-4-CF$_3$ | O |
| 3-3 | 223 | Me | H | H | H | 2,6-Cl$_2$-4-CF$_3$ | O |
| 3-4 | | Me | H | H | H | 2,6-Cl$_2$-4-CF$_3$ | S |
| 3-5 | 224 | Me | H | H | H | 2-Cl-6-F-4-CF$_3$ | O |
| 3-6 | | Me | H | H | H | 2-Cl-6-F-4-CF$_3$ | S |
| 3-7 | | Me | H | H | H | 2-Cl-4-NO$_2$-6-CF$_3$ | O |
| 3-8 | 226 | Me | H | H | H | 3-CF$_3$ | O |
| 3-9 | | Me | H | H | H | 4-NO$_2$-2-CF$_3$ | O |
| 3-10 | | Me | H | H | H | 4-NO$_2$-3-CF$_3$ | O |
| 3-11 | | Me | H | H | H | 2-NO$_2$-4-CF$_3$ | O |
| 3-12 | 118 | Me | H | Me | H | 2-Cl-6-F-4-CF$_3$ | O |
| 3-13 | | Me | H | Me | H | 2-Cl-6-F-4-CF$_3$ | S |
| 3-14 | 105 | Me | H | Me | H | 2,6-Cl$_2$-4-CF$_3$ | O |
| 3-15 | 179 | Me | H | Me | H | 2,6-Cl$_2$-4-CF$_3$ | S |
| 3-16 | | Me | H | Me | Me | 2,6-Cl$_2$-4-CF$_3$ | O |
| 3-17 | | Me | H | Me | Me | 2,6-Cl$_2$-4-CF$_3$ | S |
| 3-18 | | Me | H | Me | Et | 2,6-Cl$_2$-4-CF$_3$ | O |
| 3-19 | | Me | H | Me | Et | 2,6-Cl$_2$-4-CF$_3$ | S |
| 3-20 | | Me | H | Me | MeOCH$_2$ | 2,6-Cl$_2$-4-CF$_3$ | O |
| 3-21 | | Me | H | Me | MeOCH$_2$ | 2,6-Cl$_2$-4-CF$_3$ | S |
| 3-22 | | Me | H | Me | EtOCH$_2$ | 2,6-Cl$_2$-4-CF$_3$ | O |
| 3-23 | | Me | H | Me | EtOCH$_2$ | 2,6-Cl$_2$-4-CF$_3$ | S |
| 3-24 | 127 | Me | H | Me | H | 2-Cl-4-NO$_2$-6-CF$_3$ | O |

TABLE 3-continued

Synthesis of 3-(substituted Phenyloxy)pyrazole derivatives

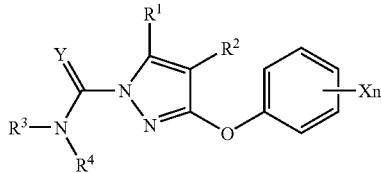

| Compound No. | Example No. | R¹ | R² | R³ | R⁴ | Xn | Y |
|---|---|---|---|---|---|---|---|
| 3-25 |  | Me | H | Me | H | 2-Cl-4-NO$_2$-6-CF$_3$ | S |
| 3-26 |  | Me | H | Me | H | 4-NH$_2$-2-CF$_3$ | O |
| 3-27 |  | Me | H | Me | H | 4-NH$_2$-3-CF$_3$ | O |
| 3-28 | 242 | Me | H | Me | H | 2-NH$_2$-4-CF$_3$ | O |
| 3-29 | 92 | Me | H | Me | H | 4-NO$_2$-2-CF$_3$ | O |
| 3-30 |  | Me | H | Me | H | 4-NO$_2$-2-CF$_3$ | S |
| 3-31 | 103 | Me | H | Me | H | 4-NO$_2$-3-CF$_3$ | O |
| 3-32 |  | Me | H | Me | H | 4-NO$_2$-3-CF$_3$ | S |
| 3-33 | 87 | Me | H | Me | H | 2-NO$_2$-4-CF$_3$ | O |
| 3-34 |  | Me | H | Me | Me | 2-NO$_2$-4-CF$_3$ | O |
| 3-35 |  | Me | H | Me | H | 2-NO$_2$-4-CF$_3$ | S |
| 3-36 |  | Me | H | Me | H | 2,4-(NO$_2$)$_2$-6-CF$_3$ | O |
| 3-37 |  | Me | H | Me | H | 2,4-(NO$_2$)$_2$-6-CF$_3$ | S |
| 3-38 |  | Me | H | Me | H | 4-NO$_2$ | O |
| 3-39 |  | Me | H | Me | H | 4-NO$_2$ | S |
| 3-40 | 53 | Me | H | Et | H | H | O |
| 3-41 | 97 | Me | H | Et | H | 3-Me-4-NO$_2$ | O |
| 3-42 | 98 | Me | H | Et | H | 3-EtO-4-NO$_2$ | O |
| 3-43 | 99 | Me | H | Et | H | 5-EtO-2-NO$_2$ | O |
| 3-44 | 106 | Me | H | Et | H | 2,6-Cl$_2$-4-CF$_3$ | O |
| 3-45 | 180 | Me | H | Et | H | 2,6-Cl$_2$-4-CF$_3$ | S |
| 3-46 | 119 | Me | H | Et | H | 2-Cl-6-F-4-CF$_3$ | O |
| 3-47 | 186 | Me | H | Et | H | 2-Cl-6-F-4-CF$_3$ | S |
| 3-48 |  | Me | H | Et | H | 2-Cl-4-CF$_3$ | O |
| 3-49 |  | Me | H | Et | H | 2-Cl-4-CF$_3$ | S |
| 3-50 | 84 | Me | H | Et | H | 4-Cl-2-CF$_3$ | O |
| 3-51 | 101 | Me | H | Et | H | 4-Cl-3-CF$_3$ | O |
| 3-52 | 124 | Me | H | Et | H | 2,6-F$_2$-4-CF$_3$ | O |
| 3-53 |  | Me | H | Et | Me | 2,6-Cl$_2$-4-CF$_3$ | O |
| 3-54 |  | Me | H | Et | Et | 2,6-Cl$_2$-4-CF$_3$ | O |
| 3-55 |  | Me | H | Et | MeOCH$_2$ | 2,6-Cl$_2$-4-CF3 | O |
| 3-56 |  | Me | H | Et | EtOCH$_2$ | 2,6-Cl2-4-CF3 | O |
| 3-57 | 126 | Me | H | Et | H | 2-Cl-4-NO$_2$-6-CF$_3$ | O |
| 3-58 |  | Me | H | Et | H | 2-Cl-4-NO$_2$-6-CF$_3$ | S |
| 3-59 | 85 | Me | H | Et | H | 4-F-2-NO$_2$ | O |
| 3-60 | 57 | Me | H | Et | H | 3-CF$_3$ | O |
| 3-61 | 95 | Me | H | Et | H | 4-CN-2-CF$_3$ | O |
| 3-62 |  | Me | H | Et | H | 4-NH$_2$-2-CF$_3$ | O |
| 3-63 | 100 | Me | H | Et | H | 4-NH$_2$-3-CF$_3$ | O |
| 3-64 |  | Me | H | Et | H | 2-NH$_2$-4-CF$_3$ | O |
| 3-65 | 93 | Me | H | Et | H | 4-NO$_2$-2-CF$_3$ | O |
| 3-66 | 104 | Me | H | Et | H | 4-NO$_2$-3-CF$_3$ | O |
| 3-67 | 88 | Me | H | Et | H | 2-NO$_2$-4-CF$_3$ | O |
| 3-68 | 125 | Me | H | Et | H | 2,4-(NO$_2$)$_2$-6-CF$_3$ | O |
| 3-69 | 54 | Me | H | Et | H | 4-NO$_2$ | O |
| 3-70 |  | Me | H | Pr | H | 2-Cl-4-CF$_3$ | O |
| 3-71 |  | Me | H | Pr | H | 4-Cl-3-CF$_3$ | O |
| 3-72 | 121 | Me | H | Pr | H | 2-Cl-6-F-4-CF$_3$ | O |
| 3-73 |  | Me | H | Pr | H | 2-Cl-6-F-4-CF$_3$ | S |
| 3-74 | 107 | Me | H | Pr | H | 2,6-Cl$_2$-4-CF$_3$ | O |
| 3-75 | 181 | Me | H | Pr | H | 2,6-Cl$_2$-4-CF$_3$ | S |
| 3-76 | 128 | Me | H | Pr | H | 2,Cl-4-NO$_2$-6-CF$_3$ | O |
| 3-77 |  | Me | H | Pr | H | 2-Cl-4-NO$_2$-6-CF$_3$ | S |
| 3-78 | 91 | Me | H | Pr | H | 4-NO$_2$-2-CF$_3$ | O |
| 3-79 |  | Me | H | Pr | H | 4-NO$_2$-2-CF$_3$ | S |
| 3-80 | 102 | Me | H | Pr | H | 4-NO$_2$-3-CF$_3$ | O |
| 3-81 |  | Me | H | Pr | H | 4-NO$_2$-3-CF$_3$ | S |
| 3-82 | 89 | Me | H | Pr | H | 2-NO$_2$-4-CF$_3$ | O |
| 3-83 |  | Me | H | Pr | H | 2-NO$_2$-4-CF$_3$ | S |
| 3-84 | 56 | Me | H | i-Pr | H | 3-CF$_3$ | O |
| 3-85 |  | Me | H | i-Pr | H | 2-Cl-4-CF$_3$ | O |
| 3-86 |  | Me | H | i-Pr | H | 4-Cl-3-CF$_3$ | O |
| 3-87 | 120 | Me | H | i-Pr | H | 2-Cl-6-F-4-CF$_3$ | O |

TABLE 3-continued

Synthesis of 3-(substituted Phenyloxy)pyrazole derivatives

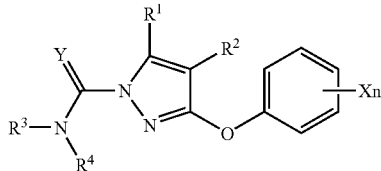

| Compound No. | Example No. | $R^1$ | $R^2$ | $R^3$ | $R^4$ | Xn | Y |
|---|---|---|---|---|---|---|---|
| 3-88 |  | Me | H | i-Pr | H | 2-Cl-6-F-4-CF$_3$ | S |
| 3-89 | 108 | Me | H | i-Pr | H | 2,6-Cl$_2$-4-CF$_3$ | O |
| 3-90 | 182 | Me | H | i-Pr | H | 2,6-Cl$_2$-4-CF$_3$ | S |
| 3-91 | 94 | Me | H | i-Pr | H | 2-NO$_2$-2-CF$_3$ | O |
| 3-92 |  | Me | H | i-Pr | H | 4-NO$_2$-2-CF$_3$ | S |
| 3-93 | 90 | Me | H | i-Pr | H | 2-NO$_2$-4-CF$_3$ | O |
| 3-94 |  | Me | H | i-Pr | H | 2-NO$_2$-4-CF$_3$ | S |
| 3-95 | 132 | Me | H | i-Pr | i-Pr | 2-NO$_2$-4-CF$_3$ | O |
| 3-96 |  | Me | H | Bu | H | 2-Cl-6-F-4-CF$_3$ | O |
| 3-97 |  | Me | H | Bu | H | 2-Cl-6-F-4-CF$_3$ | S |
| 3-98 |  | Me | H | Eu | H | 2,6-Cl$_2$-4-CF$_3$ | O |
| 3-99 | 183 | Me | H | Bu | H | 2,6-Cl$_2$4-CF$_3$ | S |
| 3-100 |  | Me | H | i-Bu | H | 2-Cl-6-F-4-CF$_3$ | O |
| 3-101 |  | Me | H | i-Bu | H | 2-Cl-6-F-4-CF3 | S |
| 3-102 |  | Me | H | i-Eu | H | 2,6-Cl$_2$-4-CF$_3$ | O |
| 3-103 |  | Me | H | s-Bu | H | 2-Cl-6-F-4-CF$_3$ | O |
| 3-104 |  | Me | H | s-Bu | H | 2-Cl-6-F-4-CF$_3$ | S |
| 3-105 | 202 | Me | H | s-Bu | H | 2,6-Cl$_2$-4-CF$_3$ | O |
| 3-106 | 58 | Me | H | t-Bu | H | 3-CF$_3$ | O |
| 3-107 | 109 | Me | H | t-Bu | H | 2,6-Cl$_2$-4-CF$_3$ | O |
| 3-108 |  | Me | H | t-Bu | H | 2-Cl-6-F-4-CF$_3$ | O |
| 3-109 | 86 | Me | H | t-Bu | H | 2-NO$_2$-4-CF$_3$ | O |
| 3-110 |  | Me | H | Pent | H | 2,6-Cl$_2$-4-CF$_3$ | O |
| 3-111 |  | Me | H | 3-Pent | H | 2-Cl-6-F-4-CF$_3$ | O |
| 3-112 | 203 | Me | H | 3-Pent | H | 2,6-Cl$_2$-4-CF$_3$ | O |
| 3-113 | 59 | Me | H | Hex | H | 3-CF$_3$ | O |
| 3-114 | 110 | Me | H | Hex | H | 2,6-Cl$_2$-4-CF$_3$ | O |
| 3-115 |  | Me | H | Hex | H | 2-Cl-6-F-4-CF$_3$ | O |
| 3-116 |  | Me | H | Hep | H | 2,6-Cl$_2$-4-CF$_3$ | O |
| 3-117 |  | Me | H | Hep | H | 2-Cl-6-F-4-CF$_3$ | O |
| 3-118 | 111 | Me | H | Oct | H | 2,6-Cl$_2$-4-CF$_3$ | O |
| 3-119 |  | Me | H | Oct | H | 2-Cl-6-F-4-CF$_3$ | O |
| 3-120 |  | Me | H | Dod | H | 2,6-Cl$_2$-4-CF$_3$ | O |
| 3-121 |  | Me | H | Dod | H | 2-Cl-6-F-4-CF$_3$ | O |
| 3-122 | 201 | Me | H | c-Pr | H | 2,6-Cl$_2$-4-CF$_3$ | O |
| 3-123 |  | Me | H | c-Pr | H | 2,6-Cl$_2$-4-CF$_3$ | S |
| 3-124 |  | Me | H | c-Pr | H | 2-Cl-6-F-4-CF$_3$ | O |
| 3-125 | 204 | Me | H | c-Pent | H | 2,6-Cl$_2$-4-CF$_3$ | O |
| 3-126 |  | Me | H | c-Pent | H | 2-Cl-6-F-4-CF$_3$ | O |
| 3-127 | 60 | Me | H | c-Hex | H | 3-CF$_3$ | O |
| 3-128 |  | Me | H | c-Hex | H | 2,6-Cl$_2$-4-CF$_3$ | O |
| 3-129 |  | Me | H | c-Hex | H | 2-Cl-6-F-4-CF$_3$ | O |
| 3-130 | 112,234 | Me | H | H$_2$C=CHCH$_2$ | H | 2,6-Cl$_2$-4-CF$_3$ | O |
| 3-131 |  | Me | H | H$_2$C=CHCH$_2$ | H | 2,6-Cl$_2$-4-CF$_3$ | S |
| 3-132 | 122 | Me | H | H$_2$C=CHCH$_2$ | H | 2-Cl-6-F-4-CF$_3$ | O |
| 3-133 |  | Me | H | H$_2$C=CHCH$_2$ | H | 2-Cl-6-F-4-CF$_3$ | S |
| 3-134 | 61 | Me | H | H$_2$C=CHCH$_2$ | H | 3-CF$_3$ | O |
| 3-135 |  | Me | H | H$_2$C=CHCH$_2$ | H | 3-CF$_3$ | S |
| 3-136 | 205 | Me | H | HC≡CCH$_2$ | H | 2,6-Cl$_2$-4-CF$_3$ | O |
| 3-137 |  | Me | H | HC≡CCH$_2$ | H | 2-Cl-6-F-4-CF$_3$ | O |
| 3-138 | 229 | Me | H | HCOCH$_2$ | H | 2,6-Cl$_2$-4-CF$_3$ | O |
| 3-139 |  | Me | H | HCOCH$_2$ | H | 2-Cl-6-F-4-CF$_3$ | O |
| 3-140 | 211 | Me | H | CF$_3$CH$_2$ | H | 2,6-Cl$_2$-4-CF$_3$ | O |
| 3-141 |  | Me | H | CF$_3$CH$_2$ | H | 2-Cl-6-F-4-CF$_3$ | O |
| 3-142 | 62 | Me | H | 2-ClC$_2$H$_4$ | H | 3-CF$_3$ | O |
| 3-143 | 113 | Me | H | 2-ClC$_2$H$_4$ | H | 2,6-Cl$_2$-4-CF$_3$ | O |
| 3-144 |  | Me | H | 2-ClC$_2$H$_4$ | H | 2,6-Cl$_2$-4-CF$_3$ | S |
| 3-145 |  | Me | H | 2-ClC$_2$H$_4$ | H | 2-Cl-6-F-4-CF$_3$ | O |
| 3-146 | 114 | Me | H | 2-BrC$_2$H$_4$ | H | 2,6-Cl$_2$-4-CF$_3$ | O |
| 3-147 |  | Me | H | 2-BrC$_2$H$_4$ | H | 2,6-Cl$_2$-4-CF$_3$ | S |
| 3-148 | 123 | Me | H | 2-BrC$_2$H$_4$ | H | 2-Cl-6-F-4-CF$_3$ | O |
| 3-149 |  | Me | H | 2-FC$_2$H$_4$ | H | 2,6-Cl$_2$-4-CF$_3$ | O |
| 3-150 |  | Me | H | 2-FC$_2$H$_4$ | H | 2-Cl-6-F-4-CF$_3$ | O |

TABLE 3-continued

Synthesis of 3-(substituted Phenyloxy)pyrazole derivatives

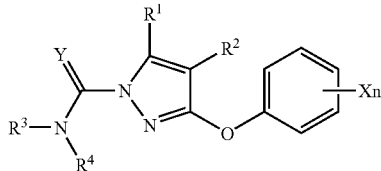

| Compound No. | Example No. | R¹ | R² | R³ | R⁴ | Xn | Y |
|---|---|---|---|---|---|---|---|
| 3-151 | 210 | Me | H | 2-HOC$_2$H$_4$ | H | 2,6-Cl$_2$-4-CF$_3$ | O |
| 3-152 | | Me | H | 2-HOC$_2$H$_4$ | H | 2-Cl-6-F-4-CF$_3$ | O |
| 3-153 | | Me | H | MeO | H | 2,6-Cl$_2$-4-CF$_3$ | O |
| 3-154 | | Me | H | MeO | H | 2,6-Cl$_2$-4-CF$_3$ | S |
| 3-155 | | Me | H | MeO | H | 2-Cl-6-F-4-CF$_3$ | O |
| 3-156 | | Me | H | MeO | H | 2-Cl-6-F-4-CF$_3$ | S |
| 3-157 | 198 | Me | H | EtO | H | 3-CF$_3$ | O |
| 3-158 | 206 | Me | H | EtO | H | 2,6-Cl$_2$-4-CF$_3$ | O |
| 3-159 | | Me | H | EtO | H | 2,6-Cl$_2$-4-CF$_3$ | S |
| 3-160 | | Me | H | EtO | H | 2-Cl-6-F-4-CF$_3$ | O |
| 3-161 | | Me | H | EtO | H | 2-Cl-6-F-4-CF$_3$ | S |
| 3-162 | 207 | Me | H | t-BuO | H | 2,6-Cl$_2$-4-CF$_3$ | O |
| 3-163 | | Me | H | t-BuO | H | 2-Cl-6-F-4-CF$_3$ | O |
| 3-164 | 208 | Me | H | H$_2$C=CHCH$_2$O | H | 2,6-Cl$_2$-4-CF$_3$ | O |
| 3-165 | | Me | H | H$_2$C=CHCH$_2$O | H | 2-Cl-6-F-4-CF$_3$ | O |
| 3-166 | 209 | Me | H | C$_6$H$_5$CH$_2$O | H | 2,6-Cl$_2$-4-CF$_3$ | O |
| 3-167 | | Me | H | H$_2$C=CHCH$_2$O | H | 2-Cl-6-F-4-CF$_3$ | O |
| 3-168 | | Me | H | MeOCH$_2$ | H | 2,6-Cl$_2$-4-CF$_3$ | O |
| 3-169 | 178 | Me | H | MeOCH$_2$ | H | 2,6-Cl$_2$-4-CF$_3$ | S |
| 3-170 | | Me | H | MeOCH$_2$ | H | 2-Cl-6-F-4-CF$_3$ | O |
| 3-171 | | Me | H | MeOCH$_2$ | H | 2-Cl-6-F-4-CF$_3$ | S |
| 3-172 | 177 | Me | H | MeOCH$_2$ | H | 4-CN-2-CF$_3$ | S |
| 3-173 | | Me | H | MeOCH$_2$ | H | 4-NO$_2$-2-CF$_3$ | O |
| 3-174 | | Me | H | MeOCH$_2$ | H | 2-NO$_2$-4-CF$_3$ | O |
| 3-175 | | Me | H | MeOCH$_2$CH$_2$ | H | 2,6-Cl$_2$-4-CF$_3$ | O |
| 3-176 | 184 | Me | H | MeOCH$_2$CH$_2$ | H | 2,6-Cl$_2$-4-CF$_3$ | S |
| 3-177 | | Me | H | MeOCH$_2$CH$_2$ | H | 2-Cl-6-F-4-CF$_3$ | O |
| 3-178 | | Me | H | MeOCH$_2$CH$_2$ | H | 2-Cl-6-F-4-CF$_3$ | S |
| 3-179 | 232 | Me | H | (MeO)$_2$CHCH$_2$ | H | 2,6-Cl$_2$-4-CF$_3$ | O |
| 3-180 | | Me | H | (MeO)$_2$CHCH$_2$ | H | 2-Cl-6-F-4-CF$_3$ | O |
| 3-181 | 199 | Me | H | *1) | H | 3-CF$_3$ | O |
| 3-182 | 200 | Me | H | *1) | H | 4-Cl-2-CF$_3$ | O |
| 3-183 | 212 | Me | H | *1) | H | 2,6-Cl$_2$-4-CF$_3$ | O |
| 3-184 | 185 | Me | H | *1) | H | 2,6-Cl$_2$-4-CF$_3$ | S |
| 3-185 | 217 | Me | H | *1) | H | 2-Cl-6-F-4-CF$_3$ | O |
| 3-186 | 230 | Me | H | *2) | H | 2,6-Cl$_2$-4-CF$_3$ | O |
| 3-187 | | Me | H | *2) | H | 2,Cl-6-F-4-CF$_3$ | O |
| 3-188 | 231 | Me | H | *3) | H | 2,6-Cl$_2$-4-CF$_3$ | O |
| 3-189 | | Me | H | *3) | H | 2,Cl-6-F-4-CF$_3$ | O |
| 3-190 | 213 | Me | H | *4) | H | 2,6-Cl$_2$-4-CF$_3$ | O |
| 3-191 | | Me | H | *4) | H | 2-Cl-6-F-4-CF$_3$ | O |
| 3-192 | 214 | Me | H | *5) | H | 2,6-Cl$_2$-4-CF$_3$ | O |
| 3-193 | | Me | H | *5) | H | 2-Cl-6-F-4-CF$_3$ | O |
| 3-194 | 215 | Me | H | *6) | H | 2,6-Cl$_2$-4-CF$_3$ | O |
| 3-195 | | Me | H | *6) | H | 2-Cl-6-F-4-CF$_3$ | O |
| 3-196 | 216 | Me | H | *7) | H | 2,6-Cl$_2$-4-CF$_3$ | O |
| 3-197 | | Me | H | *7) | H | 2-Cl-6-F-4-CF$_3$ | O |
| 3-198 | 116 | Me | H | EtO$_2$CCH$_2$ | H | 2,6-Cl$_2$-4-CF$_3$ | O |
| 3-199 | | Me | H | EtO$_2$CCH$_2$ | H | 2-Cl-6-F-4-CF$_3$ | O |
| 3-200 | 63 | Me | H | EtO$_2$CCH$_2$ | H | 3-CF$_3$ | O |
| 3-201 | 117 | Me | H | EtO$_2$C(CH$_2$)$_2$ | H | 2,6-Cl$_2$-4-CF$_3$ | O |
| 3-202 | | Me | H | EtO$_2$C(CH$_2$)$_2$ | H | 2-Cl-6-F-4-CF$_3$ | O |
| 3-203 | 264 | Me | H | EtO$_2$C(CH$_2$)$_2$ | Me | 2,6-Cl$_2$-4-CF$_3$ | O |
| 3-204 | 83 | Me | H | C$_6$H$_5$ | H | 3-Cl | O |
| 3-205 | 55 | Me | H | C$_6$H$_5$ | H | 2-CF$_3$ | O |
| 3-206 | 64 | Me | H | C$_6$H$_5$ | H | 3-CF$_3$ | O |
| 3-207 | 67 | Me | H | 3-Me-C$_6$H$_4$ | H | 3-CF$_3$ | O |
| 3-208 | 76 | Me | H | 2-Cl-4-Me-C$_6$H$_3$ | H | 3-CF$_3$ | O |
| 3-209 | 78 | Me | H | 2-Cl-6-Me-C$_6$H$_3$ | H | 3-CF$_3$ | O |
| 3-210 | 77 | Me | H | 2-Me-4-NO$_2$-C$_6$H$_3$ | H | 3-CF$_3$ | O |
| 3-211 | 65 | Me | H | 2-Cl-C$_6$H$_4$ | H | 3-CF$_3$ | O |
| 3-212 | 66 | Me | H | 3-Cl-C$_6$H$_4$ | H | 3-CF$_3$ | O |
| 3-213 | | Me | H | 3-Cl-C$_6$H$_4$ | H | 2,6-Cl$_2$-4-CF$_3$ | O |

TABLE 3-continued

Synthesis of 3-(substituted Phenyloxy)pyrazole derivatives

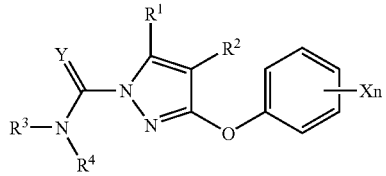

| Compound No. | Example No. | $R^1$ | $R^2$ | $R^3$ | $R^4$ | Xn | Y |
|---|---|---|---|---|---|---|---|
| 3-214 | 69 | Me | H | 4-Cl-C$_6$H$_4$ | H | 3-CF$_3$ | O |
| 3-215 | | Me | H | 4-Cl-C$_6$H$_4$ | H | 2,6-Cl$_2$-4-CF$_3$ | O |
| 3-216 | 80 | Me | H | *8) | H | 3-CF$_3$ | O |
| 3-217 | 70 | Me | H | 4-F-C$_6$H$_4$ | H | 3-CF$_3$ | O |
| 3-218 | | Me | H | 4-F-C$_6$H$_4$ | H | 2,6-Cl$_2$-4-CF$_3$ | O |
| 3-219 | 72 | Me | H | 2,4-Cl$_2$-C$_6$H$_3$ | H | 3-CF$_3$ | O |
| 3-220 | | Me | H | 2,4-Cl$_2$-C$_6$H$_3$ | H | 2,6-Cl$_2$-4-CF$_3$ | O |
| 3-221 | | Me | H | 2,4-Cl$_2$-C$_6$H$_3$ | H | 2-Cl-6-F-4-CF$_3$ | O |
| 3-222 | 75 | Me | H | 2,6-Cl$_2$-C$_6$H$_3$ | H | 3-CF$_3$ | O |
| 3-223 | | Me | H | 2,6-Cl$_2$-C$_6$H$_3$ | H | 2,6-Cl$_2$-4-CF$_3$ | O |
| 3-224 | | Me | H | 2,6-Cl$_2$-C$_6$H$_3$ | H | 2,Cl-6-F-4-CF$_3$ | O |
| 3-225 | | Me | H | 3,4-Cl$_2$-C$_6$H$_3$ | H | 3-CF$_3$ | O |
| 3-226 | | Me | H | 3,4-Cl$_2$-C$_6$H$_3$ | H | 2,6-Cl$_2$-4-CF$_3$ | O |
| 3-227 | | Me | H | 3,4-Cl$_2$-C$_6$H$_3$ | H | 2,Cl-6-F-4-CF$_3$ | O |
| 3-228 | 74 | Me | H | 3,4-Cl$_2$-C$_6$H$_3$ | H | 3-CF$_3$ | O |
| 3-229 | 73 | Me | H | 2,4-F$_2$-C$_6$H$_3$ | H | 3-CF$_3$ | O |
| 3-230 | 79 | Me | H | 2,3,4-Cl$_3$-C$_6$H$_2$ | H | 3-CF$_3$ | O |
| 3-231 | | Me | H | 3-CF$_3$-C$_6$H$_4$ | H | 2,6-Cl$_2$-4-CF$_3$ | O |
| 3-232 | | Me | H | 3-CF$_3$-C$_6$H$_3$ | H | 2-Cl-6-F-4-CF$_3$ | O |
| 3-233 | 71 | Me | H | 4-CF$_3$-C$_6$H$_4$ | H | 3-CF$_3$ | O |
| 3-234 | | Me | H | 4-CF$_3$-C$_6$H$_4$ | H | 2,6-Cl$_2$-4-CF$_3$ | O |
| 3-235 | | Me | H | 4-CF$_3$-C$_6$H$_3$ | H | 2-Cl-6-F-4-CF$_3$ | O |
| 3-236 | 70 | Me | H | 3-NO$_2$-C$_6$H$_4$ | H | 3-CF$_3$ | O |
| 3-237 | | Me | H | 3-NO$_2$-C$_6$H$_4$ | H | 2,6-Cl$_2$-4-CF$_3$ | O |
| 3-238 | | Me | H | 3-NO$_2$-C$_6$H$_4$ | H | 2-Cl-6-F-4-CF$_3$ | O |
| 3-239 | | Me | H | 4-NO$_2$-C$_6$H$_4$ | H | 2,6-Cl$_2$-4-CF$_3$ | O |
| 3-240 | 81 | Me | H | C$_6$H$_5$CH$_2$ | H | 3-CF$_3$ | O |
| 3-241 | 115 | Me | H | C$_6$H$_5$CH$_2$ | H | 2,6-Cl$_2$-4-CF$_3$ | O |
| 3-242 | | Me | H | C$_6$H$_5$CH$_2$ | H | 2-Cl-6-F-4-CF$_3$ | O |
| 3-243 | | Me | H | 3-Cl-C$_6$H$_4$CH$_2$ | H | 2,6-Cl$_2$-4-CF$_3$ | O |
| 3-244 | | Me | H | 3-Cl-C$_6$H$_4$CH$_2$ | H | 2-Cl-6-F-4-CF$_3$ | O |
| 3-245 | | Me | H | 4-Cl-C$_6$H$_4$CH$_2$ | H | 2,6-Cl$_2$-4-CF$_3$ | O |
| 3-246 | | Me | H | 4-Cl-C$_6$H$_4$CH$_2$ | H | 2-Cl-6-F-4-CF$_3$ | O |
| 3-247 | 82 | Me | H | C$_6$H$_5$C(CH$_3$)H | H | 3-CF$_3$ | O |
| 3-248 | | Me | Cl | H | H | 2,6-Cl$_2$-4-CF$_3$ | O |
| 3-249 | 247 | Me | Cl | Me | H | 2,6-Cl$_2$-4-CF$_3$ | O |
| 3-250 | | Me | Cl | Me | H | 2-Cl-6-F-4-CF$_3$ | O |
| 3-251 | 245 | Me | Cl | Me | H | 4-NO$_2$-2-CF$_3$ | O |
| 3-252 | 244 | Me | Cl | Me | H | 2-NO$_2$-4-CF$_3$ | O |
| 3-253 | 248 | Me | Cl | Et | H | 2,6-Cl$_2$-4-CF$_3$ | O |
| 3-254 | | Me | Cl | Et | H | 2,-6-Cl$_2$-4-CF$_3$ | S |
| 3-255 | | Me | Cl | Et | H | 2-Cl-6-F-4-CF$_3$ | O |
| 3-256 | | Me | Cl | Et | H | 2-Cl-6-F-4-CF$_3$ | S |
| 3-257 | | Me | Cl | Pr | H | 2,6-Cl$_2$-4-CF$_3$ | O |
| 3-258 | | Me | Cl | Pr | H | 2-Cl-6-F-4-CF$_3$ | O |
| 3-259 | 249 | Me | Cl | i-Pr | H | 2,6-Cl$_2$-4-CF$_3$ | O |
| 3-260 | | Me | Cl | i-Pr | H | 2-Cl-6-F-4-CF$_3$ | O |
| 3-261 | 243 | Me | Cl | i-Pr | H | 2-NO$_2$-4-CF$_3$ | O |
| 3-262 | | Me | Cl | Bu | H | 2,6-Cl$_2$-4-CF$_3$ | O |
| 3-263 | | Me | Cl | Bu | H | 2-Cl-6-F-4-CF$_3$ | O |
| 3-264 | | Me | Cl | s-Bu | H | 2,6-Cl$_2$-4-CF$_3$ | O |
| 3-265 | | Me | Cl | s-Bu | H | 2-Cl-6-F-4-CF$_3$ | O |
| 3-266 | 246 | Me | Cl | Hex | H | 2,6-Cl$_2$-4-CF$_3$ | O |
| 3-267 | | Me | Cl | Hex | H | 2-Cl-6-F-4-CF$_3$ | O |
| 3-268 | | Me | Cl | c-Pr | H | 2,6-Cl$_2$-4-CF$_3$ | O |
| 3-269 | | Me | Cl | c-Pr | H | 2,Cl-6-F-4-CF$_3$ | O |
| 3-270 | 160 | Me | Cl | ClC$_2$H$_4$ | H | 2,6-Cl$_2$-4-CF$_3$ | O |
| 3-271 | | Me | Cl | ClC$_2$H$_4$ | H | 2-Cl-6-F-4-CF$_3$ | O |
| 3-272 | | Me | Cl | MeOCH$_2$ | H | 2,6-Cl$_2$-4-CF$_3$ | O |
| 3-273 | | Me | Cl | MeOCH$_2$ | H | 2-Cl-6-F-4-CF$_3$ | O |
| 3-274 | | Me | Cl | MeOCH$_2$CH$_2$ | H | 2,6-Cl$_2$-4-CF$_3$ | O |
| 3-275 | | Me | Cl | MeOCH$_2$CH$_2$ | H | 2-Cl-6-F-4-CF$_3$ | O |
| 3-276 | | Me | Br | H | H | 2,6-Cl$_2$-4-CF$_3$ | O |

TABLE 3-continued

Synthesis of 3-(substituted Phenyloxy)pyrazole derivatives

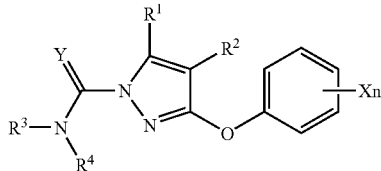

| Compound No. | Example No. | R¹ | R² | R³ | R⁴ | Xn | Y |
|---|---|---|---|---|---|---|---|
| 3-277 | | Me | Br | H | H | 2,6-Cl₂-4-CF₃ | S |
| 3-278 | | Me | Br | H | H | 2-Cl-6-F-4-CF₃ | O |
| 3-279 | | Me | Br | H | H | 2-Cl-6-F-4-CF₃ | S |
| 3-280 | | Me | Br | Me | H | 2,6-Cl₂-4-CF₃ | O |
| 3-281 | | Me | Br | Me | H | 2-Cl-6-F-4-CF₃ | O |
| 3-282 | | Me | Br | Et | H | 2,6-Cl₂-4-CF₃ | O |
| 3-283 | | Me | Br | Et | H | 2-Cl-6-F-4-CF₃ | O |
| 3-284 | | Me | Br | Pr | H | 2,6-Cl₂-4-CF₃ | O |
| 3-285 | | Me | Br | Pr | H | 2-Cl-6-F-4-CF₃ | O |
| 3-286 | | Me | Me | H | H | 2,6-Cl₂-4-CF₃ | O |
| 3-287 | | Me | Me | H | H | 2,6-Cl₂-4-CF₃ | S |
| 3-288 | | Me | Me | H | H | 2-Cl-6-F-4-CF₃ | O |
| 3-289 | | Me | Me | H | H | 2-Cl-6-F-4-CF₃ | S |
| 3-290 | | Me | Me | Me | H | 2,6-Cl₂-4-CF₃ | O |
| 3-291 | | Me | Me | Me | H | 2,6-Cl₂4-CF₃ | S |
| 3-292 | | Me | Me | Me | H | 2-Cl-6-F-4-CF₃ | O |
| 3-293 | | Me | Me | Me | H | 2-Cl-6-F-4-CF₃ | S |
| 3-294 | 152 | Me | Me | Me | H | 4-NO₂-2-CF₃ | O |
| 3-295 | 151 | Me | Me | Me | H | 2-NO₂-4-CF₃ | O |
| 3-296 | | Me | Me | Et | H | 2,6-Cl₂-4-CF₃ | O |
| 3-297 | | Me | Me | Et | H | 2,6-Cl₂-4-CF₃ | S |
| 3-298 | | Me | Me | Et | H | 2-Cl-6-F-4-CF₃ | O |
| 3-299 | | Me | Me | Et | H | 2-Cl-6-F-4-CF₃ | S |
| 3-300 | | Me | Me | Et | H | 4-NO₂-2-CF₃ | O |
| 3-301 | | Me | Me | Et | H | 2-NO₂-4-CF₃ | O |
| 3-302 | | Me | Me | Pr | H | 2,6-Cl₂-4-CF₃ | O |
| 3-303 | | Me | Me | Pr | H | 2,6-Cl₂-4-CF₃ | S |
| 3-304 | | Me | Me | Pr | H | 2-Cl-6-F-4-CF₃ | O |
| 3-305 | | Me | Me | Pr | H | 2-Cl-6-F-4-CF₃ | S |
| 3-306 | | Me | Me | i-Pr | H | 2,6-Cl₂-4-CF₃ | O |
| 3-307 | | Me | Me | i-Pr | H | 2,6-Cl₂-4-CF₃ | S |
| 3-308 | | Me | Me | i-Pr | H | 2-Cl-6-F-4-CF₃ | O |
| 3-309 | | Me | Me | i-Pr | H | 2-Cl-6-F-4-CF₃ | S |
| 3-310 | | Me | Et | H | H | 2,6-Cl₂-4-CF₃ | O |
| 3-311 | | Me | Et | H | H | 2-Cl-6-F-4-CF₃ | O |
| 3-312 | | Me | Et | Me | H | 2,6-Cl₂-4-CF₃ | O |
| 3-313 | | Me | Et | Me | H | 2,6-Cl₂-4-CF₃ | S |
| 3-314 | | Me | Et | Me | H | 2-Cl-6-F-4-CF₃ | O |
| 3-315 | | Me | Et | Me | H | 2-Cl-6-F-4-CF₃ | S |
| 3-316 | 157 | Me | Et | Me | H | 4-NO₂-2-CF₃ | O |
| 3-317 | 156 | Me | Et | Me | H | 2-NO₂-4-CF₃ | O |
| 3-318 | 169 | Me | Et | Et | H | 2,6-Cl₂-4-CF₃ | O |
| 3-319 | 227 | Me | H | —CH₂CH₂CH₂CH₂— | | 2,6-Cl₂4-CF₃ | O |
| 3-320 | | Me | H | —CH₂CH₂CH₂CH₂— | | 2-Cl-6-F-4-CF₃ | O |
| 3-321 | 228 | Me | H | —CH₂C (CH₂) OC (CH₂) CH₂— | | 2,6-Cl₂-4-CF₃ | O |
| 3-322 | | Me | H | —CH₂C (CH₂) OC (CH₂) CH₂— | | 2-Cl-6-F-4-CF₃ | O |
| 3-323 | | Et | H | H | H | 2,6-Cl₂-4-CF₃ | O |
| 3-324 | | Et | H | H | H | 2-Cl-6-F-4-CF₃ | O |
| 3-325 | | Et | H | Me | H | 2,6-Cl₂-4-CF₃ | O |
| 3-323 | | Et | H | Me | H | 2-Cl-6-F-4-CF₃ | O |
| 3-327 | 162 | Et | H | Me | H | 4-NO₂-2-CF₃ | O |
| 3-328 | | Et | H | Me | H | 2-Cl-6-F-4-CF₃ | O |
| 3-329 | 161 | Et | H | Me | H | 2-NO₂-4-CF₃ | O |
| 3-330 | 163 | Et | H | Et | H | 2,6-Cl₂-4-CF₃ | O |
| 3-331 | | Et | H | Et | H | 2,6-Cl₂-4-CF₃ | S |
| 3-332 | | Et | H | Et | H | 2-Cl-6-F-4-CF₃ | O |
| 3-333 | | Et | H | Et | H | 2-Cl-6-F-4-CF₃ | S |
| 3-334 | | Et | H | Pr | H | 2,6-Cl₂-4-CF₃ | O |
| 3-335 | | Et | H | Pr | H | 2-Cl-6-F-4-CF₃ | O |
| 3-336 | | Pr | H | H | H | 2,6-Cl₂-4-CF₃ | O |
| 3-337 | | Pr | H | H | H | 2-Cl-6-F-4-CF₃ | O |
| 3-338 | | Pr | H | Me | H | 2,6-Cl₂-4-CF₃ | O |
| 3-339 | | Pr | H | Me | H | 2-Cl-6-F-4-CF₃ | O |

TABLE 3-continued

Synthesis of 3-(substituted Phenyloxy)pyrazole derivatives

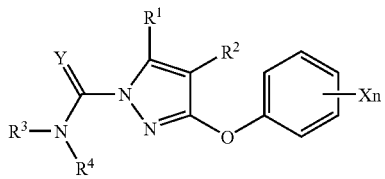

| Compound No. | Example No. | R¹ | R² | R³ | R⁴ | Xn | Y |
|---|---|---|---|---|---|---|---|
| 3-340 | | Pr | H | Et | H | 2,6-Cl$_2$-4-CF$_3$ | O |
| 3-341 | | i-Pr | H | H | H | 2,6-Cl$_2$-4-CF$_3$ | O |
| 3-342 | | i-Pr | H | H | H | 2-Cl-6-F-4-CF$_3$ | O |
| 3-343 | | i-Pr | H | Me | H | 2,6-Cl$_2$-4-CF$_3$ | O |
| 3-344 | | i-Pr | H | Me | H | 2-Cl-6-F-4-CF$_3$ | O |
| 3-345 | 167 | i-Pr | H | Et | H | 2,6-Cl$_2$-4-CF$_3$ | 0 |
| 3-346 | | i-Pr | H | Et | H | 2-Cl-6-F-4-CF$_3$ | O |
| 3-347 | | s-Bu | H | Et | H | 2,6-Cl$_2$-4-CF$_3$ | O |
| 3-348 | | s-Bu | H | Et | H | 2-Cl-6-F-4-CF$_3$ | O |
| 3-349 | 168 | t-Bu | H | Et | H | 2,6-Cl$_2$-4-CF$_3$ | O |
| 3-350 | | t-Bu | H | Et | H | 2-Cl-6-F-4-CF$_3$ | O |
| 3-351 | | Hex | H | Et | H | 2,6-Cl$_2$-4-CF$_3$ | O |
| 3-352 | | Hex | H | Et | H | 2-Cl-6-F-4-CF$_3$ | O |
| 3-353 | 166 | c-Pr | H | Et | H | 2,6-Cl$_2$-4-CF$_3$ | O |
| 3-354 | | c-Pr | H | Et | H | 2-Cl-6-F-4-CF$_3$ | O |
| 3-355 | | c-Hex | H | Et | H | 2,6-Cl$_2$-4-CF$_3$ | O |
| 3-356 | | c-Hex | H | Et | H | 2-Cl-6-F-4-CF$_3$ | O |
| 3-357 | | MeOCH$_2$ | H | H | H | 2,6-Cl$_2$-4-CF$_3$ | O |
| 3-358 | | MeOCH$_2$ | H | H | H | 2-Cl-6-F-4-CF$_3$ | O |
| 3-359 | | MeOCH$_2$ | H | Me | H | 2,6-Cl$_2$-4-CF$_3$ | O |
| 3-360 | | MeOCH$_2$ | H | Me | H | 2-Cl-6-F-4-CF$_3$ | O |
| 3-361 | 170 | MeOCH$_2$ | H | Et | H | 2,6-Cl$_2$-4-CF$_3$ | O |
| 3-362 | | MeOCH$_2$ | H | Et | H | 2-Cl-6-F-4-CF$_3$ | O |
| 3-363 | | CF$_3$ | H | H | H | 2,6-Cl$_2$-4-CF$_3$ | O |
| 3-364 | | CF$_3$ | H | H | H | 2-Cl-6-F-4-CF$_3$ | O |
| 3-365 | | CF$_3$ | H | Me | H | 2,6-Cl$_2$-4-CF$_3$ | O |
| 3-366 | | CF$_3$ | H | Me | H | 2-Cl-6-F-4-CF$_3$ | O |
| 3-367 | 172 | CF$_3$ | H | Me | H | 2-NO$_2$-4-CF$_3$ | O |
| 3-368 | | CF$_3$ | H | Et | H | 2,6-Cl$_2$-4-CF$_3$ | O |
| 3-369 | | CF$_3$ | H | Et | H | 2-Cl-6-F-4-CF$_3$ | O |
| 3-370 | 241 | CF$_3$ | H | i-Pr | i-Pr | 2-NO$_2$-4-CF$_3$ | O |
| 3-371 | 250 | CCl$_3$ | H | Pr | H | 2,6-Cl$_2$-4-CF$_3$ | O |
| 3-372 | 249 | CCl$_3$ | H | i-Pr | H | 2,6-Cl$_2$-4-CF$_3$ | O |
| 3-373 | 171 | EtO$_2$CH$_2$ | H | Et | H | 2,6-Cl$_2$-4-CF$_3$ | O |
| 3-374 | | EtO$_2$CH$_2$ | H | Et | H | 2-Cl-6-F-4-CF$_3$ | O |
| 3-375 | 175 | MeO$_2$C | H | Et | H | 2,6-Cl$_2$-4-CF$_3$ | O |
| 3-373 | | MeO$_2$C | H | Et | H | 2-Cl-6-F-4-CF$_3$ | O |
| 3-377 | | 3-Cl-C$_6$H$_5$ | H | Et | H | 2,6-Cl$_2$-4-CF$_3$ | O |
| 3-378 | | 3-Cl-C$_6$H$_5$ | H | Et | H | 2-Cl-6-F-4-CF$_3$ | O |
| 3-379 | 176 | 4-Cl-C$_6$H$_5$ | H | Et | H | 2,6-Cl$_2$-4-CF$_3$ | O |
| 3-380 | | 4-Cl-C$_6$H$_5$ | H | Et | H | 2-Cl-6-F-4-CF$_3$ | O |
| 3-381 | | 4-Br-C$_6$H$_5$ | H | Et | H | 2,6-Cl$_2$-4-CF$_3$ | O |
| 3-382 | | 4-Br-C$_6$H$_5$ | H | Et | H | 2-Cl-6-F-4-CF$_3$ | O |

TABLE 4

Synthesis of 3-(substituted Pyridyloxy) pyrazole derivatives

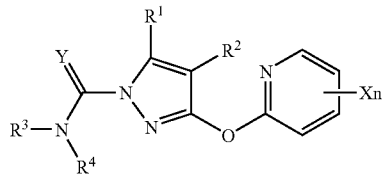

| Compound No. | Example No. | R¹ | R² | R³ | R⁴ | Xn | Y |
|---|---|---|---|---|---|---|---|
| 4-1 | | Me | H | H | H | 3,5-Cl₂ | O |
| 4-2 | 225 | Me | H | H | H | 3-Cl-5-CF₃ | O |
| 4-3 | | Me | H | H | H | 3-Cl-5-CF₃ | S |
| 4-4 | | Me | H | H | H | 5-CF₃ | O |
| 4-5 | | Me | H | Me | H | 3,5-Cl₂ | O |
| 4-6 | 133 | Me | H | Me | H | 3-Cl-5-CF₃ | O |
| 4-7 | 187 | Me | H | Me | H | 3-Cl-5-CF₃ | S |
| 4-8 | | Me | H | Me | H | 5-CF₃ | O |
| 4-9 | | Me | H | Me | H | 3,5-(NO₂)₂ | O |
| 4-10 | 237 | Me | H | Me | Me | 3-Cl-5-CF₃ | O |
| 4-11 | 265 | Me | H | Me | MeOCH₂ | 3-Cl-5-CF₃ | O |
| 4-12 | | Me | H | Me | MeOCH₂ | 3-Cl-5-CF₃ | O |
| 4-13 | 131 | Me | H | Et | H | 4-Me-6-NO₂ | O |
| 4-14 | 130 | Me | H | Et | H | 3-NO₂-6-MeO | O |
| 4-15 | 129 | Me | H | Et | H | 3,5-Cl₂ | O |
| 4-16 | 134 | Me | H | Et | H | 3-Cl-5-CF₃ | O |
| 4-17 | 188 | Me | H | Et | H | 3-Cl-5-CF₃ | S |
| 4-18 | | Me | H | Et | H | 5-CF₃ | O |
| 4-19 | | Me | H | Et | H | 3,5-(NO₂)₂ | O |
| 4-20 | | Me | H | Et | Me | 3-Cl-5-CF₃ | O |
| 4-21 | 235 | Me | H | Et | Et | 3-Cl-5-CF₃ | O |
| 4-22 | | Me | H | Et | MeOCH₂ | 3-Cl-5-CF₃ | O |
| 4-23 | 135 | Me | H | Pr | H | 3-Cl-5-CF₃ | O |
| 4-24 | 189 | Me | H | Pr | H | 3-Cl-5-CF₃ | S |
| 4-25 | 132 | Me | H | i-Pr | H | 3-Cl-5-CF₃ | O |
| 4-26 | 190 | Me | H | i-Pr | H | 3-Cl-5-CF₃ | S |
| 4-27 | 236 | Me | H | i-Pr | i-Pr | 3-Cl-5-CF₃ | O |
| 4-28 | 233 | Me | H | Bu | H | 3-Cl-5-CF₃ | C |
| 4-29 | 191 | Me | H | Bu | H | 3-Cl-5-CF₃ | S |
| 4-30 | 218 | Me | H | s-Bu | H | 3-Cl-5-CF₃ | O |
| 4-31 | 220 | Me | H | i-Bu | H | 3-Cl-5-CF₃ | O |
| 4-32 | 136 | Me | H | t-Bu | H | 3-Cl-5-CF₃ | O |
| 4-33 | 137 | Me | H | Pent | H | 3-Cl-5-CF₃ | O |
| 4-34 | | Me | H | 2-Pent | H | 3-Cl-5-CF₃ | O |
| 4-35 | 138 | Me | H | Hex | H | 3-Cl-5-CF₃ | O |
| 4-36 | 139 | Me | H | Hep | H | 3-Cl-5-CF₃ | O |
| 4-37 | 140 | Me | H | Oct | H | 3-Cl-5-CF₃ | O |
| 4-38 | 141 | Me | H | Dod | H | 3-Cl-5-CF₃ | O |
| 4-39 | 219 | Me | H | c-Pr | H | 3-Cl-5-CF₃ | O |
| 4-40 | 142 | Me | H | c-Hex | H | 3-Cl-5-CF₃ | O |
| 4-41 | 197 | Me | H | H₂C=CH | H | 3-Cl-5-CF₃ | S |
| 4-42 | 143 | Me | H | H₂C=CHCH₂ | H | 3-Cl-5-CF₃ | O |
| 4-43 | 192 | Me | H | H₂C=CHCH₂ | H | 3-Cl-5-CF₃ | S |
| 4-44 | | Me | H | HC≡CCH₂ | H | 3-Cl-5-CF₃ | O |
| 4-45 | | Me | H | CF₃CH₂ | H | 3-Cl-5-CF₃ | O |
| 4-46 | 144 | Me | H | 2-ClO₂H₄ | H | 3-Cl-5-CF₃ | O |
| 4-47 | | Me | H | 2-BrC₂H₄ | H | 3-Cl-5-CF₃ | O |
| 4-48 | | Me | H | 2-FC₂H₄ | H | 3-Cl-5-CF₃ | O |
| 4-49 | | Me | H | —HOC₂H₄ | H | 3-Cl-5-CF₃ | O |
| 4-50 | 221 | Me | H | MeO | H | 3-Cl-5-CF₃ | O |
| 4-51 | 222 | Me | H | EtC | H | 3-Cl-5-CF₃ | O |
| 4-52 | | Me | H | H₂O=CHCH₂O | H | 3-Cl-5-CF₃ | O |
| 4-53 | | Me | H | C₆H₅CH₂O | H | 3-Cl-5-CF₃ | O |
| 4-54 | 193 | Me | H | MeOCH₂ | H | 3-Cl-5-CF₃ | S |
| 4-55 | 194 | Me | H | MeOCH₂CH₂ | H | 3-Cl-5-CF₃ | S |
| 4-56 | 195 | Me | H | (CH₃)₂CH(CO₂Me)H | H | 3-Cl-5-CF₃ | S |
| 4-57 | 145 | Me | H | C₆H₅ | H | 3-Cl-5-CF₃ | O |
| 4-58 | 146 | Me | H | 3-Cl-C₆H₄ | H | 3-Cl-5-CF₃ | O |
| 4-59 | | Me | H | 4-Cl-C₆H₄ | H | 3-Cl-5-CF₃ | O |
| 4-60 | | Me | H | 2,4-Cl₂-C₆H₃ | H | 3-Cl-5-CF₃ | O |
| 4-61 | 147 | Me | H | 3,4-Cl₂-C₆H₃ | H | 3-Cl-5-CF₃ | O |

TABLE 4-continued

Synthesis of 3-(substituted Pyridyloxy) pyrazole derivatives

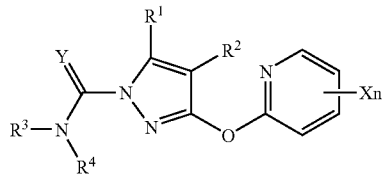

| Compound No. | Example No. | R¹ | R² | R³ | R⁴ | Xn | Y |
|---|---|---|---|---|---|---|---|
| 4-62 | 148 | Me | H | 3-CF₃-C₆H₄ | H | 3-Cl-5-CF₃ | O |
| 4-63 | 149 | Me | H | 4-CF₃-C₆H₄ | H | 3-Cl-5-CF₃ | O |
| 4-64 | 150 | Me | H | 3-NO₂-C₆H₄ | H | 3-Cl-5-CF₃ | O |
| 4-65 | 196 | Me | H | 4-Cl-C₆H₄CH₂ | H | 3-Cl-5-CF₃ | S |
| 4-66 | 252 | Me | Cl | Me | H | 3-Cl-5-CF₃ | O |
| 4-67 | 251 | Me | Cl | Et | H | 3-Cl-5-CF₃ | O |
| 4-68 | 253 | Me | Cl | Pr | H | 3-Cl-5-CF₃ | O |
| 4-69 | 254 | Me | Cl | i-Pr | H | 3-Cl-5-CF₃ | O |
| 4-70 | 255 | Me | Cl | Pent | H | 3-Cl-5-CF₃ | O |
| 4-71 | 256 | Me | Cl | Hex | H | 3-Cl-5-CF₃ | O |
| 4-72 | 257 | Me | Cl | Hep | H | 3-Cl-5-CF₃ | O |
| 4-73 | 258 | Me | Cl | Oct | H | 3-Cl-5-CF₃ | O |
| 4-74 | 259 | Me | Cl | Dod | H | 3-Cl-5-CF₃ | O |
| 4-75 | 260 | Me | Cl | c-Hex | H | 3-Cl-5-CF₃ | O |
| 4-76 |  | Me | Cl | HC≡CCH₂ | H | 3-Cl-5-CF₃ | O |
| 4-77 | 261 | Me | Cl | ClC₂H₄ | H | 3-Cl-5-CF₃ | O |
| 4-78 | 263 | Me | Br | Et | H | 3-Cl-5-CF₃ | O |
| 4-79 |  | Me | Me | H | H | 3-Cl-5-CF₃ | O |
| 4-80 | 154 | Me | Me | Me | H | 3-Cl-5-CF₃ | O |
| 4-81 | 155 | Me | Me | Et | H | 3-Cl-5-CF₃ | O |
| 4-82 | 153 | Me | Me | i-Pr | H | 3-Cl-5-CF₃ | O |
| 4-83 |  | Me | Et | H | H | 3-Cl-5-CF₃ | O |
| 4-84 | 158 | Me | Et | Me | H | 3-Cl-5-CF₃ | O |
| 4-85 | 159 | Me | Et | Et | H | 3-Cl-5-CF₃ | O |
| 4-86 |  | Et | H | H | H | 3-Cl-5-CF₃ | O |
| 4-87 | 164 | Et | H | Me | H | 3-Cl-5-CF₃ | O |
| 4-88 | 165 | Et | H | Et | H | 3-Cl-5-CF₃ | O |
| 4-89 | 262 | Et | Cl | Me | H | 3-Cl-5-CF₃ | O |
| 4-90 |  | CF₃ | H | H | H | 3-Cl-5-CF₃ | O |
| 4-91 | 176 | CF₃ | H | Me | H | 3-Cl-5-CF₃ | O |
| 4-92 | 238 | CF₃ | H | Me | Me | 3-Cl-S-CF₃ | O |
| 4-93 | 173 | CF₃ | H | Et | H | 3-Cl-5-CF₃ | O |
| 4-94 | 239 | CF₃ | H | Et | Et | 3-Cl-5-CF₃ | O |
| 4-95 | 240 | CF₃ | H | i-Pr | i-Pr | 3-Cl-5-CF₃ | O |

When the compound of the present invention is used as a herbicide, it can be used as it is. It can be also used in the form of a herbicide containing one or more adjuvants in combination. Generally, as adjuvants, various carriers, extenders, solvents, surfactants and stabilizers are incorporated, and the compound of the present invention is preferably formed into preparations in the form of a wettable powder, an emulsifiable concentrate, a dust, granules, a flowable agent or the like.

The solvent as one adjuvant in the herbicide containing the compound of the present invention as an active ingredient is properly selected from water, alcohols, ketones, ethers, aliphatic and aromatic hydrocarbons, halogenated hydrocarbons, acid amides, esters or nitriles. One of these solvents may be used, or a mixture of two or more solvents of these may be used.

The extender is selected from mineral powders including clays such as kaolin and bentonite, talcs such as talc and pyrophyllite, oxides such as diatomite and white carbon or plant powders such as soybean powder and CMC. Further, a surfactant may be used as a spreading agent, a dispersant, an emulsifier or a penetrant. The surfactant includes, for example, nonionic surfactants, cationic surfactants and amphoteric surfactants. These surfactants are used alone or as a mixture of at least two members of these depending upon an end in use.

The method of use of a herbicide containing the compound of the present invention as an active ingredient includes soil treatment, water surface treatment, foliar treatment, and the herbicide can produce an excellent effect when applied before and during germination.

Further, the herbicide containing the compound of the present invention as an active ingredient may contain other active components such as other herbicide, an insecticide, a fungicide, a plant growth regulator, etc., in combination, or may be used in combination with these.

The present invention will be explained further in detail with reference to Preparation Examples of herbicides containing the compound of the present invention as an active ingredient and Examples of testing herbicides for herbicidal efficacy. In addition, "part" stands for "part by weight".

Preparation Example 1

Emulsifiable Concentrate

20 Parts of a compound of the present invention, 35 parts of xylene, 40 parts of cyclohexanone and 5 parts of Sorpol 900A (supplied by Toho Chemical Co., Ltd.) were homogeneously mixed, to give an emulsifiable concentrate.

Preparation Example 2

Wettable Powder

50 Parts of a compound of the present invention, 25 parts of diatomite, 22 parts of clay and 3 parts of Lunox 1000C (supplied by Toho Chemical Co., Ltd.) were homogenously mixed and pulverized, to give a wettable powder.

Preparation Example 3

Granules

A mixture containing 5 parts of a compound of the present invention, 35 parts of bentonite, 55 parts of talc, 5 parts of sodium ligninsulfonate was homogenously mixed and pulverized, and then water was added. The mixture was kneaded and granulated with an extrusion granulator, and the granulated product was dried and particle-size-adjusted, to give granules.

The compound of the present invention was tested for herbicidal efficacy according to those methods shown in the following Test Examples with regard to preparations prepared according to the above-shown methods. The herbicidal efficacy thereof on test weeds and their phytotoxicity to test crops were evaluated on the basis of five ratings in which 1 shows no influence and 5 shows complete die.

Test Example 1

Herbicidal Efficacy Test by Pre-Emergence Treatment Under Submergence Condition A 1/10,000-are pot was filled with paddy field soil, and, after plowing, seeds of *Echinochloa oryzicola, Cyperus difformis, Monochoria vaginalis, Scirpus juncoides, Eleocharis acicularis* and other annual broadleaf weeds such as *Lindernia procumbens, Rotala indica* and *Elatine triandra* were sown. Rice (*oryza sativa*) seedlings (cultiver "Koshihikari") at a 2.5-leaf stage were transplanted and kept under a submergence condition. After one day, the wettable powder or emulsifiable concentrate of the compound of the present invention, prepared according to Preparation Example, was diluted and dropped on a water surface at a predetermined dose. On the 15$^{th}$ day after the treatment, the herbicidal efficacy on the test weeds and the injury to the rice were investigated on the basis of the ratings of 1 to 5, and Table 5 shows the results.

TABLE 5

| | | Herbicidal efficacy test by pre-emergence treatment under submergence condition | | | | | | |
|---|---|---|---|---|---|---|---|---|
| Comp'd | Dose | Herbicidal efficacy | | | | | | Injury |
| No. | kg/ha | Eo | Cd | Blw | Mv | Sj | Ea | Os |
| 3-3 | 1 | 5 | 5 | 5 | 5 | 5 | 5 | 1.5 |
| | 0.5 | 5 | 5 | 5 | 5 | 5 | 5 | 1.5 |

TABLE 5-continued

| | | Herbicidal efficacy test by pre-emergence treatment under submergence condition | | | | | | |
|---|---|---|---|---|---|---|---|---|
| Comp'd | Dose | Herbicidal efficacy | | | | | | Injury |
| No. | kg/ha | Eo | Cd | Blw | Mv | Sj | Ea | Os |
| 3-14 | 1 | 5 | 5 | 5 | 5 | 5 | 5 | 2.5 |
| | 0.5 | 5 | 5 | 5 | 5 | 5 | 5 | 2.3 |
| 3-15 | 1 | 5 | 5 | 5 | 5 | 5 | 5 | 1.5 |
| | 0.5 | 5 | 5 | 5 | 5 | 5 | 5 | 1.3 |
| 3-44 | 1 | 5 | 5 | 5 | 5 | 5 | 5 | 3.5 |
| | 0.5 | 5 | 5 | 5 | 5 | 5 | 5 | 2.5 |
| 3-45 | 1 | 5 | 5 | 5 | 5 | 5 | 5 | 1.7 |
| | 0.5 | 5 | 5 | 5 | 5 | 4 | 5 | 1.5 |
| 3-74 | 1 | 5 | 5 | 5 | 5 | 5 | 5 | 1.8 |
| | 0.5 | 5 | 5 | 5 | 5 | 5 | 5 | 1.8 |
| 3-89 | 1 | 5 | 5 | 5 | 5 | 5 | 5 | 1.5 |
| | 0.5 | 5 | 5 | 5 | 5 | 5 | 5 | 1.3 |
| 3-130 | 1 | 5 | 5 | 5 | 5 | 5 | 5 | 1.8 |
| | 0.5 | 5 | 5 | 5 | 5 | 5 | 5 | 1.5 |
| 3-143 | 1 | 5 | 5 | 5 | 5 | 5 | 5 | 1.5 |
| | 0.5 | 5 | 5 | 5 | 5 | 4 | 5 | 1.3 |
| 3-146 | 1 | 5 | 5 | 5 | 5 | 5 | 5 | 1 |
| | 0.5 | 5 | 5 | 5 | 5 | 5 | 5 | 1 |
| 3-158 | 1 | 5 | 5 | 5 | 5 | 5 | 5 | 2 |
| | 0.5 | 5 | 5 | 5 | 5 | 5 | 5 | 1.5 |
| 3-169 | 1 | 5 | 5 | 5 | 5 | 4.2 | 5 | 1 |
| | 0.5 | 5 | 5 | 5 | 5 | 4 | 5 | 1 |
| 3-183 | 1 | 5 | 5 | 5 | 5 | 5 | 5 | 2 |
| | 0.5 | 5 | 5 | 5 | 5 | 5 | 5 | 2 |
| 3-249 | 1 | 5 | 5 | 5 | 5 | 5 | 5 | 1.5 |
| | 0.5 | 5 | 5 | 5 | 5 | 5 | 5 | 1.2 |
| 3-253 | 1 | 5 | 5 | 5 | 5 | 5 | 5 | 1.6 |
| | 0.5 | 5 | 5 | 5 | 5 | 5 | 5 | 1.4 |
| 3-330 | 1 | 5 | 5 | 5 | 5 | 5 | 5 | 1.5 |
| | 0.5 | 5 | 5 | 5 | 5 | 5 | 5 | 1.2 |
| 4-6 | 1 | 5 | 5 | 5 | 5 | 5 | 5 | 1.4 |
| | 0.5 | 4.8 | 5 | 5 | 5 | 4.6 | 5 | 1.2 |
| 4-16 | 1 | 5 | 5 | 5 | 5 | 5 | 5 | 2.5 |
| | 0.5 | 5 | 5 | 5 | 5 | 4.8 | 5 | 2 |
| 4-17 | 1 | 5 | 5 | 5 | 5 | 4.8 | 5 | 1.8 |
| | 0.5 | 5 | 5 | 4.8 | 5 | 4.5 | 5 | 1.5 |
| 4-23 | 1 | 5 | 5 | 5 | 5 | 5 | 5 | 1.3 |
| | 0.5 | 5 | 5 | 4.8 | 5 | 4.9 | 5 | 1.1 |

Eo: *Echinochloa oryzicola*, Cd: *Cyperus difformis*, Blw: annual broadleaf weeds, Mv: *Monochoria vaginalis*, Sj: *Scirpus juncoides*, Ea: *Eleocharis acicularis*, Os: *Oryza sativa*

Test Example 2

Herbicidal Efficacy Test by Soil Treatment Before Germination Under Upland Field Condition A vat having an area of 5×10 cm$^2$ and a depth of 5 cm was filled with upland field soil, and seeds of *Chenopodium album, Echinochloa crus-galli, Amaranthus viridis, Digitaria ciliaris* and sweet corn (*Zea mays*) were sown thereon and covered with soil by a depth of 0.5 cm. Next day, the wettable powder or emulsifiable concentrate of the compound of the present invention, prepared according to Preparation Example, was diluted and sprayed uniformly onto the covering soil at a predetermined dose. On the 21st day after the treatment, the herbicidal efficacy on the test weeds and the injury to the corn were investigated on the basis of the ratings of 1 to 5, and Table 6 shows the results.

TABLE 6

Herbicidal efficacy test by soil treatment
before germination under upland field condition

| Comp'd No. | Dose kg/ha | Herbicidal activity | | | | Injury |
|---|---|---|---|---|---|---|
| | | Ca | Ec | Av | Dc | Zm |
| 3-3 | 1 | 5 | 3.5 | 5 | 4.5 | 1.5 |
| 3-14 | 1 | 5 | 4.9 | 5 | 5 | — |
| 3-44 | 1 | 5 | 5 | 5 | 5 | 3 |
| 3-45 | 1 | 5 | 5 | 5 | 5 | 2 |
| 3-74 | 1 | 5 | 4.9 | 5 | 5 | 1 |
| 3-183 | 1 | 5 | 3 | 5 | 4 | 1 |
| 3-249 | 1 | 5 | 4.5 | 5 | 5 | 1.2 |
| 3-253 | 1 | 5 | 4 | 5 | 5 | 1.5 |
| 3-330 | 1 | 5 | 3.5 | 5 | 5 | 1.5 |

Ca: *Chenopodium album*, Ec: *Echinochloa crus-galli*, Av: *Amaranthus viridis*, Dc: *Digitaria ciliaris*, Zm: *Zea mays*.

Test Example 3

Herbicidal Efficacy Test by Foliar Treatment After Germination Under Upland Field Condition A vat having an area of 5×10 cm² and a depth of 5 cm was filled with upland field soil, and seeds of *Chenopodium album*, *Echinochloa crus-galli*, *Amaranthus viridis* and *Abutilon theophrasti* were sown thereon and covered with soil by a depth of 0.5 cm. Water was sprayed as required to grow them for 14 days. The wettable powder or emulsifiable concentrate of the compound of the present invention, prepared according to Preparation Example, was diluted and sprayed uniformly to shoot of the plants at a dose of 1,000 liters/ha. On the 14$^{th}$ day after the treatment, the herbicidal efficacy on the test weeds were investigated on the basis of the ratings of 1 to 5, and Table 7 shows the results.

TABLE 7

Herbicidal efficacy test by foliar treatment
after germination under upland field condition

| Comp'd No. | Dose kg/ha | Herbicidal activity | | | |
|---|---|---|---|---|---|
| | | Ca | Ec | Av | Dc |
| 3-3 | 1 | 5 | 4.5 | 5 | 5 |
| 3-14 | 1 | 5 | 5 | 5 | 5 |
| 3-15 | 1 | 5 | 5 | 5 | 5 |
| 3-44 | 1 | 5 | 5 | 5 | 5 |
| 3-45 | 1 | 5 | 5 | 5 | 5 |
| 3-67 | 1 | 5 | 4.9 | 5 | 5 |
| 3-74 | 1 | 5 | 4.9 | 5 | 5 |
| 3-82 | 1 | 5 | 3.8 | 5 | 5 |
| 3-89 | 1 | 5 | 5 | 5 | 5 |
| 3-130 | 1 | 5 | 5 | 5 | 5 |
| 3-158 | 1 | 5 | 5 | 5 | 5 |
| 3-183 | 1 | 5 | 5 | 5 | 5 |
| 3-249 | 1 | 5 | 5 | 5 | 5 |
| 3-253 | 1 | 5 | 5 | 5 | 5 |
| 3-330 | 1 | 5 | 5 | 5 | 5 |
| 4-30 | 1 | 5 | 5 | 5 | 5 |

Ca: *Chenopodium album*, Ec: *Echinochloa crus-galli*, Av: *Amaranthus viridis*, Dc: *Digitaria ciliaris*.

INDUSTRIAL UTILITY

The pyrazole derivative of the present invention exhibits excellent herbicidal activity at a low dosage without causing phytotoxicity on crops and has utility as a herbicide.

The invention claimed is:

1. A pyrazole of formula (I),

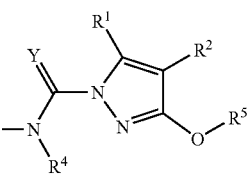

wherein:

R$^1$ is a hydrogen atom; an alkyl group having 1 to 6 carbon atoms which is unsubstituted or substituted by halogen, alkoxy having 1 to 6 carbon atoms or alkyloxycarbonyl having 1 to 6 carbon atoms; a cycloalkyl group having 3 to 8 carbon atoms; an alkyloxycarbonyl group having 1 to 6 carbon atoms; or a phenyl group which is unsubstituted or substituted by alkyl having 1 to 12 carbon atoms or halogen;

R$^2$ is a hydrogen atom;

R$^3$ is a hydrogen atom; an alkyl group having 1 to 12 carbon atoms which is unsubstituted or substituted by halogen, hydroxyl, formyl, alkoxy having 1 to 6 carbon atoms, alkyloxycarbonyl having 1 to 6 carbon atoms, or heterocyclic ring selected from the group consisting of 2-furyl, 2-tetrahydrofuryl, 2-thienyl, 1,3-dioxolan-2-yl, 1,3-dioxinan-2-yl, morpholino, and 2-pyridyl; a cycloalkyl group having 3 to 8 carbon atoms; an aralkyl group having 7 to 11 carbon atoms; an alkenyl group having 3 to 6 carbon atoms; an alkynyl group having 3 to 6 carbon atoms; a phenyl group which is unsubstituted or substituted by halogen, alkyl having 1 to 12 carbon atoms, trifluoromethyl, or nitro; an alkyloxy group having 1 to 6 carbon atoms; a cycloalkyloxy group having 3 to 8 carbon atoms; an aralkyloxy group having 7 to 11 carbon atoms; an alkenyloxy group having 3 to 6 carbon atoms; an alkynyloxy group having 3 to 6 carbon atom; or a phenyloxy group;

R$^4$ is a hydrogen atom;

R$^5$ is a 4-trifluoromethyl phenyl group which is unsubstituted or substituted by a halogen atom or nitro; and Y is an oxygen atom or a sulfur atom.

2. A herbicide containing, as an active ingredient, a pyrazole of claim 1.

3. The pyrazole of claim 1, wherein R$^1$ is a hydrogen atom, or an alkyl group having 1 to 6 carbon atoms which is unsubstituted or substituted by halogen, alkoxy having 1 to 6 carbon atoms, or alkyloxycarbonyl having 1 to 6 carbon atoms.

4. The pyrazole of claim 1, wherein R$^3$ is a hydrogen atom; an alkyl group having 1 to 12 carbon atoms which is unsubstituted or substituted by halogen, hydroxyl, formyl, alkoxy having 1 to 6 carbon atoms, alkyloxycarbonyl having 1 to 6 carbon atoms, or a heterocyclic ring selected from the group consisting of 2-furyl, 2-tetrahydrofuryl, 2-thienyl, 1,3-dioxolan-2-yl, 1,3-dioxinan-2-yl, morpholino, and 2-pyridyl; a cycloalkyl group having 3 to 8 carbon atoms; an aralkyl group having 7 to 11 carbon atoms selected from the group consisting of benzyl, 1-phenylethyl and 2-phenylethyl; an alkenyl group having 3 to 6 carbon atoms; an alkynyl group having 3 to 6 carbon atoms; a phenyl group which is unsubstituted or substituted by halogen, alkyl having 1 to 12 carbon atoms, trifluoromethyl or nitro; an alkyloxy group having 1 to 6 carbon atoms; or a cycloalkyloxy group having 3 to 8 carbon atoms.

5. The pyrazole of claim 4, wherein $R^3$ is a hydrogen atom, or an alkyl group having 1 to 12 carbon atoms which is unsubstituted or substituted by halogen, hydroxyl, formyl, alkoxy having 1 to 6 carbon atoms, alkyloxycarbonyl having 1 to 6 carbon atoms, or a heterocyclic ring selected from the group consisting of 2-furyl, 2-tetrahydrofuryl, 2-thienyl, 1,3-dioxolan-2-yl, 1,3-dioxinan-2-yl, morpholino, and 2-pyridyl.

6. The pyrazole of claim 1, wherein Y is an oxygen atom.

7. The pyrazole of claim 1, having the formula:

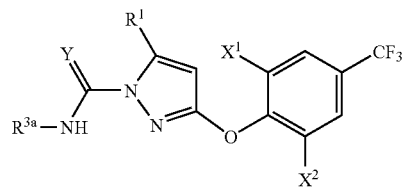

wherein $X^1$ and $X^2$ are each independently a halogen.

8. The pyrazole of claim 7, wherein $X^1$ and $X^2$ are each independently chlorine or fluorine.

\* \* \* \* \*